United States Patent
Li et al.

(10) Patent No.: US 11,725,012 B2
(45) Date of Patent: *Aug. 15, 2023

(54) IMIDAZO[1,5-A]PYRAZINE DERIVATIVES AS PI3K δ INHIBITORS

(71) Applicant: BEIGENE, LTD., Grand Cayman (KY)

(72) Inventors: Jing Li, Beijing (CN); Haibo Zhao, Beijing (CN); Zhiwei Wang, Beijing (CN)

(73) Assignee: BEIGENE, LTD., Grand Cayman (KY)

( * ) Notice: Subject to any disclaimer, the term of this patent is extended or adjusted under 35 U.S.C. 154(b) by 0 days.

This patent is subject to a terminal disclaimer.

(21) Appl. No.: 17/370,728

(22) Filed: Jul. 8, 2021

(65) Prior Publication Data

US 2022/0098202 A1 Mar. 31, 2022

Related U.S. Application Data

(63) Continuation of application No. 16/466,621, filed as application No. PCT/CN2017/114970 on Dec. 7, 2017, now Pat. No. 11,136,323.

(30) Foreign Application Priority Data

Dec. 7, 2016 (WO) ................ PCT/CN2016/108897

(51) Int. Cl.
*C07D 487/04* (2006.01)
(52) U.S. Cl.
CPC .................... *C07D 487/04* (2013.01)
(58) Field of Classification Search
CPC .......... C07D 487/04; A61K 31/4985
See application file for complete search history.

(56) References Cited

U.S. PATENT DOCUMENTS

| 11,136,323 | B2* | 10/2021 | Li ........................ C07D 487/04 |
| 11,220,506 | B2 | 1/2022 | Li et al. |
| 2019/0367523 | A1 | 12/2019 | Li et al. |
| 2020/0207774 | A1 | 7/2020 | Li et al. |
| 2022/0081447 | A1 | 3/2022 | Li et al. |

FOREIGN PATENT DOCUMENTS

| WO | WO-2005037836 A2 | 4/2005 |
| WO | WO-2010119264 A1 | 10/2010 |
| WO | WO-2012107465 A1 | 8/2012 |
| WO | WO-2013104610 A1 | 7/2013 |
| WO | WO-2014071109 A1 | 5/2014 |
| WO | WO-2014194254 A1 | 12/2014 |
| WO | WO-2015058084 A1 | 4/2015 |
| WO | WO-2016024130 A1 | 2/2016 |
| WO | WO-2018103688 A1 | 6/2018 |
| WO | WO-2019047915 A1 | 3/2019 |

OTHER PUBLICATIONS

ChemSpider (ChemZoo, Inc.) Registry Compound RN 1025939-56-3, 1 page (2008).
Extended European Search Report for European Application No. 18853233.7, dated Dec. 10, 2020, 6 pages.
Fry, M. J., "Review: Phosphoinositide 3-kinase signaling in breast cancer: how big a role might it play?," Breast Cancer Res 2001, 3:304-312.
Gonzalez, S. M. et al., "Imidazo[1,2-a]pyrazines as novel PI3K inhibitors," Bioorganic & Medicinal Chemistry Letters, vol. 22, No. 5, Mar. 2012, pp. 1874-1878.
Gura, T., Cancer Models: "Systems for identifying new drugs are often faulty," Science, vol. 278, No. 5340, pp. 1041-1042 (Nov. 1997).
International Search Report and Written Opinion for International Application No. PCT/CN2017/114970, dated Mar. 6, 2018, 13 pages.
International Search Report and Written Opinion for International Application No. PCT/CN2018/104559, dated Nov. 30, 2018, 11 pages.
Johnson, J. et al., "Relationships between drug activity in NCI preclinical in vitro and in vivo models and early clinical trials," British Journal of Cancer (2001) 84(10):1424-1431.
Pearce, H. L. et al., "Failure modes in anticancer drug discovery and development," Cancer Drug Design and Discovery, Neidle, S. (ed.), Chapter 18 in Cancer Drug Design and Discovery, Elsevier Inc., pp. 424-435 (2008).
Simone, J. V., Part XIV Oncology, 154 Introduction, In: Cecil Textbook of Medicine, 20th Edition, vol. 1, Bennett, J. C. (ed.) (1996) pp. 1004-1010.
The Merck Manual, "Acute Leukemia," (Online Edition), 6 pages (2013).

* cited by examiner

*Primary Examiner* — Deepak R Rao
(74) *Attorney, Agent, or Firm* — Cooley LLP

(57) ABSTRACT

Disclosed is a compound of Formula (I), or a stereoisomer thereof, or a pharmaceutically acceptable salt thereof, and pharmaceutical compositions comprising thereof. Also disclosed is a method of treating PI3Kδ related disorders or diseases by using the compound disclosed herein.

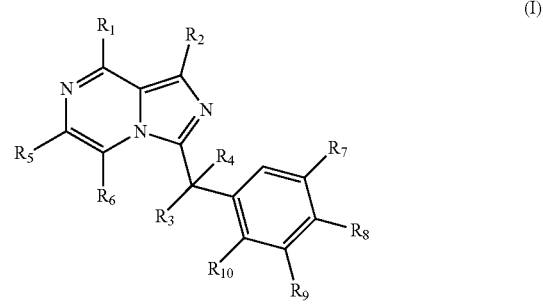

(I)

28 Claims, 1 Drawing Sheet

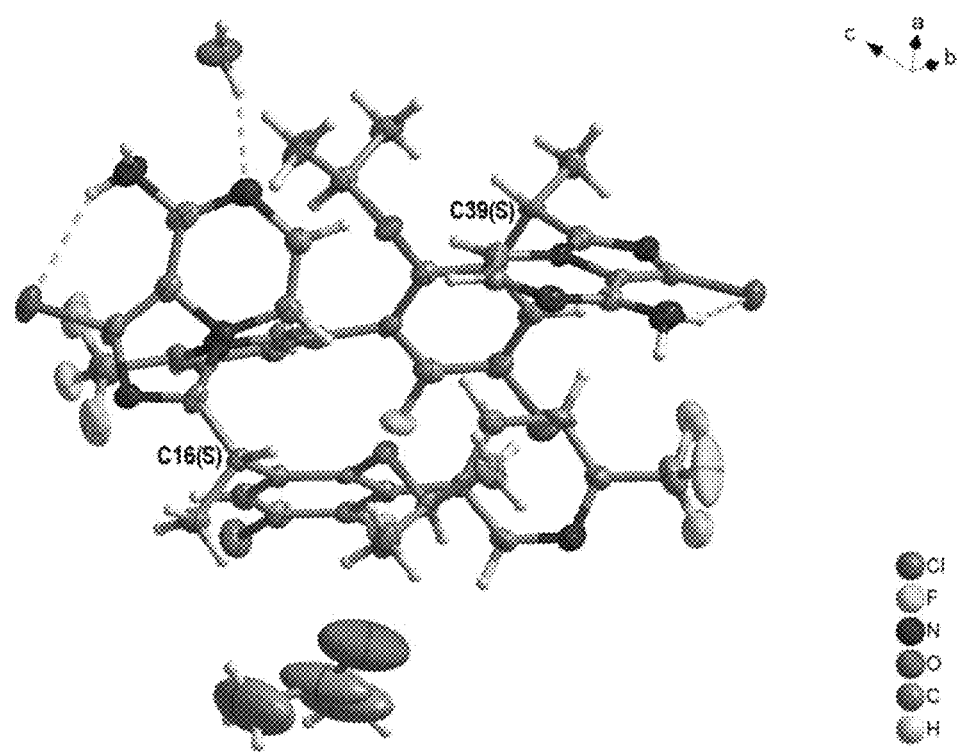

IMIDAZO[1,5-A]PYRAZINE DERIVATIVES AS PI3K δ INHIBITORS

CROSS-REFERENCE TO RELATED APPLICATIONS

This application is a continuation of U.S. patent application Ser. No. 16/466,621, filed on Jun. 4, 2019, which is a U.S. National Stage Application under 35 U.S.C. § 371 of International Application No. PCT/CN2017/114970, filed on Dec. 7, 2017, which claims the benefit of priority to International Patent Application No. PCT/CN2016/108897 filed on Dec. 7, 2016, the disclosures of each of the aforementioned patent applications are hereby incorporated by reference in their entireties for all purposes.

FIELD OF THE INVENTION

Disclose herein is an imidazo[1,5-a]pyrazine derivative, or a stereoisomer thereof, or a pharmaceutically acceptable salt thereof, and a pharmaceutical composition comprising thereof. Also disclosed herein is a method of treating PI3K-related disorders (in particular PI3Kδ-related disorders) using the imidazo[1,5-a]pyrazine derivative disclosed herein, or a stereoisomer thereof, or a pharmaceutically acceptable salt thereof. Also disclosed herein is the imidazo[1,5-a]pyrazine derivative, or a stereoisomer thereof, or a pharmaceutically acceptable salt thereof for use in the treatment of PI3K-related disorders (in particular PI3Kδ-related disorders).

BACKGROUND OF THE INVENTION

Phosphatidylinositol-4,5-bisphosphate 3-kinases (PI3Ks) are a family of enzymes involved in various of primary cellular functions, including cell growth, proliferation, differentiation, motility, survival, metabolism and intracellular trafficking [Vanhaesebroeck, B., L. Stephens, and P. Hawkins, *PI3K signalling: the path to discovery and understanding*. Nat Rev Mol Cell Biol, 2012, 13(3): p. 195-203.]. They are kinases capable of phosphorylating phosphatidylinositol [Whitman, M., et al., *Type I phosphatidylinositol kinase makes a novel inositol phospholipid, phosphatidylinositol-3-phosphate*. Nature, 1988. 332(6165): p. 644-6; Auger, K. R., et al., *PDGF-dependent tyrosine phosphorylation stimulates production of novel polyphosphoinositides in intact cells*. Cell, 1989. 57(1): p. 167-75.]. Phosphorylated phosphatidylinositols, which are called phosphoinositides, play important roles in signaling transduction and membrane trafficking [Martin, T. F., *Phosphoinositide lipids as signaling molecules: common themes for signal transduction, cytoskeletal regulation, and membrane trafficking*. Annu Rev Cell Dev Biol, 1998. 14: p. 231-64.].

PI3K family is divided into three classes (I, II, and III) based on structure, regulation and substrate specificity [Vanhaesebroeck, B., et al., *The emerging mechanisms of isoform-specific PI3K signalling*. Nat Rev Mol Cell Biol, 2010. 11(5): p, 329-41.]. Class I PI3Ks are further divided based on sequence similarity into class IA and class IB. The class IA PI3Ks comprise three closely related kinases, PI3Kα, PI3Kβ, and PI3Kδ, which exist as heterodimers composed of a catalytic subunit (p110α, p110β, or p110δ) and a regulatory subunit (p85) [Yu, J., et al., *Regulation of the p85/p110 phosphatidylinositol 3'-kinase: stabilization and inhibition of the p110alpha catalytic subunit by the p85 regulatory subunit*. Mol Cell Biol, 1998. 18(3): p. 1379-37; Carpenter, C. L., et al., *Phosphoinositide 3-kinase is activated by phosphopeptides that bind to the SH2 domains of the 85-kDa subunit*. J Biol Chem, 1993. 268(13): p. 9478-83; Zhang, X., et al., *Structure of lipid kinase p110beta/p85beta elucidates an unusual SH2-domain-mediated inhibitory mechanism*. Mol Cell, 2011. 41(5): p. 567-78; Burke, J. E., et al., *Dynamics of the phosphoinositide 3-kinase p110delta interaction with p85alpha and membranes reveals aspects of regulation distinct from p110alpha*. Structure, 2011. 19(8): p. 1127-37.]. The class IB PI3K includes only PI3Kγ, which is composed of a p110γ [Stoyanov, B., et al., *Cloning and characterization of a G protein-activated human phosphoinositide-3 kinase*. Science, 1995. 269(5224): p. 690-3.] catalytic subunit that can associate with a p101 [Stephens, L. R., et al., *The G beta gamma sensitivity of a PI3K is dependent upon a tightly associated adaptor, p101*. Cell, 1997. 89(1): p. 105-14; Brock, C., et al., *Roles of G beta gamma in membrane recruitment and activation of p110 gamma/p101 phosphoinositide 3-kinase gamma*. J Cell Biol, 2003, 160(1): p. 89-99.] or p84 [Suire, S., et al., *p84, a new Gbetagamma-activated regulatory subunit of the type IB phosphoinositide 3-kinase p110gamma*. Curr Biol, 2005. 15(6): p. 566-70.] regulatory subunit. PI3Kα and PI3Kδ respond to signaling generally through receptor tyrosine kinases (RTKs) [Inukai, K., et al., *Five isoforms of the phosphatidylinositol 3-kinase regulatory subunit exhibit different associations with receptor tyrosine kinases and their tyrosine phosphorylations*. FEBS Lett, 2001. 490(1-2): p. 32-8.], while PI3Kγ signals through G-protein-coupled receptors (GPCRs) [Stoyanov, B., et al., *Cloning and characterization of a G protein-activated human phosphoinositide-3 kinase*. Science, 1995. 269(5224): p. 690-3; Maier, U., A. Babich, and B. Nurnberg, *Roles of non-catalytic subunits in gbetagamma-induced activation of class I phosphoinositide 3-kinase isoforms beta and gamma*. J Biol Chem, 1999. 274(41): p. 29311-7.] and PI3Kβ signals through both [Kurosu, H., et al., *Heterodimeric phosphoinositide 3-kinase consisting of p85 and p110beta is synergistically activated by the betagamma subunits of G proteins and phosphotyrosyl peptide*. J Biol Chem, 1997. 272(39): p. 24252-6.]. Expression of the PI3Kα and PI3Kβ isoforms is ubiquitous, while the expression pattern of PI3Kδ and PI3Kγ seems more restricted, with both isoforms found primarily in leukocytes [Kok, K., B. Geering, and B. Vanhaesebroeck, *Regulation of phosphoinositide 3-kinase expression in health and disease*. Trends Biochem Sci, 2009. 34(3): p. 115-27.].

The relatively restricted expression pattern of PI3Kδ, in addition to data accumulated from studies in mice, where PI3Kδ was either genetically inactivated or hyper-activated or pharmacologically inactivated, suggests that this isoform plays a major role in the adaptive immune systems [Lucas, C. L., et al., *PI3Kdelta and primary immunodeficiencies*. Nat Rev Immunol, 2016.]. In mice, the loss of function of PI3Kδ in B cells impairs the T cell-independent antibody response but has no effect on class-switch recombination (CSR) and somatic hypermutation (SHM) [Rolf, J., et. al., *Phosphoinositide 3-kinase activity in T cells regulates the magnitude of the germinal center reaction*. J Immunol, 2010. 185(7): p. 4042-52.], both of which are essential for antibody maturation and diversity [Stavnezer, J., J. E. Guikema, and C. E. Schrader, *Mechanism and regulation of class switch recombination*. Annu Rev Immunol, 2008. 26: p, 261-92; Li, Z., et al., *The generation of antibody diversity through somatic hypermutation and class switch recombination*. Genes Dev, 2004. 18(1): p. 1-11.]; while the hyperactivation of PI3Kδ in mature B cells interferes with CSR and SHM and inhibits the proliferation of antigen-specific B cell populations [Janas, M. L., et al., *The effect of deleting p110delta on the phenotype and function of PTEN-deficient B cells.* J Immunol, 2008. 180(2): p. 739-46; Omori, S. A., et al., *Regulation of class-switch recombination and plasma, cell differentiation by phosphatidylinositol 3-kinase signaling.* Immunity, 2006. 25(4): p. 545-57; Sander, S., et al., *PI3 Kinase and FOXO1 Transcription Factor Activity Differentially Control B Cells in the Germinal Center Light and Dark Zones.* Immunity, 2015. 43(6): p. 1075-86.]. Besides, PI3Kδ is also a key signaling transduction component for malignant B cells, which makes it an attractive drug target for B cell malignancies [Wei, M., et al., *Targeting PI3Kdelta: emerging therapy for chronic lymphocytic leukemia and beyond.* Med Res Rev, 2015. 35(4): p. 720-52.].

Meanwhile, PI3Kδ is required for the differentiation of naïve T cell towards T helper cells, including $T_{FH}$ (follicular helper) [Rolf, J., et al., *Phosphoinositide 3-kinase activity in T cells regulates the magnitude of the germinal center reaction.* J Immunol, 2010. 185(7): p. 4042-52,], $T_H1$, $T_H2$ and $T_H17$ [Okkenhaug, K., et al., *The p110delta isoform of phosphoinositide 3-kinase, controls clonal expansion and differentiation of Th cells.* J Immunol, 2006. 177(8): p. 5122-8; Soond, D. R., et al., *PI3K p110delta regulates T-cell cytokine production during primary and secondary immune, responses in mice and humans.* Blood, 2010. 115(11): p. 2203-13; Kurebayashi, Y., et al., *PI3K-Akt-mTORC1-S6K1/2 axis controls Th17 differentiation by regulating Gfi1 expression and nuclear translocation of RORgamma.* Cell Rep, 2012. 1(4): p. 360-73.]. The interference on $T_{FH}$ development leads to severe attenuation of T cell-dependent CSR and SHM in B cells [Rolf, J., et al., *Phosphoinositide 3-kinase activity in T cells regulates the magnitude of the germinal center reaction.* J Immunol, 2010. 185(7): p. 4042-52,], whereas the reduction on $T_H2$ and $T_H17$ cells induced by PI3Kδ deficiency could provide protections on mice with asthma [Nashed, B. F., et al., *Role of the phosphoinositide 3-kinase p110delta in generation of type 2 cytokine responses and allergic airway inflammation.* Eur J Immunol, 2007, 37(2): p, 416-24,] or multiple sclerosis [Haylock-Jacobs, S., et al., *PI3Kdelta drives the pathogenesis of experimental autoimmune encephalomyelitis by inhibiting effector T cell apoptosis and promoting Th17 differentiation.* J Autoimmun, 2011, 36(3-4): p. 278-87.] respectively. PI3Kδ is also essential for the homeostasis and function of Foxp$^{3+}$ T regulatory cells ($T_{reg}$) [Patton, D. T., et al., *Cutting edge: the phosphoinositide 3-kinase p110 delta, is critical for the function of CD4+CD25+Foxp3+ regulatory T cells.* J Immunol, 2006. 177(10): p. 6598-602.]. PI3Kδ deficient mice develop colitis [Patton, D. T., et al., *Cutting edge: the phosphoinositide 3-kinase p110 delta is critical for the function of CD4+CD25+Foxp3+ regulatory T cells.* J Immunol, 2006, 177(10): p. 6598-602.] due to the reduced $T_{reg}$ functions but have increased immune response against tumors [Ali, K., et al., *Inactivation of PI(3)K p110delta breaks regulatory T-cell-mediated immune tolerance to cancer.* Nature, 2014. 510(7505): p. 407-11,]. PI3Kδ also contributes to, but is not necessary for the reprogramming of CD8+ T cells to fully activated effector cells [Pearce, V. Q., et al., *PI3Kdelta Regulates the Magnitude, of CD8+ T Cell Responses after Challenge with Listeria monocytogenes.* J Immunol, 2015. 195(7): p. 3206-17; Gracias, D. T., et al., *Phosphatidylinositol 3-Kinase p110delta Isoform Regulates CD8+ T Cell Responses during Acute Viral and Intracellular Bacterial Infections.* J Immunol, 2016. 196(3): p, 1186-98.]. In contrast, the generation of memory CD8+ T cells requires the suppression of PI3Kδ signaling [Pearce, V. Q., et al., *PI3Kdelta Regulates the Magnitude of CD8+ T Cell Responses after Challenge with Listeria monocytogenes.* J Immunol, 2015. 195(7): p. 3206-17.].

PI3Kδ mutations, both gain of function (GOF) and loss of function (LOF), can induce primary immunodeficiency in human [Lucas, C. L., et al., *PI3Kdelta and primary immunodeficiencies.* Nat Rev Immunol, 2016.]. Patients lacking of PI3Kδ function presented with recurrent infections and severe B cell lymphopenia [Conley, M. E., et al., *Agammaglobulinemia and absent B lineage cells in a patient lacking the p85alpha subunit of PI3K.* J Exp Med, 2012. 209(3): p. 463-70; Conley, M. E., et al., *Agammaglobulinemia and absent B lineage cells in a patient lacking the p85alpha subunit of PI3K.* J Exp Med, 2012. 209(3): p. 463-70.], while GOF mutations in PI3Kδ genes can cause a syndrome of combined immune-deficiency, which is referred to as activated PI3Kδ syndrome (APDS) [Angulo, L, et ah, *Phosphoinositide 3-kinase delta gene mutation predisposes to respiratory infection and airway damage.* Science, 2013. 342(6160): p, 866-71; Lucas, C. L., et al., *Dominant-activating germline, mutations in the gene encoding the PI(3)K catalytic subunit p110delta result in T cell senescence and human immunodeficiency.* Nat Immunol, 2014. 15(1): p. 88-97; Deau, M. C., et al., *A human immunodeficiency caused by mutations in the PIK3R1 gene.* J Clin Invest, 2015. 125(4): p. 1764-5; Lucas, C. L., et al., *Heterozygous splice mutation in PIK3R1 causes human immunodeficiency with lymphoproliferation due to dominant activation of PI3K.* J Exp Med, 2014. 211(13): p. 2537-47.]. Patients with APDS were characterized with senescent T cells, lymphadenopathy and frequent infections [Elgizouli, M., et al., *Activating PI3Kdelta mutations in a cohort of 669 patients with primary immunodeficiency.* Clin Exp Immunol, 2016, 183(2): p, 221-9; Elkaim, E., et al., *Clinical and immunologic phenotype associated with activated phosphoinositide 3-kinase delta syndrome 2: A cohort study.* J Allergy Clin Immunol, 2016. 138(1): p. 210-218 e9; Coulter, T. I., et al., *Clinical spectrum and features of activated phosphoinositide 3-kinase delta syndrome: A large patient cohort study.* J Allergy Clin Immunol, 2016.].

Because of the specific and critical functions of PI3Kδ in adaptive immune responses, the inhibitors of PI3Kδ are being developed for the treatment of autoimmune (such as multiple sclerosis, systemic lupus erythematosus, rheumatoid arthritis and psoriasis) and inflammatory disorders (such as asthma and chronic obstructive pulmonary disease), hematological and solid tumors as well as APDS [Lucas, C. L., et al., *PI3Kdelta and primary immunodeficiencies.* Nat Rev Immunol, 2016; Stark, A. K., et al., *PI3K inhibitors in inflammation, autoimmunity and cancer.* Curr Opin Pharmacol, 2015. 23: p. 82-91.]. Idelalisib is the first PI3Kδ inhibitor approved in 2014 for the treatment of B cell malignancies [Yang, Q., et al., *Idelalisib: First-in-Class PI3K Delta Inhibitor for the Treatment of Chronic Lymphocytic Leukemia, Small Lymphocytic Leukemia, and Follicular Lymphoma.* Clin Cancer Res, 2015, 21(7): p. 1537-42,]. In addition to idelalisib, at least 9 δ-specific and 5 δγ, δβ or δα-dual inhibitors are under clinical development [Wei, M., et al., *Targeting PI3Kdelta: emerging therapy for chronic lymphocytic leukemia and beyond.* Med Res Rev, 2015. 35(4): p. 720-52.], Among them, a δγ-dual inhibitor duvelisib (NCT02004522) and a δ-specific inhibitor TGR-1202 (NCT02612311) are being evaluated in phase III clinical trials.

Recently, both idelalisib and duvelisib were noted with the risk of increasing infections in lung [Okkenhaug, K., M. Graupera, and B. Vanhaesebroeck, *Targeting PI3K in Cancer: Impact on Tumor Cells, Their Protective Stroma, Angio-* genesis, and Immunotherapy. Cancer Discov, 2016. 6(10): p. 1090-1105.], which was inferred to be associated with their relatively low selectivity to PI3Kγ [Ruckle, T., M. K. Schwarz, and C. Rommel, *PI3Kgamma inhibition: towards an 'aspirin of the 21st century'*? Nat Rev Drug Discov, 2006. 5(11): p. 903-18.]. PI3Kγ is important for immune cell chemotaxis [Hawkins, P. T. and L. R. Stephens, *PI3K signalling in inflammation*. Biochem Biophys Acta, 2015. 1851(6): p. 882-97,] and plays major roles in innate immune system [Ruckle, T., M. K. Schwarz, and C. Rommel, *PI3Kgamma inhibition: towards an 'aspirin of the 21st century'*? Nat Rev Drug Discov, 2006. 5(11): p. 903-18.]. PI3Kγ knock-out mice displayed increased susceptibility to pneumococcal infection [Maus, U. A., et al., *Importance of phosphoinositide 3-kinase gamma in the host defense against pneumococcal infection*. Am J Respir Crit Care Med, 2007. 175(9): p. 958-66.]. It also works in concert with PI3Kδ in multiple immune surveillance processes, including neutrophil recruitment [Liu, L., et al., *Leukocyte PI3Kgamma and PI3Kdelta have temporally distinct roles for leukocyte recruitment in vivo*. Blood, 2007. 110(4): p. 1191-8.] and T-cell development [Webb, L. M., et al., *Cutting edge: T cell development requires the combined activities of the p110gamma and p110delta catalytic isoforms of phosphatidylinositol 3-kinase*. J Immunol, 2005. 175(5): p. 2783-7.]. The simultaneous genetic inactivation of PI3Kδ and PI3Kγ in mice leads to more severe impairment of thymocyte development and multiple organ inflammation [Ji, H., et al., *Inactivation of PI3Kgamma and PI3Kdelta distorts T-cell development and causes multiple organ inflammation*. Blood, 2007. 110(8): p. 2940-7.] than in the mice with the deficiency of each isoform alone [Swat, W., et al., *Essential role of PI3Kdelta and PI3Kgamma in thymocyte survival*. Blood, 2006. 107(6): p. 2415-22.]. Thus PI3Kδ inhibitors with higher selectivity against PI3Kγ is expected to have improved safety profile and would provide new therapeutic options for APDS, autoimmune and inflammatory disorders as well as cancer, e.g., glioblastoma. The compounds, compositions and methods described herein are directed toward these needs and others.

SUMMARY OF THE INVENTION

Provided is a compound of Formula (I),

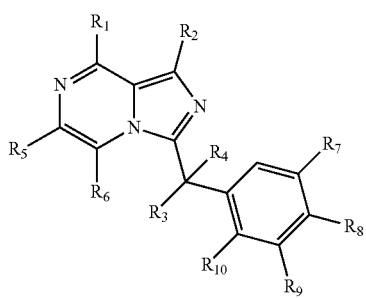

(I)

or a stereoisomer thereof, or a pharmaceutically acceptable salt thereof,
wherein:
$R_1$ is $-NR_aR_b$, wherein $R_a$ and $R_b$ are each independently hydrogen or $C_{1-6}$alkyl;
$R_2$ is hydrogen, F, Cl, Br, $-C_{1-6}$alkyl, $-C_{2-6}$alkenyl, $-C_{2-6}$alkynyl, cycloalkyl, heterocyclyl, aryl, heteroaryl, $-CN$, $-NO_2$, $-OR_{12}$, $-SO_2R_{12}$, $-COR_{12}$, $-CO_2R_{12}$, $-CONR_{12}R_{13}$, $-C(=NR_{12})NR_{13}R_{14}$, $-NR_{12}R_{13}$, $-NR_{12}COR_{13}$, $-NR_{12}CONR_{13}R_{14}$, $-NR_{12}CO_2R_{13}$, $-NR_{12}SONR_{13}R_{14}$, $-NR_{12}SO_2NR_{13}R_{14}$, or $-NR_{12}SO_2R_{13}$; wherein said $-C_{1-6}$alkyl, $-C_{2-6}$alkenyl, $-C_{2-6}$alkynyl, cycloalkyl, heterocyclyl, aryl or heteroaryl are each independently optionally substituted with at least one substituent $R_{11a}$;

$R_3$ and $R_4$, which may be the same or different, are each independently hydrogen, $-C_{1-6}$alkyl, cycloalkyl, heterocyclyl, aryl, or heteroaryl;

$R_5$ and $R_6$, which may be the same or different, are each independently hydrogen, halogen, $-C_{1-6}$alkyl, $-C_{2-6}$alkenyl, $-C_{2-6}$alkynyl, cycloalkyl, heterocyclyl, aryl, heteroaryl, $-CN$, $-NO_2$, $-OR_{12}$, $-SO_2R_{12}$, $-COR_{12}$, $-CO_2R_{12}$, $-CONR_{12}R_{13}$, $-C(=NR_{12})NR_{13}R_{14}$, $-NR_{12}R_{13}$, $-NR_{12}COR_{13}$, $-NR_{12}CONR_{13}R_{14}$, $-NR_{12}CO_2R_{13}$, $-NR_{12}SONR_{13}R_{14}$, $-NR_{12}SO_2NR_{13}R_{14}$, or $-NR_{12}SO_2R_{13}$; wherein said $-C_{1-6}$alkyl, $-C_{2-6}$alkenyl, $-C_{2-6}$alkynyl, cycloalkyl, heterocyclyl, aryl or heteroaryl are each independently optionally substituted with at least one substituent $R_{11b}$;

$R_7$, $R_8$ and $R_{10}$, which may be the same or different, are each independently hydrogen, halogen, $-C_{1-6}$alkyl, $-C_{2-6}$alkenyl, $-C_{2-6}$alkynyl, cycloalkyl, heterocyclyl, aryl, heteroaryl, $-CN$, $-NO_2$, $-OR_{12}$, $-SO_2R_{12}$, $-COR_{12}$, $-CO_2R_{12}$, $-CONR_{12}R_{13}$, $-C(=NR_{12})NR_{13}R_{14}$, $-NR_{12}R_{13}$, $-NR_{12}COR_{13}$, $-NR_{12}CONR_{13}R_{14}$, $-NR_{12}CO_2R_{13}$, $-NR_{12}SONR_{13}R_{14}$, $-NR_{12}SO_2NR_{13}R_{14}$, or $-NR_{12}SO_2R_{13}$; wherein said $-C_{1-6}$alkyl, $-C_{2-6}$alkenyl, $-C_{2-6}$alkynyl, cycloalkyl, heterocyclyl, aryl or heteroaryl are each independently optionally substituted with at least one substituent $R_{11c}$;

$R_9$ is hydrogen, halogen, $-C_{1-6}$alkyl, $-C_{2-6}$alkenyl, $-C_{2-6}$alkynyl, cycloalkyl, heterocyclyl, aryl, or heteroaryl; wherein said $-C_{1-6}$alkyl, $-C_{2-6}$alkenyl, $-C_{2-6}$alkynyl, cycloalkyl, heterocyclyl, aryl or heteroaryl are each independently optionally substituted with at least one substituent $R_{11d}$;

$R_{11a}$, $R_{11b}$, $R_{11c}$ and $R_{11d}$, which may be the same or different, are each independently hydrogen, halogen, $-C_{1-6}$alkyl, $-C_{2-6}$alkenyl, $-C_{2-6}$alkynyl, halo$C_{1-6}$alkyl, halo$C_{2-6}$alkenyl, halo$C_{2-6}$alkynyl, cycloalkyl, heterocyclyl, aryl, heteroaryl, $-CN$, $-NO_2$, oxo, $-OR_{12}$, $-SO_2R_{12}$, $-COR_{12}$, $-C_2R_{12}$, $-CONR_{12}R_{13}$, $-C(=NR_{12})NR_{13}R_{14}$, $-NR_{12}R_{13}$, $-NR_{12}COR_{13}$, $-NR_{12}CONR_{13}R_{14}$, $-NR_{12}CO_2R_{13}$, $-NR_{12}SONR_{13}R_{14}$, $-NR_{12}SO_2NR_{13}R_{14}$, or $-NR_{12}SO_2R_{13}$; and $R_{12}$, $R_{13}$, and $R_{14}$, which may be the same or different, are each independently hydrogen, $-C_{1-6}$alkyl, $-C_{2-6}$alkenyl, $-C_{2-6}$alkynyl, $C_{1-6}$alkyloxy$C_{1-6}$alkyl-, cycloalkyl, heterocyclyl, aryl, heteroaryl or $-OR_{15}$, wherein $R_{15}$ is hydrogen, $C_{1-6}$alkyl, $-C_{2-6}$alkenyl, $-C_{2-6}$alkynyl, $C_{1-6}$alkyloxy$C_{1-6}$alkyl-, cycloalkyl, heterocyclyl, aryl, or heteroaryl, and wherein said $C_{1-6}$alkyl, $-C_{2-6}$alkenyl, $-C_{2-6}$alkynyl, $C_{1-6}$alkyloxy$C_{1-6}$alkyl-, cycloalkyl, heterocyclyl, aryl, or heteroaryl as $R_{12}$, $R_{13}$, or $R_{14}$, or as a moiety of $-OR_{15}$ are each independently optionally substituted with at least one substituent $R_{16}$;

Alternatively, ($R_{12}$ and $R_{13}$), or ($R_{13}$ and $R_{14}$), or ($R_{12}$ and $R_{14}$), together with the atom(s) to which they are attached, form a 3- to 8-membered saturated, partially or fully unsaturated ring comprising 0, 1 or 2 additional heteroatoms independently selected from $-NH$, $-O-$, $-S-$, $-SO-$ or $-SO_2-$, and said ring is optionally substituted with at least one substituent $R_{16}$;

$R_{16}$, at each of its occurrences, is independently hydrogen, halogen, —$C_{1-6}$alkyl optionally substituted with hydroxyl, —$C_{2-6}$alkenyl, —$C_{2-6}$alkynyl, halo$C_{1-6}$alkyl, halo$C_{2-6}$alkenyl, halo$C_{2-6}$alkynyl, cycloalkyl, heterocyclyl, aryl, heteroaryl, —CN, —$NO_2$, oxo, —$OR_a$, —$SO_2R_a$, —$COR_a$, —$CO_2R_a$, —$CONR_aR_b$, —$C(=NR_a)NR_bR_c$, —$NR_aR_b$, —$NR_aCOR_b$, —$NR_aCONR_bR_c$, —$NR_aCO_2R_b$, —$NR_aSONR_bR_c$, —$NR_aSO_2NR_bR_c$, or —$NR_aSO_2R_b$; wherein $R_a$, $R_b$, or $R_c$ is independently hydrogen, halogen, —$C_{1-6}$alkyl, —$C_{2-6}$alkenyl, —$C_{2-6}$alkynyl, halo$C_{1-6}$alkyl, halo$C_{2-6}$alkenyl, halo$C_{2-6}$alkynyl, cycloalkyl, heterocyclyl, aryl, or heteroaryl; or ($R_a$ and $R_b$), or ($R_a$ and $R_b$), or ($R_b$ and $R_c$), together with the atom(s) to which they are attached, form a 3- to 8-membered saturated, partially or fully unsaturated ring comprising 0, 1 or 2 additional heteroatoms independently selected from —NH, —O—, —S—, —SO— or —$SO_2$—.

In an embodiment, provided herein is a compound of Formula (II)

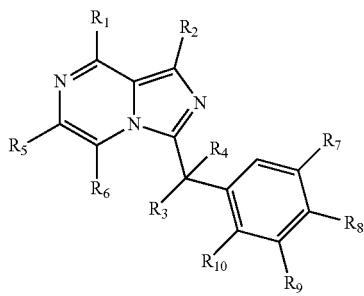

(II)

or a stereoisomer thereof, or a pharmaceutically acceptable salt thereof,
wherein:

$R_1$ is —$NR_aR_b$, wherein $R_a$ and $R_b$ are each independently hydrogen or $C_{1-6}$alkyl;

$R_2$ is hydrogen, F, Cl, Br, —$C_{1-6}$alkyl, —$C_{2-6}$alkenyl, —$C_{2-6}$alkynyl, cycloalkyl, heterocyclyl, aryl, heteroaryl, —CN, —$NO_2$, —$OR_{12}$, —$SO_2R_{12}$, —$COR_{12}$, —$CO_2R_{12}$, —$CONR_{12}R_{13}$, —$C(=NR_{12})NR_{13}R_{14}$, —$NR_{12}R_{13}$, —$NR_{12}COR_{13}$, —$NR_{12}CONR_{13}R_{14}$, —$NR_{12}CO_2R_{13}$, —$NR_{12}SONR_{13}R_{14}$, —$NR_{12}SO_2NR_{13}R_{14}$, or —$NR_{12}SO_2R_{13}$; wherein said —$C_{1-6}$alkyl, —$C_{2-6}$alkenyl, —$C_{2-6}$alkynyl, cycloalkyl, heterocyclyl, aryl or heteroaryl are each independently optionally substituted with at least one substituent $R_{11a}$;

$R_3$ and $R_4$, which may be the same or different, are each independently hydrogen, —$C_{1-6}$alkyl, cycloalkyl, heterocyclyl, aryl, or heteroaryl;

$R_5$ and $R_6$, which may be the same or different, are each independently hydrogen, halogen, —$C_{1-6}$alkyl, —$C_{2-6}$alkenyl, —$C_{2-6}$alkynyl, cycloalkyl, heterocyclyl, aryl, heteroaryl, —CN, —$NO_2$, —$OR_{12}$, —$SO_2R_{12}$, —$COR_{12}$, —$CO_2R_{12}$, —$CONR_{12}R_{13}$, —$C(=NR_{12})NR_{13}R_{14}$, —$NR_{12}R_{13}$, —$NR_{12}COR_{13}$, —$NR_{12}CONR_{13}R_{14}$, —$NR_{12}CO_2R_{13}$, —$NR_{12}SONR_{13}R_{14}$, —$NR_{12}SO_2NR_{13}R_{14}$, or —$NR_{12}SO_2R_{13}$; wherein said —$C_{1-6}$alkyl, —$C_{2-6}$alkenyl, —$C_{2-6}$alkynyl, cycloalkyl, heterocyclyl, aryl or heteroaryl are each independently optionally substituted with at least one substituent $R_{11b}$;

$R_7$, $R_8$ and $R_{10}$, which may be the same or different, are each independently hydrogen, halogen, —$C_{1-6}$alkyl, —$C_{2-6}$alkenyl, —$C_{2-6}$alkynyl, cycloalkyl, heterocyclyl, aryl, heteroaryl, —CN, —$NO_2$, —$OR_{12}$, —$SO_2R_{12}$, —$COR_{12}$, —$CO_2R_{13}$, —$CONR_{12}R_{13}$, —$C(=NR_{12})NR_{13}R_{14}$, —$NR_{12}R_{13}$, —$NR_{12}COR_{13}$, —$NR_{12}CONR_{13}R_{14}$, —$NR_{12}CO_2R_{13}$, —$NR_{12}SONR_{13}R_{14}$, —$NR_{12}SO_2NR_{13}R_{14}$, or —$NR_{12}SO_2R_{13}$; wherein said —$C_{1-6}$alkyl, —$C_{2-6}$alkenyl, —$C_{2-6}$alkynyl, cycloalkyl, heterocyclyl, aryl or heteroaryl are each independently optionally substituted with at least one substituent $R_{11c}$;

$R_9$ is hydrogen, halogen, —$C_{1-6}$alkyl, —$C_{2-6}$alkenyl, —$C_{2-6}$alkynyl, cycloalkyl, heterocyclyl, aryl, or heteroaryl; wherein said —$C_{1-6}$alkyl, —$C_{2-6}$alkenyl, —$C_{2-6}$alkynyl, cycloalkyl, heterocyclyl, aryl or heteroaryl are each independently optionally substituted with at least one substituent $R_{11d}$;

$R_{11a}$, $R_{11b}$, $R_{11c}$ and $R_{11d}$, which may be the same or different, are each independently hydrogen, halogen, —$C_{1-6}$alkyl, —$C_{2-6}$alkenyl, —$C_{2-6}$alkynyl, halo$C_{1-6}$alkyl, halo$C_{2-6}$alkenyl, halo$C_{2-6}$alkynyl, cycloalkyl, heterocyclyl, aryl, heteroaryl, —CN, —$NO_2$, oxo, —$OR_{12}$, —$SO_2R_{12}$, —$COR_{12}$, —$CO_2R_{12}$, —$CONR_{12}R_{13}$, —$C(=NR_{12})NR_{13}R_{14}$, —$NR_{12}R_{13}$, —$NR_{12}COR_{13}$, —$NR_{12}CONR_{13}R_{14}$, —$NR_{12}CO_2R_{13}$, —$NR_{12}SONR_{13}R_{14}$, —$NR_{12}SO_2NR_{13}R_{14}$, or —$NR_{12}SO_2R_{13}$; and $R_{12}$, $R_{13}$, and $R_{14}$, which may be the same or different, are each independently hydrogen, —$C_{1-6}$alkyl, —$C_{2-6}$alkenyl, —$C_{2-6}$alkynyl, halo$C_{1-6}$alkyl, halo$C_{2-6}$alkenyl, halo$C_{2-6}$alkynyl, $C_{1-6}$alkyloxy$C_{1-6}$alkyl-, cycloalkyl, heterocyclyl, aryl, or heteroaryl.

Provided also is a pharmaceutical composition, comprising a therapeutically effective amount of a compound of Formula (I), or a stereoisomer thereof or a pharmaceutically acceptable salt thereof disclosed herein, and a pharmaceutically acceptable excipient.

The compound of Formula (I) disclosed herein is useful as a PI3K inhibitor, in particular, a PI3Kδ inhibitor. The compound of Formula (I) disclosed herein is thus useful in treating or preventing idiopathic thrombocytopenic purpura (ITP), autoimmune hemolytic anemia, vasculitis, systemic lupus erythematosus, lupus nephritis, pemphigus, membranous nephropathy, chronic lymphocytic leukemia (CLL), Non-Hodgkin lymphoma (NHL), hairy cell leukemia, Mantle cell lymphoma, small lymphocytic lymphoma, follicular lymphoma, lymphoplasmacytic lymphoma, extranodal marginal zone lymphoma, activated B-cell like (ABC) diffuse large B cell lymphoma, or germinal center B cell (GCB) diffuse large B cell lymphoma in a subject. Thus, compositions and methods for treating various disorders or diseases mentioned above using the compound of Formula (I) are disclosed herein, and use of the compound of Formula (I) in manufacturing medicine for treating various disorders or diseases mentioned above, are also provided.

BRIEF DESCRIPTION OF THE DRAWINGS

FIG. 1 shows single crystal of Compound 40A used to determine the stereochemistry of Compound 40A.

DETAILED DESCRIPTION OF THE INVENTION

In the first aspect, provided is a compound of Formula (I),

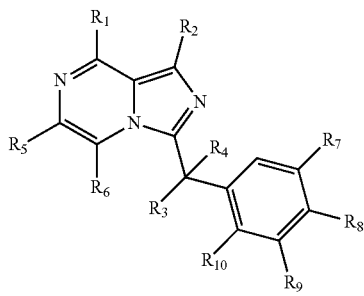

(I)

or a stereoisomer thereof, or a pharmaceutically acceptable salt thereof,
wherein:

$R_1$ is —$NR_aR_b$, wherein $R_a$ and $R_b$ are each independently hydrogen or $C_{1-6}$alkyl;

$R_2$ is hydrogen, F, Cl, Br, —$C_{1-6}$alkyl, —$C_{2-6}$alkenyl, —$C_{2-6}$alkynyl, cycloalkyl, heterocyclyl, aryl, heteroaryl, —CN, —$NO_2$, —$OR_{12}$, —$SO_2R_{12}$, —$COR_{12}$, —$CO_2R_{12}$, —$CONR_{12}R_{13}$, —$C(=NR_{12})NR_{13}R_{14}$, —$NR_{12}R_{13}$, —$NR_{12}COR_{13}$, —$NR_{12}CONR_{13}R_{14}$, —$NR_{12}CO_2R_{13}$, —$NR_{12}SONR_{13}R_{14}$, —$NR_{12}SO_2NR_{13}R_{14}$, or —$NR_{12}SO_2R_{13}$; wherein said —$C_{1-6}$alkyl, —$C_{2-6}$alkenyl, —$C_{2-6}$alkynyl, cycloalkyl, heterocyclyl, aryl or heteroaryl are each independently optionally substituted with at least one substituent $R_{11a}$;

$R_3$ and $R_4$, which may be the same or different, are each independently hydrogen, —$C_{1-6}$alkyl, cycloalkyl, heterocyclyl, aryl, or heteroaryl;

$R_5$ and $R_6$, which may be the same or different, are each independently hydrogen, halogen, —$C_{1-6}$alkyl, —$C_{2-6}$alkenyl, —$C_{2-6}$alkynyl, cycloalkyl, heterocyclyl, aryl, heteroaryl, —CN, —$NO_2$, —$OR_{12}$, —$SO_2R_{12}$, —$COR_{12}$, —$CO_2R_{12}$, —$CONR_{12}R_{13}$, —$C(=NR_{12})NR_{13}R_{14}$, —$NR_{12}R_{13}$, —$NR_{12}COR_{13}$, —$NR_{12}CONR_{13}R_{14}$, —$NR_{12}CO_2R_{13}$, —$NR_{12}SONR_{13}R_{14}$, —$NR_{12}SO_2NR_{13}R_{14}$, or —$NR_{12}SO_2R_{13}$; wherein said —$C_{1-6}$alkyl, —$C_{2-6}$alkenyl, —$C_{2-6}$alkynyl, cycloalkyl, heterocyclyl, aryl or heteroaryl are each independently optionally substituted with at least one substituent $R_{11b}$;

$R_7$, $R_8$ and $R_{10}$, which may be the same or different, are each independently hydrogen, halogen, —$C_{1-6}$alkyl, —$C_{2-6}$alkenyl, —$C_{2-6}$alkynyl, cycloalkyl, heterocyclyl, aryl, heteroaryl, —CN, —$NO_2$, —$OR_{12}$, —$SO_2R_{12}$, —$COR_{12}$, —$CO_2R_{12}$, —$CONR_{12}R_{13}$, —$C(=NR_{12})NR_{13}R_{14}$, —$NR_{12}R_{13}$, —$NR_{12}COR_{13}$, —$NR_{12}CONR_{13}R_{14}$, —$NR_{12}CO_2R_{13}$, —$NR_{12}SONR_{13}R_{14}$, —$NR_{12}SO_2NR_{13}R_{14}$, or —$NR_{12}SO_2R_{13}$; wherein said —$C_{1-6}$alkyl, —$C_{2-6}$alkenyl, —$C_{2-6}$alkynyl, cycloalkyl, heterocyclyl, aryl or heteroaryl are each independently optionally substituted with at least one substituent $R_{11c}$;

$R_9$ is hydrogen, halogen, —$C_{1-6}$alkyl, —$C_{2-6}$alkenyl, —$C_{2-6}$alkynyl, cycloalkyl, heterocyclyl, aryl, or heteroaryl; wherein said —$C_{1-6}$alkyl, —$C_{2-6}$alkenyl, —$C_{2-6}$alkynyl, cycloalkyl, heterocyclyl, aryl or heteroaryl are each independently optionally substituted with at least one substituent $R_{11d}$;

$R_{11a}$, $R_{11b}$, $R_{11c}$ and $R_{11d}$, which may be the same or different, are each independently hydrogen, halogen, —$C_{1-6}$alkyl, —$C_{2-6}$alkenyl, —$C_{2-6}$alkynyl, halo$C_{1-6}$alkyl, halo$C_{2-6}$alkenyl, halo$C_{2-6}$alkynyl, cycloalkyl, heterocyclyl, aryl, heteroaryl, —CN, —$NO_2$, oxo, —$OR_{12}$, —$SO_2R_{12}$, —$COR_{12}$, —$CO_2R_{12}$, —$CONR_{12}R_{13}$, —$C(=NR_{12})NR_{13}R_{14}$, —$NR_{12}R_{13}$, —$NR_{12}COR_{13}$, —$NR_{12}CONR_{13}R_{14}$, —$NR_{12}CO_2R_{13}$, —$NR_{12}SONR_{13}R_{14}$, —$NR_{12}SO_2NR_{13}R_{14}$, or —$NR_{12}SO_2R_{13}$; and $R_{12}$, $R_{13}$, and $R_{14}$, which may be the same or different, are each independently hydrogen, —$C_{1-6}$alkyl, —$C_{1-6}$alkenyl, —$C_{2-6}$alkynyl, $C_{1-6}$alkyloxy$C_{1-6}$alkyl-, cycloalkyl, heterocyclyl, aryl, heteroaryl or —$OR_{15}$, wherein $R_{15}$ is hydrogen, $C_{1-6}$alkyl, —$C_{2-6}$alkenyl, —$C_{2-6}$alkynyl, $C_{1-6}$alkyloxy$C_{1-6}$alkyl-, cycloalkyl, heterocyclyl, aryl, or heteroaryl, and wherein said $C_{1-6}$alkyl, —$C_{2-6}$alkenyl, —$C_{2-6}$alkynyl, $C_{1-6}$alkyloxy$C_{1-6}$alkyl-, cycloalkyl, heterocyclyl, aryl, or heteroaryl as $R_{12}$, $R_{13}$, or $R_{14}$, or as a moiety of —$OR_{15}$ are each independently optionally substituted with at least one substituent $R_{16}$;

Alternatively, ($R_{12}$ and $R_{13}$), or ($R_{13}$ and $R_{14}$), or ($R_{12}$ and $R_{14}$), together with the atom(s) to which they are attached, form a 3- to 8-membered saturated, partially or fully unsaturated ring comprising 0, 1 or 2 additional heteroatoms independently selected from —NH, —O—, —S—, —SO— or —$SO_2$—, and said ring is optionally substituted with at least one substituent $R_{16}$;

$R_{16}$, at each of its occurrences, is independently hydrogen, halogen, —$C_{1-6}$alkyl optionally substituted with hydroxyl, —$C_{2-6}$alkenyl, —$C_{2-6}$alkynyl, halo$C_{1-6}$alkyl, halo$C_{2-6}$alkenyl, halo$C_{2-6}$alkynyl, cycloalkyl, heterocyclyl, aryl, heteroaryl, —CN, —$NO_2$, oxo, —$OR_a$, —$SO_2R_a$, —$COR_a$, —$CO_2R_a$, —$CONR_aR_b$, —$C(=NR_a)NR_bR_c$, —$NR_aR_b$, —$NR_aCOR_b$, —$NR_aCONR_bR_c$, —$NR_aCO_2R_b$, —$NR_aSONR_bR_c$, —$NR_aSO_2NR_bR_c$, or —$NR_aSO_2R_b$, wherein $R_a$, $R_b$, or $R_c$ is independently hydrogen, halogen, —$C_{1-6}$alkyl, —$C_{2-6}$alkenyl, —$C_{2-6}$alkynyl, halo$C_{1-6}$alkyl, halo$C_{2-6}$alkenyl, halo$C_{2-6}$alkynyl, cycloalkyl, heterocyclyl, aryl, or heteroaryl; or ($R_a$ and $R_b$), or ($R_a$ and $R_b$), or ($R_b$ and $R_c$), together with the atom(s) to which they are attached, form a 3- to 8-membered saturated, partially or fully unsaturated ring comprising 0, 1 or 2 additional heteroatoms independently selected from —NH, —O—, —S—, —SO— or —$SO_2$—.

In a preferred embodiment of this first aspect, provided is a compound of Formula (II),

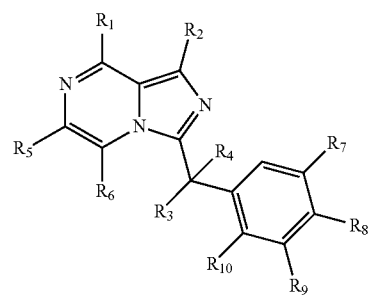

(II)

or a stereoisomer thereof, or a pharmaceutically acceptable salt thereof,
wherein:

$R_1$ is —$NR_aR_b$, wherein $R_a$ and $R_b$ are each independently hydrogen or $C_{1-6}$alkyl;

$R_2$ is hydrogen, F, Cl, Br, —$C_{1-6}$alkyl, —$C_{2-6}$alkenyl, —$C_{2-6}$alkynyl, cycloalkyl, heterocyclyl, aryl, heteroaryl, —CN, —$NO_2$, —$OR_{12}$, —$SO_2R_{12}$, —$COR_{12}$, —$CO_2R_{12}$, —$CONR_{12}R_{13}$, —$C(=NR_{12})NR_{13}R_{14}$, —$NR_{12}R_{13}$, —$NR_{12}COR_{13}$, —$NR_{12}CONR_{13}R_{14}$, —$NR_{12}CO_2R_{13}$, —$NR_{12}SONR_{13}R_{14}$, —$NR_{12}SO_2NR_{13}R_{14}$, or —$NR_{12}SO_2R_{13}$; wherein said —$C_{1-6}$alkyl, —$C_{2-6}$alkenyl, —$C_{2-6}$alkynyl, cycloalkyl, heterocyclyl, aryl or heteroaryl are each independently optionally substituted with at least one substituent $R_{11a}$;

$R_3$ and $R_4$, which may be the same or different, are each independently hydrogen, —$C_{1-6}$alkyl, cycloalkyl, heterocyclyl, aryl, or heteroaryl;

$R_5$ and $R_6$, which may be the same or different, are each independently hydrogen, halogen, —$C_{1-6}$alkyl, —$C_{2-6}$alkenyl, —$C_{2-6}$alkynyl, cycloalkyl, heterocyclyl, aryl, heteroaryl, —CN, —$NO_2$, —$OR_{12}$, —$SO_2R_{12}$, —$COR_{12}$, —$CO_2R_{12}$, —$CONR_{12}R_{13}$, —$C(=NR_{12})NR_{13}R_{14}$, —$NR_{12}R_{13}$, —$NR_{12}COR_{13}$, —$NR_{12}CONR_{13}R_{14}$, —$NR_{12}CO_2R_{13}$, —$NR_{12}SONR_{13}R_{14}$, —$NR_{12}SO_2NR_{13}R_{14}$, or —$NR_{12}SO_2R_{13}$; wherein said —$C_{1-6}$alkyl, —$C_{2-6}$alkenyl, —$C_{2-6}$alkynyl, cycloalkyl, heterocyclyl, aryl or heteroaryl are each independently optionally substituted with at least one substituent $R_{11b}$;

$R_7$, $R_8$ and $R_{10}$, which may be the same or different, are each independently hydrogen, halogen, —$C_{1-6}$alkyl, —$C_{2-6}$alkenyl, —$C_{2-6}$alkynyl, cycloalkyl, heterocyclyl, aryl, heteroaryl, —CN, —$NO_2$, —$OR_{12}$, —$SO_2R_{12}$, —$COR_{12}$, —$CO_2R_{12}$, —$CONR_{12}R_{13}$, —$C(=NR_{12})NR_{13}R_{14}$, —$NR_{12}R_{13}$, —$NR_{12}COR_{13}$, —$NR_{12}CONR_{13}R_{14}$, —$NR_{12}CO_2R_{13}$, —$NR_{12}SONR_{13}R_{14}$, —$NR_{12}SO_2NR_{13}R_{14}$, or —$NR_{12}SO_2R_{13}$; wherein said —$C_{1-6}$alkyl, —$C_{2-6}$alkenyl, —$C_{2-6}$alkynyl, cycloalkyl, heterocyclyl, aryl or heteroaryl are each independently optionally substituted with at least one substituent $R_{11c}$;

$R_9$ is hydrogen, halogen, —$C_{1-6}$alkyl, —$C_{2-6}$alkenyl, —$C_{2-6}$alkynyl, cycloalkyl, heterocyclyl, aryl, or heteroaryl; wherein said —$C_{1-6}$alkyl, —$C_{2-6}$alkenyl, —$C_{2-6}$alkynyl, cycloalkyl, heterocyclyl, aryl or heteroaryl are each independently optionally substituted with at least one substituent $R_{11d}$;

$R_{11a}$, $R_{11b}$, $R_{11c}$ and $R_{11a}$, which may be the same or different, are each independently hydrogen, halogen, —$C_{1-6}$alkyl, —$C_{2-6}$alkenyl, —$C_{2-6}$alkynyl, halo$C_{1-6}$alkyl, halo$C_{2-6}$alkenyl, halo$C_{2-6}$alkynyl, cycloalkyl, heterocyclyl, aryl, heteroaryl, —CN, —$NO_2$, oxo (i.e., =O), —$OR_{12}$, —$SO_2R_{12}$, —$COR_{12}$, —$CO_2R_{12}$, —$CONR_{12}R_{13}$, —$C(=NR_{12})NR_{13}R_{14}$, —$NR_{12}R_{13}$, —$NR_{12}COR_{13}$, —$NR_{12}CONR_{13}R_{14}$, —$NR_{12}CO_2R_{13}$, —$NR_{12}SONR_{13}R_{14}$, —$NR_{12}SO_2NR_{13}R_{14}$, or —$NR_{12}SO_2R_{13}$; and $R_{12}$, $R_{13}$, and $R_{14}$, which may be the same or different, are each independently hydrogen, —$C_{1-6}$alkyl, —$C_{2-6}$alkenyl, —$C_{2-6}$alkynyl, halo$C_{1-6}$alkyl, halo$C_{2-6}$alkenyl, halo$C_{2-6}$alkynyl, $C_{1-6}$alkyloxy$C_{1-6}$alkyl-, cycloalkyl, heterocyclyl, aryl, or heteroaryl.

In a preferred embodiment of the first aspect, provided is the compound of Formula (I), wherein:

$R_1$ is —$NH_2$;
$R_2$ is methyl or Cl or Br;
$R_3$ and $R_4$, which may be the same or different, are each independently hydrogen, —$C_{1-6}$alkyl;
$R_5$ and $R_6$ are both hydrogen;
$R_7$ and $R_8$, which may be the same or different, are each independently hydrogen, halogen, or —$C_{1-6}$alkyl;
$R_{10}$ is —$OR_{12}$, wherein $R_{12}$ is $C_{1-6}$alkyl, preferably $C_{1-3}$alkyl, e.g., methyl, ethyl, propyl or isopropyl;

$R_9$ is hydrogen, 5- to 6-membered heterocyclyl comprising one nitrogen atom and 0 or 1 additional heteroatom selected from N, O and S, or 5- to 6-membered heteroaryl comprising one nitrogen atom and 0 or 1 additional heteroatom selected from N, O and S; wherein said heterocyclyl or heteroaryl are each independently optionally substituted with one or two $R_{11d}$;

$R_{11d}$ is halogen, —$C_{1-6}$alkyl, halo$C_{1-6}$alkyl, oxo, —$OR_{12}$, —$CO_2R_{12}$, or —$CONR_{12}R_{13}$; and $R_{12}$ and $R_{13}$, which may be the same or different, are each independently hydrogen, —$C_{1-6}$alkyl, or $C_{1-6}$alkyloxy$C_{1-6}$alkyl-.

In an embodiment of the first aspect, $R_1$ is —$NH_2$.

In an embodiment of the first aspect, $R_2$ is independently hydrogen, F, Cl, Br, —$C_{1-6}$alkyl, $C_{3-6}$cycloalkyl or $C_{6-10}$ aryl, and wherein —$C_{1-6}$alkyl, $C_{3-6}$cycloalkyl and $C_{6-10}$ aryl are each independently optionally substituted with $R_{11a}$. In another embodiment of the first aspect, wherein $R_2$ is $C_{6-10}$ aryl, optionally substituted with $R_{11a}$, wherein $R_{11a}$ is OH or —$OC_{1-6}$alkyl. In a further another embodiment of the first aspect, $R_2$ is hydrogen, —F, —Cl, —Br, methyl, ethyl, 1-propyl, 2-propyl or isopropyl, 1-butyl or n-butyl, 2-methyl-1-propyl, 1-methylpropyl, 1,1-dimethylethyl, I-pentyl, 2-pentyl, 3-pentyl, 2-methyl-2-butyl, 3-methyl-2-butyl, 3-methyl-1-butyl or 2-methyl-1-butyl, cyclopropyl, cyclobutyl, cyclopentyl, cyclohexyl, cycloheptyl, cyclooctyl, phenyl, or phenyl substituted with hydroxyl or methoxy. In a preferred embodiment of the first aspect, $R_2$ is Cl or Br or methyl.

In an embodiment of the first aspect, $R_3$ and $R_4$ are each independently hydrogen or —$C_{1-6}$ alkyl. In another embodiment of the first aspect, $R_3$ and $R_4$ are each independently hydrogen, methyl, ethyl, 1-propyl, 2-propyl or isopropyl, 1-butyl or n-butyl, 2-methyl-1-propyl, 1-methylpropyl, 1,1-dimethylethyl, 1-pentyl, 2-pentyl, 3-pentyl, 2-methyl-2-butyl, 3-methyl-2-butyl, 3-methyl-1-butyl or 2-methyl-1-butyl.

In an embodiment of the first aspect, $R_3$ is hydrogen, and $R_4$ is —$C_{1-6}$alkyl. In an embodiment of the first aspect, $R_3$ is hydrogen, and $R_4$ is methyl, ethyl, 1-propyl, 2-propyl or isopropyl, 1-butyl or n-butyl, 2-methyl-1-propyl, I-methylpropyl, 1,1-dimethylethyl, 1-pentyl, 2-pentyl, 3-pentyl, 2-methyl-2-butyl, 3-methyl-2-butyl, 3-methyl-1-butyl or 2-methyl-1-butyl.

In a preferred embodiment of the first aspect, $R_3$ is hydrogen, and $R_4$ is methyl.

In a preferred embodiment of the first aspect, the compound of Formula (I) has the following (R) and (S) configurations, when $R_3$ and $R_4$ are different:

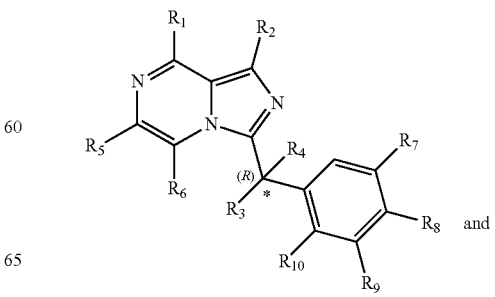

and

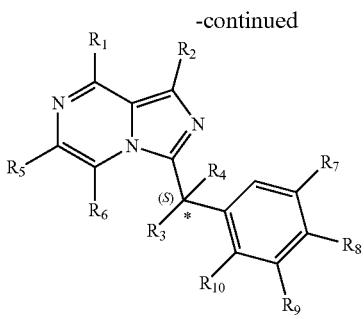

* indicates the chiral carbon atom.

In an embodiment of the first aspect, $R_5$ and $R_6$ are each independently hydrogen, or halogen. In another embodiment of the first aspect, $R_5$ and $R_6$ are each independently hydrogen, —F, —Cl, or —Br. In a further another embodiment of the first aspect, $R_5$ is hydrogen, $R_6$ is —F, —Cl or —Br. In a preferred embodiment of the first aspect, $R_5$ and $R_6$ are both hydrogen.

In an embodiment of the first aspect, $R_7$, $R_8$ and $R_{10}$, which may be the same or different, are each independently hydrogen, halogen, —$C_{1-6}$alkyl, —$C_{2-6}$alkenyl, —$C_{2-6}$alkynyl, cycloalkyl, heterocyclyl, aryl, heteroaryl, or —$OR_{12}$; wherein said —$C_{1-6}$alkyl, —$C_{2-6}$alkenyl, —$C_{2-6}$alkynyl, cycloalkyl, heterocyclyl, aryl or heteroaryl are each independently optionally substituted with at least one substituent $R_{11c}$, wherein $R_{11c}$ is as defined above. In a preferred embodiment, $R_{11c}$ is halogen.

In an embodiment of the first aspect, $R_7$, $R_8$ and $R_{10}$, which may be the same or different, are each independently hydrogen, halogen, —$C_{1-6}$alkyl, —$C_{2-6}$alkenyl, —$C_{2-6}$alkynyl, or —$OR_{12}$. In another embodiment of the first aspect, $R_7$, $R_8$, and $R_{10}$ are each independently hydrogen, halogen, —$C_{1-6}$alkyl, or —$OR_{12}$. In a further another embodiment of the first aspect, $R_7$, $R_8$, and $R_{10}$ are each independently hydrogen, —F, —Cl, —Br, methyl, ethyl, 1-propyl, 2-propyl or isopropyl, 1-butyl or n-butyl, 2-methyl-1-propyl, 1-methylpropyl, 1,1-dimethylethyl, 1-pentyl, 2-pentyl, 3-pentyl, 2-methyl-2-butyl, 3-methyl-2-butyl, 3-methyl-1-butyl, 2-methyl-1-butyl, methoxy, ethoxy, propoxy, isopropoxy, n-butoxy, tert-butoxy, pentoxy and hexoxy. In a preferred embodiment of the first aspect, $R_7$ and $R_8$ are each independently halogen or —$C_{1-6}$ alkyl. In a preferred embodiment of the first aspect, $R_{10}$ is methoxy, ethoxy, propoxy, or isopropoxy. In a further preferred embodiment of the first aspect, $R_{10}$ is isopropoxy.

In an embodiment of the first aspect, $R_9$ is hydrogen, cycloalkyl, heterocyclyl, aryl, or heteroaryl; wherein said cycloalkyl, heterocyclyl, aryl or heteroaryl are each independently optionally substituted with at least one substituent $R_{11d}$, wherein $R_{11d}$ is defined as in Formula (I). In another embodiment, the heterocyclyl is 5- to 6-membered heterocyclyl comprising one nitrogen atom and 0 or 1 additional heteroatom selected from N, O and S, and heteroaryl is 5- to 6-membered heteroaryl comprising one nitrogen atom and 0 or 1 additional heteroatom selected from N, O and S. In a preferred embodiment, $R_9$ is 5- to 6-membered heterocyclyl comprising one nitrogen atom and 0 or 1 additional heteroatom selected from N, O and S, or 5- to 6-membered heteroaryl comprising one nitrogen atom and 0 or 1 additional heteroatom selected from N, O and S; wherein said heterocyclyl or heteroaryl are each independently optionally substituted with at least one substituent $R_{11d}$. In a further preferred embodiment, $R_9$ is 5-membered heterocyclyl comprising one nitrogen atom, or 6-membered heterocyclyl comprising one or two nitrogen atoms, or 5- or 6-membered heteroaryl comprising one nitrogen atom, wherein said heterocyclyl or heteroaryl are each independently optionally substituted with at least one substituent $R_{11d}$.

In some embodiment, $R_{11d}$ is hydrogen, halogen, —$C_{1-6}$alkyl, halo$C_{1-6}$alkyl, oxo, —$OR_{12}$, —$CO_2R_{12}$, —$CONR_{12}R_{13}$ or 5- to 6-membered heterocyclyl comprising 1 or 2 heteroatoms selected from N and O, wherein $R_{12}$ and $R_{13}$ are each independently hydrogen, —$C_{1-6}$alkyl, or $C_{1-6}$alkyloxy$C_{1-6}$alkyl-. In another embodiment, $R_{11d}$ is methyl, trifluoromethyl, chloro, N,N-dimethylaminocarbonyl, N,N-diethylaminocarbonyl, aminocarbonyl, carboxyl, hydroxyl, oxo, methoxy, or 2-methoxyethoxy.

In one embodiment, $R_9$ is 5- or 6-membered heteroaryl comprising one nitrogen atom, wherein said heteroaryl is optionally substituted with a substituent $R_{11d}$. In a preferred embodiment, $R_9$ is pyridinyl optionally substituted with a substituent $R_{11d}$. Preferably, $R_{11d}$ is —$CONR_{12}R_{13}$, wherein $R_{12}$ and $R_{13}$ are as defined in Formula (I). In one example of this embodiment, $R_{11d}$ is —$CONR_{12}R_{13}$, wherein $R_{12}$ is hydrogen, and $R_{13}$ is cycloalkyl optionally substituted with at least one substituent $R_{16}$, preferably $R_{13}$ is a $C_3$-$C_8$ cycloalkyl optionally substituted with at least one substituent $R_{16}$, more preferably $R_{13}$ is a cyclopropyl optionally substituted with at least one substituent $R_{16}$. In another example of this embodiment, $R_{11d}$ is —$CONR_{12}R_{13}$, wherein $R_{12}$ and $R_{13}$ together with the nitrogen atom to which they are attached, form a 3- to 8-membered saturated, partially or fully unsaturated ring comprising 0, 1 or 2 additional heteroatoms independently selected from —NH, —O—, —S—, —SO— or —$SO_2$—, and said ring is optionally substituted with at least one substituent $R_{16}$. Preferably, $R_{11d}$ is —$CONR_{12}R_{13}$, wherein $R_{12}$ and $R_{13}$ together with the nitrogen atom to which they are attached, form a 4-, or 5- or 6-membered saturated ring comprising 0 or 1 additional heteroatoms independently selected from —NH, —O—, —S—, —SO— or —$SO_2$—, and said ring is optionally substituted with at least one substituent $R_{16}$. More preferably, $R_{11d}$ is —$CONR_{12}R_{13}$, wherein $R_{12}$ and $R_{13}$ together with the nitrogen atom to which they are attached, form a 4-, or 5- or 6-membered saturated ring comprising 0 additional heteroatoms independently selected from —NH, —O—, —S—, —SO— or —$SO_2$— and said ring is optionally substituted with at least one substituent $R_{16}$; alternatively, $R_{11d}$ is —$CONR_{12}R_{13}$, wherein $R_{12}$ and $R_{13}$ together with the nitrogen atom to which they are attached, form a 4-, or 5- or 6-membered saturated ring comprising 1 additional heteroatoms independently selected from —NH, —O—, —S—, —SO— or —$SO_2$—, and said ring is optionally substituted with at least one substituent $R_{16}$. In the above embodiments or examples, $R_{16}$ is as defined in Formula (I); preferably, $R_{16}$, at each of its occurrences, is independently hydrogen, halogen, —$C_{1-6}$alkyl optionally substituted with hydroxyl, —$C_{2-6}$alkenyl, —$C_{2-6}$alkynyl, halo$C_{1-6}$alkyl, halo$C_{2-6}$alkenyl, halo$C_{2-6}$alkynyl, cycloalkyl, heterocyclyl, aryl, heteroaryl, —CN, —$NO_2$, oxo, —$OR_a$, —$SO_2R_a$, —$COR_a$, —$CO_2R_a$, —$CONR_aR_b$, —C(=$NR_a$)$NR_bR_c$, —$NR_aR_b$, —$NR_aCOR_b$, —$NR_aCONR_bR_c$, —$NR_aCO_2R_b$, —$NR_aSONR_bR_c$, —$NR_aSO_2NR_bR_c$, or —$NR_aSO_2R_b$, wherein $R_a$, $R_b$, or $R_c$ is independently hydrogen, halogen, —$C_{1-6}$alkyl, —$C_{2-6}$alkenyl, —$C_{2-6}$alkynyl, halo$C_{1-6}$alkyl, halo$C_{2-6}$alkenyl, halo$C_{2-6}$alkynyl, cycloalkyl, heterocyclyl, aryl, or heteroaryl; more preferably, $R_{16}$, at each of its occurrences, is independently hydrogen, halogen, —$C_{1-6}$ alkyl optionally substituted with hydroxyl, —OH, or —$CO_2H$.

In an embodiment of the first aspect, R₉ is
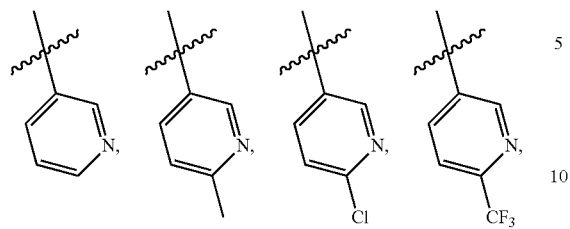
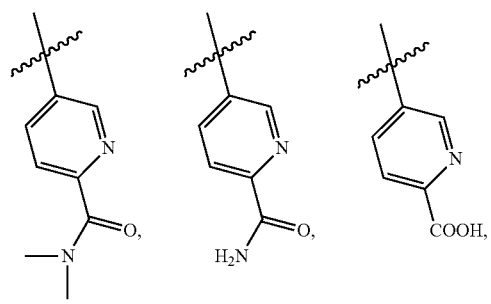
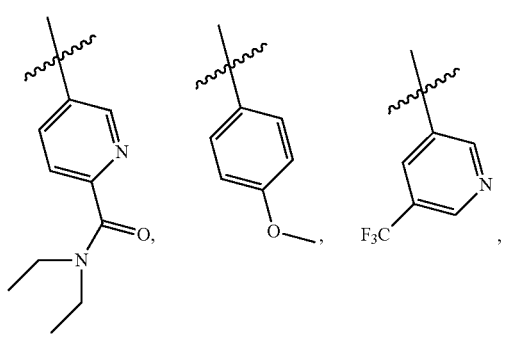
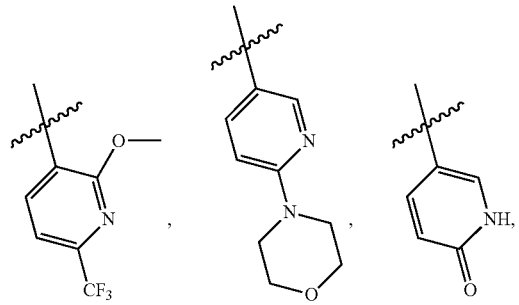
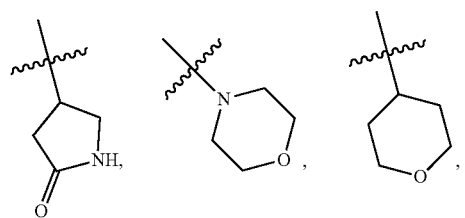
-continued
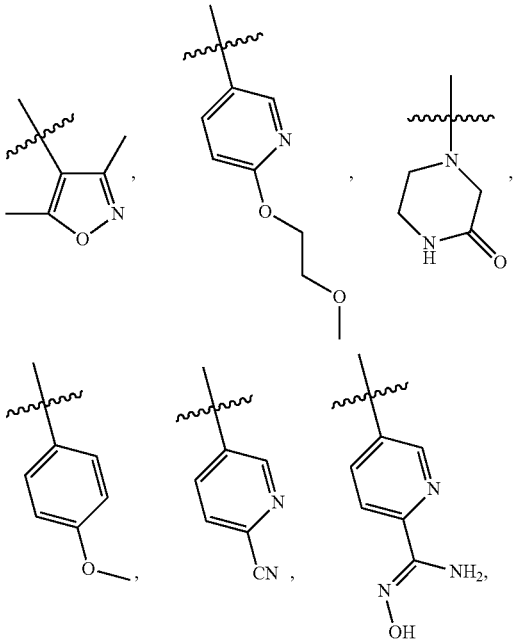
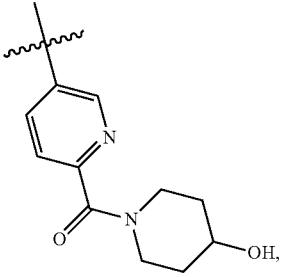
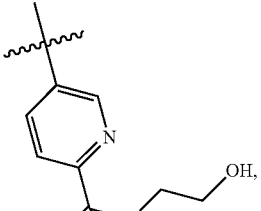
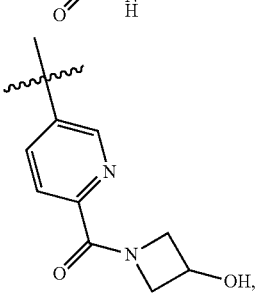
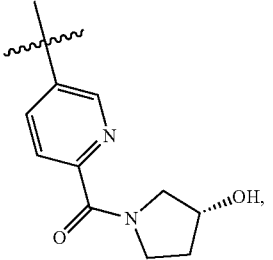

-continued
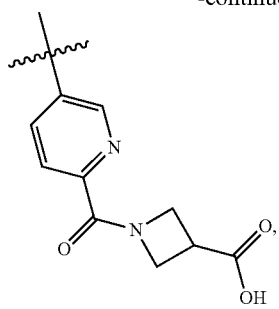
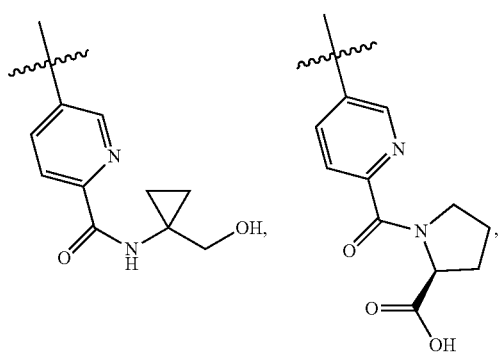
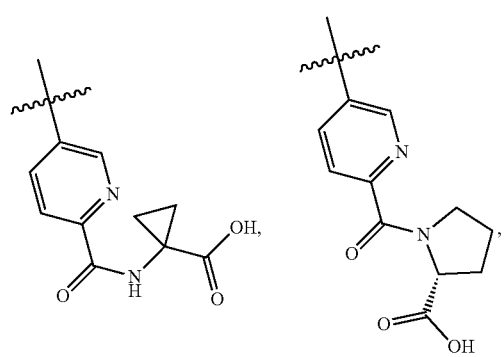
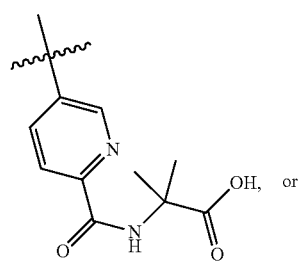
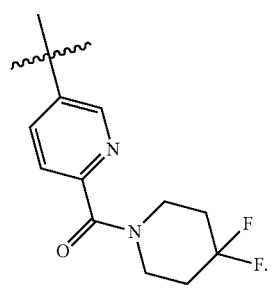
In another embodiment, R$_9$ is substituted heteroaryl or heterocyclyl, which is
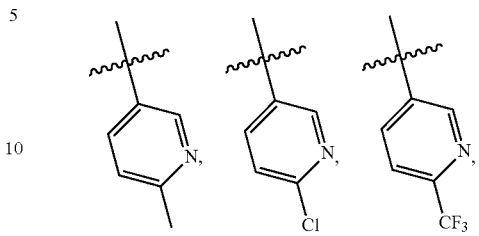
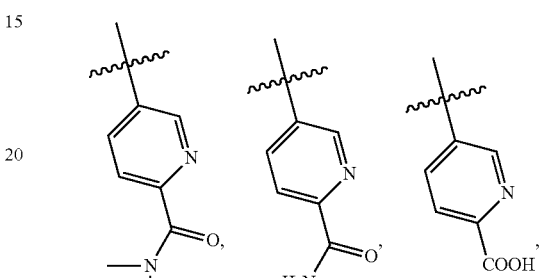
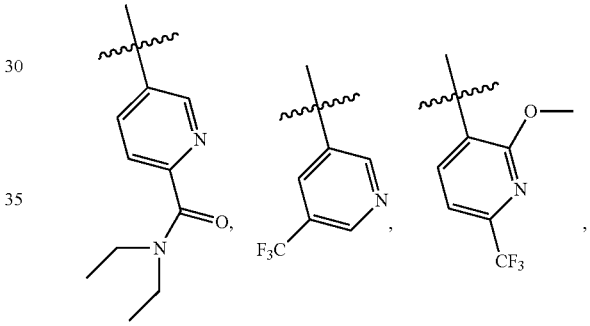
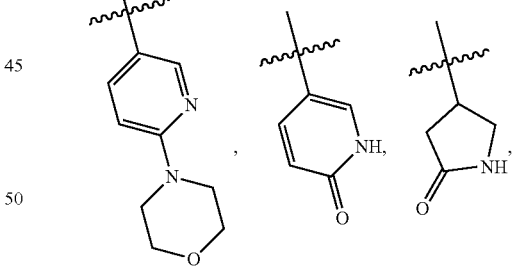
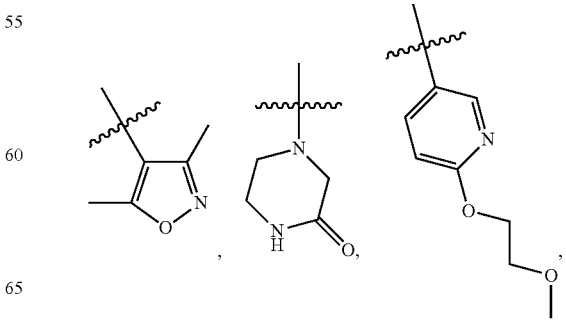

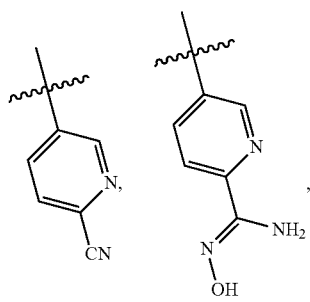 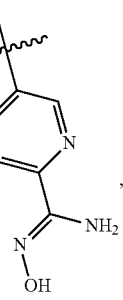, 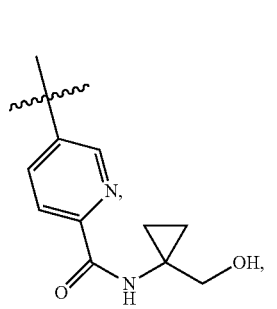, 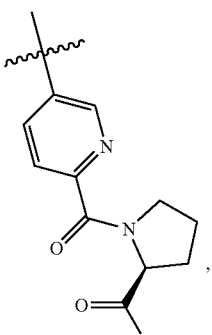,
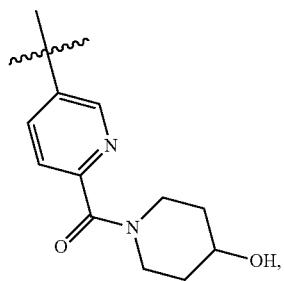, 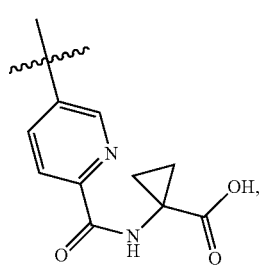, 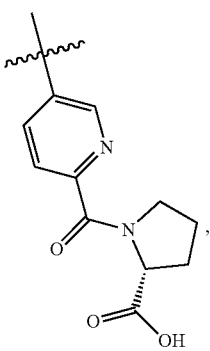,
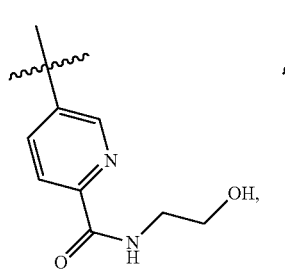, 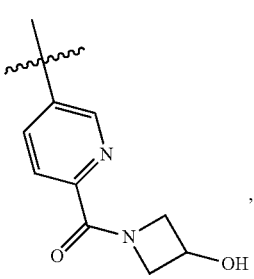, 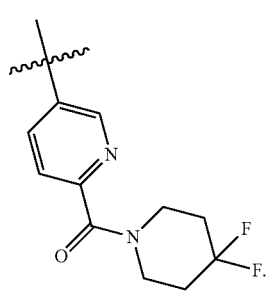 or
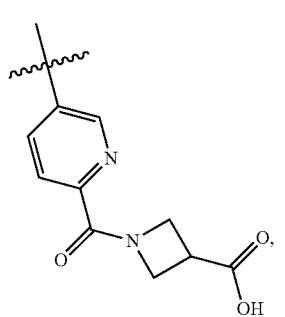, 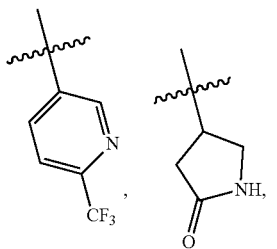.
In an embodiment of the first aspect, R₉ is
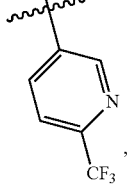, 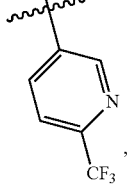, 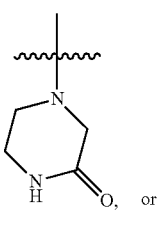 or

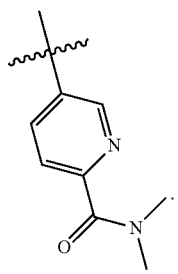

In a preferred embodiment, provided is the compound of Formula (I),
wherein:

$R_1$ is —$NH_2$;

$R_2$ is methyl or Cl or Br;

$R_3$ and $R_4$, which may be the same or different, are each independently hydrogen, —$C_{1-6}$alkyl; preferably $R_3$ is hydrogen, and $R_4$ is —$C_{1-6}$alkyl, e.g., —$C_{1-4}$alkyl;

$R_5$ and $R_6$ are both hydrogen;

$R_7$ and $R_8$, which may be the same or different, are each independently hydrogen, halogen, or —$C_{1-6}$alkyl;

$R_{10}$ is —$OR_{12}$, wherein $R_{12}$ is $C_{1-6}$alkyl; preferably $C_{1-3}$alkyl, e.g., methyl, ethyl, propyl or isopropyl;

$R_9$ is

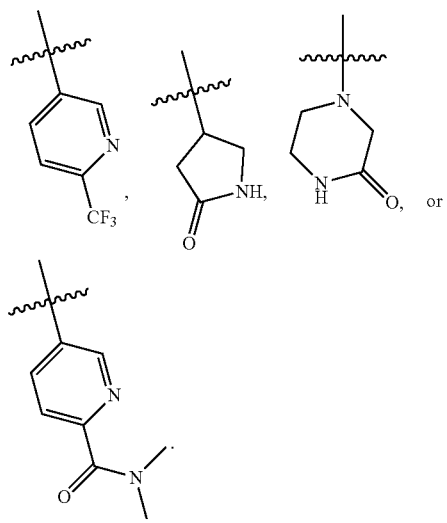

In an embodiment of the first aspect, $R_2$ is Cl or Br, and $R_9$ is hydrogen, 5- to 6-membered heterocyclyl comprising one nitrogen atom and 0 or 1 additional heteroatom selected from N, O and S, or 5- to 6-membered heteroaryl comprising one nitrogen atom and 0 or 1 additional heteroatom selected from N, O and S, wherein said heterocyclyl or heteroaryl are each independently optionally substituted with at least one substituent $R_{11a}$; preferably, $R_9$ is 5- or 6-membered heterocyclyl comprising one nitrogen atom, or 5- or 6-membered heteroaryl comprising one nitrogen atom, wherein said heterocyclyl or heteroaryl are each independently optionally substituted with at least one substituent $R_{11a}$; more preferably, $R_9$ is

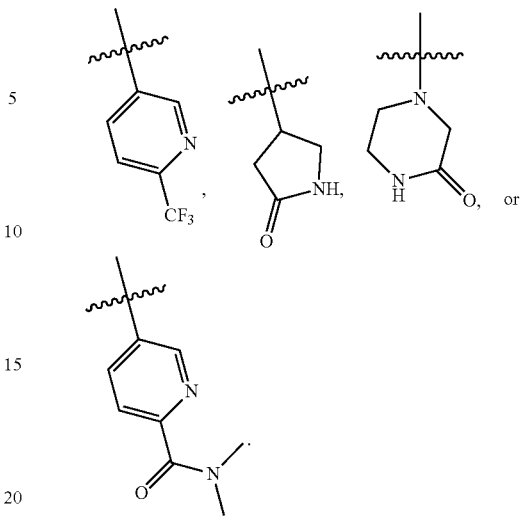

In another embodiment of the first aspect, $R_2$ and $R_9$ are defined as above and $R_{10}$ is ethoxy or isopropoxy; preferably $R_{10}$ is isopropoxy.

As shown in Table 1, the compounds disclosed herein are effective inhibitors against PI3Kδ. The compounds disclosed herein wherein $R_2$ in Formula (I) is Cl or Br are more active against PI3Kδ as shown in Table 1.

The compounds disclosed herein, wherein $R_2$ is Cl or Br and $R_9$ is substituted or unsubstituted 5- to 6-membered heterocyclyl comprising one nitrogen atom and 0 or 1 additional heteroatom selected from N, O and S, or substituted or unsubstituted 5- to 6-membered heteroaryl comprising one nitrogen atom and 0 or 1 additional heteroatom selected from N, O and S, have been found to be selective inhibitors against PI3Kδ over PI3Kα, β and/or γ as shown in Table 1. The compounds disclosed herein, wherein $R_2$ is Cl or Br, $R_9$ is substituted or unsubstituted 5- to 6-membered heterocyclyl comprising one nitrogen atom and 0 or 1 additional heteroatom selected from N, O and S, or substituted or unsubstituted 5- to 6-membered heteroaryl comprising one nitrogen atom and 0 or 1 additional heteroatom selected from N, O and S, and $R_{10}$ is ethoxy or isopropoxy (preferably isopropoxy) show better selectivity for PI3Kδ over each of PI3Kα, β and γ as shown in Table 1.

The compound disclosed herein is a potentially important diagnostic and therapeutic agent to the brain due to its better Brain/Plasma Conc. Ratio.

In the second aspect, provided is a pharmaceutical composition comprising a therapeutically effective amount of the compound disclosed herein, or a stereoisomer thereof or a pharmaceutically acceptable salt thereof, and a pharmaceutically acceptable excipient.

In the third aspect, provided is a method for treating or preventing the following a disorders or a disease responsive to the inhibition of PI3Kδ activity by using the compound disclosed herein or a stereoisomer thereof or a pharmaceutically acceptable salt thereof; the use of the compound disclosed herein in the manufacture of a medicament for treating or preventing a disorders or a disease responsive to the inhibition of PI3Kδ activity; and the compound disclosed herein or a stereoisomer thereof or a pharmaceutically acceptable salt thereof for use in treating or preventing a disorders or a disease responsive to the inhibition of PI3Kδ activity, wherein the disorder or disease is an inflammatory disorder, an autoimmune disease or a cancer. In some embodiments, the disorder or disease is selected from the group consisting of idiopathic thrombocytopenic purpura (ITP), autoimmune hemolytic anemia, vasculitis, systemic lupus erythematosus, lupus nephritis, pemphigus, membranous nephropathy, acute lymphocytic hemolytic (ALL), acute myeloid leukemia (AML), chronic lymphocytic leukemia (CLL), Non-Hodgkin lymphoma (NHL), chronic myeloid leukemia (CML), multiple myeloma (MM), hairy cell leukemia, Mantle cell lymphoma (MCL), small lymphocytic lymphoma (SLL), follicular lymphoma, lymphoplasmacytic lymphoma, extranodal marginal zone lymphoma, activated B-cell like (ABC) diffuse large B cell lymphoma (DLBCL), or germinal center B cell (GCB) diffuse large B cell lymphoma (DLBCL), T-cell lymphoma, B-cell lymphoma, myelodysplasia syndrome (MDS), myeloproliferative disease (MPD) follicular lymphoma, Waldestrom's macroglobulinemia (WM), pancreatic cancer, bladder cancer, colorectal cancer, breast cancer, prostate cancer, renal cancer, hepatocellular cancer, lung cancer, ovarian cancer, cervical cancer, gastric cancer, esophageal cancer, head and neck cancer, melanoma, neuroendocrine cancer, CNS cancer, brain cancer, bone cancer, soft tissue sarcoma, non-small cell lung cancer, small-cell lung cancer, colon cancer, systemic lupus erythematosus (SLE), myestenia gravis, rheumatoid arthritis (RA), acute disseminated encephalomyelitis, idiopathic thrombocytopenic purpura, multiple sclerosis (MS), Sjoegren's syndrome, autoimmune hemolytic anemia, asthma, rheumatoid arthritis, multiple sclerosis, or lupus.

Definitions

The following terms have the indicated meanings throughout the specification:

As used herein, including the appended claims, the singular forms of words such as "a", "an", and "the", include their corresponding plural references unless the context clearly dictates otherwise.

The term "or" is used to mean, and is used interchangeably with, the term "and/or" unless the context clearly dictates otherwise.

The term "alkyl" herein refers to a hydrocarbon group selected from linear and branched saturated hydrocarbon groups comprising from 1 to 18, such as from 1 to 12, further such as from 1 to 10, more further such as from 1 to 8, or from 1 to 6, or from 1 to 4, carbon atoms. Examples of alkyl groups comprising from 1 to 6 carbon atoms (i.e., $C_{1-6}$ alkyl) include, but not limited to methyl, ethyl, 1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Bu"), 1,1-dimethylethyl or t-butyl ("t-Bu"), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl and 3,3-dimethyl-2-butyl groups.

The term "halogen" herein refers to fluoro (F), chloro (Cl), bromo (Br) and iodo (I).

The term "haloalkyl" herein refers to an alkyl group in which one or more hydrogen is/are replaced by one or more halogen atoms such as fluoro (F), chloro (Cl), bromo (Br), and iodo (I). Examples of the haloalkyl include haloC$_{1-8}$ alkyl, haloC$_{1-6}$alkyl or halo C$_{1-4}$alkyl, but not limited to —CF$_3$, —CH$_2$Cl, —CH$_2$CF$_3$, —CCl$_2$, CF$_3$, and the like.

The term "alkenyl" herein refers to a hydrocarbon group selected from linear and branched hydrocarbon groups comprising at least one C=C double bond and from 2 to 18, such as from 2 to 8, further such as from 2 to 6, carbon atoms. Examples of the alkenyl group, e.g., $C_{2-6}$ alkenyl, include, but not limited to ethenyl or vinyl, prop-1-enyl, prop-2-enyl, 2-methylprop-1-enyl, but-1-enyl, but-2-enyl, but-3-enyl, buta-1,3-dienyl, 2-methylbuta-1,3-dienyl, hex-1-enyl, hex-2-enyl, hex-3-enyl, hex-4-enyl, and hexa-1,3-dienyl groups.

The term "alkynyl" herein refers to a hydrocarbon group selected from linear and branched hydrocarbon group, comprising at least one CEC triple bond and from 2 to 18, such as 2 to 8, further such as from 2 to 6, carbon atoms. Examples of the alkynyl group, e.g., $C_{2-6}$ alkynyl, include, but not limited to ethynyl, 1-propynyl, 2-propynyl (propargyl), 1-butynyl, 2-butynyl, and 3-butynyl groups.

The term "alkyloxy" herein refers to an alkyl group as defined above bonded to oxygen, represented by —Oalkyl. Examples of an alkyloxy, e.g., $C_{1-6}$alkyloxy or $C_{1-4}$ alkyloxy includes, but not limited to, methoxy, ethoxy, isopropoxy, propoxy, n-butoxy, tert-butoxy, pentoxy and hexoxy and the like.

The term "cycloalkyl" herein refers to a hydrocarbon group selected from saturated and partially unsaturated cyclic hydrocarbon groups, comprising monocyclic and polycyclic (e.g., bicyclic and tricyclic) groups. For example, the cycloalkyl group may comprise from 3 to 12, such as from 3 to 10, further such as 3 to 8, further such as 3 to 6, 3 to 5, or 3 to 4 carbon atoms. Even further for example, the cycloalkyl group may be selected from monocyclic group comprising from 3 to 12, such as from 3 to 10, further such as 3 to 8, 3 to 6 carbon atoms. Examples of the monocyclic cycloalkyl group include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, and cyclododecyl groups. In particular, Examples of the saturated monocyclic cycloalkyl group, e.g., $C_{3-8}$ cycloalkyl, include, but not limited to cyclopropyl, cyclobutyl, cyclopentyl, cyclohexyl, cycloheptyl, and cyclooctyl groups. In a preferred embodiment, the cycloalkyl is a monocyclic ring comprising 3 to 6 carbon atoms (abbreviated as $C_{3-6}$ cycloalkyl), including but not limited to, cyclopropyl, cyclobutyl, cyclopentyl, and cyclohexyl. Examples of the bicyclic cycloalkyl groups include those having from 7 to 12 ring atoms arranged as a bicyclic ring selected from [4,4], [4,5], [5,5], [5,6] and [6,6] ring systems, or as a bridged bicyclic ring selected from bicyclo[2.2.1]heptane, bicyclo[2.2.2]octane, and bicyclo[3.2.2]nonane. Further Examples of the bicyclic cycloalkyl groups include those arranged as a bicyclic ring selected from [5,6] and [6,6] ring systems, such as and

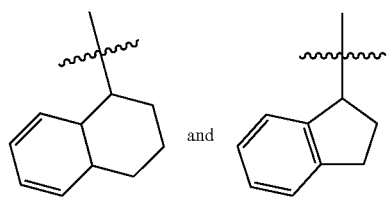 [SMILES: *C1CCCC2C=CC=CC12 ; *C1CCc2ccccc21]

wherein the wavy lines indicate the points of attachment. The ring may be saturated or have at least one double bond (i.e. partially unsaturated), but is not fully conjugated, and is not aromatic, as aromatic is defined herein.

The term "aryl" used alone or in combination with other terms refers to a group selected from: 5- and 6-membered carbocyclic aromatic rings, e.g., phenyl; bicyclic ring systems such as 7 to 12 membered bicyclic ring systems, wherein at least one ring is carbocyclic and aromatic, e.g., naphthyl and indanyl; and, tricyclic ring systems such as 10 to 15 membered tricyclic ring systems wherein at least one ring is carbocyclic and aromatic, e.g., fluorenyl. The terms "aromatic hydrocarbon ring" and "aryl" are used interchangeable throughout the disclosure herein. In some embodiments, a monocyclic or bicyclic aromatic hydrocarbon ring has 5 to 10 ring-forming carbon atoms (i.e., $C_{5-10}$ aryl). Examples of a monocyclic or bicyclic aromatic hydrocarbon ring includes, but not limited to, phenyl, naphth-1-yl, naphth-2-yl, anthracenyl, phenanthrenyl, and the like. In some embodiments, the aromatic hydrocarbon ring is a naphthalene ring (naphth-1-yl or naphth-2-yl) or phenyl ring. In some embodiments, the aromatic hydrocarbon ring is a phenyl ring.

The term "heteroaryl" herein refers to a group selected from: 5-, 6- or 7-membered aromatic, monocyclic rings comprising at least one heteroatom, for example, from 1 to 4, or, in some embodiments, from 1 to 3, in some embodiments, from 1 to 2, heteroatoms, selected from nitrogen (N), sulfur (S) and oxygen (O), with the remaining ring atoms being carbon; 8- to 12-membered bicyclic rings comprising at least one heteroatom, for example, from 1 to 4, or, in some embodiments, from 1 to 3, or, in other embodiments, 1 or 2, heteroatoms, selected from N, O, and S, with the remaining ring atoms being carbon and wherein at least one ring is aromatic and at least one heteroatom is present in the aromatic ring; and 11- to 14-membered tricyclic rings comprising at least one heteroatom, for example, from 1 to 4, or in some embodiments, from 1 to 3, or, in other embodiments, 1 or 2, heteroatoms, selected from N, O, and S, with the remaining ring a toms being carbon and wherein at least one ring is aromatic and at least one heteroatom is present in an aromatic ring. In a preferred embodiment, heteroaryl is 5- to 6-membered heteroaryl comprising one nitrogen atom and 0 or 1 additional heteroatom selected from N, O and S, including but not limited to pyridinyl, isoxazolyl, and oxazolyl.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1. When the heteroaryl group contains more than one heteroatom ring member, the heteroatoms may be the same or different. The nitrogen atoms in the ring(s) of the heteroaryl group can be oxidized to form N-oxides.

The terms "aromatic heterocyclic ring" and "heteroaryl" are used interchangeable throughout the disclosure herein. In some embodiments, a monocyclic or bicyclic aromatic heterocyclic ring has 5-, 6-, 7-, 8-, 9- or 10-ring forming members with 1, 2, 3, or 4 heteroatom ring members independently selected from nitrogen (N), sulfur (S) and oxygen (O) and the remaining ring members being carbon. In some embodiments, the monocyclic or bicyclic aromatic heterocyclic ring is a monocyclic or bicyclic ring comprising 1 or 2 heteroatom ring members independently selected from nitrogen (N), sulfur (S) and oxygen (O). In some embodiments, the monocyclic or bicyclic aromatic heterocyclic ring is a 5- to 6-membered heteroaryl ring, which is monocyclic and which has 1 or 2 heteroatom ring members independently selected from nitrogen (N), sulfur (S) and oxygen (O). In some embodiments, the monocyclic or bicyclic aromatic heterocyclic ring is a 8- to 10-membered heteroaryl ring, which is bicyclic and which has 1 or 2 heteroatom ring members independently selected from nitrogen, sulfur and oxygen.

Examples of the heteroaryl group or the monocyclic or bicyclic aromatic heterocyclic ring include, but are not limited to, (as numbered from the linkage position assigned priority 1) pyridyl (such as 2-pyridyl, 3-pyridyl, or 4-pyridyl), cinnolinyl, pyrazinyl, 2,4-pyrimidinyl, 3,5-pyrimidinyl, 2,4-imidazolyl, imidazopyridinyl, isoxazolyl, oxazolyl, thiazolyl, isothiazolyl, thiadiazolyl (such as 1,2,3-thiadiazolyl, 1,2,4-thiadiazolyl, or 1,3,4-thiadiazolyl), tetrazolyl, thienyl (such as thien-2-yl, thien-3-yl), triazinyl, benzothienyl, furyl or furanyl, benzofuryl, benzoimidazolyl, indolyl, isoindolyl, indolinyl, oxadiazolyl (such as 1,2,3-oxadiazolyl, 1,2,4-oxadiazolyl, or 1,3,4-oxadiazolyl), phthalazinyl, pyrazinyl, pyridazinyl, pyrrolyl, triazolyl (such as 1,2,3-triazolyl, 1,2,4-triazolyl, or 1,3,4-triazolyl), quinolinyl, isoquinolinyl, pyrazolyl, pyrrolopyridinyl (such as 1H-pyrrolo[2,3-b]pyridin-5-yl), pyrazolopyridinyl (such as 1H-pyrazolo[3,4-b]pyridin-5-yl), benzoxazolyl (such as benzo[d]oxazol-6-yl), pteridinyl, purinyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, furazanyl (such as furazan-2-yl, furazan-3-yl), benzofurazanyl, benzothiophenyl, benzothiazolyl, benzoxazolyl, quinazolinyl, quinoxalinyl, naphthyridinyl, furopyridinyl, benzothiazolyl (such as benzo[d]thiazol-6-yl), indazolyl (such as 1H-indazol-5-yl) and 5,6,7,8-tetrahydroisoquinoline.

The term "heterocyclic" or "heterocycle" or "heterocyclyl" herein refers to a ring selected from 4-, 5-, 6-, 7-, 8-, 9-, 10-, 11- or 12-membered monocyclic, bicyclic and tricyclic, saturated and partially unsaturated rings comprising at least one carbon atoms in addition to at least one heteroatom, such as from 1-4 heteroatoms, further such as from 1-3, or further such as 1 or 2 heteroatoms, selected from nitrogen (N), sulfur (S) and oxygen (O). In some embodiments, a heterocyclyl group is 4-, 5-, 6- or 7-membered monocyclic ring with at least one heteroatom selected from N, O and S. "Heterocycle" herein also refers to a 5- to 7-membered heterocyclic ring comprising at least one heteroatom selected from N, O, and S fused with 5-, 6-, and/or 7-membered cycloalkyl, carbocyclic aromatic or heteroaromatic ring, provided that the point of attachment is at the heterocyclic ring when the heterocyclic ring is fused with a carbocyclic aromatic or a heteroaromatic ring, and that the point of attachment can be at the cycloalkyl or heterocyclic ring when the heterocyclic ring is fused with cycloalkyl. "Heterocycle" herein also refers to an aliphatic spirocyclic ring comprising at least one heteroatom selected from N, O, and S, provided that the point of attachment is at the heterocyclic ring. The rings may be saturated or have at least one double bond (i.e. partially unsaturated). The heterocycle may be substituted with oxo. The point of the attachment may be carbon or heteroatom in the heterocyclic ring. A heterocycle is not a heteroaryl as defined herein. In a preferred embodiment, heterocyclyl is 5- to 6-membered heterocyclyl comprising one nitrogen atom and 0 or 1 additional heteroatom selected from N, O and S, including but not limited to pyrrolyl, dihydropyridine, morpholino, morpholinyl and tetrahydropyranyl. In other embodiment, the substituted 5- to 6-membered heterocyclyl comprising one nitrogen atom and 0 or 1 additional heteroatom selected from N, O and S, includes, but not limited, γ-butyrolactam, δ-valerolactam, piperazin-2-one, pyrrolidine-2,5-dione, pyridin-2(1H)-one, 1,5-dihydro-2H-pyrrol-2-one, pyrrolidin-2-one or 1H-pyrrole-2,5-dione group.

Examples of the heterocycle include, but not limited to, (as numbered from the linkage position assigned priority 1) 1-pyrrolidinyl, 2-pyrrolidinyl, 2,4-imidazolidinyl, 2,3-pyrazolidinyl, I-piperidinyl, 2-piperidinyl, 3-piperidinyl, 4-piperidinyl, 2,5-piperazinyl, pyranyl, morpholinyl, morpholino, 2-morpholinyl, 3-morpholinyl, oxiranyl, aziridinyl, thiiranyl, azetidinyl, oxetanyl, thietanyl, 1,2-dithietanyl, 1,3-dithietanyl, dihydropyridinyl, tetrahydropyridinyl, thiomorpholinyl, thioxanyl, piperazinyl, homopiperazinyl, homopiperidinyl, azepanyl, oxepanyl, thiepanyl, 1,4-oxathiinyl, 1,4-dioxepanyl, 1,4-oxathiepanyl, 1,4-oxaazepanyl, 1,4-dithiepanyl, 1,4-thiazepanyl and 1,4-diazepanyl, 1,4-dithianyl, 1,4-azathianyl, oxazepinyl, diazepinyl, thiazepinyl, dihydrothienyl, dihydropyranyl, dihydrofuranyl, tetrahydrofuranyl, tetrahydrothienyl, tetrahydropyranyl, tetrahydrothiopyranyl, 1-pyrrolinyl, 2-pyrrolinyl, 3-pyrrolinyl, indolinyl, 2H-pyranyl, 4H-pyranyl, 1,4-dioxanyl, 1,3-dioxolanyl, pyrazolinyl, pyrazolidinyl, dithianyl, dithiolanyl, pyrazolidinyl, imidazolinyl, pyrimidinonyl, 1,1-dioxo-thiomorpholinyl, 3-azabicyclo[3.1.0]hexanyl, 3-azabicyclo[4.1.0]heptanyl and azabicyclo[2.2.2]hexanyl. A substituted heterocycle also includes a ring system substituted with one or more oxo moieties, such as piperidinyl N-oxide, morpholinyl-N-oxide, I-oxo-1-thiomorpholinyl and 1,1-dioxo-1-thiomorpholinyl.

Compounds disclosed herein may contain an asymmetric center and may thus exist as enantiomers. "Enantiomers" refer to two stereoisomers of a compound which are non-superimposable mirror images of one another. Where the compounds disclosed herein possess two or more asymmetric centers, they may additionally exist as diastereomers. Enantiomers and diastereomers fall within the broader class of stereoisomers. All such possible stereoisomers as substantially pure resolved enantiomers, racemic mixtures thereof, as well as mixtures of diastereomers are intended to be included. All stereoisomers of the compounds disclosed herein and/or pharmaceutically acceptable salts thereof are intended to be included. Unless specifically mentioned otherwise, reference to one isomer applies to any of the possible isomers. Whenever the isomeric composition is unspecified, all possible isomers are included.

The term "substantially pure" as used herein means that the target stereoisomer contains no more than 35%, such as no more than 30%, further such as no more than 25%, even further such as no more than 20%, by weight of any other stereoisomer(s). In some embodiments, the term "substantially pure" means that the target stereoisomer contains no more than 10%, for example, no more than 5%, such as no more than 1%, by weight of any other stereoisomer(s).

When compounds disclosed herein contain olefinic double bonds, unless specified otherwise, such double bonds are meant to include both E and Z geometric isomers.

Some of the compounds disclosed herein may exist with different points of attachment of hydrogen, referred to as tautomers. For example, compounds including carbonyl —$CH_2C(O)$— groups (keto forms) may undergo tautomerism to form hydroxyl —CH=C(OH)— groups (enol forms). Both keto and enol forms, individually as well as mixtures thereof, are also intended to be included where applicable.

It may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed ("SMB") and preparative thin or thick layer chromatography, as well as techniques of small scale thin layer and flash chromatography. One skilled in the art will apply techniques most likely to achieve the desired separation.

"Diastereomers" refers to stereoisomers of a compound with two or more chiral centers but which are not mirror images of one another. Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Enantiomers can also be separated by use of a chiral HPLC column.

A single stereoisomer, e.g., a substantially pure enantiomer, may be obtained by resolution of the racemic mixture using a method such as formation of diastereomers using optically active resolving agents (Eliel, E. and Wilen, S. *Stereochemistry of Organic Compounds*. New York: John Wiley & Sons, Inc., 1994; Lochmuller, C. H., et al. *"Chromatographic resolution of enantiomers: Selective review." J. Chromatogr.,* 113(3) (1975): pp. 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: Wainer, Irving W., Ed. *Drug Stereochemistry: Analytical Methods and Pharmacology*. New York: Marcel Dekker, Inc., 1993.

"Pharmaceutically acceptable salts" refers to those salts which are, within the scope of sound medical judgment, suitable for use in contact with the tissues of humans and lower animals without undue toxicity, irritation, allergic response and the like, and are commensurate with a reasonable benefit/risk ratio. A pharmaceutically acceptable salt may be prepared in situ during the final isolation and purification of the compounds disclosed herein, or separately by reacting the free base function with a suitable organic acid or by reacting the acidic group with a suitable base.

In addition, if a compound disclosed herein is obtained as an acid addition salt, the free base can be obtained by basifying a solution of the acid salt. Conversely, if the product is a free base, an addition salt, such as a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used without undue experimentation to prepare non-toxic pharmaceutically acceptable addition salts.

As defined herein, "a pharmaceutically acceptable salt thereof" include salts of at least one compound of Formula (I), and salts of the stereoisomers of the compound of Formula (I), such as salts of enantiomers, and/or salts of diastereomers.

The terms "administration", "administering", "treating" and "treatment" herein, when applied to an animal, human, experimental subject, cell, tissue, organ, or biological fluid, mean contact of an exogenous pharmaceutical, therapeutic, diagnostic agent, or composition to the animal, human, subject, cell, tissue, organ, or biological fluid. Treatment of a cell encompasses contact of a reagent to the cell, as well as contact of a reagent to a fluid, where the fluid is in contact with the cell. The term "administration" and "treatment" also means in vitro and ex vivo treatments, e.g., of a cell, by a reagent, diagnostic, binding compound, or by another cell. The term "subject" herein includes any organism, preferably an animal, more preferably a mammal (e.g., rat, mouse, dog, cat, rabbit) and most preferably a human.

The term "effective amount" or "therapeutically effective amount" refers to an amount of the active ingredient, such as compound that, when administered to a subject for treating a disease, or at least one of the clinical symptoms of a disease or disorder, is sufficient to affect such treatment for the disease, disorder, or symptom. The "therapeutically effective amount" can vary with the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be apparent to those skilled in the art or can be determined by routine experiments. In some embodiments, "therapeutically effective amount" is an amount of at least one compound and/or at least one stereoisomer thereof, and/or at least one pharmaceutically acceptable salt thereof disclosed herein effective to "treat" as defined above, a disease or disorder in a subject.

The term "at least one substituent" disclosed herein includes, for example, from 1 to 5, such as from 1 to 4, further as 1, 2 or 3, substituents, provided that the valence allows. For example, "at least one substituent $R_{11a}$" disclosed herein includes from 1 to 4, such as from 1 to 3, further as 1 or 2, substituents selected from the list of $R_{11d}$ as disclosed herein. In the case of combination therapy, the "therapeutically effective amount" refers to the total amount of the combination objects for the effective treatment of a disease, a disorder or a condition.

The pharmaceutical composition comprising the compound disclosed herein can be administrated via oral, inhalation, rectal, parenteral or topical administration to a subject in need thereof. For oral administration, the pharmaceutical composition may be a regular solid formulation such as tablets, powder, granule, capsules and the like, a liquid formulation such as water or oil suspension or other liquid formulation such as syrup, solution, suspension or the like; for parenteral administration, the pharmaceutical composition may be solution, water solution, oil suspension concentrate, lyophilized powder or the like. Preferably, the formulation of the pharmaceutical composition is selected from tablet, coated tablet, capsule, suppository, nasal spray or injection, more preferably tablet or capsule. The pharmaceutical composition can be a single unit administration with an accurate dosage. In addition, the pharmaceutical composition may further comprise additional active ingredients.

All formulations of the pharmaceutical composition disclosed herein can be produced by the conventional methods in the pharmaceutical field. For example, the active ingredient can be mixed with one or more excipients, then to make the desired formulation. The "pharmaceutically acceptable excipient" refers to conventional pharmaceutical carriers suitable for the desired pharmaceutical formulation, for example: a diluent, a vehicle such as water, various organic solvents, etc, a filler such as starch, sucrose, etc a binder such as cellulose derivatives, alginates, gelatin and polyvinylpyrrolidone (PVP); a wetting agent such as glycerol; a disintegrating agent such as agar, calcium carbonate and sodium bicarbonate; an absorption enhancer such as quaternary ammonium compound; a surfactant such as hexadecanol; an absorption carrier such as Kaolin and soap clay; a lubricant such as talc, calcium stearate, magnesium stearate, polyethylene glycol, etc. In addition, the pharmaceutical composition further comprises other pharmaceutically acceptable excipients such as a decentralized agent, a stabilizer, a thickener, a complexing agent, a buffering agent, a permeation enhancer, a polymer, aromatics, a sweetener, and a dye.

The term "disease" refers to any disease, discomfort, illness, symptoms or indications, and can be interchangeable with the term "disorder" or "condition".

Throughout this specification and the claims which follow, unless the context requires otherwise, the term "comprise", and variations such as "comprises" and "comprising" are intended to specify the presence of the features thereafter, but do not exclude the presence or addition of one or more other features. When used herein the term "comprising" can be substituted with the term "containing", "including" or sometimes "having".

Throughout this specification and the claims which follow, the term "$C_{n-m}$" indicates a range which includes the endpoints, wherein n and m are integers and indicate the number of carbons. Examples include $C_{1-8}$, $C_{1-6}$, and the like.

Unless specifically defined elsewhere in this document, all other technical and scientific terms used herein have the meaning commonly understood by one of ordinary skill in the art to which this invention belongs.

General Synthesis

Compounds described herein, including salts thereof, can be prepared using known organic synthesis techniques and can be synthesized according to any of numerous possible synthetic routes.

The reaction for preparing compounds described herein can be carried out in suitable solvents which can be readily selected by one of skill in the art of organic synthesis. Suitable solvents can be substantially non-reactive with the starting materials, the intermediates, or products at the temperatures at which the reactions are carried out, e.g., temperatures which can range from the solvent's boiling temperature. A given reaction can be carried out in one solvent or mixture of solvents.

The selection of appropriate protecting group, can be readily determined by one skilled in the art.

Reactions can be monitored according to any suitable method known in the art, such as NMR, UV, HPLC, LC-MS and TLC. Compounds can be purified by a variety of methods, including HPLC and normal phase silica chromatography.

Scheme I

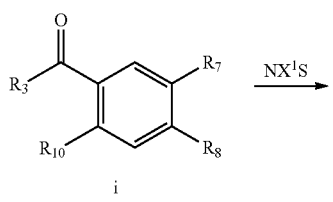

i

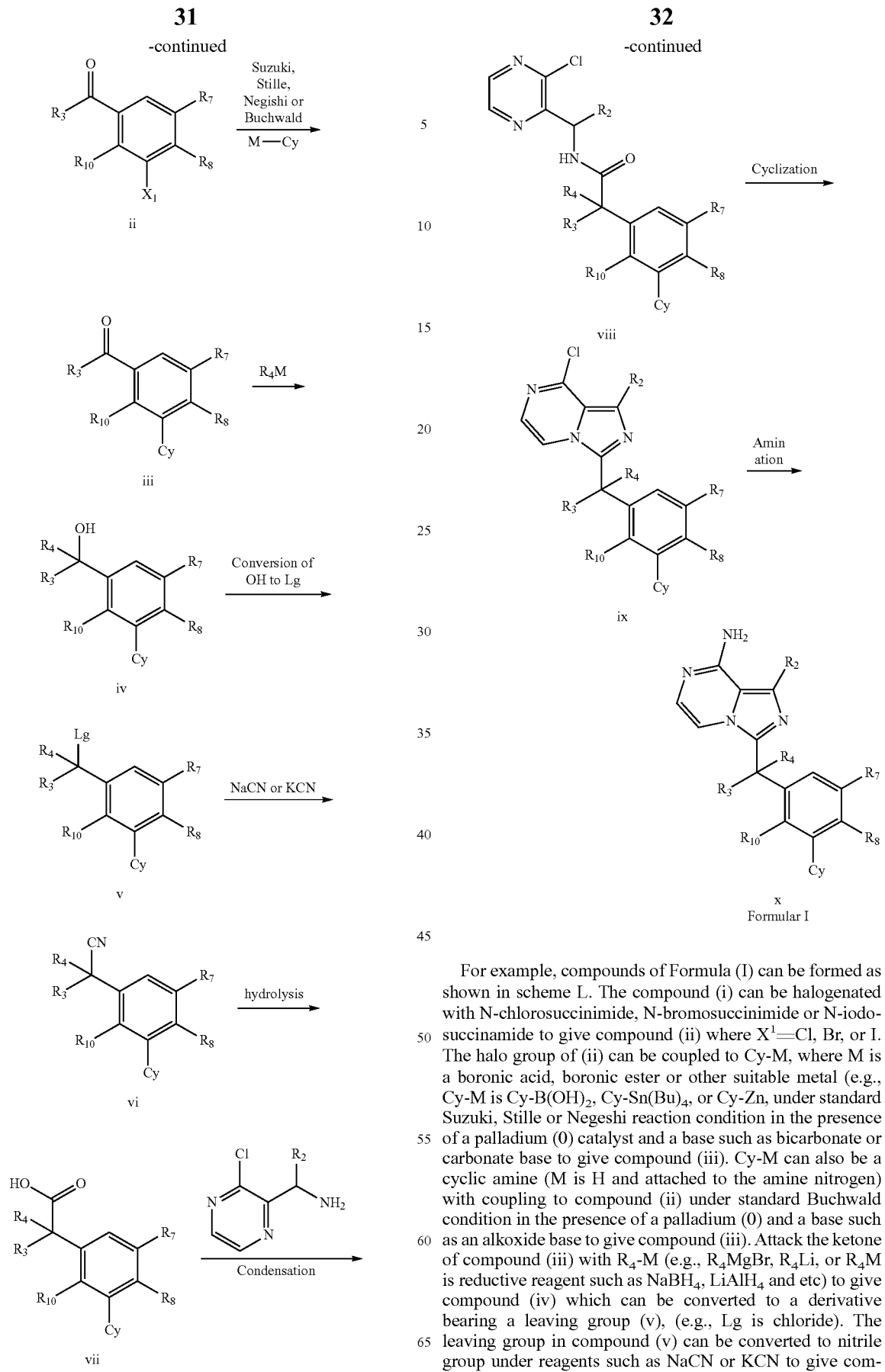

For example, compounds of Formula (I) can be formed as shown in scheme L. The compound (i) can be halogenated with N-chlorosuccinimide, N-bromosuccinimide or N-iodosuccinamide to give compound (ii) where $X^1$=Cl, Br, or I. The halo group of (ii) can be coupled to Cy-M, where M is a boronic acid, boronic ester or other suitable metal (e.g., Cy-M is Cy-B(OH)$_2$, Cy-Sn(Bu)$_4$, or Cy-Zn, under standard Suzuki, Stille or Negeshi reaction condition in the presence of a palladium (0) catalyst and a base such as bicarbonate or carbonate base to give compound (iii). Cy-M can also be a cyclic amine (M is H and attached to the amine nitrogen) with coupling to compound (ii) under standard Buchwald condition in the presence of a palladium (0) and a base such as an alkoxide base to give compound (iii). Attack the ketone of compound (iii) with R$_4$-M (e.g., R$_4$MgBr, R$_4$Li, or R$_4$M is reductive reagent such as NaBH$_4$, LiAlH$_4$ and etc) to give compound (iv) which can be converted to a derivative bearing a leaving group (v), (e.g., Lg is chloride). The leaving group in compound (v) can be converted to nitrile group under reagents such as NaCN or KCN to give compound (vi) which was hydrolyzed under acidic condition (e.g., HCl) or basic condition (KOH) to give acid (vii). Condensation of compound (vii) with the suitable amine in scheme I under standard condition such as HOBt, EDCI with a base such as trimethylamine to give compound (viii) that can be used for cyclization directly under Tf$_2$O or POCl$_3$ to give compound (ix). Finally, amination of compound (ix) by condition such as NH$_3$/i-prOH to give a compound of Formula (I) (x).

Scheme II

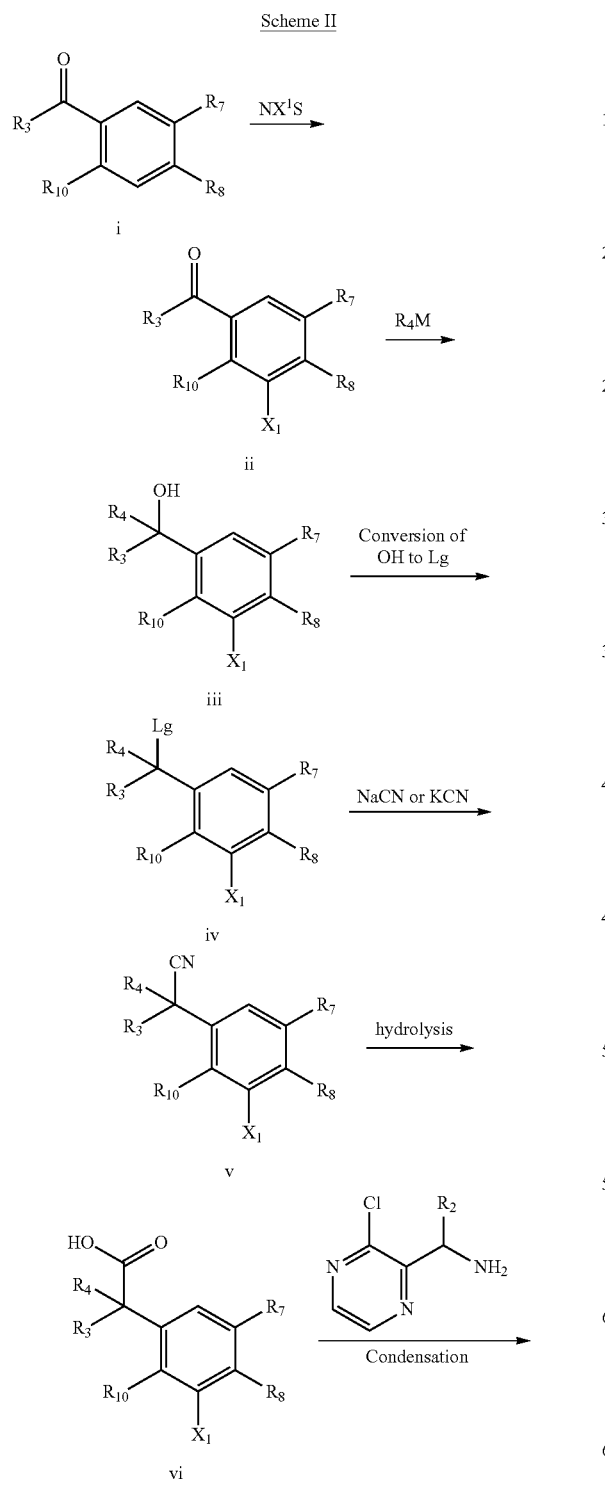

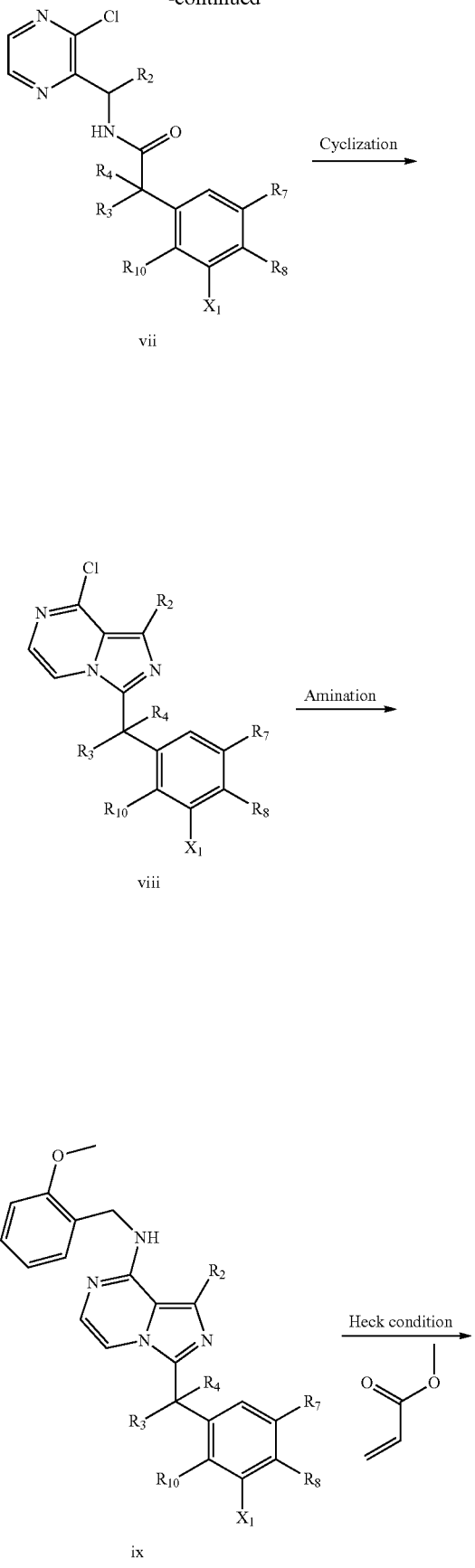

-continued

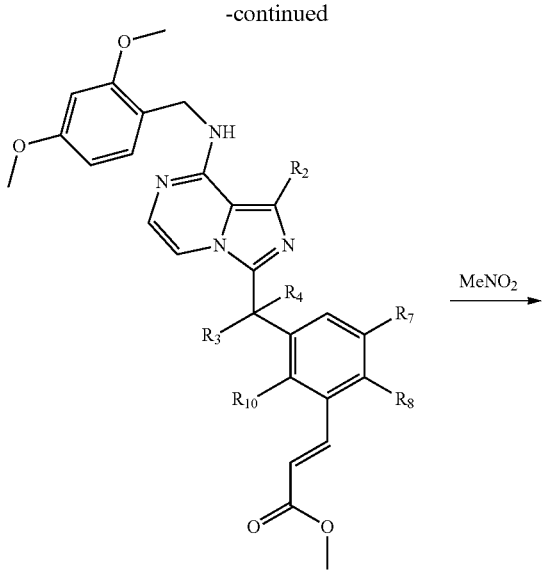

x

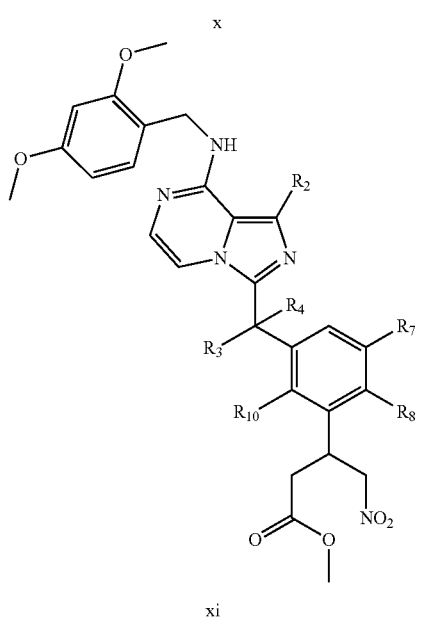

xi

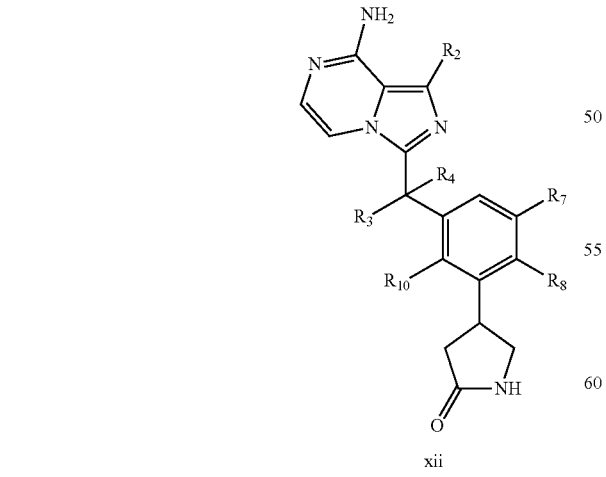

xii

For example, compounds of Formula (I) can also be formed as shown in scheme II. The compound (i) can be halogenated with N-chlorosuccinamide, N-bromosuccinamide or N-iodosuccinamide to give compound (ii) where $X^1$=Cl, Br, or I. Attack the ketone of compound (ii) with $R_4$-M (e.g., $R_4$MgBr, $R_4$Li or $R_4$M is reductive reagent such as $NaBH_4$, $LiAlH_4$ and etc) to give compound (iii) which can be converted to a derivative bearing a leaving group (iv), (e.g., Lg is chloride). The leaving group in compound (iv) can be converted to nitrile group under reagents such as NaCN or KCN to give compound (v) which was hydrolyzed under acidic condition (e.g., HCl) or basic condition (KOH) to give acid (vi). Condensation of compound (vi) with the suitable amine in scheme II under standard condition such as HOBt, EDCI with a base such as trimethylamine to give compound (vii) that can be used for cyclization directly under $Tf_2O$ or $POCl_3$ to give compound (viii). Amination of compound (viii) with suitable protecting amine (e.g., (2,4-dimethoxyphenyl)methanamine) that is easy to remove under reductive conditions to give compound (ix) which was used for coupling under Heck reaction condition such as a palladium (0) and bicarbonate or carbonate base with methyl acrylate to give compound (x). Reaction of compound (x) with nitromethane in the presence of DBU can afford the nitro derivative (xi) which can be reduced under standard conditions (e.g., Fe/HOAc, Zn/HOAc or $NiCL_2/NaBH_4$) to give Formula (I) (xii).

Scheme III

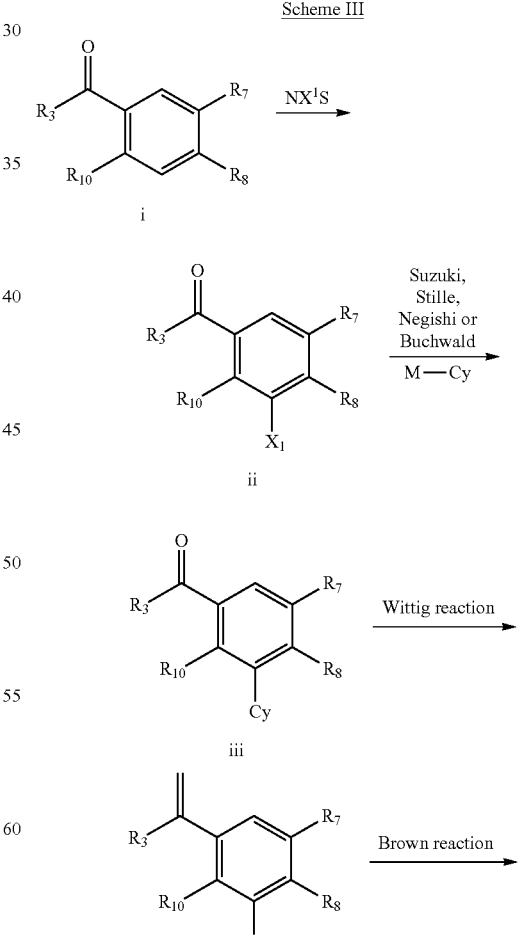

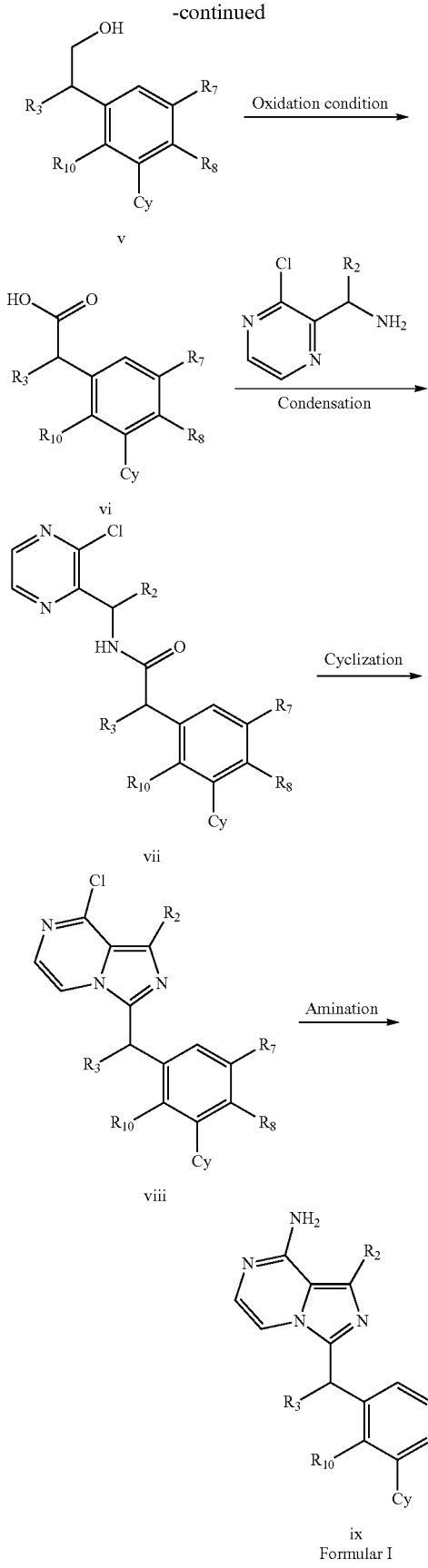

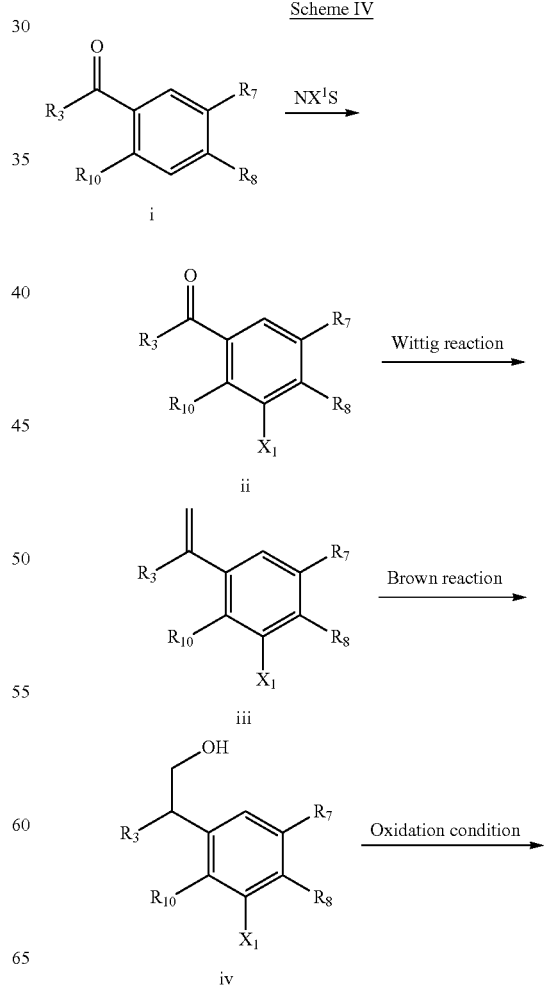

For example, compounds of Formula (I) can also be formed as shown in scheme III. The compound (i) can be halogenated with N-chlorosuccinamide, N-bromosuccinamide or N-iodosuccinamide to give compound (ii) where $X^1$=Cl, Br, or I. The halo group of (ii) can be coupled to Cy-M, where M is a boronic acid, boronic ester or other suitable metal (e.g., Cy-M is Cy-B(OH)$_2$, Cy-Sn(Bu)$_4$, or Cy-Zn, under standard Suzuki, Stille or Negeshi reaction condition in the presence of a palladium (0) catalyst and a base such as bicarbonate or carbonate base to give compound (iii). Cy-M can also be a cyclic amine (M is H and attached to the amine nitrogen) with coupling to compound (ii) under standard Buchwald condition in the presence of a palladium (0) and a base such as an alkoxide base to give compound (iii). A Wittig reaction was run from compound (iii) under standard condition (e.g., Ph$_3$PCH$_3$Br/nBuLi or other bases such as NaH) to give compound (iv) which was run under standard Brown reaction condition using BH$_3$/H$_2$O$_2$ to give compound (v) which was oxidized directly by NaClO/NaClO$_2$ or Jones reagent to afford the acid compound (vi), the compound (vi) was used for condensation under HOBt or EDCI with suitable amine in scheme III to give compound (vii) that was cyclized directly by Tf$_2$O or POCl$_3$ to afford compound (viii). Finally, amination of compound (viii) under NH$_3$/i-PrOH to give Formula (I) (ix).

39
-continued
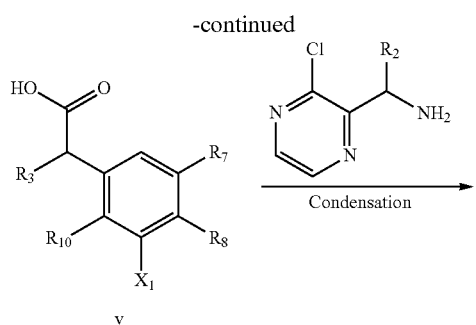
v
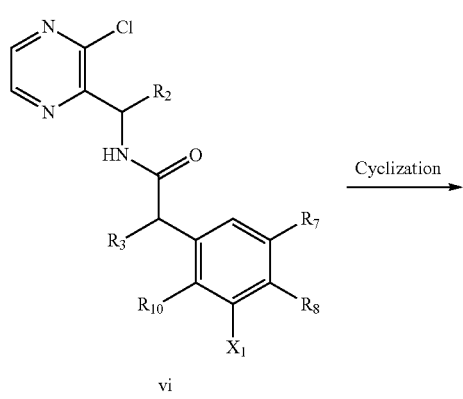
vi
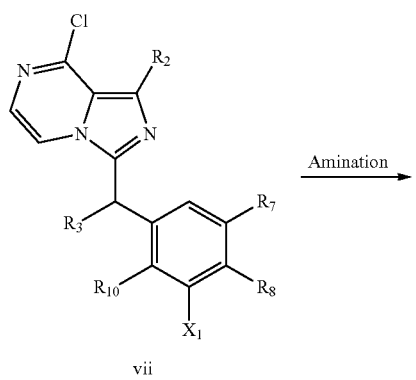
vii
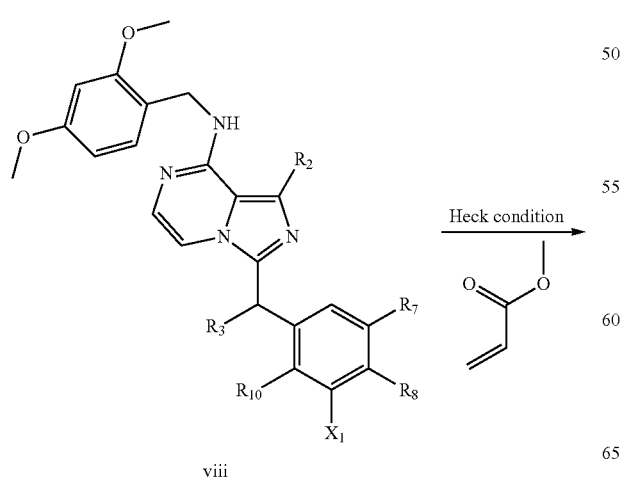
viii
40
-continued
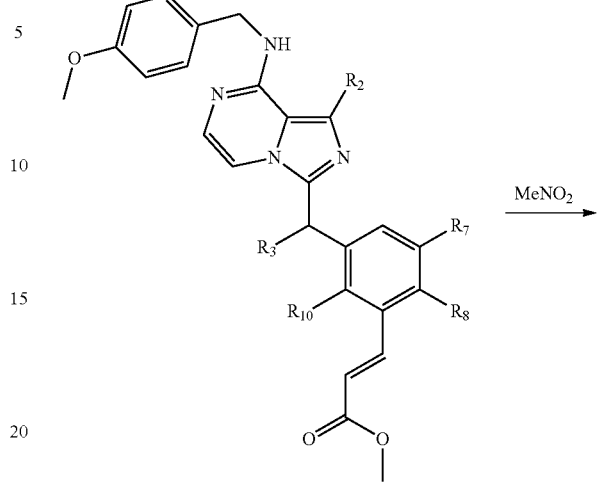
ix
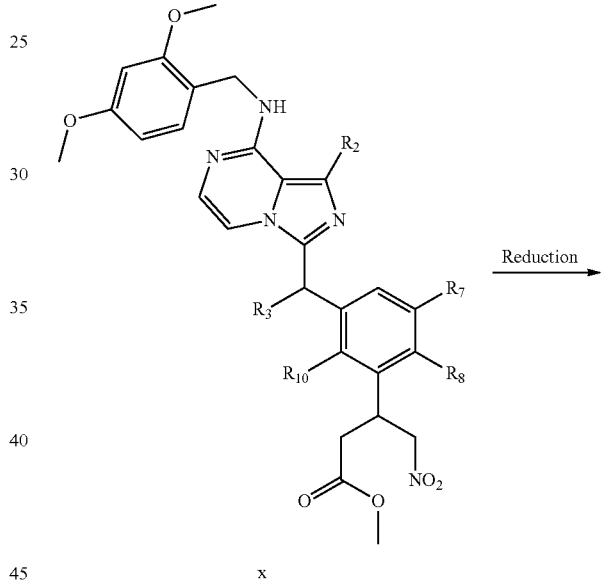
x
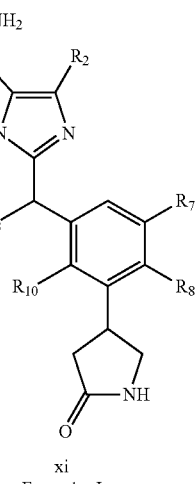
xi
Formular I
For example, compounds of Formula (I) can also be formed as shown in scheme IV. The compound (i) can be halogenated with N-chlorosuccinamide, N-bromosuccinamide or N-iodosuccinamide to give compound (ii) where $X^1$=Cl, Br, or I. A Wittig reaction was run from compound (ii) under standard condition (e.g., $Ph_3PCH_3Br/nBuLi$ or other bases such as NaH) to give compound (iii) which was run under standard Brown reaction condition using $BH_3/H_2O_2$ to give compound (iv) which was oxidized directly by $NaClO/NaClO_2$ or Jones reagent to afford the acid compound (v), the compound (v) was used for condensation under HOBt or EDCI with suitable amine in scheme IV to give compound (vi) that was cyclized directly by $Tf_2O$ or $POCl_3$ to afford compound (vii). Amination of compound (vii) with suitable protecting amine (e.g., (2,4-dimethoxyphenyl)methanamine) that is easy to remove under reductive conditions to give compound (viii) which was used for coupling under Fleck reaction condition such as a palladium (0) and bicarbonate or carbonate base with methyl acrylate to give compound (ix). Reaction of compound (ix) with nitromethane in the presence of DBU can afford the nitro derivative (x) which can be reduced under standard conditions (e.g., Fe/HOAc, Zn/HOAc or $NiCL_2/NaBH_4$) to give Formula (I) (xi).

different position, a carbonyl insertion reaction was run under carbon monoxide, a palladium (0), bases (e.g., bicarbonate, carbonate or organic amine such as trimethylamine) to give an ester which followed by an amine ester exchange reaction by dimethylamine under $AlMe_3$ to afford Formula (I) (ii).

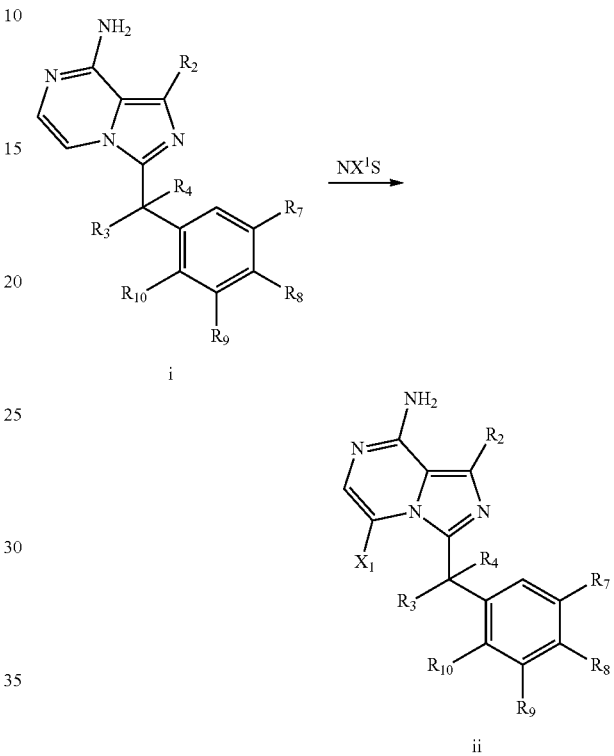

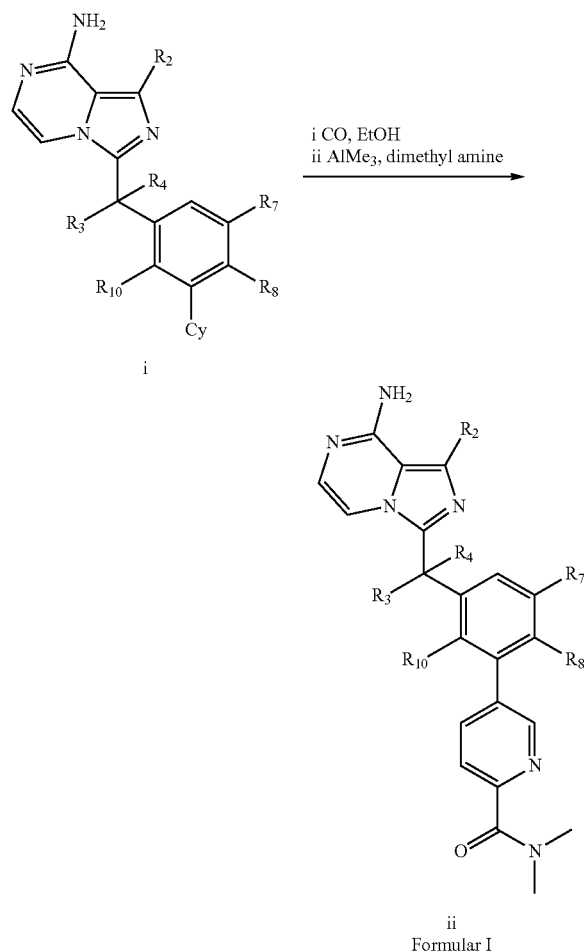

For example, compounds of Formula (I) can also be formed as shown in scheme V. Starting from compound (i) in which the Cy include substituted aromatic or heterocyclic ring with halogen such as chloride, bromide or iodide at For example, compounds of Formula (I) can also be formed as shown in scheme VI. A halogenation reaction was done from compound (i) under N-chlorosuccinamide, N-bromosuccinamide, N-iodosuccinamide or N-fluorosuccinamide to give Formula (I) (ii), $X_1$ is F, Cl Br or I.

Abbreviations

The following abbreviations used in the present application have the following meanings unless specified otherwise:
AcOH: acetic acid;
DMF: dimethylformamide;
MeOH: methanol;
Pd(dppf)Cl$_2$: [1,1'-bis(diphenylphosphino)ferrocene]dichloropalladium(II);
aq.s: aqueous saturated solution;
EtON: ethanol;
HOBt: 1-hydroxybenzotriazole;
EDCI: 1-ethyl-3-(3-dimethylaminopropyl)carbodiimide;
DIPEA: diisopropylethylamine;
THF: tetrahydrofuran;
DCM: dichloromethane;
NBS: N-bromosuccinimide;
NCS: N-chlorosuccinimide;
Tf$_2$O: trifluoromethanesulfonic anhydride;
Et$_3$N: triethylamine;
Xantphos: 4,5-bis(diphenylphosphino)-9,9-dimethylxanthene;

NIS: N-iodosuccinimide;
PE: petroleum ether;
EA: ethyl acetate;
DMA: dimethyl acetylamide;

EXAMPLE

Example 1

3-(1-(5-chloro-2-methoxy-4-methyl-3-(pyridin-3-yl) phenyl)ethyl)imidazo[1,5-a]pyrazine-8-amine (Compound 1)

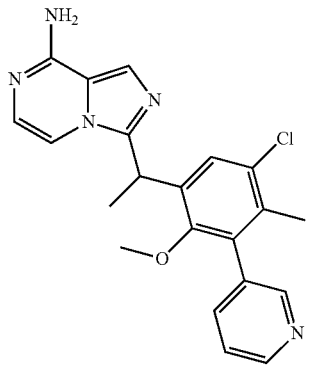 [SMILES: COc1c(C(C)c2ncc3c(N)nccn23)cc(Cl)c(C)c1-c1cccnc1]

Step 1: 1-(5-chloro-2-hydroxy-3-iodo-4-methylphenyl)ethan-1-one (1-1)

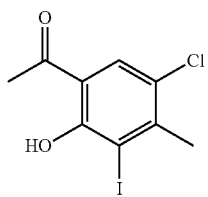

1-(5-chloro-2-hydroxy-4-methylphenyl)ethan-1-one (10 g, 54.165 mmol) was dissolved in AcOH (100 mL) and 1-iodopyrrolidine-2,5-dione (24.4 g, 108.33 mmol) was added, the reaction was stirred at 80° C. for 4 hrs and then at room temperature for overnight. Solvent was removed in vacuo, water (100 mL) was added and extracted with ethyl acetate. The combined organic layers were washed with aqueous $Na_2S_2O_3$ solution, aqueous $Na_2CO_3$ solution and brine, and dried over $Na_2SO_4$, to give a product (20 g). MS (ESI) m/e $(M+1)^+$ 311.0.

Step 2: 1-(5-chloro-3-iodo-2-methoxy-4-methylphenyl)ethan-1-one (1-2)

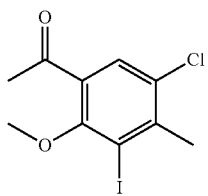

1-(5-chloro-2-hydroxy-3-iodo-4-methylphenyl)ethan-1-one (20 g, 64.41 mmol) was dissolved in DMF (200 mL), $K_2CO_3$ (18 g, 128.82 mmol) and $CH_3I$ (10.3 g, 72.48 mmol) were added, the reaction was stirred at room temperature for overnight, then DMF was removed in vacuo and the product (9 g in 51% yield) was got by chromatography column on silica gel. $^1H$ NMR (400 MHz, DMSO-d6) δ 7.69 (s, 1H), 3.72 (s, 3H), 2.60 (s, 3H), 2.58 (s, 3H). MS (ESI) m/e $(M+1)^+$ 325.0.

Step 3: 1-(5-chloro-3-iodo-2-methoxy-4-methylphenyl)ethan-1-ol (1-3)

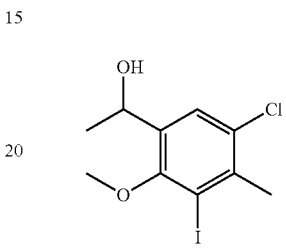

1-(5-chloro-3-iodo-2-methoxy-4-methylphenyl)ethan-1-one (2.2 g, 6.163 mmol) was dissolved in MeOH/$CH_2Cl_2$ (15 mL/15 mL), $NaBH_4$ (0.7 g, 18.49 mmol) was added and the mixture was stirred at room temperature for 30 mins. Solvent was removed in vacuo, water (20 mL) was added and extracted with ethyl acetate. The combined organic layers were washed with water and brine, and dried over $Na_2SO_4$, to give a product (2.31 g in 100% yield). MS (ESI) m/e $(M-18)^+$ 309.0.

Step 4: 1-(5-chloro-2-methoxy-4-methyl-3-(pyridin-3-yl)phenyl)ethan-1-ol (1-4)

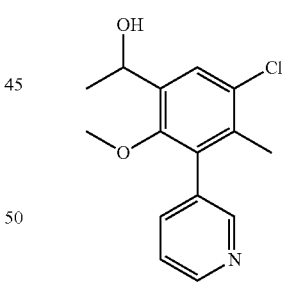

1-(5-chloro-3-iodo-2-methoxy-4-methylphenyl)ethan-1-ol (2.31 g, 21.06 mmol), Pd(dppf)Cl$_2$ (517 mg, 0.7074 mmol), 3-(4,4,5,5-tetramethyl-1,3,2-dioxaborolan-2-yl) pyridine (4.751 g, 23.17 mmol) and $K_2CO_3$ (5.81 g, 42.12 mmol) were dissolved in 1,4-dioxane/$H_2O$ (25 mL/25 mL) and refluxed under $N_2$ for overnight. Pd(PPh$_3$)$_4$ (1.22 g, 1.053 mmol) was added and stirred for 5 hrs at 100° C. under $N_2$. Solvent was removed by in vacuo and extracted with ethyl acetate. The combined organic layers were washed with brine and dried over $Na_2SO_4$. The product (3.6 g in 72% yield) was got by chromatography column on silica gel ($CH_2Cl_2$/MeOH=50/1). MS (ESI) m/e $(M+1)^+$ 278.0.

Step 5: 3-(3-chloro-5-(1-chloroethyl)-6-methoxy-2-methylphenyl)pyridine (1-5)

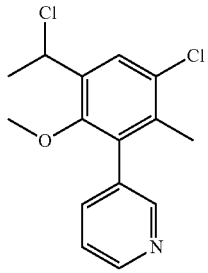 [SMILES: COc1c(C(C)Cl)cc(Cl)c(C)c1-c1cccnc1]

1-(5-chloro-2-methoxy-4-methyl-3-(pyridin-3-yl)phenyl) ethan-1-ol (1.37 g, 4.092 mmol) was dissolved in dry CH$_2$Cl$_2$ (20 mL) and SOCl$_2$ (974 mg, 8.184 mmol) was added dropwise at 0° C. The reaction was stirred at room temperature for 3 hrs, then solvent was removed in vacuo, ethyl acetate (50 mL) was added and washed with NaHCO$_3$ (aq.s) and brine, to give a product (1.1 g). MS (ESI) in/e (W-+296.0.

Step 6: 2-(5-chloro-2-methoxy-4-methyl-3-(pyridin-3-yl)phenyl)propanenitrile (1-6)

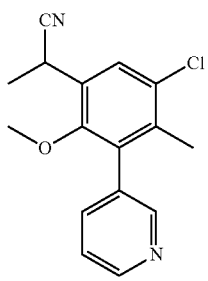 [SMILES: COc1c(C(C)C#N)cc(Cl)c(C)c1-c1cccnc1]

3-(3-chloro-5-(1-chloroethyl)-6-methoxy-2-methylphenyl)pyridine (200 mg, 0.675 mmol), NaCN (50 mg, 1.0204 mmol) and KI (5.6 mg. 0.03376 mmol) were dissolved in DMF (5 mL) and heated to 75° C. for overnight under N2, and then the mixture was cooled to room temperature, water (20 mL) was added and extracted with ethyl acetate. The combined organic layers were washed with water and brine and dried over Na$_2$SO$_4$. The product (150 mg in 77.5% yield) was got by chromatography column on silica gel (CH2Cl2/MeOH=50/1). MS (ESI) m/e (M+1)+ 287.0.

Step 7: 2-(5-chloro-2-methoxy-4-methyl-3-(pyridin-3-yl)phenyl)propanoic acid (1-7)

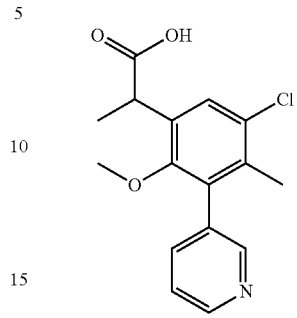

2-(5-chloro-2-methoxy-4-methyl-3-(pyridin-3-yl)phenyl) propanenitrile (150 mg, 0.523 mmol) was dissolved in EtOH (3 mL) and KOH (aq. 5 N, 3 mL) was added. The reaction was refluxed for overnight, then the solvent was removed in vacuo. The pH was adjusted to about 4 and extracted with ethyl acetate. The combine organic layers were washed with brine and dried over Na$_2$SO$_4$, to give a product (140 mg, 87.5%). MS (ESI) m/e (M+1)$^+$ 306.0.

Step 8: 2-(5-chloro-2-methoxy-4-methyl-3-(pyridin-3-yl)phenyl)-N-((3-chloropyrazin-2-yl)methyl)propanamide (1-8)

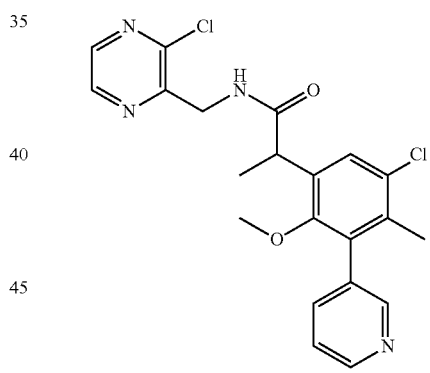

2-(5-chloro-2-methoxy-4-methyl-3-(pyridin-3-yl)phenyl) propanoic acid (140 mg, 0.458 mmol), (3-chloropyrazin-2-yl)methanamine (85.5 mg, 0.595 mmol), HOBt (80.43 mg, 0.595 mmol), EDCI (114.2 mg, 0.595 mmol) and DIPEA (178 mg, 1.374 mmol) were dissolved in THF (10 ml) and stirred at room temperature under N$_2$ for overnight. Water (20 mL) was added and extracted with ethyl acetate. The combined organic layers were washed with brine and dried over Na$_2$SO$_4$. The product (75 mg in 38.4% yield) was got by chromatography column on silica gel and prep-TLC (DCM/MeOH=50/1). $^1$H NMR (400 MHz, CDCl$_3$) δ 8.74-8.63 (m, 1H), 8.58 (d, J=1.7 Hz, 1H), 8.49 (s, 1H), 8.32 (d, J=2.3 Hz, 1H), 7.76 (s, 1H), 7.52 (s, 1H), 7.00 (s, 1H), 4.68 (d, J=2.6 Hz, 2H), 4.11-4.02 (m, 1H), 3.29 (s, 3H), 2.14 (s, 3H), 1.56 (dd, J=15.2, 6.9 Hz, 3H). MS (ESI) m/e (M+1)$^+$ 431.0.

Step 9: 8-chloro-3-(1-(5-chloro-2-methoxy-4-methyl-3-(pyridin-3-yl)phenyl)ethyl)imidazo[1,5-a]pyrazine (1-9)

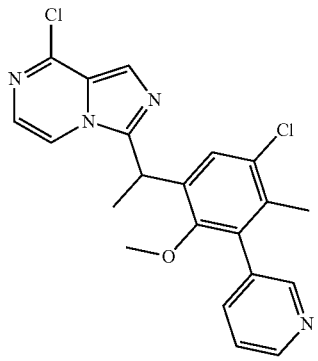

2-(5-chloro-2-methyoxy-4-methyl-3-(pyridin-3-yl)phenyl)-N-((3-chloropyrazin-2-yl)methyl) propanamide (15 mg, 0.0348 mmol) was dissolved in acetonitrile (5 mL), POCl3 (3 drops) was added and the tube was heated to 80° C. for overnight. Solvent was removed by reduced pressure, water (20 ml) was added and the pH was adjusted to 9 by NaHCO$_{13}$ (aq. s). The reaction was extracted with ethyl acetate. The combined organic layers were washed with brine and dried over Na$_2$SO$_4$. The product (12 mg in 83% yield) was got. MIS (ESI) m/e (M+1)+ 413.0.

Step 10: 3-(1-(5-chloro-2-methoxy-4-menthyl-3-(pyridin-3-yl)phenyl)ethyl)imidazo[1,5-a]pyrazin-8-amine (1-10)

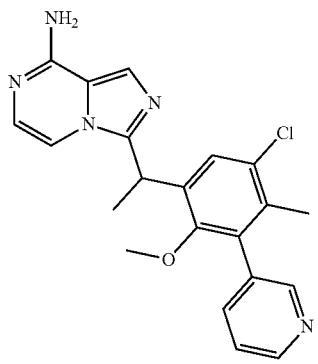

8-chloro-3-(1-(5-chloro-2-methoxy-4-menthyl-3-(pyridin-3-yl)phenyl)ethyl)imidazo[1,5-a]pyrazine (12 mg, 0.029 mmol) was dissolved in NH$_3$/H$_2$O, (5 mL). The mixture was heated to 100° C. for overnight. The desired product (3.67 mg in 32% yield) was got by prep-HPLC. $^1$H NMR (400 MHz, CD$_3$OD) δ 8.61 (brs, 2H), 8.19 (brs, 2H), 7.80 (brs, 1H), 7.50 (d, J=5.9 Hz, 1H), 7.32 (s, 1H), 6.84 (d, J=6.0 Hz, 1H), 4.88 (q, J=4.0 Hz, 1H), 3.22 (s, 3H), 2.03 (s, 3H), 1.75 (d, J=7.1 Hz, 3H). MS (ESI) m/e (M+1)$^+$ 394.0.

Prep-HPLC:

| Column | Gilson GX-281 |
|---|---|
| Column size | 21.2*150 5 μm GIMINI |
| Flow rate | 20 ml/min |
| Wave length | 214 nm + 254 nm |
| Method | 0.1% TFA in water, CH$_3$CN from 15 to 25% in 11 min, then from 25 to 90% in 1 min, 90% hold 2 min, then balance 2 min. Total run time 18 min. Single gradient method. |

Example 2

1-bromo-3-(1-(5-chloro-2-methoxy-4-methyl-3-(pyridin-3-yl)phenyl)ethyl)imidazo[1,5-a]pyrazin-8-amine (Compound 2)

Compound 2

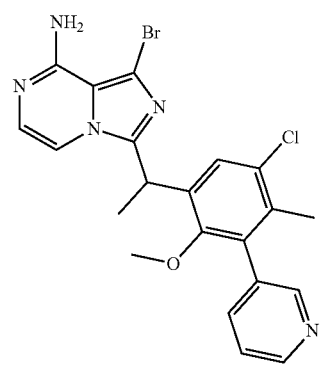

Compound 2A

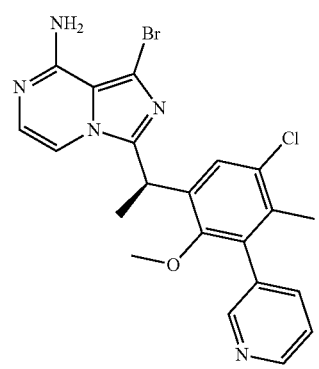

Compound 2B

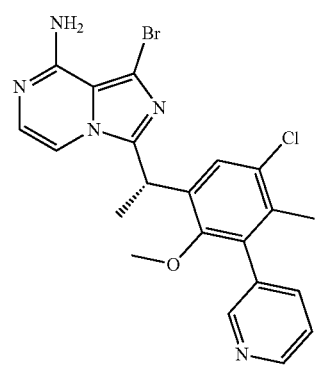

Step 1: 1-bromo-8-chloro-3-(1-(5-chloro-2-methoxy-4-methyl-3-(pyridin-3-yl)phenyl)ethyl)imidazo[1,5-a]pyrazine (2-1)

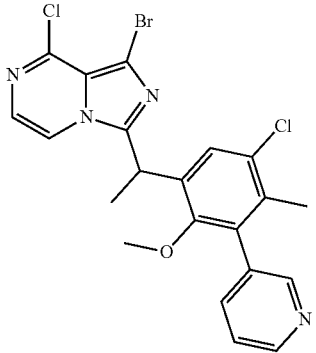

8-chloro-3-(1-(5-chloro-2-methoxy-4-methyl-3-(pyridin-3-yl)phenyl)ethyl)imidazo[1,5-a]pyrazine (compound (1-9), 100 mg, 0.242 mmol) was dissolved in dry DMF (2.5 mL), NBS (51.7 mg, 0.290 mmol) was added at 0° C. and stirred at 0° C. for 20 mins. Water (20 mL) was added. The product (80 mg in 67.2% yield) was got by filtration. MS (ESI) m/e (M+1)⁺ 493.0.

Step 2: 1-bromo-3-(1-(5-chloro-2-methoxy-4-methyl-3-(pyridin-3-yl)phenyl)ethyl)imidazo[1,5-a]pyrazin-8-amine (2-2)

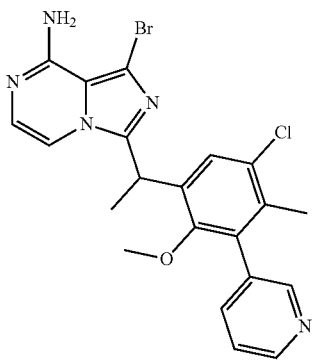

1-bromo-8-chloro-3(1-(5-chloro-2-methoxy-4-methyl-3-(pyridin-3-yl)phenyl)ethyl) imidazo[1,5-a]pyrazine (80 mg, 0.163 mmol) was dissolved in NH₃/H₂O (4 M, 8 mL) and heated to 100° C. in tube for 18 hrs. Solvent was removed in vacuo and the desired product (21 mg, 27.3% yield) was got by prep-TLC (CH₂Cl₂/MeOH=50/1). ¹H NMR (400 MHz, DMSO-d6) δ 8.62 (d, J=3.5 Hz, 1H), 8.49 (d, J=27.9 Hz, 1H), 7.76 (dd, J=29.9, 6.8 Hz, 1H), 7.52 (s, 1H), 7.39 (s, 1H), 7.25 (d, J=8.0 Hz, 1H), 7.01 (d, J=4.0 Hz, 1H), 6.69 (s, 2H), 4.84 (d, J 6.9 Hz, 1H), 3.15 (s, 3H), 2.02 (s, 3H), 1.67 (d, J=7.0 Hz, 3H). MS (ESI) m/e (M+1)⁺ 472.1.

Compound 2 was separated by chiral column to afford two compounds, Compound 2A (the first and fast isomer) and Compound 2B (the second and slow isomer), as white solids. Compound 2B was assigned as a (S)-configuration in a similar manner to Compound 40A as disclosed below.

Compound 2A: ¹H NMR (400 MHz, DMSO-d₆) δ 8.62 (d, J=4.9 Hz, 1H), 8.49 (d, J=27.4 Hz, 1H), 7.76 (d, J=21.8 Hz, 1H), 7.52 (s, 1H), 7.39 (s, 1H), 7.25 (d, J=8.0 Hz, 1H), 7.01 (s, 1H), 6.68 (s, 2H), 4.84 (d, J=6.7 Hz, 1H), 3.15 (s, 3H), 2.02 (s, 3H), 1.67 (d, J=7.1 Hz, 3H). MS (ESI) m/e (M+1)⁺ 472.1.

Compound 2B: ¹H NMR (400 MHz, DMSO-d6) δ 8.62 (d, J=3.3 Hz, 1H), 8.49 (d, J=27.1 Hz, 1H), 7.75 (d, J=30.4 Hz, 1H), 7.52 (s, 1H), 7.39 (s, 1H), 7.25 (d, J=8.5 Hz, 1H), 7.01 (s, 1H), 6.68 (s, 2H), 4.84 (d, J=6.8 Hz, 1H), 3.15 (s, 4H), 2.02 (s, 3H), 1.67 (d, J=7.1 Hz, 3H). MS (ESI) m/e (M+1)⁺ 472.1.

Chiral Separation:

| Column | CHIRALART OJ |
|---|---|
| Column size | 3.0 cm*5 μm |
| Injection | 0.4 ML |
| Mobile phase | CO₂/MeOH 0.1% DEA = 75/25 |
| Flow rate | 60 ml/min |
| Wave length | UV 210 nm |
| Temperature | 35° C. |

Example 3

3-(1-(5-chloro-2-methoxy-4-methyl-3-(pyridin-3-yl)phenyl)ethyl)-1-phenylimidazo[1,5-a]pyrazin-8-amine (Compound 3)

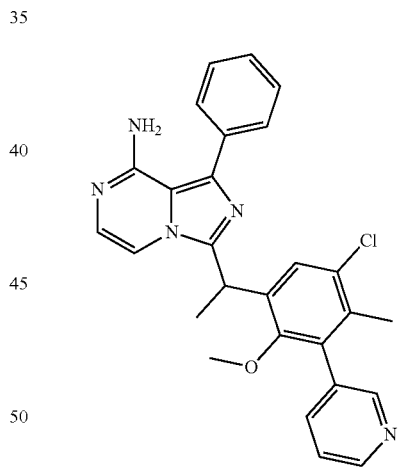

1-bromo-3-(1-(5-chloro-2-methoxy-4-methyl-3-(pyridin-3-yl)phenyl)ethyl)imidazo[1,5-a]pyrazin-8-amine (compound 2, 47 mg, 0.09941 mmol), phenylboronic acid (18.2 mg, 0.1491 mmol), Pd(dppf)Cl₂ (3.64 mg, 0.004971 mmol) and K₂CO₃ (41.155 mg, 0.2982 mmol) were dissolved in 1,4-dioxane/H₂O (5 mL/2 mL) and refluxed under N₂ for 2 hrs. Solvent was removed in vacuo and the product (35 mg in 53.5% yield) was got by prep-TLC. ¹H NMR (400 MHz, DMSO-d6) δ 8.63 (d, J=3.4 Hz, 1H), 8.50 (m, 1H), 7.62 (d, J=11.6 Hz, 2H), 7.53 (t, J=7.4 Hz, 3H), 7.43 (dd, J=19.4, 6.2 Hz, 2H), 7.30 (s, 1H), 7.06 (s, 1H), 6.13 (s, 2H), 4.90 (d, J=7.1 Hz, 1H) 3.19 (brs, 3H), 2.01 (s, 3H), 1.75 (d, J=6.9 Hz, 3H), MS (ESI) m/e (M+1)⁺ 470.0.

Example 4

3-(8-amino-3-(1-(5-chloro-2-methoxy-4-methyl-3-(pyridin-3-yl)phenyl)ethyl)imidazo[1,5-a]pyrazin-1-yl)phenol (Compound 4)

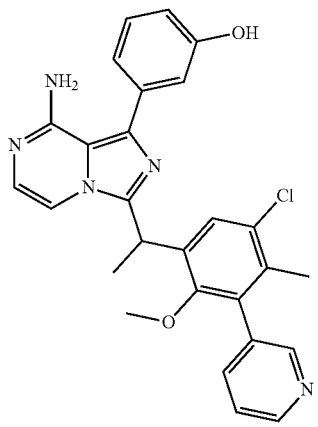

1-bromo-3-(1-(5-chloro-2-methoxy-4-methyl-3-(pyridin-3-yl)phenyl)ethyl)imidazo[1,5-a]pyrazin-8-amine (compound 2, 26 mg, 0.055 mmol), (3-hydroxyphenyl)boronic acid (9.1 mg, 0.066 mmol), $K_2CO_3$ (15.18 mg, 0.11 mmol), Pd(dppf)Cl$_2$ (2.0 mg, 0.00275 mmol) were dissolved in 1,4-dioxane/H$_2$O (1 mL/1 mL) and refluxed for 3 hrs under N$_2$. Solvent was removed in vacuo and extracted with ethyl acetate. The combined organic layers were washed with brine and dried over Na$_2$SO$_4$. The product (4.07 mg in 15.2% yield) was got by prep-TLC. $^1$H NMR (400 MHz, CD$_3$OD) δ 8.61 (d, J=4.5 Hz, 1H), 8.49 (m, 1H), 7.87-7.67 (m, 1H), 7.60-7.57 (m, 2H), 7.47 (m, 1H), 7.43-7.29 (m 3H), 7.13 (d, J=7.1 Hz, 2H) 7.06-6.89 (m, 2H), 4.87 (q, J=7.0 Hz, 1H), 3.35 (s, 4H), 2.11 (s, 3H), 1.89 (d, J=7.1 Hz, 3H). MS (ESI) m/e (M+1)$^+$ 486.0.

Example 5

1-bromo-5-chloro-3-(1-(5-chloro-2-methoxy-4-methyl-3-(pyridin-3-yl)phenyl)ethyl) imidazo[1,5-a]pyrazin-8-amine (Compound 5)

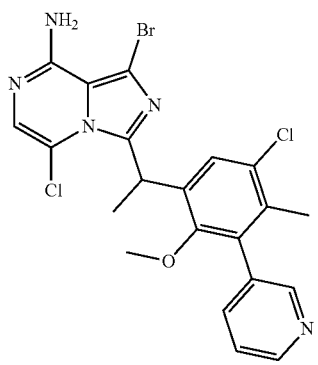

1-bromo-3-(1-(5-chloro-2-methoxy-4-methyl-3-(pyridin-3-yl)phenyl)ethyl)imidazo[1,5-a]pyrazin-8-amine (compound 2, 15 mg, 0.032 mmol) was dissolved in AcOH (2 mL) and NCS (5 mg, 0.038 mmol) was added. The reaction was heated to 80° C. for 2 hrs. Solvent was removed in vacuo and water (15 mL) was added. The reaction was extracted with ethyl acetate and the combined organic layers were washed with brine. The product (4.29 mg in 26.65% yield) was got by prep-HPLC. $^1$H NMR (400 MHz, CD$_3$OD) δ 8.64 (m, 2H), 7.85 (d, J=24.6 Hz, 1H), 7.66 (d, J=12.3 Hz, 1H), 7.20 (s, 1H), 6.93 (s, 1H), 5.61 (q, J=7.0 Hz, 1H), 3.20 (s, 3H), 2.14 (s, 3H), 1.80 (d, J=7.0 Hz, 3H). MS (ESI) m/e (M+1)$^+$ 506.0.

Prep-HPLC:

| Column | Gilson GX-281 |
|---|---|
| Column size | 21.2*150 5 μm GIMINI |
| Flow rate | 20 ml/min |
| Wave length | 214 nm + 254 nm |
| Method | 0.1% TFA in water, CH$_3$CN from 22 to 38% in 11 min, then from 38 to 90% in 1 min, 90% hold 2 min, then balance 2 min. Total run time 18 win. Single gradient method. |

Example 6

1-chloro-3-(1-(5-chloro-2-methoxy-4-methyl-3-(pyridin-3-yl)phenyl)ethyl)imidazo[1,5-a]pyrazin-8-amine (Compound 6)

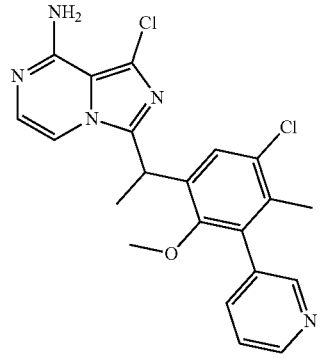

Step 1: 1,8-dichloro-3-(1-(5-chloro-2-methoxy-4-methyl-3-(pyridin-3-yl)phenyl)ethyl) imidazo[1,5-a]pyrazine (6-1)

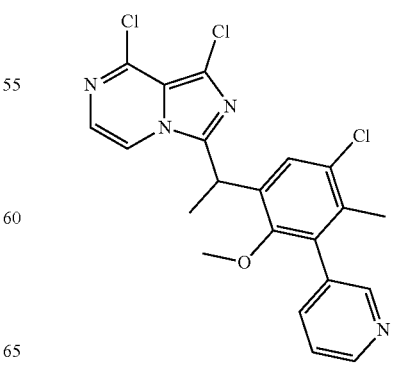

8-chloro-3-(1-(5-chloro-2-methoxy-4-methyl-3-(pyridin-3-yl)phenyl)ethyl)imidazo[1,5-a]pyrazine (compound (1-9), 100 mg, 0.242 mmol) and 1-chloropyrrolidine-2,5-dione (49 mg, 0.363 mmol) were dissolved in DMF (1 mL) and heated to 60° C. for overnight. Solvent was removed in vacuo and water (20 mL) was added. The reaction was extracted with ethyl acetate and washed with brine. The product (90 mg in 83% yield) was got. MS (ESI) m/e (M+1)+ 447.0.

Step 2: 1-chloro-3-(1-(5-chloro-2-methoxy-4-methyl-3-(pyridin-3-yl)phenyl)ethyl) imidazo[1,5-a]pyrazin-8-amine (6-2)

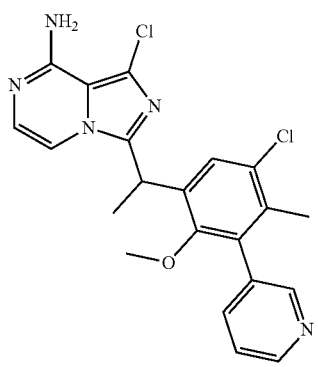

1,8-dichloro-3-(1-(5-chloro-2-methoxy-4-methyl-3-(pyridin-3-yl)phenyl)ethyl)imidazo[1,5-a]pyrazine (90 mg, 0.201 mmol) was dissolved in Ammonia in propan-2-ol (4 N, 10 mL) and heated to 90° C. in tube for 24 hrs. The solvent was removed by reduced pressure and the product (15 mg in 17.4% yield) was got by prep-HPLC. $^1$H NMR (400 MHz, DMSO-d6) δ 8.67 (d, J=3.9 Hz, 1H), 8.53 (d, J=39.5 Hz, 1H), 7.83 (d, J=43.0 Hz, 1H), 7.60 (s, 2H), 7.40 (d, J=10.9 Hz, 1H), 7.05 (d, J=5.6 Hz, 1H), 4.93 (dd, J=13.8, 6.8 Hz, 1H), 3.13 (d, J=11.1 Hz, 3H), 2.04 (s, 3H), 1.68 (d, J=7.0 Hz, 3H). MS (ESI) m/e (M+1)+ 428.0.

Example 7

1-bromo-3-(1-(5-chloro-2-ethoxy-4-methyl-3-(6-methylpyridin-3-yl)phenyl)ethyl) imidazo[1,5-a]pyrazin-8-amine (Compound 7)

Compound 7

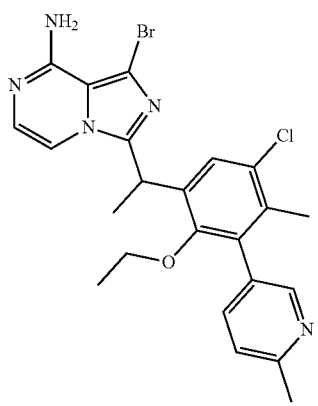

Compound 7A

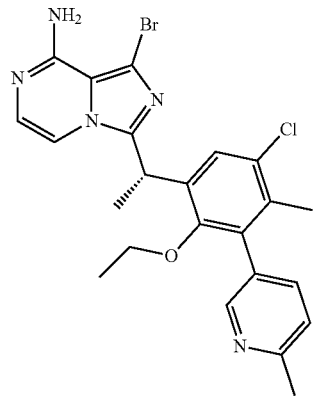

Compound 7B

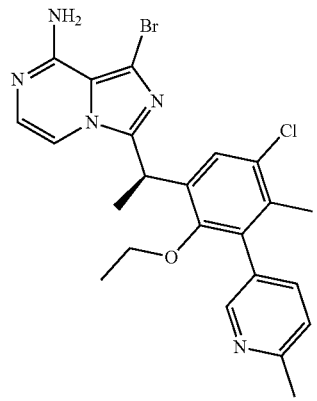

Step 1: 1-(5-chloro-2-hydroxy-3-iodo-4-methylphenyl)ethan-1-one (7-1)

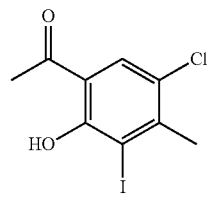

1-(5-chloro-2-hydroxy-4-methylphenyl)ethan-1-one (34 g, 184.16 mmol) was dissolved in AcOH (400 mL), 1-iodopyrrolidine-2,5-dione (83 g, 368.32 mmol) was added and the reaction was heated to 80° C. for 4 hrs. AcOH was removed by reduced pressure, ethyl acetate (400 mL) was added, Na$_2$S$_2$O$_3$ (aq.s) (400 mL) was added and stirred for 10 mins. The organic layers were washed with water, NaHCO$_3$ (aq. s) and brine and dried over anhydrous Na$_2$SO$_4$. The product (46 g in 80.42% yield) was got. MS (ESI) m/e (M+1)+ 310.

Step 2: 1-(5-chloro-2-ethoxy-3-iodo-4-methylphenyl)ethan-1-one (7-2)

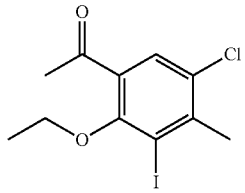

1-(5-chloro-2-hydroxy-3-iodo-4-methylphenyl)ethan-1-one (41 g, 132.64 mmol), iodoethane (24.72 g, 158.44 mmol) and $K_2CO_3$ (36.5 g, 264.1 mmol) were dissolved in DMF (400 mL) and stirred at room temperature for overnight. Solvent was removed by reduced pressure, water (300 mL) was added and extracted with ethyl acetate. The combined organic layers were washed with water and brine and dried over $Na_2SO_4$. The product (29 g in 65% yield) was got by chromatography column on silica gel. $^1$H NMR (400 MHz, DMSO-d6) δ 7.65 (s, 1H), 3.86 (q, J=7.0 Hz, 2H), 2.60 (s, 3H), 2.57 (s, 3H), 1.38 (t, J=7.0 Hz, 3H). MS (ESI) m/e $(M+1)^+$ 338.

Step 3: 1-(5-chloro-2-ethoxy-3-iodo-4-methylphenyl)ethan-1-ol (7-3)

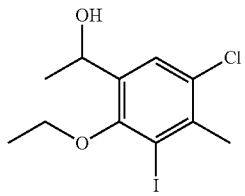

1-(5-chloro-2-ethoxy-3-iodo-4-methylphenyl)ethan-1-one (2 g, 5.91 mmol) was dissolved in MeOH (20 mL), $Na_3BH_4$ (0.894 g, 23.63 mmol) was added and stirred for 30 mins, MeOH was removed by reduced pressure, water (20 mL) was added and extracted with ethyl acetate. The combined organic layers were washed with brine and dried over $Na_2SO_4$. The product (2 g in 99.4% yield) was got. MS(ESI) m/e $[M-18]^+$ 322.4.

Step 4: 1-(5-chloro-2-ethoxy-4-methyl-3-(6-methylpyridin-3-yl)phenyl)ethan-1-ol (7-4)

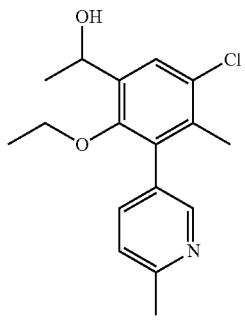 [SMILES: CCOc1c(C(C)O)cc(Cl)c(C)c1-c1ccc(C)nc1]

1-(5-chloro-2-ethoxy-3-iodo-4-methylphenyl)ethan-1-ol (5 g, 14.7 mmol), (6-methylpyridin-3-yl)boronic acid (2.42 g, 17.6 mmol), $Pd(PPh_3)_4$ (85 mg, 0.734 mmol) and $K_2CO_3$ (6.1 g, 44 mmol) were dissolved in 1,4-dioxane (30 mL)/$H_2O$ (20 mL) and heated to 100° C. under $N_2$ for overnight. Solvent was removed and extracted with ethyl acetate. The combined organic layers were washed with brine and dried over $Na_2SO_4$. The product (4.3 g in 95.77% yield) was got by chromatography column on silica gel ($CH_2Cl_2$/MeOH=50/1). H NMR (400 MHz, DMSO-d6) δ 8.32 (d, J=1.7 Hz, 1H), 7.64-7.58 (m, 1H), 7.52 (s, 1H), 7.35 (d, J=7.9 Hz, 1H), 5.20 (d, J=4.5 Hz, 1H), 5.07-4.86 (m, 1H), 3.54-3.37 (m, 1H), 2.53 (s, 3H), 2.04 (s, 3H), 1.34 (t, J=6.4 Hz, 3H), 0.84 (t, J=7.0 Hz, 3H). MS (ESI) m/e $(M+1)^+$ 306.

Step 5: 5-(3-chloro-5-(1-chloroethyl)-6-ethoxy-2-methylphenyl)-2-methylpyridine (7-5)

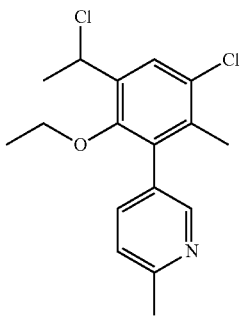 [SMILES: CCOc1c(C(C)Cl)cc(Cl)c(C)c1-c1ccc(C)nc1]

1-(5-chloro-2-ethoxy-4-methyl-3-(6-methylpyridin-3-yl)phenyl)ethan-1-ol (4.3 g, 14.06 mmol) was dissolved in $CH_2Cl_2$ (40 mL) and $SOCl_2$ (5.020 g, 42.19 mmol) was added. The reaction was stirred at rt for 3 hrs. Solvent was removed by reduced pressure, ethyl acetate (50 mL) was added and $NaHCO_3$ (aq. s, 30 mL) was added. The reaction was extracted with ethyl acetate. The combined organic layers were washed with brine and dried over $Na_2SO_4$, The product (4.56 g in 100% yield) was got. MS (ESI) m/e $(M+1)^+$ 324.

Step 6: 2-(5-chloro-2-ethoxy-4-methyl-3-(6-methylpyridin-3-yl)phenyl)propanenitrile (7-6)

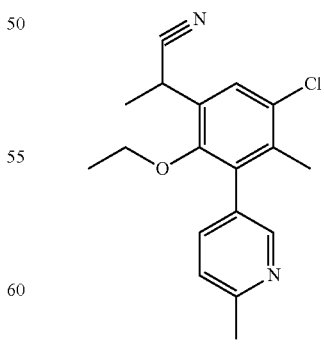

5-(3-chloro-5-(1-chloroethyl)-6-ethoxy-2-methylphenyl)-2-methylpyridine (5.47 g, 16.87 mmol) and NaCN (1.45 g, 29.6 mmol) were dissolved in DMF (50 mL) and heated to 80° C. for overnight. Water (50 mL) was added and extracted with ethyl acetate. The combined organic layers were washed with brine and dried over Na$_2$SO$_4$. The product (3.147 g in 59.3% yield) was got. MS (ESI) m/e (M+1)$^+$ 315.

Step 7: 2-(5-chloro-2-ethoxy-4-methyl-3-(6-methylpyridin-3-yl)phenyl)propanoic acid (7-7)

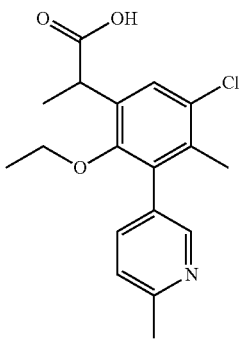 [SMILES: CCOc1c(C(C)C(=O)O)cc(Cl)c(C)c1-c1ccc(C)nc1]

2-(5-chloro-2-ethoxy-4-methyl-3-(6-methylpyridin-3-yl)phenyl)propanenitrile (3.147 g, 9,997 mmol) was dissolved in EtOH (25 mL) and KOH (aq. 5 N, 25 mL) was added. The reaction was refluxed for overnight and EtOH was removed by reduced pressure. The pH was adjusted to 3-5 by HC (2 N) and the product (2.7 g in 80.8% yield) was got by filtration.

Step 8: 2-(5-chloro-2-ethoxy-4-methyl-3-(6-methylpyridin-3-yl)phenyl)-N-((3-chloropyrazin-2-yl)methyl)propanamide (7-8)

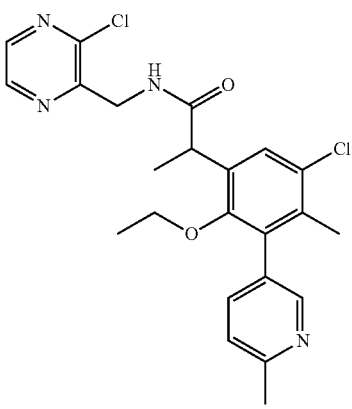 [SMILES: CCOc1c(C(C)C(=O)NCc2nccnc2Cl)cc(Cl)c(C)c1-c1ccc(C)nc1]

2-(5-chloro-2-ethoxy-4-methyl-3-(6-methylpyridin-3-yl)phenyl)propanoic acid (2.7 g, 8.09 mmol), (3-chloropyrazin-2-yl)methanamine hydrochloride (1.4 g, 9.71 mmol, HOBt (1.32 g, 24.27 mmol), EDCI (1.86 g, 9.71 mmol) and DIPEA (3.14 g, 24.27 mmol) were dissolved in THF (30 mL) and stirred at room temperature tinder N$_2$ for overnight, brine (20 mL) was added and extracted with ethyl acetate. The combined organic layers were washed with brine and dried over Na$_2$SO$_4$. The product (3.2 g in 86.1% yield) was got. MS (ESI) m/e (M+1)$^+$ 459.

Step 9: 8-chloro-3-(1-(5-chloro-2-ethoxy-4-methyl-3-(6-methylpyridin-3-yl)phenyl)ethyl)imidazo[1,5-a]pyrazine (7-9)

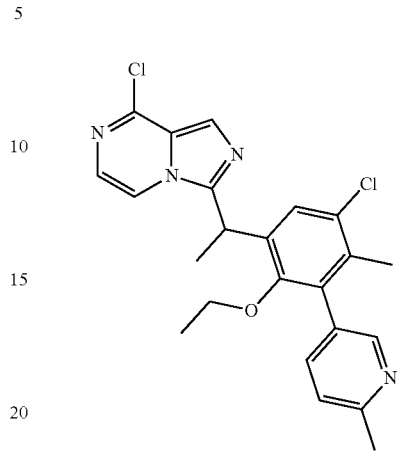

2-(5-chloro-2-ethoxy-4-methyl-3-(6-methylpyridin-3-yl)phenyl)-N-((3-chloropyrazin-2-yl)methyl)propanamide (3.2 g, 6.97 mmol) was dissolved in CH$_2$Cl$_2$ (40 mL), pyridine (5.9 g, 20.9 mmol) was added, Tf$_2$O (5.9 g, 20.9 mmol) was added dropwise slowly and stirred at rt for 6 hrs. Water (30 mL) was added and extracted with ethyl acetate. The combined organic layers were washed with brine and dried over Na$_2$SO$_4$. The product (1.5 g in 51% yield) was got. MS (ESI) m/e (M+1)$^+$ 441.

Step 10: 1-bromo-8-chloro-3-(1-(5-chloro-2-ethoxy-4-methyl-3-(6-methylpyridin-3-yl)phenyl)ethyl)imidazo[1,5-a]pyrazine (7-10)

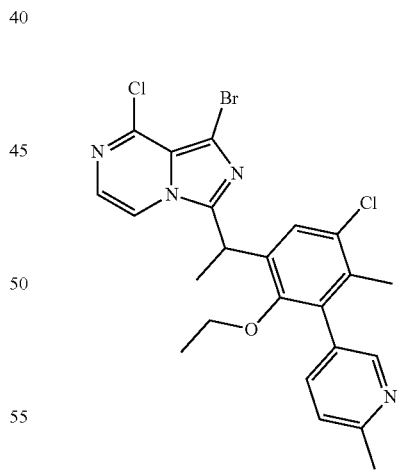

8-chloro-3-(1-(5-chloro-2-ethoxy-4-methyl-3-(6-methylpyridin-3-yl)phenyl)ethyl)imidazo[1,5-a]pyrazine (500 mg, 1.133 mmol) was dissolved in DMF (5 mL), 1-bromopyrrolidine-2,5-dione (303 mg, 1.699 mmol) was added at 0° C. and stirred for 30 mins at 0° C. Water (30 mL) was added and the product (518 mg in 88% yield) was got by filtration. MS (ESI) m/e (M+1)$^+$ 519.

Step 11: 1-bromo-3-(1-(5-chloro-2-ethoxy-4-methyl-3-(6-methylpyridin-3-yl)phenyl)ethyl)imidazo[1,5-a]pyrazin-8-amine (7-11)

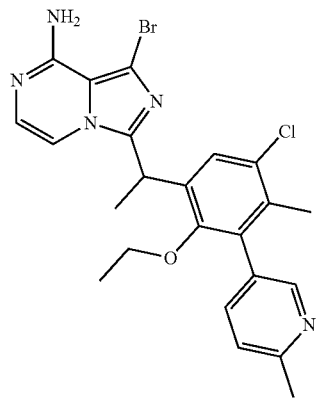 [SMILES: CCOc1c(C(C)c2nc(Br)c3c(N)nccn23)cc(Cl)c(C)c1-c1ccc(C)nc1]

1-bromo-8-chloro-3-(1-(5-chloro-2-ethoxy-4-methyl-3-(6-methylpyridin-3-yl)phenyl)ethyl)imidazo[1,5-a]pyrazine (518 mg, 0.996 mmol) was dissolved in $NH_3$/propan-2-ol (7 N, 20 mL) and heated to 90° C. for overnight. Solvent was removed in vacuo and the product (239 mg in 47.8% yield) was got by chromatography column on silica gel. $^1$H NMR (400 MHz, DMSO-d6) δ 8.33 (d, J=22.0 Hz, 1H), 7.90-7.50 (m, 1H), 7.37 (d, J=12.2 Hz, 1H), 7.22 (d, J=8.8 Hz, 1H), 7.02 (d, J=4.9 Hz, 1H), 6.69 (s, 1H), 4.83 (q, J=7.2 Hz, 1H), 3.40 (brs, 1H), 3.20 (brs, 1H), 2.03 (s, 3H), 2.53 (s, 3H), 1.65 (d, J=7.0 Hz, 3H), 0.82 (t, J=4.0 Hz, 3H). MS (ESI) m/e (M+1)$^+$ 500.

Compound 7 was separated by chiral column to afford two compounds, Compound 7A (the first and fast isomer) and Compound 7B (the second and slow isomer), as white solids. Compound 7A was assigned as a (S)-configuration in a similar manner to Compound 40A as disclosed below.

Compound 7A: $^1$H NMR (400 MHz, DMSO-d6) δ 8.33 (d, J=24.0 Hz, 1H), 7.64 (d, J=19.5 Hz, 1H), 7.39 (dd, J=20.0, 5.4 Hz, 2H), 7.24 (d, J=8.8 Hz, 1H), 7.03 (d, J=5.0 Hz, 3H), 4.84 (q, J=6.8 Hz, 1H), 3.41 (s, 1H), 3.21 (s, 1H), 2.54 (s, 3H), 2.03 (s, 3H), 1.66 (d, J=7.0 Hz, 3H), 0.80 (t, J=6.8 Hz, 3H). MS (ESI) m/e (M+1)$^+$ 500.

Compound 7B: $^1$H NMR (400 MHz, DMSO-d6) δ 8.33 (d, J=24.0 Hz, 1H), 7.64 (d, J=19.5 Hz, 1H), 7.39 (dd, J=20.0, 5.4 Hz, 2H), 7.24 (d, J=8.8 Hz, 1H), 7.03 (d, J=5.0 Hz, 3H), 4.84 (q, J=6.8 Hz, 1H), 3.41 (s, 1H), 3.21 (s, 1H), 2.54 (s, 3H), 2.03 (s, 3H), 1.66 (d, J=7.0 Hz, 3H), 0.80 (t, J=6.8 Hz, 3H). MS (ESI) m/e (M+1)$^+$ 500.

Chiral Separation:

| Column | Lux Cellulose-4 |
|---|---|
| Column size | 2.12 cm × 25 cm |
| Injection | 1 ml |
| Mobile phase | Hex:EtOH = 50:50 |
| Flow rate | 20 ml/min |
| Wave length | UV 220 nm |
| Temperature | 35° C. |
| Sample solution | 10 mg/ml in mobile phase |
| Prep-HPLC equipment | BJ-Prep-Gilson-HPLC |

Example 8

1-chloro-3-(1-(5-chloro-2-ethoxy-4-methyl-3-(6-methylpyridin-3-yl)phenyl)ethyl) imidazo[1,5-a]pyrazin-8-amine (Compound 8)

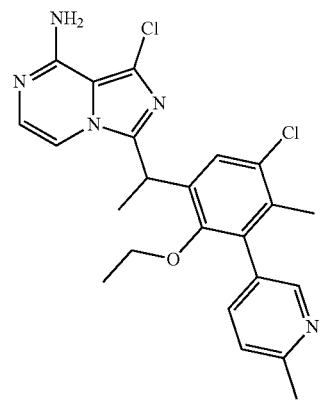

Compound 8

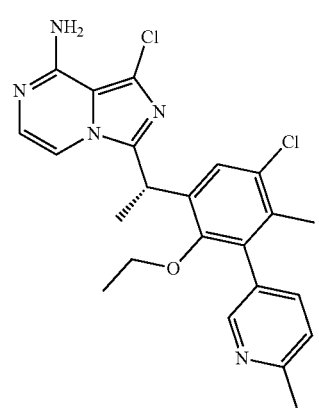

Compound 8A

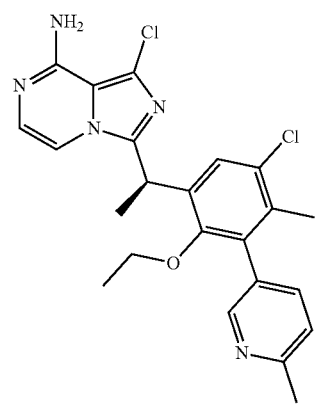

Compound 8B

Step 1: 1,8-dichloro-3-(1-(5-chloro-2-ethoxy-4-methyl-3-(6-methylpyridin-3-yl)phenyl)ethyl)imidazo[1,5-a]pyrazine (8-1)

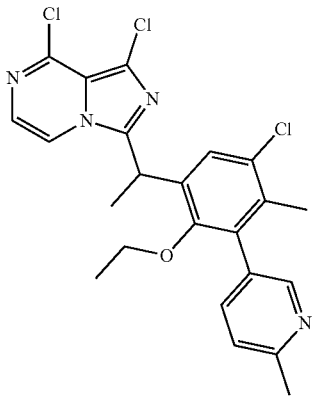 [SMILES: CCOc1c(C(C)c2nc(Cl)c3c(Cl)nccn23)cc(Cl)c(C)c1-c1ccc(C)nc1]

8-chloro-3-(1-(5-chloro-2-ethoxy-4-methyl-3-(6-methylpyridin-3-yl)phenyl)ethyl)imidazo[1,5-a]pyrazine (compound (7-9), 500 mg, 1.133 mmol) and 1-chloropyrrolidine-2,5-dione (227 mg, 1.7 mmol) were dissolved in DMF (10 mL) and heated 60° C. for overnight. Water (30 mL) was added and extracted with ethyl acetate. The combined organic layers were washed with brine and dried over Na₂SO₄. The product (314 mg in 58.3% yield) was got. MS (ESI) m/e (M+1)⁺ 475.

Step 2: 1-chloro-3-(1-(5-chloro-2-ethoxy-4-methyl-3-(6-methylpyridin-3-yl)phenyl)ethyl) imidazo[1,5-a]pyrazin-8-amine (8-2)

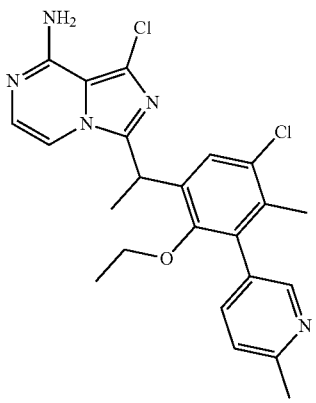 [SMILES: CCOc1c(C(C)c2nc(Cl)c3c(N)nccn23)cc(Cl)c(C)c1-c1ccc(C)nc1]

1,8-dichloro-34(1-(5-chloro-2-ethoxy-4-methyl-3-(6-methylpyridin-3-yl)phenyl)ethyl) imidazo[1,5-a]pyrazine (314 mg, 0.66 mmol) was dissolved in NH₃/propan-2-ol (7 N, 20 mL) and heated to 90° C. for overnight in tube. Solvent was removed and the product (170 mg in 56,44% yield) was got by chromatography column on silica gel. ¹H NMR (400 MHz, DMSO-d6) δ 8.33 (d, J=22.3 Hz, 1H), 7.63 (d, J=19.0 Hz, 1H), 7.35 (t, J=7.0 Hz, 2H), 7.23 (d, J=8.7 Hz, 1H), 7.00 (d, J=4.9 Hz, 1H), 6.82 (s, 2H), 4.83 (d, J=7.0 Hz, 1H), 3.43 (s, 1H), 3.21 (s, 1H), 2.53 (s, 3H), 2.02 (s, 3H), 1.65 (d, J=7.1 Hz, 3H), 0.81 (t, J=7.0 Hz, 3H). MS (ESI) m/e (M+1)⁺ 456.

Compound 8 was separated by chiral column to afford two compounds, Compound 8A (the first and fast isomer) and Compound 8B (the second and slow isomer), as white solids. Compound 8A was assigned as a (S)-configuration in a similar manner to Compound 40A as disclosed below.

Compound 8A: ¹H NMR (400 MHz, DMSO-d6) δ 8.34 (d, J=27.6 Hz, 1H), 7.68-7.60 (m, 1H), 7.42 (d, J=5.3 Hz, 1H), 7.39 (s, 1H), 7.27 (d, J=7.4 Hz, 1H), 7.02 (d, J=5.3 Hz, 1H), 4.86 (d, J=7.1 Hz, 1H), 3.22 (s, 2H), 2.54 (s, 3H), 2.03 (s, 3H), 1.66 (d, J=7.1 Hz, 3H), 0.81 (t, J=6.9 Hz, 3H). MS (ESI) m/e (M+1)⁺ 456.

Compound 8B: ¹H NMR (400 MHz, DMSO-d6) δ 8.34 (d, J=27.6 Hz, 1H), 7.68-7.60 (m, 1H), 7.42 (d, J=5.3 Hz, 1H), 7.39 (s, 1H), 7.02 (d, J=7.4 Hz, 1H), 7.02 (d, J=5.3 Hz, 1H), 4.85 (q, J=7.2 Hz, 1H), 3.22 (s, 2H), 2.54 (s, 3H), 2.03 (s, 3H), 1.65 (d, J=7.0 Hz, 3H), 0.81 (t, J=6.8 Hz, 3H). MS (ESI) m/e (M+1)⁺ 456.

Chiral Separation:

| Column | Chiral Cellulose-SB |
| --- | --- |
| Column size | 2.12 cm × 25 cm |
| Injection | 0.4 ML |
| Mobile phase | Hex:EtOH = 50:50 |
| Flow rate | 20 ml/min |
| Wave length | UV 220 nm |
| Temperature | 35° C. |
| Sample solution | 20 mg/ml in mobile phase |
| Prep-HPLC equipment | BJ-Prep-Gilson-HPLC |

Example 9

1-bromo-3-(1-(4',5-dichloro-2-ethoxy-6-methyl-[1,1'-biphenyl]-3-yl)ethyl)imidazo[1,5-a]pyrazin-8-amine (Compound 9)

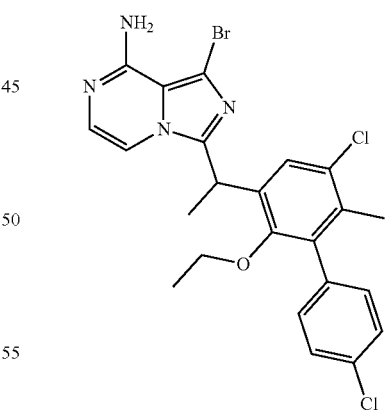

The desired compound was prepared by the similar manner as Compound 7 described in example 7 using 1-(5-chloro-2-hydroxy-4-methylphenyl)ethan-1-one as starting materials. ¹H NMR (400 MHz, DMSO-d6) δ 7.53 (t, J=6.6 Hz, 3H), 7.34 (d, J=8.3 Hz, 1H), 7.30 (s, 1H), 7.25 (d, J=8.0 Hz, 1H), 7.07 (d, J=5.7 Hz, 1H), 4.89 (d, J=7.1 Hz, 1H), 3.28-3.18 (m, 2H), 2.02 (s, 3H), 1.66 (d, J=7.1 Hz, 3H), 0.81 (t, J=6.9 Hz, 3H). MS (ESI) m/e (M+1)⁺ 519.

Prep-HPLC:

| Column | Gilson GX-281 |
|---|---|
| Column size | 21.2*150 5 μm GIMINI |
| Flow rate | 20 ml/min |
| Wave length | 214 nm + 254 nm |
| Method | 0.1% TFA in water, CH₃CN from 20 to 50% in 11 min, then from 50 to 90% in 1 min, 90% hold 2 min, then balance 2 min. Total run time 18 min. Single gradient method. |

Example 10

3-(8-amino-3-(1-(5-chloro-2-ethoxy-4-methyl-3-(6-(trifluoromethyl)pyridin-3-yl)phenyl)ethyl)imidazo[1,5-a]pyrazin-1-yl)phenol (Compound 10)

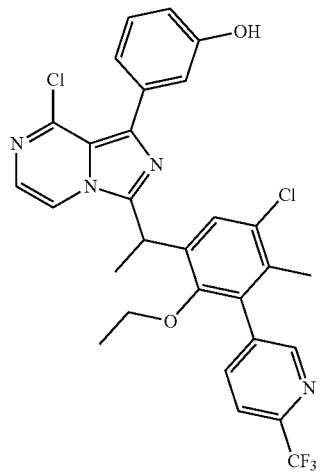 [SMILES: CCOc1c(C(C)c2nc(-c3cccc(O)c3)c3c(Cl)nccn23)cc(Cl)c(C)c1-c1ccc(C(F)(F)F)nc1]

Compound 24 (100 mg, 0.180 mmol), (3-hydroxyphenyl)boronic acid (30 mg, 0.216 mmol), Pd(dppf)Cl₂ (6.6 g, 0.009 mmol) and K₂CO₃ (50 mg, 0.360 mmol) were dissolved in H₂O/1,4-dioxane (5 mL/5 mL) and heated to 90° C. under N₂ for 3 hrs. Solvent was removed by reduced pressure and extracted with ethyl acetate. The combined organic layers were washed with brine and dried over Na₂SO₄. The product (66 mg in 64.5% yield) was got by prep-HPLC. ¹H NMR (400 MHz, DMSO-d6) δ 9.67 (s, 1H), 8.74 (d, J=36.3 Hz, 1H), 8.25-7.93 (m, 2K), 7.39 (d, J=5.0 Hz, 1H), 7.38-7.25 (m, 2H), 7.03 (t, J=9.6 Hz, 3H), 6.91-6.73 (m, 1H), 6.13 (s, 2H), 4.89 (d, J=6.9 Hz, 1H), 3.51 (s, 1H), 3.30 (d, J=9.6 Hz, 1H), 204 (s, 3H), 1.74 (d, J=7.0 Hz, 3H), 0.81 (t, J=6.9 Hz, 3H). MS (ESI) m/e (M+1)⁺ 568.

Prep-HPLC:

| Column | Gilson GX-281 |
|---|---|
| Column size | 21.2*150 5 μm GIMINI |
| Flow rate | 20 ml/min |
| Wave length | 214 nm + 254 nm |
| Method | 0.1% TFA in water, CH₃CN from 10 to 90% in 11 min, then from 90 to 90% in 1 min, 90% hold 2 min, then balance 2 min. Total run time 18 min. |

Example 11

(S)-5-(3-(1-(8-amino-1-chloroimidazo[1,5-a]pyrazin-3-yl)ethyl)-5-chloro-2-ethoxy-6-methylphenyl)-N,N-dimethylpicolinamide (Compound 11)

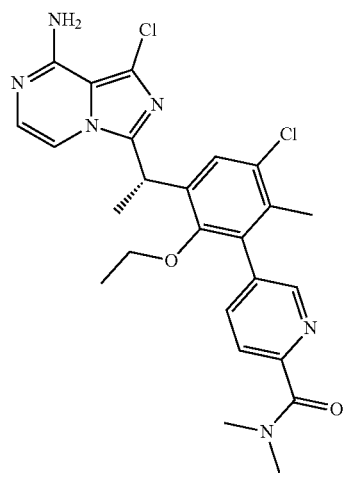 [SMILES: CCOc1c([C@H](C)c2nc(Cl)c3c(N)nccn23)cc(Cl)c(C)c1-c1ccc(C(=O)N(C)C)nc1]

Compound 27A (400 mg, 0.839 mmol), Pd(OAc)₂ (9.42 mg, 0.042 mmol) and Et₃N (10 mL) were dissolved in dimethylamine/THF (3 N, 20 mL). The reaction was stirred under CO (0.6 MPa) at 85° C. for overnight. Solvent was removed in vacuo. Water (20 mL) added and extracted with ethyl acetate. The combined organic layers were washed with brine and dried over Na₂SO₄. The product (110 mg in 25.5% yield) was got by chromatography column on silica gel. ¹H NMR (400 MHz, DMSO-d6) δ 8.50 (d, J=24.8 Hz, 1H), 7.89 (dd, J=28.8, 7.3 Hz, 1H), 7.66 (s, 1H), 7.31 (dd, J=29.0, 5.3 Hz, 2H), 7.01 (s, 1H), 6.79 (s, 2H), 4.84 (q, J=6.7 Hz, 1H), 3.56-3.40 (m, 1H), 3.23 (dd, J=15.1, 7.9 Hz, 1H), 3.01 (ds, 61H), 2.06 (s, 3H), 1.66 (d, J=7.0 Hz, 3H), 0.80 (t, J=6.5 Hz, 3H). MS (ESI) m/e (M+1)⁺ 513.

Example 12

((S)-5-(3-(1-(8-amino-1-chloroimidazo[1,5-a]pyrazin-3-yl)ethyl)-5-chloro-2-ethoxy-6-methylphenyl)picolinic Acid (Compound 12)

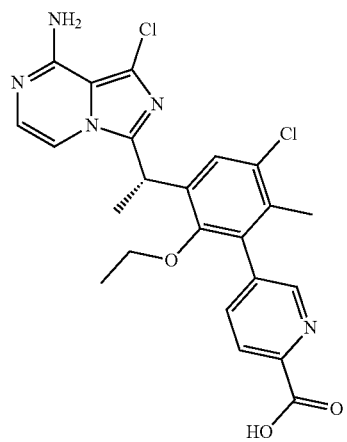 [SMILES: CCOc1c([C@H](C)c2nc(Cl)c3c(N)nccn23)cc(Cl)c(C)c1-c1ccc(C(=O)O)nc1]

Compound 11 (28 mg, 54.54 mmol) was dissolved in EtOH (3 mL), KOH (5 N, 3 mL) was added and heated to 60° C. for 1 hr. Solvent was removed in vacuo. The pH was adjusted to 7 and extracted with ethyl acetate. The product (26.5 mg in 100% yield) was got. MS (ESI) m/e (M+1)$^+$ 513. $^1$H NMR (400 MHz, DMSO-d6) δ 8.62 (d, J=35.4 Hz, 1H), 8.15 (s, 1H), 7.98 (d, J=39.2 Hz, 1H), 7.61 (s, 1H), 7.43 (d, J=13.3 Hz, 1H), 7.14 (d, J=5.8 Hz, 1H), 4.93 (d, J=7.0 Hz, 1H), 3.53-3.33 (m, 1H), 3.21 (s, 1H), 2.06 (s, 3H), 1.68 (d, J=7.0 Hz, 3H), 0.78 (t, J=6.7 Hz, 3H).

Example 13

5-(3-(1-(8-amino-1-chloroimidazo[1,5-a]pyrazin-3-yl)ethyl)-5-chloro-2-ethoxy-6-fluorophenyl)-N,N-dimethylpicolinamide (Compound 13)

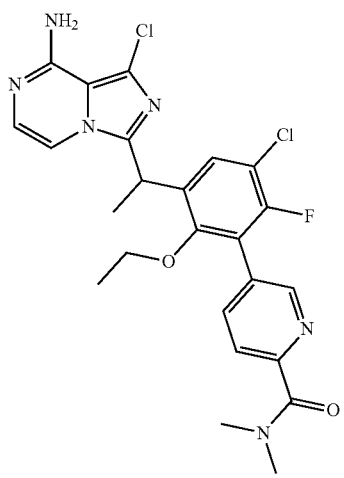 [SMILES: CCOc1c(C(C)c2nc(Cl)c3c(N)nccn23)cc(Cl)c(F)c1-c1ccc(C(=O)N(C)C)nc1]

The desired compound was prepared by the similar method as compound 11 described in example 11 using 1-(5-chloro-4-fluoro-2-hydroxyphenyl)ethan-1-one as starting materials. $^1$H NMR (400 MHz, DMSO-d6) δ 8.14 (s, 1H), 7.58 (d, J=8.9 Hz, 1H), 7.41 (d, J=5.1 Hz, 1H), 7.32 (d, J=8.3 Hz, 1H), 7.02 (d, J=5.0 Hz, 1H), 6.86-6.64 (m, 3H), 4.87 (d, J=7.1 Hz, 1H), 3.45 (dd, J=9.1, 7.0 Hz, 1H), 3.27 (dd, J=9.1, 7.1 Hz, 1H), 3.07 (s, 6H), 1.64 (d, J=7.0 Hz, 3H), 0.93 (t, J=7.0 Hz, 3H). MS (ESI) m/e (M+1)$^+$ 517.

Example 14

(S)-5-(3-(1-(8-amino-1-chloroimidazo[1,5-a]pyrazin-3-yl)ethyl)-5-chloro-2-ethoxy-6-methylphenyl)-N,N-diethylnicotinamide (Compound 14)

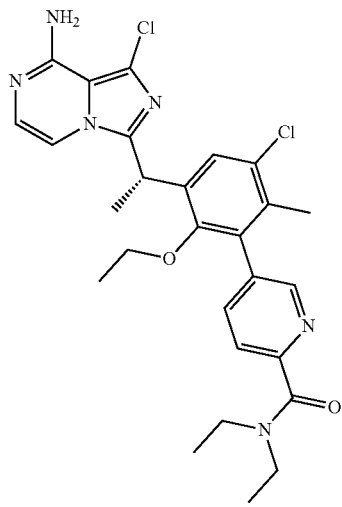 [SMILES: CCOc1c([C@H](C)c2nc(Cl)c3c(N)nccn23)cc(Cl)c(C)c1-c1ccc(C(=O)N(CC)CC)nc1]

Compound 27A (200 mg, 0.42 mmol), diethylamine (1 mL), Et$_3$N (10 mL), Pd(OAc) (4.7 mg, 0.021 mmol) and xantphos (24.3 mg, 0.042 mmol) were dissolved in THF (10 mL) and stirred under CO (0.85 MPa) at 80° C. for 48 hrs. Solvent was removed in vacuo. Water (20 mL) was added and extracted with ethyl acetate. The combined organic layers were washed with brine and dried over Na$_2$SO$_4$. The product (85 mg in 37.4% yield) was got by column (DCM/MeOH=50/1). $^1$H NMR (400 MHz, DMSO-d6) δ 8.55 (d, J=21.6 Hz, 1H), 8.12-7.84 (m, 1H), 7.70 (s, 1H), 7.51-7.24 (m, 2H), 7.07 (s, 1H), 6.81 (s, 2H), 4.90 (d, J 6.9 Hz, 1H), 3.72-3.45 (m, 4H), 3.29 (dd, J=16.6, 9.2 Hz, 2H), 2.13 (d, J=4.6 Hz, 3H), 1.72 (d, J=6.9 Hz, 3H), 1.19 (dt, J=40.5, 7.0 Hz, 6H), 0.85 (s, 3H). MS (ESI) m/e (M+1)$^+$ 541.

Example 15

5-(3-(1-(8-amino-1-chloroimidazo[1,5-a]pyrazin-3-yl)ethyl)-5-chloro-2-ethoxy-6-methylphenyl)pyridin-2(1H)-one (Compound 15)

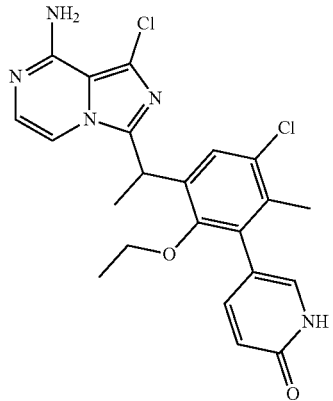 [SMILES: CCOc1c(C(C)c2nc(Cl)c3c(N)nccn23)cc(Cl)c(C)c1-c1ccc(=O)[nH]c1]

1-chloro-3-(1-(5-chloro-2-ethoxy-3-iodo-4-methylphenyl)ethyl)imidazo[1,5-a]pyrazin-8-amine (compound (46-6), 150 mg, 0.3054 mmol), 5-(4,4,5,5-tetramethyl-1,3,2-dioxaborolan-2-yl)pyridin-2(1H)-one (74.3 mg, 0.336 mmol), Na$_2$CO$_3$ (97.11 mg, 0.9162 mmol) and Pd(PPh$_3$)$_4$ (18 mg, 0.0153 mmol) were dissolved in 1,4-dioxane/H$_2$O (10 mL/10 mL) and heated to 80° C. under N$_2$ for 24 hrs. 1,4-dioxane was removed in vacuo and extracted with ethyl acetate. The combined organic layers were washed with brine and dried over Na$_2$SO$_4$. The product (30 mg in 21.5% yield) was got by chromatography column on silica gel. $^1$H NMR (400 MHz, DMSO-d6) δ 11.76 (s, 1H), 7.57-7.20 (m, 3H), 7.16 (s, 1H), 6.99 (d, J=4.9 Hz, 1H), 6.72 (s, 2H), 6.40 (d, J=9.4 Hz, 1H), 4.81 (q, J=6.8 Hz, 1H), 3.66-3.47 (m, 2H), 2.12 (s, 3H), 1.63 (d, J=7.0 Hz, 3H), 1.00 (t, J=6.9 Hz, 3H). MS (ESI) m/e (M+1)$^+$ 458.

Example 16

5-(3-(1-(8-amino-1-chloroimidazo[1,5-a]pyrazin-3-yl)ethyl)-5-chloro-6-fluoro-2-isopropoxyphenyl)-N,N-dimethylpicolinamide (Compound 16)

Compound 16

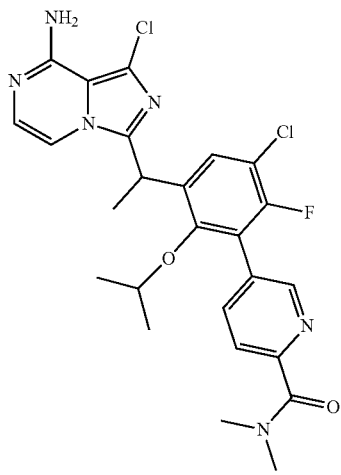

Compound 16A

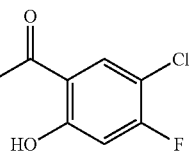

Compound 16B

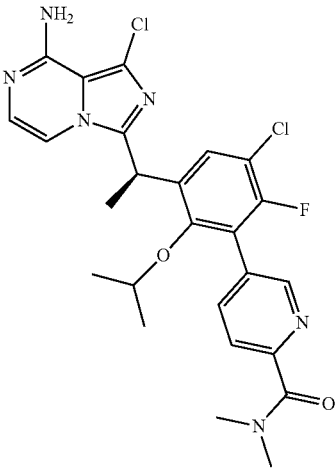

Step 1: 1-(5-chloro-4-fluoro-2-hydroxyphenyl)ethan-1-one (16-1)

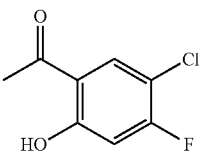

4-chloro-3-fluorophenol (100 g, 68.26 mmol) was dissolved in acetyl chloride (80.4 g, 102.42 mmol). AlCl$_3$ (1136.2 g, 102.42 mmol) was added slowly. The reaction was heated to 180° C. for 2 hrs. Cooled to room temperature, HCl (2N, 800 ml) was added slowly and stirred for 2 hrs. The product (130 g, 100% yield) was received by filtration and washed with water. MS (ESI) m/e [M+$^1$1]$^+$ 189.0.

Step 2: 1-(5-chloro-4-fluoro-2-hydroxy-3-iodophenyl)ethan-1-one (16-2)

1-(5-chloro-4-fluoro-2-hydroxyphenyl)ethan-1-one (130 g 689.7 mmol) was dissolved in AcOH (700 ml), NIS (186.2 g, 827.6 mmol) was added and heated to 70° C. for overnight, another batch NIS (65 g, 288.9 mmol) was added and heated to 70° C. for 12 hrs. AcOH was removed in vacuo. Ethyl acetate (1 L) was added Na$_2$S$_2$O$_3$ (s.aq, 1 L) was added. The reaction was stirred for 20 min at room temperature and extracted with ethyl acetate. The combined organic layers were washed with Brine and dried over Na$_2$SO$_4$. The product (128 g, 59% yield) was received by chromatography column on silica gel. MS (ESI) m/e [M+1]$^+$ 315.0.

Step 3: 1-(5-chloro-3-(6-chloropyridin-3-yl)-4-fluoro-2-hydroxyphenyl)ethan-1-one (16-3)

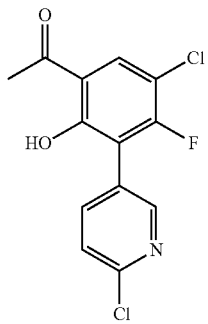 [SMILES: CC(=O)c1cc(Cl)c(F)c(-c2ccc(Cl)nc2)c1O]

1-(5-chloro-4-fluoro-2-hydroxy-3-iodophenyl)ethan-1-one (10 g, 31.8 mmol), (6-chloropyridin-3-yl)boronic acid (5 g, 31.8 mmol), Pd(PPh$_3$)$_4$ (1.84 g, 1.59 mmol) and K$_2$CO$_3$ (8.78 g, 63.6 mmol) was dissolved in 1,4-dioxane/H$_2$O (50 ml/30 ml) and refluxed under N$_2$. 1,4-dioxane was removed in vacuo and extracted with ethyl acetate. The combined organic layers were washed with brine and dried over Na$_2$SO$_4$. The product (2.6 g, 27.2% yield) was received by chromatography column on silica gel. MS (ESI) m/e [M+1]$^+$ 300.0.

Step 4: 1-(5-chloro-3-(6-chloropyridin-3-yl)-4-fluoro-2-isopropoxyphenyl)ethan-1-one (16-4)

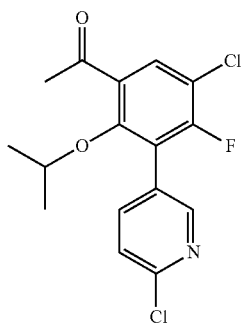 [SMILES: CC(=O)c1cc(Cl)c(F)c(-c2ccc(Cl)nc2)c1OC(C)C]

1-(5-chloro-3-(6-chloropyridin-3-yl)-4-fluoro-2-hydroxyphenyl)ethan-1-one (2.6 g, 8.663 mmol), 2-iodopropane (2.95 g, 17.33 mmol) and K$_2$CO$_3$ (3.6 g, 25.99 mmol) were dissolved in DMF (25 mL) and heated to 60° C. for 2 hrs. Cooled to room temperature, water (30 mL) was added and extracted with ethyl acetate. The combined organic layers were washed with brine and dried over Na$_2$SO$_4$. The product (2.5 g, 84.5% yield) was received by chromatography column on silica gel. $^1$H NMR (400 MHz, DMSO-d6) δ 8.56 (d, J=1.1 Hz, 1H), 8.05 (m, J=8.3, 1.7 Hz, 1H), 7.81 (d, J=8.6 Hz, 1H), 7.72 (d, J=8.3 Hz, 1H), 3.69 (m, 1H), 2.61 (s, 3H), 0.89 (d, J=6.1 Hz, 6H). MS (ESI) m/e [M+1]$^+$ 342.0.

Step 5: 2-chloro-5-(3-chloro-2-fluoro-6-isopropoxy-5-(prop-1-en-2-yl)phenyl)pyridine (16-5)

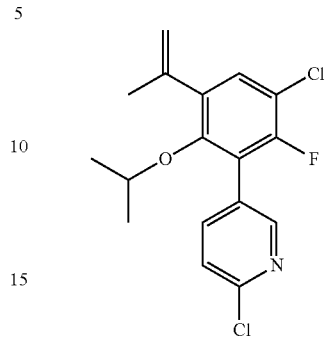

CH$_3$PPh$_3$Br (6.3 g, 17.53 mmol) was dissolved in dry THF (30 mL), n-BuLi (1.6 M, 9 mL) was added dropwise at 0° C. under N$_2$ and stirred at 0° C. for 1 h, then a solution of 1-(5-chloro-3-(6-chloropyridin-3-yl)-4-fluoro-2-isopropoxyphenyl)ethan-1-one (2.0 g, 5.84 mmol) in dry THF was added to the mixture dropwise and stirred at for overnight. Water (20 ml) was added and extracted with ethyl acetate. The combined organic layers were washed with Brine and dried over Na$_2$SO$_4$. The product (1.3 g, 52.2% yield) was received. $^1$H NMR (400 MHz, DMSO-d6) δ 8.49 (s, 1H), 7.98 (m, 1H), 7.67 (d, J=8.2 Hz, 1H), 7.50 (d, J=8.7 Hz, 1H), 5.23 (ds, 2H), 3.89 (m, 1H), 2.12 (s, 3H), 0.84 (d, J=6.1 Hz, 3H). MS (ESI) m/e [M+1]$^+$ 340.0.

Step 6: 2-(5-chloro-3-(6-chloropyridin-3-yl)-4-fluoro-2-isopropoxyphenyl)propan-1-ol (16-6)

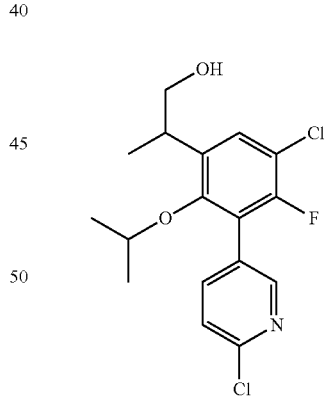

2-chloro-5-(3-chloro-2-fluoro-6-isopropoxy-5-(prop-1-en-2-yl)phenyl)pyridine (13 g, 3.82 mmol) was dissolved in BH$_3$/THF (1M, 30 mL) and stirred at r.t for overnight. NaOH (1M, 10 mL) was added dropwise at 0° C. H$_2$O$_2$ (30%, 20 mL) was added dropwise at 0° C. for 1 h. The reaction was extracted with ethyl acetate. The combined organic layers were washed with Na$_2$S$_2$O$_3$ and brine and dried over Na$_2$SO$_4$. The product (1.37 g, 100% yield) was received. MS (ESI) m/e [M+1]$^+$ 358.0.

Step 7: 2-(5-chloro-3-(6-chloropyridin-3-yl)-4-fluoro-2-isopropoxyphenyl)propanoic Acid (16-7)

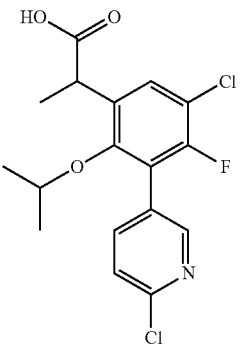 [SMILES: CC(C)Oc1c(C(C)C(=O)O)cc(Cl)c(F)c1-c1ccc(Cl)nc1]

2-(5-chloro-3-(6-chloropyridin-3-yl)-4-fluoro-2-isopropoxyphenyl)propan-1-ol (1.37 g, 3.824 mmol) was dissolved in $CH_3CN$ (50 mL). $Na_2HPO_4/NaH_2PO_4$ (0.25 mol/0.5 mol/L) (50 mL) was added. TEMPO (119.5 mg, 0.765 mmol) was added. $NaClO_2$ (3.46 g, 38.24 mmol) in NaClO (6%, 50 mL) was added dropwise at room temperature. The reaction was stirred at room temperature for overnight and extracted with ethyl acetate. The combined organic layers were washed with brine and dried over $Na_2SO_4$. The product (770 mg, 54.23% yield) was received. MS (ESI) m/e $[M+1]^+$ 372.0.

Step 8: 2-(5-chloro-3-(6-chloropyridin-3-yl)-4-fluoro-2-isopropoxyphenyl)-N-((3-chloropyrazin-2-yl)methyl)propanamide (16-8)

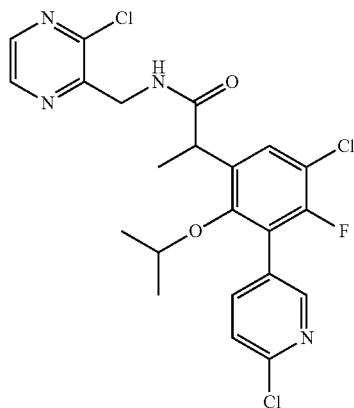 [SMILES: CC(C)Oc1c(C(C)C(=O)NCc2nccnc2Cl)cc(Cl)c(F)c1-c1ccc(Cl)nc1]

2-(5-chloro-3-(6-chloropyridin-3-yl)-4-fluoro-2-isopropoxyphenyl)propanoic acid (770 mg, 2.07 mmol), (3-chloropyrazin-2-yl)methanamine hydrochloride (356.4 mg, 2.48 mmol), HOBt (335.42 mg, 2.48 mmol), EDCI (475 mg, 2.48 mmol) and DIPEA (803 mg, 6.21 mmol) were dissolved in TH F (15 mL) and stirred at room temperature for overnight under $N_2$. Water (20 mL) was added and extracted with ethyl acetate. The combined organic layers were washed with brine and dried over $Na_2SO_4$. The product (680 mg, 66% yield) was received by chromatography column on silica gel (PE:EA=1:1). MS (ESI) m/e $[M+1]^+$ 497.0.

Step 9: 8-chloro-3-(1-(5-chloro-3-(6-chloropyridin-3-yl)-4-fluoro-2-isopropoxyphenyl)ethyl)imidazo[1,5-a]pyrazine (16-9)

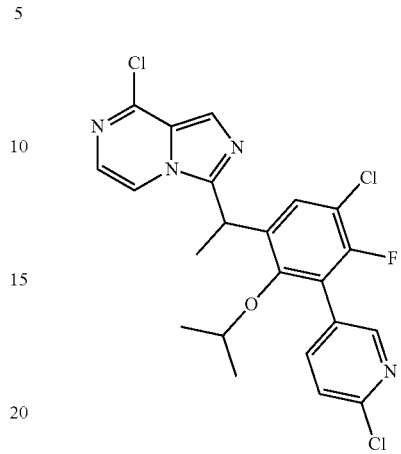

2-(5-chloro-3-(6-chloropyridin-3-yl)-4-fluoro-2-isopropoxyphenyl)-N-((3-chloropyrazin-2-yl)methyl)propanamide (680 mg, 1.37 mmol) was dissolved in $CH_2Cl_2$ (20 mL). $Tf_2O$ (0.8 mL) was added and pyridine (1.2 mL) was added dropwise. The reaction was stirred at room temperature for 1 h. Water (20 mL) was added at 0° C. and extracted with $CH_2Cl_2$. The combined organic layers were washed with brine and dried over $Na_2SO_4$. The product (506 mg, 77.2% yield) was received by chromatography column on silica gel (PE:EA 20:1), MS (ESI) m/e $[M+1]^+$ 479.0.

Step 10: 1,8-dichloro-3-(1-(5-chloro-3-(6-chloropyridin-3-yl)-4-fluoro-2-isopropoxyphenyl)ethyl)imidazo[1,5-a]pyrazine (16-10)

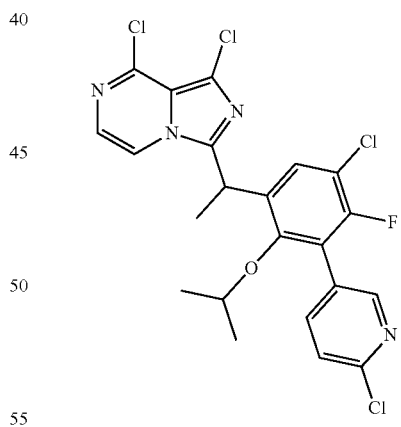

8-chloro-3-(1-(5-chloro-3-(6-chloropyridin-3-yl)-4-fluoro-2-isopropoxyphenyl)ethyl)imidazo[1,5-a]pyrazine (506 mg, 1,055 mmol) and NCS (169 mg, 1.266 mmol) were dissolved in DMF (10 mL) and heated to 60° C. for 1 h. Water (20 mL) was added and extracted with ethyl acetate. The combined organic layers were washed with brine and dried over $Na_2SO_4$. The product (450 mg, 83% yield) was received by chromatography column on silica gel (PE:EA=15:1). $^1H$ NMR (400 MHz, DMSO-d6) δ 8.50 (s, 1H), 8.19 (d, J=5.0 Hz, 1H), 7.99 (m, 1H), 7.69 (d, J=8.3 Hz, 1H), 7.62 (d, J=8.4 Hz, 1H), 7.50 (d, J 5.0 Hz, 1H), 5.04 (q, J=7.0

Hz, 1H), 3.62 (m, 1H), 1.70 (d, J=7.1 Hz, 3H), 1.00 (d, J=6.1 Hz, 3H), 0.81 (d, J=6.1 Hz, 3H). MS (ESI) m/e [M+1]⁺ 513.0.

Step 11: 1-chloro-3-(1-(5-chloro-3-(6-chloropyridin-3-yl)-4-fluoro-2-isopropoxyphenyl)ethyl)imidazo[1,5-a]pyrazin-8-amine (16-11)

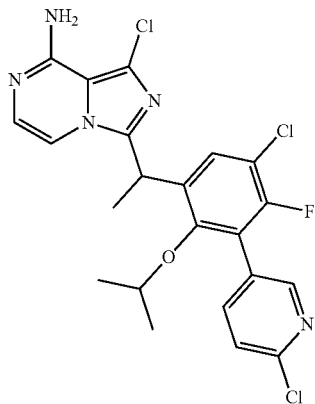 [SMILES: CC(C)Oc1c(C(C)c2nc(Cl)c3c(N)nccn23)cc(Cl)c(F)c1-c1ccc(Cl)nc1]

1,8-dichloro-3-(1-(5-chloro-3-(6-chloropyridin-3-yl)-4-fluoro-2-isopropoxyphenyl)ethyl) imidazo[1,5-a]pyrazine (450 mg, 0.875 mmol) was dissolved in NH/propan-2-ol (4N, 30 mL). The reaction was heated to 85° C. for overnight in tube. Solvent was removed in vacuo and ethyl acetate (30 mL) was added. The reaction was extracted with ethyl acetate and the combined organic layers were washed with brine. The product (360 mg, 83% yield) was received. MS (ESI) m/e [M+1]⁺ 494.

Step 12: ethyl 5-(3-(1-(8-amino-1-chloroimidazo[1,5-a]pyrazin-3-yl)ethyl)-5-chloro-6-fluoro-2-isopropoxyphenyl)picolinate (16-12)

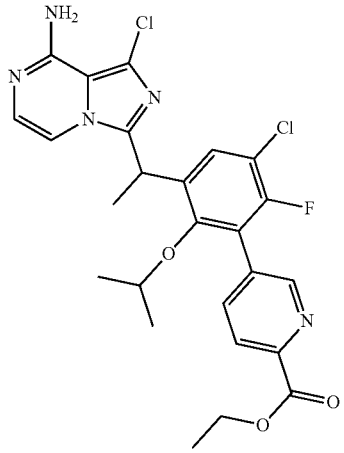 [SMILES: CCOC(=O)c1ccc(-c2c(F)c(Cl)cc(C(C)c3nc(Cl)c4c(N)nccn34)c2OC(C)C)cn1]

1-chloro-3-(1-(5-chloro-3-(6-chloropyridin-3-yl)-4-fluoro-2-isopropoxyphenyl)ethyl) imidazo[1,5-a]pyrazin-8-amine (335 mg, 0.677 mmol), Pd(OAc)₂ (7.6 mg, 0.0339 mmol) and Xantphos (39.2 mg, 0.0677 mmol) were dissolved in EtOH/Et₃N (8 mL/8 mL) in tube. The reaction was heated to 70° C. under CO (0.5-0.8 MPa) for 48 hrs. Solvent was removed in vacuo and extracted with ethyl acetate. The combined organic layers were washed with brine and dried over Na₂SO₄. The product (280 mg in 77.8% yield) was got by chromatography column on silica gel. MS (ESI) m/e (M+1)⁺ 532.

Step 13: 5-(3-(1-(8-amino-1-chloroimidazo[1,5-a]pyrazin-3-yl)ethyl)-5-chloro-6-fluoro-2-isopropoxyphenyl)-N,N-dimethylpicolinamide (16-13)

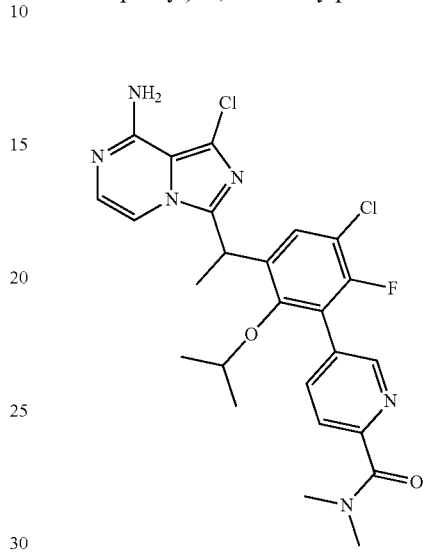

To a 0° C. solution of dimethylamine (2 N, 0.65 mL, 1.296 mmol) in THF was added trimethylaluminum (2 M, 0.65 mL, 1.296 mmol). Gas evolution is observed and the reaction was then allowed to warm to room temperature and stirred for 1 hr. Ethyl 5-(3-(1-(8-amino-1-chloroimidazo[1,5-a]pyrazin-3-yl)ethyl)-5-chloro-6-fluoro-2-isopropoxyphenyl) picolinate (230 mg, 0.432 mmol) was added to the aluminum reagent and the mixture was heated to reflux for 1 hr. Cooled to 0° C., the reaction was quenched with water and extracted with ethyl acetate. The combined organic layers were washed with brine and dried over Na₂SO₄. The product (80 mg, 28.62% yield) was got by chromatography column on silica gel (CH₂Cl₂/MeOH=50/1). ¹H NMR (400 MHz, CDCl₃) δ 8.66 (s, 1H), 7.90 (d, J=8.1 Hz, 1H), 7.81 (d, J=8.0 Hz, 1H), 7.45-7.38 (m, 2H), 6.95 (d, J=5.4 Hz, 1H), 4.83 (d, J=7.1 Hz, 1H), 3.84-3.59 (m, 1H), 3.18 (d, J=7.3 Hz, 6H), 1.84 (d, J=7.2 Hz, 3H), 1.17-0.99 (m, 6H). MS (ESI) m/e (M+1)⁺ 531.

Compound 16 was separated by chiral column to afford two compounds, Compound 16A (the first and fast isomer) and Compound 16B (the second and slow isomer), as white solids. Compound 16A was assigned as a (S)-configuration in a similar manner to Compound 40A as disclosed below.

Compound 16A: ¹H NMR (400 MHz, DMSO-d6) δ 8.64 (s, 1H), 8.03 (d, J=8.0 Hz, 1H), 7.70 (d, J=8.0 Hz, 1H), 7.51 (dd, J=26.3, 6.7 Hz, 2H), 7.06 (d, J=5.0 Hz, 1H), 6.74 (s, 2H), 4.91 (d, J=7.1 Hz, 1H), 3.76-3.52 (m, 1H), 3.04 (s, 3H), 2.97 (s, 3H), 1.66 (d, J=7.0 Hz, 3H), 0.99 (d, J=6.0 Hz, 3H), 0.77 (d, J=6.1 Hz, 3H). MS (ESI) m/e (M+1)⁺ 531.

Compound 16B: ¹H NMR (400 MHz, DMSO-d6) δ 8.64 (s, 1H), 8.03 (d, J=8.2 Hz, 1H), 7.70 (d, J=8.0 Hz, 1H), 7.51 (dd, J=26.1, 6.8 Hz, 2H), 7.06 (d, J=5.0 Hz, 1H), 6.74 (s, 2H), 4.91 (d, J=7.1 Hz, 1H), 3.76-3.52 (m, 1H), 3.04 (s, 3H), 2.97 (s, 3H), 1.66 (d, J=7.1 Hz, 3H), 0.99 (d, J=6.1 Hz, 3H), 0.77 (d, J=6.1 Hz, 3H). MS (ESI) m/e (M+1)⁺ 531.

Chiral Separation:

| Column | CHIRALART Cellulose-SB |
|---|---|
| Column size | 2 cm × 25 cm, 5 μm |
| Injection | 0.3 ML |
| Mobile phase | Hex:EtOH = 85:15 |
| Flow rate | 20 ml/min |
| Wave length | UV 220 nm |
| Temperature | 35° C. |
| Sample solution | 10 mg/ml in mobile phase |
| Prep-HPLC equipment | BJ-Prep-Gilson-HPLC |

Example 17

5-(3-(1-(8-amino-1-chloroimidazo[1,5-a]pyrazin-3-yl)ethyl)-5-chloro-6-fluoro-2-isopropoxyphenyl)picolinamide (Compound 17)

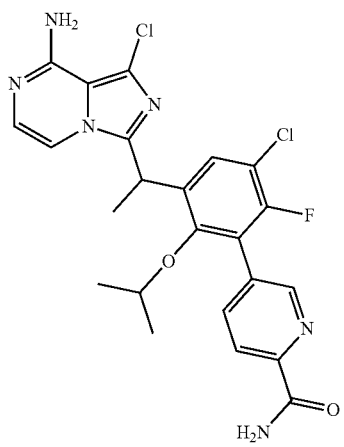

Compound 17

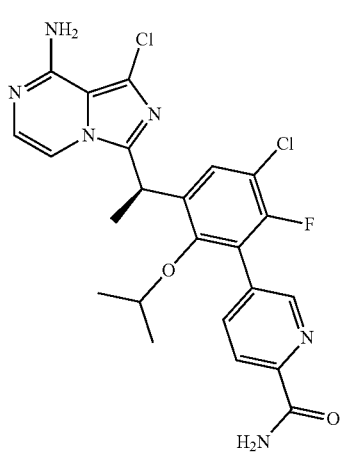

Compound 17A

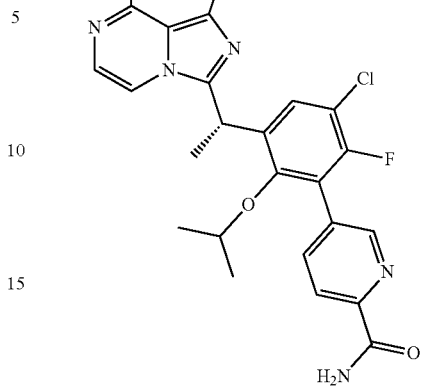

Compound 17B

Compound (16-12) (500 mg, 0.939 mmol) was dissolved in $NH_3$/i-PrOH (7 N, 10 mL) and heated to 85° C. for overnight. Solvent was removed in vacuo and extracted with ethyl acetate. The combined organic layers were washed with brine and dried over $Na_2SO_4$. The product (260 mg in 55% yield) was got by chromatography column on silica gel. $^1$H NMR (400 MHz, DMSO-d6) δ 8.69 (s, 1H), 8.22 (s, 1H), 8.16 (d, J=8.1 Hz, 1H), 8.09 (d, J=8.1 Hz, 1H), 7.75 (s, 1H), 7.52 (dd, J=30.2, 6.7 Hz, 2H), 7.06 (d, J=5.0 Hz, 1H), 6.75 (s, 2H), 4.91 (d, J=7.1 Hz, 1H), 3.71-3.51 (m, 1H), 1.67 (d, J=7.0 Hz, 3H), 0.98 (d, J=6.0 Hz, 3H), 0.77 (d, J=6.0 Hz, 3H). MS (ESI) m/e (M+1)$^+$ 503.

Compound 17 was separated by chiral column to afford two compounds, Compound 17A (the first and fast isomer) and Compound 17B (the second and slow isomer), as white solids. Compound 17B was assigned as a (S)-configuration in a similar manner to Compound 40A as disclosed below.

Compound 17A: MS (ESI) in/e (M+1)$^+$ 503. $^1$H NMR (400 MHz, DMSO-d6) δ 8.69 (s, 1H), 8.22 (s, 1H), 8.16 (d, J=8.1 Hz, 1H), 8.09 (d, J=8.0 Hz, 1H), 7.75 (s, 1H), 7.56 (d, J 8.4 Hz, 1H), 7.48 (d, J=5.0 Hz, 1H), 7.06 (d, J=5.0 Hz, 1H), 6.74 (s, 2H), 4.91 (d, J=7.0 Hz, 1H), 3.61-3.58 (m, 1H), 1.67 (d, J=7.0 Hz, 3H), 0.98 (d, J=6.0 Hz, 3H), 0.76 (d, J=6.0 Hz, 3H).

Compound 17B: MS (ESI) m/e (M+1)$^+$ 503. $^1$H NMR (400 MHz, DMSO-d6) δ 8.69 (s, 1H), 8.22 (s, 1H), 8.16 (d, J=8.0 Hz, 1H), 8.09 (d, J=7.8 Hz, 1H), 775 (s, 1H), 7.56 (d, J=8.4 Hz, 1H), 7.48 (d, J=5.0 Hz, 1H), 7.06 (d, J=4.9 Hz, 1H), 6.75 (s, 2H), 4.91 (d, J=7.0 Hz, 1H), 3.61-3.58 (m, 1H), 1.67 (d, J=6.9 Hz, 3H), 0.98 (d, J=6.0 Hz, 3H), 0.76 (d, J=6.0 Hz, 3H).

Chiral Separation:

| Column | CHIRALART Cellulose-SB |
|---|---|
| Column size | 2 cm × 25 cm, 5 μm |
| Injection | 4.0 ML |
| Mobile phase | MTBE:EtOH = 50:50 |
| Flow rate | 20 ml/min |
| Wave length | UV 220 nm |
| Temperature | 35° C. |
| Sample solution | 14.3 mg/ml in mobile phase |
| Prep HPLC equipment | BJ-Prep-Gilson-HPLC |

Example 18

5-(3-(1-(8-amino-1-chloroimidazo[1,5-a]pyrazin-3-yl)ethyl)-5-chloro-6-fluoro-2-isopropoxyphenyl) picolinic Acid (Compound 18)

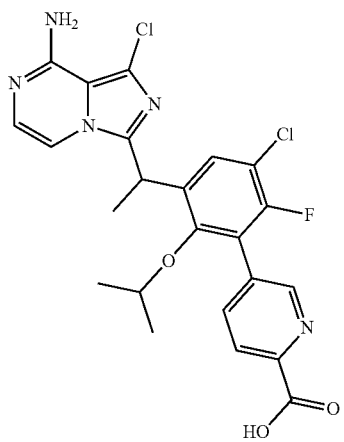

Compound 18

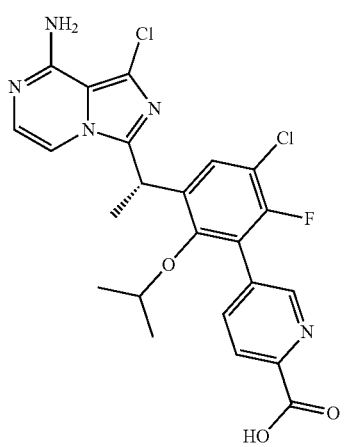

Compound 18A

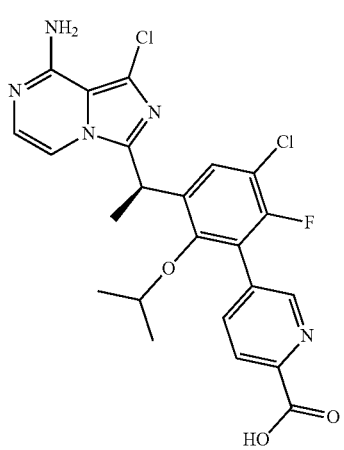

Compound 18B

Compound (16-12) (450 mg, 0.845 mmol) was dissolved in EtOH (10 mL), NaOH (169 mg, 4.23 mmol) in water (10 mL) was added and heated to 70° C. for 1 hr. Solvent was removed in vacuo. The pH was adjusted to 7. The crude product was got by filtration. The product (255 mg in 84% yield) was got by prep-HPLC. $^1$H NMR (400 MHz, DMSO-d6) d 8.77 (s, 1H), 8.14 (dd, J=29.9, 8.4 Hz, 2H), 7.53 (dd, J=31.1, 6.8 Hz, 2H), 7.06 (d, J=5.0 Hz, 1H), 6.75 (s, 2H), 4.91 (d, J=7.2 Hz, 1H), 3.65-3.54 (m, 1H), 1.67 (d, J=6.9 Hz, 3H), 0.98 (d, J=610 Hz, 3H), 0.76 (d, J=6.1 Hz, 3H). MS (ESI) m/e (M+1)$^+$ 504.

Compound 18 was separated by chiral column to afford two compounds, Compound 18A (the first and fast isomer) and Compound 1813 (the second and slow isomer), as white solids. Compound 18A was assigned as a (S)-configuration in a similar manner to Compound 40A as disclosed below.

Compound 18A: MS (ESI) m/e (M+1)$^+$ 504. $^1$H NMR (400 MHz, DMSO-d6) δ 8.80 (s, 1H), 8.11 (dd, J=33.9, 7.9 Hz, 2H), 7.52 (dd, J=28.5, 6.7 Hz, 2H), 7.08 (d, J=4.9 Hz, 1H), 6.74 (s, 2H), 4.91 (q, J=6.9 Hz, 1H), 3.67-3.53 (m, 1H), 1.67 (d, J=7.0 Hz, 3H), 0.98 (d, J=6.0 Hz, 3H), 0.77 (d, J-=6.0 Hz, 3H).

Compound 18B: MS (ESI) m/e (M+1)$^+$ 504. $^1$H NMR (400 MHz, DMSO-d6) δ 8.79 (s, 1H), 8.11 (dd, J=33.9, 7.9 Hz, 2H), 7.51 (dd, J=25.2, 6.7 Hz, 2H), 7.08 (d, J=4.8 Hz, 1H), 6.74 (s, 2H), 4.91 (q, J=7.1 Hz, 1H), 3.67-3.52 (m, 1H), 1.67 (d, J=7.0 Hz, 3H), 0.98 (d, J=6.0 Hz, 3H), 0.77 (d, J=6.1 Hz, 3H).

Chiral Separation:

| Column | CHIRALART Cellulose-SB |
| --- | --- |
| Column size | 2 cm × 25 cm, 5 μm |
| Injection | 1.0 ML |
| Mobile phase | Hex:EtOH(0.2% MSA) = 60:40 |
| Flow rate | 20 ml/min |
| Wave length | UV 220 nm |
| Temperature | 35° C. |
| Sample solution | 12.7 mg/ml in mobile phase |
| Prep-HPLC equipment | BJ-Prep-Gilson-HPLC |

Example 19

1-bromo-3-(1-(5-chloro-2-methoxy-4-methyl-3-(6-methylpyridin-3-yl)phenyl)ethyl) imidazo[1,5-a]pyrazin-8-amine (Compound 19)

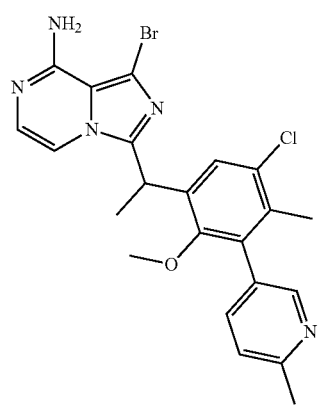 [SMILES: COc1c(C(C)c2nc(Br)c3c(N)nccn23)cc(Cl)c(C)c1-c1ccc(C)nc1]

The desired compound was prepared by the same manner as Compound 7 described in example 7 using 1-(5-chloro-2-hydroxy-4-methylphenyl)ethan-1-one as starting materials. $^1$H NMR (400 MH z, DMSO-d6): δ 8.30-8.37 (d, 1H), 7.59-7.67 (m, 1H), 7.36-7.40 (q, 2H), 7.22-7.23 (d, 1H), 7.00-7.01 (d, 1H), 6.77 (brs, 2H), 4.81-4.86 (q, 1H), 3.15 (s, 3H), 2.67 (s, 3H), 2.02 (s, 3H), 1.65-1.67 (d, 3H). MS (ESI) m/e (M+1)$^+$ 485.6.

Example 20

1-bromo-3-(1-(5-chloro-2-methoxy-3-(6-methoxy-pyridin-3-yl)-4-methylphenyl)ethyl)imidazo[1,5-a]pyrazin-8-amine (Compound 20)

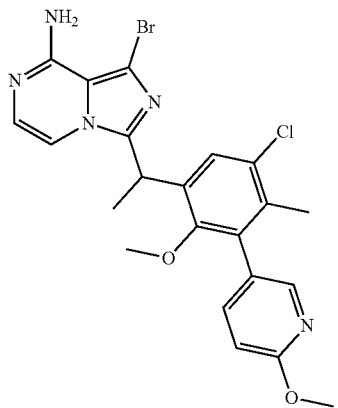 [SMILES: COc1ccc(-c2c(C)c(Cl)cc(C(C)c3nc(Br)c4c(N)nccn34)c2OC)cn1]

The desired compound was prepared by the similar manner as Compound 7 described in example 7 using 1-(5-chloro-2-hydroxy-4-methylphenyl)ethan-1-one as starting materials. $^1$H NMR (400 MHz, CD3OD): δ 7.89-7.93 (d, 1H), 7.46-7.54 (m, 1H), 7.26-7.27 (d, 1H), 7.12 (s, 1H), 6.81-6.84 (m, 3H), 3.87 (s, 3H), 3.16 (s, 3H), 2.03 (s, 3H), 1.66-1.68 (d, 3H). MS (ESI) m/e (M+1)$^+$ 501.6.

Example 21

1-bromo-3-(1-(5-chloro-3-(3,5-dimethylisoxazol-4-yl)-2-methoxy-4-methylphenyl)ethyl)imidazo[1,5-a]pyrazin-8-amine (Compound 21)

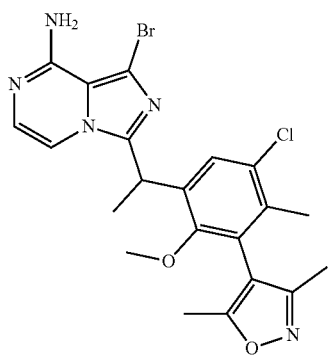 [SMILES: COc1c(C(C)c2nc(Br)c3c(N)nccn23)cc(Cl)c(C)c1-c1c(C)noc1C]

The desired compound was prepared by the similar manner as Compound 7 described in example 7 using 1-(5-chloro-2-hydroxy-4-methylphenyl)ethan-1-one as starting materials. $^1$H NMR (400 MHz, DMSO-d6): δ$_H$ 7.35-7.36 (q, 1H), 7.25 (s, 1H), 6.97-6.98 (q, 1H), 6.68 (brs, 2H), 4.81-4.84 (q, 1H), 3.22-3.30 (d, 3H), 2.16-2.25 (d, 3H), 1.94-2.04 (m, 6H), 1.66-1.70 (q, 3H). MS (ESI) m/e (M+1)$^+$ 489.6.

Example 22

1-bromo-3-(1-(5-chloro-3-(6-chloropyridin-3-yl)-2-methoxy-4-methylphenyl) ethyl) imidazo[1,5-a]pyrazin-8-amine (Compound 22)

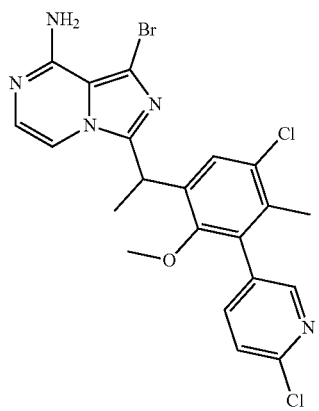 [SMILES: COc1c(C(C)c2nc(Br)c3c(N)nccn23)cc(Cl)c(C)c1-c1ccc(Cl)nc1]

The desired compound was prepared by the similar manner as Compound 7 described in example 7 using 1-(5-chloro-2-hydroxy-4-methylphenyl)ethan-1-one as starting materials. $^1$H NMR (400 MHz, DMSO-d$_6$): δ 8.33-8.39 (d, 1H), 7.81-7.90 (m, 1H), 7.65 (s, 1H), 7.38-7.39 (d, 1H), 7.26-7.28 (d, 1H), 7.00-7.01 (d, 1H), 6.68 (brs, 2H), 4.81-4.86 (q, 1H), 3.18 (s, 3H), 2.03 (s, 3H), 1.65-1.67 (d, 3H). MS (ESI) m/e (M+1)$^+$ 507.6.

Example 23

1-bromo-3-(1-(5-chloro-2-methoxy-4-methyl-3-(6-morpholinopyridin-3-yl)phenyl)ethyl)imidazo[1,5-a]pyrazin-8-amine (Compound 23)

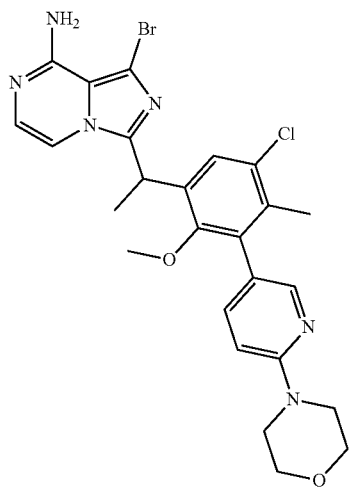 [SMILES: COc1c(C(C)c2nc(Br)c3c(N)nccn23)cc(Cl)c(C)c1-c1ccc(N2CCOCC2)nc1]

Compound 22 (20 mg, 0.04 mmol) was dissolved in morpholine (5 mL), and heated at 100° C. for 3 hrs. Then the solvent was removed in vacuo. The residue was purified by prep-HPLC to give the product (3 mg in 12% yield) as a white solid. $^1$H NMR (400 MHz, DMSO-d6): δ 8.04 (s, 1H), 7.59-7.61 (d, 1H), 7.57 (s, 1H), 7.29 (s, 1H), 7.05-7.07 (d, 1H), 6.94-6.96 (d, 1H), 4.90-4.92 (q, 1H), 3.72-3.74 (m, 4H), 3.51-3.52 (m, 4H), 3.16 (s, 3H), 2.07 (s, 3H), 1.66-1.68 (d, 3H). MS (ESI) m/e (M+1)+ 556.4.

Example 24

1-bromo-3-(1-(5-chloro-2-ethoxy-4-methyl-3-(6-(trifluoromethyl)pyridin-3-yl)phenyl)ethyl)imidazo[1,5-a]pyrazin-8-amine (Compound 24)

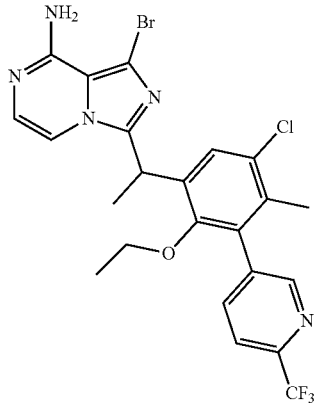 [SMILES: CCOc1c(C(C)c2nc(Br)c3c(N)nccn23)cc(Cl)c(C)c1-c1ccc(C(F)(F)F)nc1]

The desired compound was prepared by the similar manner as Compound 7 described in example 7 using 1-(5-chloro-2-hydroxy-4-methylphenyl)ethan-1-one as starting materials. $^1$H NMR (400 MHz, DMSO-d6): δ 8.69-8.76 (d, 1H), 8.04-8.15 (m, 2H), 7.40-7.41 (d, 1H), 7.30-7.33 (d, 1H), 7.03 (s, 1H), 7.00-7.01 (d, 1H), 6.69 (brs, 2H), 4.84-4.86 (q, 1H), 3.39-3.47 (m, 1H), 3.13-3.21 (m, 1H), 2.04 (s, 3H), 1.64-1.66 (d, 3H), 0.76-0.79 (t, 3H). MS (ESI) m/e (M+1)+ 554.1.

Example 25

1-chloro-3-(1-(5-chloro-2-ethoxy-4-methyl-3-(6-(trifluoromethyl)pyridin-3-yl)phenyl) ethyl)imidazo[1,5-a]pyrazin-8-amine (Compound 25)

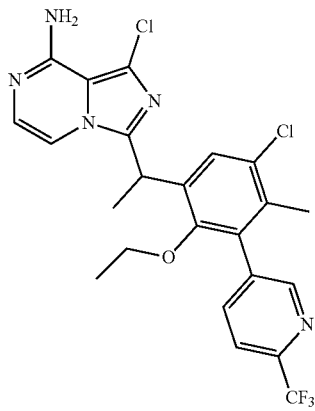 [SMILES: CCOc1c(C(C)c2nc(Cl)c3c(N)nccn23)cc(Cl)c(C)c1-c1ccc(C(F)(F)F)nc1]

The desired compound was prepared by the similar manner as Compound 8 described in example 8 using 1-(5-chloro-2-hydroxy-4-methylphenyl)ethan-1-one as starting materials. $^1$H NMR (400 MHz, DMSO-d6): δ 8.68-8.76 (d, 1H), 8.04-8.05 (m, 2H), 7.30-7.36 (m, 2H), 7.01 (s, 1H), 6.65 (brs, 2H), 4.83-4.85 (q, 1H), 3.44-3.47 (m, 1H), 3.20-3.22 (m, 1H), 2.04 (s, 3H), 1.66-1.67 (d, 3H), 0.76-0.79 (t, 3H). MS (ESI) m/e (M+1)+ 510.1.

Example 26

1-bromo-3-(1-(5-chloro-3-(6-chloropyridin-3-yl)-2-ethoxy-4-methylphenyl)ethyl) imidazo[1,5-a]pyrazin-8-amine (Compound 26)

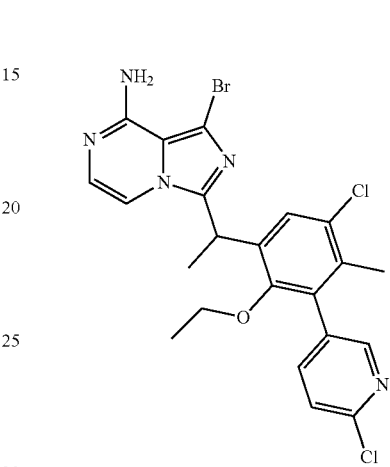

The desired compound was prepared by the similar manner as compound 7 described in example 7 using 1-(5-chloro-2-hydroxy-4-methylphenyl)ethan-1-one as starting materials. $^1$H NMR (400 MHz, DMSO-d6): δ 8.32-8.38 (d, 1H), 7.81-7.90 (m, 1H), 7.64-7.65 (m, 1H), 7.39 (s, 1H), 7.26-7.28 (d, 1H), 7.01-7.02 (d, 1H), 6.72 (brs, 2H), 4.81-4.86 (q, 1H), 3.44-3.45 (m, 1H), 3.20-3.22 (m, 1H), 2.04 (s, 3H), 1.65-1.67 (d, 3H), 0.80-0.85 (t, 3H). MS (ESI) m/e (M+1)+ 521.3.

Example 27

1-chloro-3-(1-(5-chloro-3-(6-chloropyridin-3-yl)-2-ethoxy-4-methylphenyl)ethyl)imidazo[1,5-a]pyrazin-8-amine (Compound 27)

Compound 27

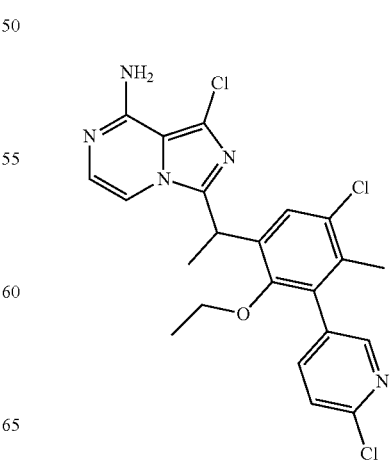

Compound 27A

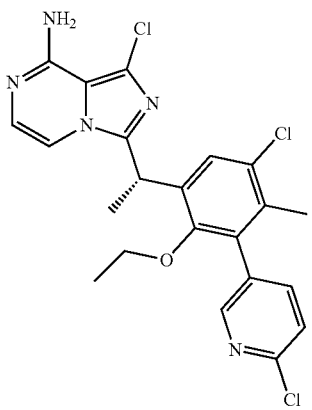

Compound 27B

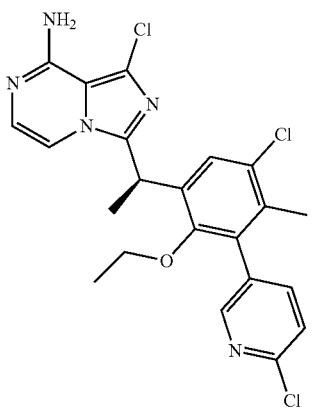

| Column | CHIRAL Cellulose-SB |
|---|---|
| Column size | 2 cm × 25 cm |
| Injection | 0.5 ML |
| Mobile phase | Hex(0.1% DEA):EtOH = 95:5 |
| Flow rate | 35 ml/min |
| Wave length | UV 220 nm |
| Temperature | 25° C. |
| Sample solution | 15 mg/ml in mobile phase |
| Prep-HPLC equipment | BJ-Prep-Gilson-HPLC |

Example 28

1-bromo-3-(1-(5-chloro-2-ethoxy-3-(6-methoxypyridin-3-yl)-4-methylphenyl)ethyl)imidazo[1,5-a]pyrazin-8-amine (Compound 28)

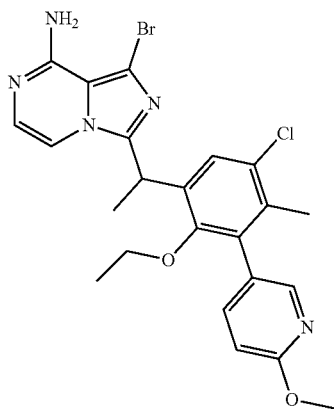 [SMILES: CCOc1c(C(C)c2nc(Br)c3c(N)nccn23)cc(Cl)c(C)c1-c1ccc(OC)nc1]

The desired compound was prepared by the similar manner as Compound 8 described in example 8 using 1-(5-chloro-2-hydroxy-4-methylphenyl)ethan-1-one as starting materials, which was separated by chiral column to give 27A (the first and fast isomer) and 27B (the second and slow isomer). Compound 27A was assigned as a (S)-configuration in a similar manner to Compound 40A as disclosed below.

Compound 27: $^1$H NMR (400 MHz, DMSO-d6): $\delta_H$ 8.32-8.39 (d, 1H), 7.81-7.90 (m, 1H), 7.64-7.65 (m, 1H), 7.37 (s, 1H), 7.27-7.30 (d, 1H), 6.97-7.02 (m, 2H), 4.81-4.86 (q, 1H), 3.43-3.48 (m, 1H), 3.20-3.22 (m, 1H), 2.04 (s, 3H), 1.65-1.70 (d, 3H), 0.82-0.85 (t, 3H). MS (ESI) m/e (M+1)$^+$ 478.1.

Compound 27A: $^1$H NMR (400 MHz, DMSO-d6): $\delta_H$ 8.32-8.39 (d, 1H), 7.81-7.90 (m, 1H), 7.64-7.65 (m, 1H), 7.37 (s, 1H), 7.27-7.30 (d, 1H), 6.97-7.02 (m, 2H), 4.81-4.86 (q, 1H), 3.43-3.48 (m, 1H), 3.20-3.22 (m, 1H), 2.04 (s, 3H), 1.65-1.70 (d, 3H), 0.82-0.85 (t, 3H). MS (ESI) m/e (M+1)$^+$ 478.1.

Compound 27B: $^1$H NMR (400 MHz, DMSO-d6): $\delta_H$ 8.32-8.39 (d, 1H), 7.81-7.90 (m, 1H), 7.64-7.65 (m, 1H), 7.37 (s, 1H), 7.27-7.30 (d, 1H), 6.97-7.02 (m, 2H), 4.81-4.86 (q, 1H), 3.43-3.48 (m, 1H), 3.20-3.22 (m, 1H), 2.04 (s, 3H), 1.65-1.70 (d, 3H), 0.82-0.85 (t, 3H). MS (ESI) m/e (M+1)$^+$ 478.1.

The desired compound was prepared by the similar manner as Compound 7 described in example 7 using 1-(5-chloro-2-hydroxy-4-methylphenyl)ethan-1-one as starting materials. $^1$H NMR (400 MHz, DMSO-d6): $\delta$ 8.04-8.10 (d, 1H), 7.61-7.69 (m, 1H), 7.38-7.40 (d, 1H), 7.20-7.21 (d, 1H), 7.01-7.03 (d, 1H), 6.92-6.94 (d, 1H), 6.74 (brs, 2H), 4.80-4.86 (q, 1H), 3.90 (s, 3H), 3.40-3.47 (m, 1H), 3.19-3.27 (m, 1H), 2.05 (s, 3H), 1.65-1.66 (d, 3H), 0.83-0.88 (t, 3H). MS (ESI) m/e (M+1)$^+$ 516.0.

Example 29

1-chloro-3-(1-(5-chloro-2-ethoxy-3-(6-methoxypyridin-3-yl)-4-methylphenyl)ethyl)imidazo[1,5-a]pyrazin-8-amine (Compound 29)

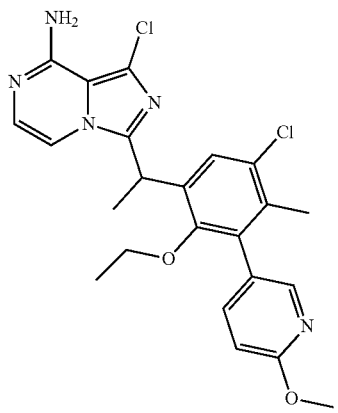 [SMILES: CCOc1c(C(C)c2nc(Cl)c3c(N)nccn23)cc(Cl)c(C)c1-c1ccc(OC)nc1]

The desired compound was prepared by the similar manner as Compound 8 described in example 8 using 1-(5-chloro-2-hydroxy-4-methylphenyl)ethan-1-one as starting materials. $^1$H NMR (400 MHz, DMSO-d6): δ 8.04-8.10 (d, 1H), 7.61-7.70 (m, 1H), 7.33-7.34 (d, 1H), 7.20-7.21 (d, 1H), 7.00-7.01 (d, 1H), 6.92-6.94 (d, 1H), 6.73 (brs, 2H), 4.80-4.85 (q, 1H), 3.90 (s, 3H), 3.40-3.46 (m, 1H), 3.21-3.27 (m, 1H), 2.05 (s, 3H), 1.64-1.66 (d, 3H), 0.83-0.86 (t, 3H). MS (ESI) m/e (M+1)$^+$ 472.1.

Example 30

1-bromo-3-(1-(5-chloro-2-ethoxy-3-(6-(2-methoxyethoxy)pyridin-3-yl)-4-methyl phenyl)ethyl)imidazo[1,5-a]pyrazin-8-amine (Compound 30)

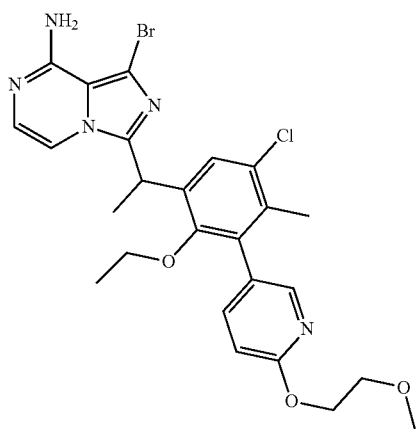 [SMILES: CCOc1c(C(C)c2nc(Br)c3c(N)nccn23)cc(Cl)c(C)c1-c1ccc(OCCOC)nc1]

The desired compound was prepared by the similar manner as Compound 7 described in example 7 using 1-(5-chloro-2-hydroxy-4-methylphenyl)ethan-1-one as starting materials. $^1$H NMR (400 MHz, DMSO-d6): δ 8.02-8.05 (d, 1H), 7.61-7.70 (m, 1H), 7.37-7.39 (d, 1H), 7.20-7.21 (d, 1H), 7.01-7.02 (d, 1H), 6.92-6.94 (d, 1H), 6.73 (brs, 2H), 4.81-4.85 (q, 1H), 4.41-4.43 (t, 2H), 3.67-3.70 (t, 2H), 3.44-3.49 (m, 1H), 3.31 (s, 3H), 3.21-3.27 (m, 1H), 2.05 (s, 3H), 1.64-1.66 (d, 3H), 0.85-0.88 (t, 3H). MS (ESI) m/e (M+1)$^+$ 560.1.

Example 31

1-chloro-3-(1-(5-chloro-2-ethoxy-3-(6-(2-methoxyethoxy)pyridin-3-yl)-4-methyl phenyl)ethyl)imidazo[1,5-a]pyrazin-8-amine (Compound 31)

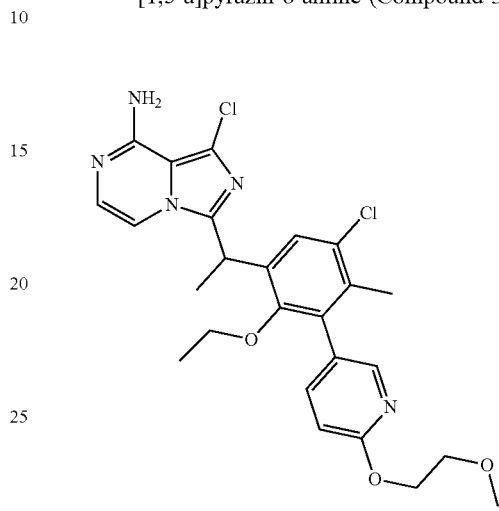

The desired compound was prepared by the similar manner as Compound 8 described in example 8 using 1-(5-chloro-2-hydroxy-4-methylphenyl)ethan-1-one as starting materials. $^1$H NMR (400 MHz, DMSO-d6): δ 8.02-8.08 (d, 1H), 7.62-7.70 (m, 1H), 7.32-7.33 (d, 1H), 7.21-7.22 (d, 1H), 7.00-7.01 (d, 1H), 6.92-6.94 (d, 1H), 6.74 (brs, 2H), 4.79-4.85 (q, 1H), 4.41-4.43 (t, 2H), 3.67-3.70 (t, 2H), 3.42-3.48 (m, 1H), 3.31 (s, 3H), 3.20-3.23 (m, 1H), 2.05 (s, 3H), 1.64-1.66 (d, 3H), 0.85-0.87 (t, 3H). MS (ESI) m/e (M+1)$^+$ 516.1.

Example 32

3-(1-(5-chloro-2-ethoxy-4-methyl-3-(6-(trifluoromethyl)pyridin-3-yl)phenyl)ethyl)-1-methylimidazo[1,5-a]pyrazin-8-amine (Compound 32)

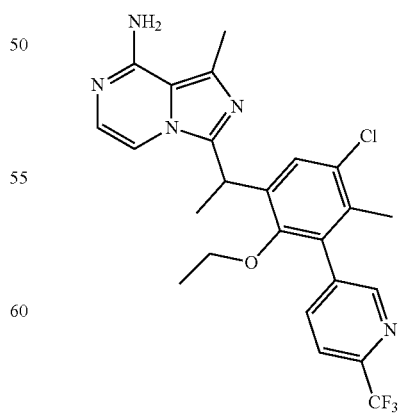

The desired compound was prepared by the similar manner as Compound 8 described in example 8 using 1-(5- chloro-2-hydroxy-4-methylphenyl)ethan-1-one as starting materials. $^1$H NMR (400 MHz, DMSO-d6): δ$_H$ 8.68-8.76 (d, 1H), 8.05-8.15 (m, 2H), 7.20-7.26 (m, 2H), 6.85-6.86 (d, 1H), 6.45 (brs, 2H), 4.74-4.77 (q, 1H), 3.44-3.48 (m, 1H), 3.23-3.26 (m, 1H), 2.60 (s, 3H), 2.03 (s, 3H), 1.66-1.67 (d, 3H), 0.78-0.82 (t, 3H). MS (ESI) m/e (M+1)$^+$ 490.1.

Example 33

1-chloro-3-(1-(4-chloro-2-ethoxy-5-fluoro-3-(6-(trifluoromethyl)pyridin-3-yl)phenyl)ethyl)imidazo[1,5-a]pyrazin-8-amine (Compound 33)

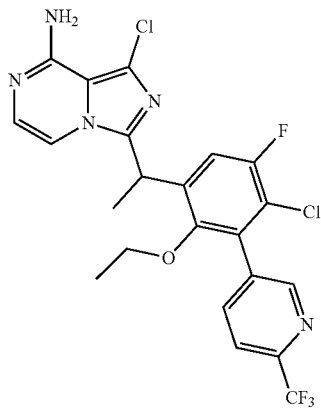

The desired compound was prepared by the similar manner as Compound 8 described in example 8 using 1-(4-chloro-5-fluoro-2-hydroxyphenyl)ethan-1-one as starting materials, $^1$H NMR (400 MHz, DMSO-d6): δ 8.81 (s, 1H), 8.19-8.20 (d, 1H), 8.07-8.09 (d, 1H), 7.41-7.43 (m, 2H), 7.02-7.03 (d, 1H), 6.75 (brs, 2H), 4.88-4.93 (q, 1H), 3.43-3.49 (m, 1H), 3.20-3.24 (m, 1H), 1.66-1.68 (d, 3H), 0.77-0.80 (t, 3H). MS (ESI) m/e (M+1)$^+$ 514.1.

Example 34

3-(1-(4-chloro-2-ethoxy-5-fluoro-3-(6-(trifluoromethyl)pyridin-3-yl)phenyl) ethyl)-1-methylimidazo[1,5-a]pyrazin-8-amine (Compound 34)

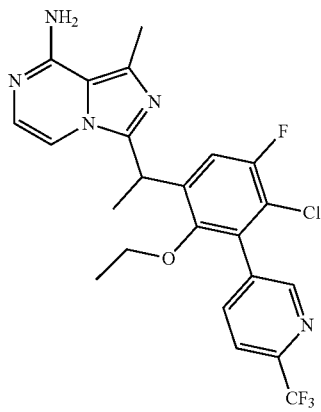 [SMILES: CCOc1c(C(C)c2nc(C)c3c(N)nccn23)cc(F)c(Cl)c1-c1ccc(C(F)(F)F)nc1]

The desired compound was prepared by the similar manner as Compound 8 described in example 8 using 1-(4- chloro-5-fluoro-2-hydroxyphenyl)ethan-1-one as starting materials. $^1$H NMR (400 MHz, DMSO-d6): δ 8.81 (s, 1H), 8.19-8.20 (d, 1H), 8.07-8.09 (d, 1H), 7.38-7.40 (m, 2H), 6.75 (brs, 2H), 4.86-4.89 (q, 1H), 3.44-3.48 (m, 1H), 3.20-3.22 (m, 1H), 2.67 (s, 3H), 1.66-1.68 (d, 3H), 0.83-0.85 (t, 3H). MS (ESI) m/e (M+1)$^+$ 494.1.

Example 35

1-chloro-3-(1-(4-chloro-5-fluoro-2-isopropoxy-3-(6-(trifluoromethyl)pyridin-3-yl)phenyl)ethyl)imidazo[1,5-a]pyrazin-8-amine (Compound 35)

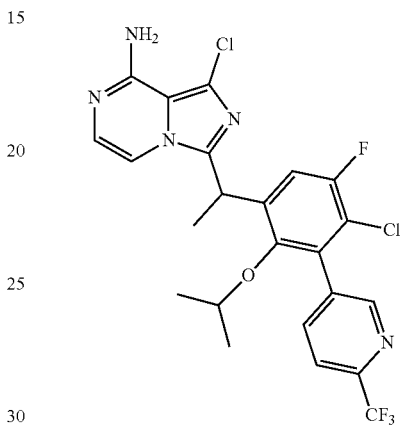

The desired compound was prepared by the similar manner as Compound 8 described in example 8 using 1-(4-chloro-5-fluoro-2-hydroxyphenyl)ethan-1-one as starting materials. $^1$H NMR (400 MHz, DMSO-d6): δ 8.72-8.87 (d, 1H), 8.10-8.26 (m, 2H), 8.07-8.09 (d, 1H), 7.47-7.48 (m, 2H), 7.05-7.12 (m, 1H), 6.71 (brs, 2H), 4.89-4.94 (q, 1H), 3.51-3.56 (m, 2H), 1.67-1.69 (d, 3H), 0.96 (s, 3H), 0.71-0.73 (t, 3H). MS (ESI) m/e (M+1)$^+$ 528.1.

Example 36

1-chloro-3-(1-(4,5-dichloro-2-ethoxy-3-(6-(trifluoromethyl)pyridin-3-yl)phenyl)ethyl)imidazo[1,5-a]pyrazin-8-amine (Compound 36)

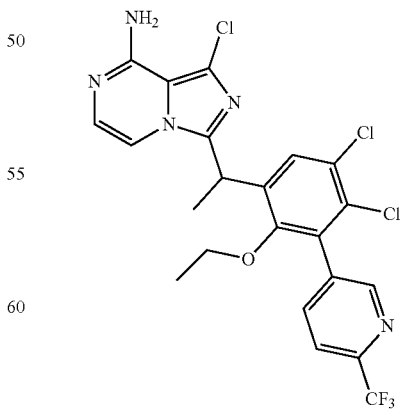

The desired compound was prepared by the similar manner as Compound 8 described in example 8 using 1-(4,5- dichloro-2-hydroxyphenyl)ethan-1-one as starting materials. ¹H NMR (400 MHz, DMSO-d6): δ 8.70-8.80 (d, 1H), 8.04-8.7 (m, 2H), 7.56-7.67 (m, 2H), 7.05-7.06 (d, 1H), 4.93-4.94 (q, 1H), 3.43-3.49 (m, 1H), 3.25-3.27 (m, 1H), 1.66-1.68 (d, 3H), 0.75-0.77 (t, 3H). MS (ESI) m/e (M+1)⁺ 530.1.

Example 37

1-chloro-3-(1-(4,5-dichloro-2-isopropoxy-3-(6-(trifluoromethyl)pyridin-3-yl)phenyl)ethyl)imidazo[1,5-a]pyrazin-amine (Compound 37)

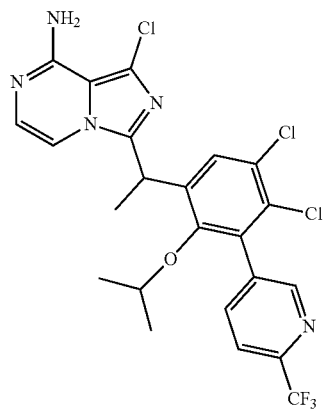 [SMILES: CC(C)Oc1c(C(C)c2nc(Cl)c3c(N)nccn23)cc(F)c(Cl)c1-c1ccc(C(F)(F)F)nc1]

The desired compound was prepared by the similar manner as Compound 8 described in example 8 using 1-(4,5-dichloro-2-hydroxyphenyl)ethan-1-one as starting materials. ¹H NMR (400 MHz, DMSO-d6): δ 8.70-8.87 (d, 1H), 8.07-8.26 (m, 2H), 7.63-7.68 (d, 1H), 7.45-7.49 (m, 1H), 7.04-7.06 (m, 1H), 6.75 (brs, 2H), 4.89-4.92 (q, 1H), 3.55-3.56 (m, 2H), 1.67-1.68 (d, 3H), 0.92-0.97 (q, 3H), 0.68-0.70 (t, 3H). MS (ESI) m/e (M+1)⁺ 544.0.

Example 38

1-bromo-3-(1-(5-chloro-2-isopropoxy-4-methyl-3-(6-(trifluoromethyl)pyridin-3-yl)phenyl)ethyl)imidazo[1,5-a]pyrazin-8-amine (Compound 38)

Compound 38

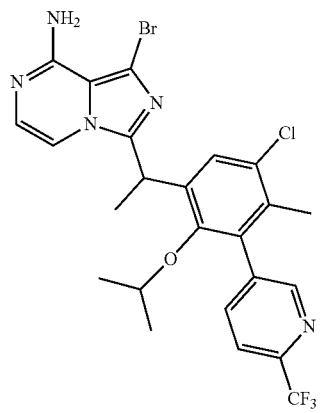

Compound 38A

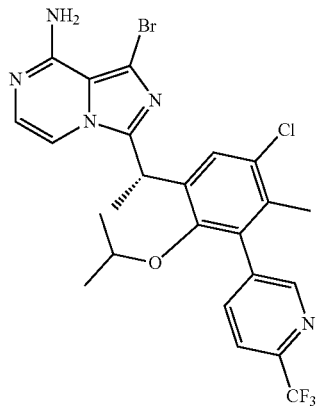

Compound 38B

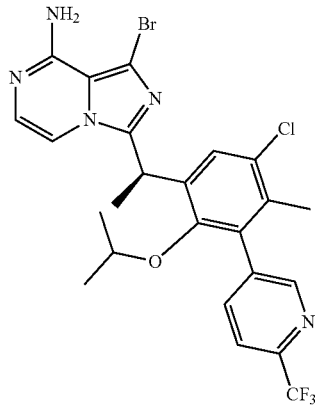

Step 1: 1-(5-chloro-2-hydroxy-3-iodo-4-methylphenyl)ethan-1-one (38-1)

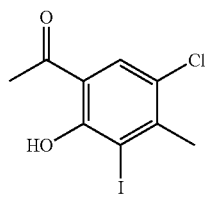

To the solution of 1-(5-chloro-2-hydroxy-4-methylphenyl)ethan-1-one (28.6 g, 155 mmol) in AcOH (250 mL) was added 1-iodopyrrolidine-2,5-dione (52.3 g, 232 mmol) and stirred at 80° C. for overnight. After completed, the solvent was evaporated in vacuo and the residue was dissolved with ethyl acetate. The resulting mixture was washed with aqueous $Na_2CO_3$ solution, aqueous $Na_2S_2O_3$ solution and brine, dried over $Na_2SO_4$, filtered and evaporated in vacuo. The residue was purified by column chromatography (PE/EA=25/1) to give the product as yellow oil. ¹H NMR (400 MHz, CDCl₃) δ 13.22 (s, 1H), 7.72 (s, 1H), 2.67 (s, 3H), 2.64 (s, 3H). MS (M+H)⁺ 310.9.

Step 2: 1-(5-chloro-2-hydroxy-4-methyl-3-(6-(trifluoromethyl)pyridin-3-yl)phenyl)ethan-1-one (38-2)

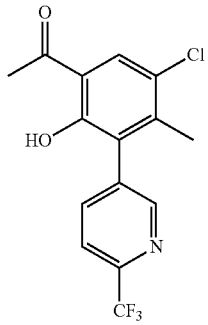

The reaction mixture of 1-(5-chloro-2-hydroxy-3-iodo-4-methylphenyl)ethan-1-one (621 mg, 2 mmol), (6-(trifluoromethyl)pyridin-3-yl)boronic acid (382 mg, 2 mmol), $K_2CO_3$ (828 mg, 6 mmol) and $Pd(PPh_3)_4$ (231 mg, 0.2 mmol) in 1,4-dioxane (20 mL) and water (4 mL) under nitrogen was stirred at 80° C. for overnight. After completed, the mixture was filtered and evaporated in vacuo. The residue was purified by column chromatography (PE/EA=20/1) to give the product (300 g in 45% yield) as a yellow solid. $^1$H NMR (400 MHz, $CDCl_3$): δ 12.51 (s, 1H), 8.60 (s, 1H), 7.84 (s, 1H), 7.79 (s, 2H), 2.67 (s, 3H), 2.21 (s, 3H). MS (M+H)$^+$ 330.0.

Step 3: 1-(5-chloro-2-isopropoxy-4-methyl-3-(6-(trifluoromethyl)pyridin-3-yl)phenyl)ethan-1-one (38-3)

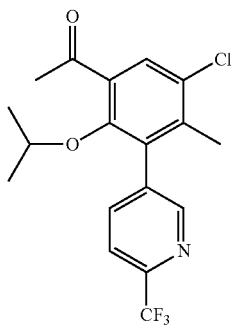 [SMILES: CC(=O)c1cc(Cl)c(C)c(-c2ccc(C(F)(F)F)nc2)c1OC(C)C]

The reaction mixture of I-(5-chloro-2-hydroxy-4-methyl-3-(6-(trifluoromethyl)pyridin-3-yl)phenyl)ethan-1-one (300 mg, 0.91 mmol), 2-Iodopropane (618 mg, 3.64 mmol) and $K_2CO_3$ (502 mg, 3.64 mmol) in DMF (15 ml) under $N_2$ was stirred at 60° C. for overnight. After completed, the mixture was poured to water and extracted with ethyl acetate. The combined organic layers were washed with $Na_2SO_4$, filtered and evaporated in vacuo. The residue was purified by column chromatography (PE/EA=10/1) to give the product as a brown solid (210 mg in 62% yield). $^1$H NMR (400 MHz, $CDCl_3$) δ 8.67 (s, 1H), 7.87-7.80 (m, 21), 7.64 (s, 1H), 3.70-3.48 (m, 1H), 2.63 (s, 3H), 2.20 (s, 3H), 0.87 (s, 6H). MS (M+H)$^+$ 372.0.

Step 4: 1-(5-chloro-2-isopropoxy-4-methyl-3-(6-(trifluoromethyl)pyridin-3-yl)phenyl)ethan-1-ol (38-4)

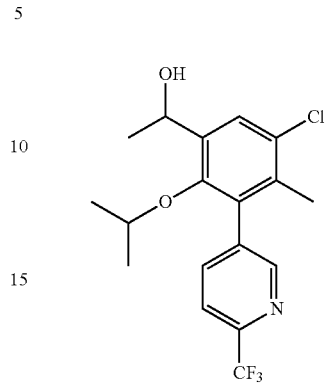

To the solution of 1-(5-chloro-2-isopropoxy-4-methyl-3-(6-(trifluoromethyl)pyridin-3-yl)phenyl)ethan-1-one (210 mg, 0.57 mmol) in MeOH (10 mL) under nitrogen was added $NaBH_4$ (32 mg, 0.85 mmol) at 0° C. and stirred while the ice was melting for overnight. Then the reaction was quenched with 1N hydrochloride to pH~7 and the mixture was evaporated in vacuo. The residue was purified by column chromatography (PE/EA=10/1) to give the product as a colorless gum (190 mg in 89% yield). $^1$H NMR (400 MHz, $CDCl_3$) δ 8.66 (s, 1H) 7.85-7.78 (m, 2H), 7.58 (d, J=9.1 Hz, 1H), 5.23 (q, J=6.4 Hz, 1H), 3.52 (dt, J=12.3, 6.1 Hz, 1H), 2.15 (s, 3H), 1.51 (d, J=6.8 Hz, 3H), 0.96-0.80 (m, 6H). LC-MS (M+H)$^+$ 374.1.

Step 5: 5-(3-chloro-5-(1-chloroethyl)-6-isopropoxy-2-methylphenyl)-2-(trifluoromethyl)pyridine (38-5)

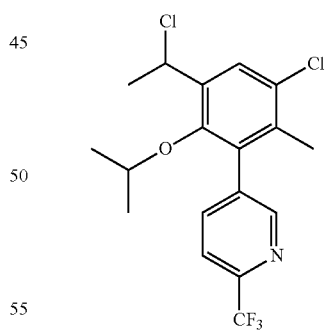

To the solution of 1-(5-chloro-2-isopropoxy-4-methyl-3-(6-(trifluoromethyl)pyridin-3-yl)phenyl)ethan-1-ol (600 mg, 1.61 mmol) in DCM (20 mL at room temperature was added $SOCl_2$ (0.5 mL) and stirred for 1 hr. After completed, the mixture was diluted with $CH_2Cl_2$ washed with saturated $NaHCO_3$ aqueous solution and brine, dried over $Na_2SO_4$, filtered and evaporated in vacuo to give the product (590 mg in 93% yield) as a brown oil. LC-MS (M+H)$^+$ 392.0.

Step 6: 2-(5-chloro-2-isopropoxy-4-methyl-3-(6-(trifluoromethyl)pyridin-3-yl)phenyl)propanenitrile (38-6)

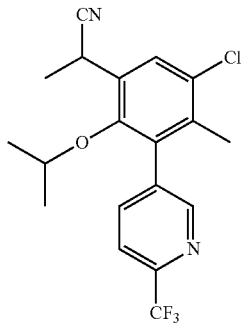 [SMILES: Cc1c(Cl)cc(C(C)C#N)c(OC(C)C)c1-c1ccc(C(F)(F)F)nc1]

The reaction of 5-(3-chloro-5-(1-chloroethyl)-6-isopropoxy-2-methylphenyl)-2-(trifluoromethyl)pyridine (590 mg, 1.51 mmol) and NaCN (111 mg, 2.26 mmol) in DMF (5 mL) was stirred at 80° C. for overnight. After completed, the reaction was quenched with aqueous KOH solution and NaClO. The resulting mixture was extracted with ethyl acetate. The combine organic layers were washed with water, brine and dried over $Na_2SO_4$, filtered and evaporated in vacuo. The residue was purified by column chromatography (PE/EA=4/1) to give the product (610 mg) as a colorless oil which was solidified at room temperature. LC-MS (M+H)$^+$ 383.1.

Step 7: 2-(5-chloro-2-isopropoxy-4-methyl-3-(6-(trifluoromethyl)pyridin-3-yl)phenyl)propanoic Acid (38-7)

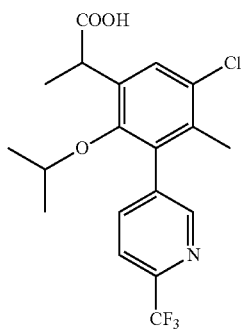 [SMILES: Cc1c(Cl)cc(C(C)C(=O)O)c(OC(C)C)c1-c1ccc(C(F)(F)F)nc1]

To the solution of 2-(5-chloro-2-isopropoxy-4-methyl-3-(6-(trifluoromethyl)pyridin-3-yl)phenyl)propanenitrile (610 mg, 1.6 mmol) in EtOH (20 mL) was added a solution of KOH (268 mg, 4.59 mmol) in water and stirred at 90° C. for overnight. After completed, the reaction mixture was neutralized by hydrochloride to pH~7 then evaporated in vacuo. The residue was dissolved with MeOH, filtered and evaporated in vacuo to give the product (680 mg). LC-MS (M+H)$^+$ 402.1.

Step 8: 2-(5-chloro-2-isopropoxy-4-methyl-3-(6-(trifluoromethyl)pyridin-3-yl)phenyl)-N-((3-chloropyrazin-2-yl)methyl)propanamide (38-8)

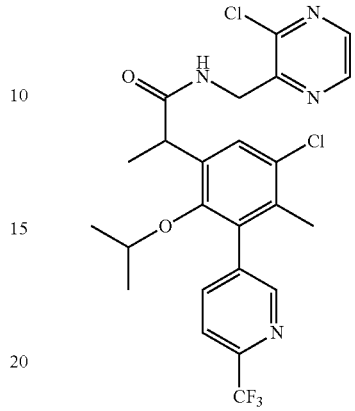

The solution of 2-(5-chloro-2-isopropoxy-4-methyl-3-(6-(trifluoromethyl)pyridin-3-yl)phenyl)propanoic acid (680 mg, 1.6 mmol), (3-chloropyrazin-2-yl)methanamine hydrochloride (366 mg, 2.56 mmol), Benzotriazole-1-yl-oxytripyrrolidinophosphonium hexafluorophosphate (1.25 g, 2.4 mmol) and N,N-Diisopropylethylamine (413 mg, 3.2 mmol) in DMF (10 mL) was stirred at room temperature for overnight. After completed, the solvent was evaporated in vacuo and the residue was dissolved with ethyl acetate. The mixture was washed with water, brine and dried over $Na_2SO_4$, filtered and evaporated in vacuo to give the product (850 mg) which was used directly for the next step without further purification. MS (M+H)$^+$ 527.1, 529.1.

Step 9: 8-chloro-3-(1-(5-chloro-2-isopropoxy-4-methyl-3-(6-(trifluoromethyl)pyridin-3-yl)phenyl)ethyl)imidazo[1,5-a]pyrazine (38-9)

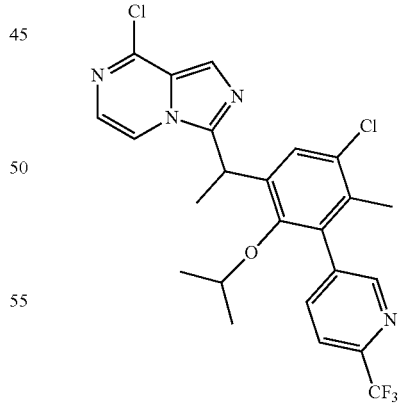

To the solution of 2-(5-chloro-2-isopropoxy-4-methyl-3-(6-(trifluoromethyl)pyridin-3-yl)phenyl)-N-((3-chloropyrazin-2-yl)methyl)propanamide (850 mg, crude) in $CH_2Cl_2$ (20 mL) was added trifluoromethanesulfonic anhydride (0.5 mL) at room temperature. Then pyridine (0.5 mL) was added dropwise slowly and the mixture was stirred for 20 mins. The mixture was washed with a saturated $NaHCO_3$ aqueous solution and brine, dried over Na$_2$SO$_4$, filtered and evaporated in vacuo. The residue was purified by column chromatography (PE/EA=6/1 to 1/1) to give the product (170 mg in 20.6% yield, for two steps) as a yellow solid. LC-MS (M+H)$^+$ 509.1.

Step 10 1-bromo-8-chloro-3-(1-(5-chloro-2-isopropoxy-4-methyl-3-(6-(trifluoromethyl)pyridin-3-yl)phenyl)ethyl)imidazo[1,5-a]pyrazine (38-10)

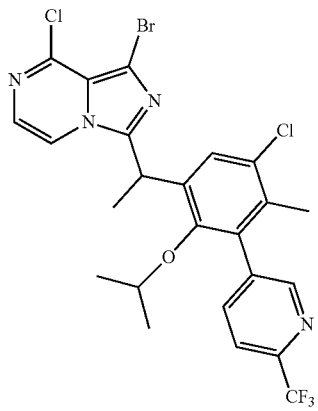 [SMILES: Cc1c(Cl)cc(C(C)c2nc(Br)c3c(Cl)nccn23)c(OC(C)C)c1-c1ccc(C(F)(F)F)nc1]

The reaction mixture of 8-chloro-3-(1-(5-chloro-2-isopropoxy-4-methyl-3-(6-(trifluoromethyl)pyridin-3-yl)phenyl)ethyl)imidazo[1,5-a]pyrazine (170 mg, 0.33 mmol) and 1-bromopyrrolidine-2,5-dione (71 mg, 0.4 mmol) in DMF (10 mL) was stirred at room temperature for overnight. After completed, the solvent was evaporated in vacuo and the residue was purified by column chromatography (PE/EA=4/1) to give the product (220 mg) as a colorless oil which solidified at room temperature. MS (M+H)$^+$ 587.0, 589.0.

Step 11: 1-bromo-3-(1-(5-chloro-2-isopropoxy-4-methyl-3-(6-(trifluoromethyl)pyridin-3-yl)phenyl)ethyl)imidazo[1,5-a]pyrazin-8-amine (38-11)

The reaction mixture of 1-bromo-8-chloro-3-(1-(5-chloro-2-isopropoxy-4-methyl-3-(6-(trifluoromethyl)pyridin-3-yl)phenyl)ethyl)imidazo[1,5-a]pyrazine (220 mg, impure) and NH$_3$ in i-PrOH (10 mL) was stirred at 90° C. for overnight. After completed, the mixture was evaporated in vacuo. The residue was purified by column chromatography (CH$_2$Cl$_2$/MeOH=30/1) to obtain the desired product (120 mg), which was further separated by chiral-HPLC to give two compounds, Compound 38A (52 mg, the first and fast isomer) and 38B (39 mg, the second and slow isomer), as white solids. Compound 38A was assigned as a (S)-configuration in a similar manner to Compound 40A as disclosed below.

Compound 38: $^1$H NMR (400 MHz, CDCl$_3$) δ 8.64 (d, J=29.8 Hz, 1H), 7.91-7.66 (m, 2H), 7.48-7.31 (m, 2H), 7.00 (s, 1H), 5.93 (s, 2H), 4.76 (q, J=6.9 Hz, 1H), 3.59 (brs, 1H), 2.09 (s, 3H), 1.86 (d, J=7.1 Hz, 3H), 1.12 (d, J=6.1 Hz, 3H), 0.85 (s, 3H). MS (M+H)$^+$ 570.0.

Compound 38A: $^1$H NMR (400 MHz, CDCl$_3$) δ 8.63 (d, J=36.6 Hz, 1H), 7.83-7.72 (m, 2H), 7.51-7.31 (m, 2H), 6.94 (d, J=5.3 Hz, 1H), 4.78 (q, J=7.1 Hz, 1H), 3.58 (brs, 1H), 2.10 (s, 3H), 1.86 (d, J=7.1 Hz, 3H), 1.12 (d, J=6.0 Hz, 3H), 0.86 (s, 3H). MS (M+H)$^+$ 570.0.

Compound 38B: $^1$H NMR (400 MHz, CDCl$_3$) δ 8.64 (d, J=32.2 Hz, 1H), 7.83-7.74 (m, 2H). 7.48-7.33 (m, 2H), 6.97 (d, J=5.2 Hz, 1H), 4.77 (q, J=7.1 Hz, 1H), 3.66-3.47 (m, 1H), 2.09 (s, 3H), 1.86 (d, J=7.1 Hz, 3H), 1.12 (d, J=6.1 Hz, 3H), 0.85 (d, J=5.1 Hz, 3H). LC-MS (M+H)$^+$ 570.0.

| Column | CHIRAL Cellulose-SB |
| --- | --- |
| Column size | 2 cm × 25 cm |
| Injection | 0.5 ML |
| Mobile phase | Hex(0.1% DEA):EtOH = 95:5 |
| Flow rate | 35 ml/min |
| Wave length | UV 220 nm |
| Temperature | 25° C. |
| Sample solution | 15 mg/ml in mobile phase |
| Prep-HPLC equipment | BJ-Prep-Gilson-HPLC |

Example 39

1-bromo-3-(1-(5-chloro-2-ethoxy-4-methyl-3-(5-(trifluoromethyl)pyridin-3-yl)phenyl)ethyl)imidazo[1,5-a]pyrazin-8-amine (Compound 39)

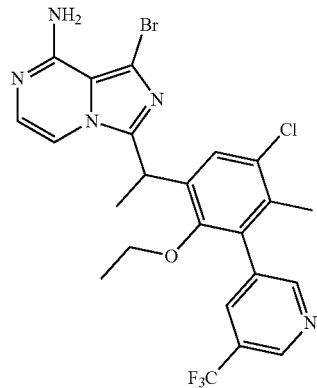

Step 1: 1-(5-chloro-2-ethoxy-4-methyl-3-(5-(trifluoromethyl)pyridin-3-yl)phenyl)ethan-1-ol (39-1)

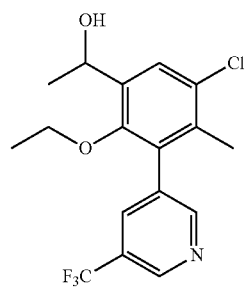 [SMILES: CCOc1c(C(C)O)cc(Cl)c(C)c1-c1cncc(C(F)(F)F)c1]

Compound (39-1) was prepared in the similar manner as compound (38-2) described in example 38 from 1-(5-chloro-2-ethoxy-3-iodo-4-methylphenyl)ethan-1-ol (650 mg). Afford compound (39-1) (370 g in 54% yield) as a yellow solid. $^1$H NMR (400 MH z, CDCl$_3$) (8.91 (s, 1H), 8.70 (d, J=25.7 Hz, 1H), 7.93 (s, 1H), 7.58 (s, 1H), 5.17 (q, J=6.3 Hz, 1H), 3.39 (brs, 2H), 2.15 (s, 3H), 1.54 (d, J=6.4 Hz, 3H), 0.94 (t, J=7.0 Hz, 3H). MS (M+H)$^+$ 360.1.

Step 2: 3-(3-chloro-5-(1-chloroethyl)-6-ethoxy-2-methylphenyl)-5-(trifluoromethyl)pyridine (39-2)

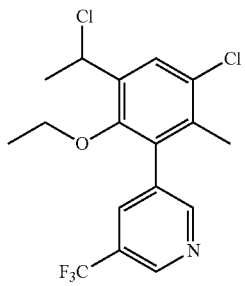 [SMILES: CCOc1c(C(C)Cl)cc(Cl)c(C)c1-c1cncc(C(F)(F)F)c1]

Compound (39-2) was prepared in the similar manner as compound (38-5) described in example 38 from 1-(5-chloro-2-ethoxy-4-methyl-3-(5-(trifluoromethyl)pyridin-3-yl)phenyl)ethan-1-ol (370 mg). Afford Compound (39-2) (367 mg in 94% yield) as a brown gum which solidified at room temperature. MS (M+H)$^+$ 378.0, 380.0.

Step 3: 2-(5-chloro-2-ethoxy-4-methyl-3-(5-(trifluoromethyl)pyridin-3-yl)phenyl) propanenitrile (39-3)

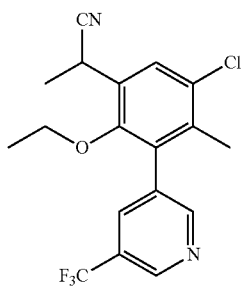 [SMILES: CCOc1c(C(C)C#N)cc(Cl)c(C)c1-c1cncc(C(F)(F)F)c1]

Compound (39-3) was prepared in the similar manner as compound (38-6) described in example 38 from 3-(3-chloro-5-(I-chloroethyl)-6-ethoxy-2-methylphenyl)-5-(trifluoromethyl)pyridine (367 mg). Afford Compound (39-3) (200 mg in 55% yield) as a colorless oil which was solidified at room temperature. MS (M+H)$^+$ 369.0, 371.0.

Step 4: 2-(5-chloro-2-ethoxy-4-methyl-3-(5-(trifluoromethyl)pyridin-3-yl)phenyl)propanoic Acid (39-4)

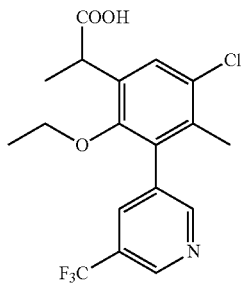 [SMILES: CCOc1c(C(C)C(=O)O)cc(Cl)c(C)c1-c1cncc(C(F)(F)F)c1]

Compound (39-4) was prepared in the similar manner as compound (38-7) described in example 38 from 2-(5-chloro-2-ethoxy-4-methyl-3-(5-(trifluoromethyl)pyridin-3-yl)phenyl)propanenitrile (200 mg). Afford Compound (39-4) (190 mg, in 91% yield). MS (M+H)$^+$ 388.1.

Step 5: 2-(5-chloro-2-ethoxy-4-methyl-3-(5-(trifluoromethyl)pyridin-3-yl)phenyl)-N-((3-chloropyrazin-2-yl)methyl)propanamide (39-5)

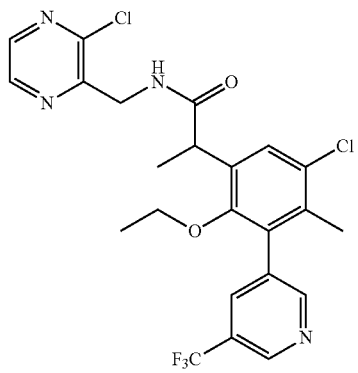 [SMILES: CCOc1c(C(C)C(=O)NCc2nccnc2Cl)cc(Cl)c(C)c1-c1cncc(C(F)(F)F)c1]

Compound (39-5) was prepared in the similar manner as compound (38-8) described in example 38 from 2-(5-chloro-2-ethoxy-4-methyl-3-(5-(trifluoromethyl)pyridin-3-yl)phenyl)propanoic acid (190 mg). Afford crude product (850 mg) which was used directly for the next step without further purification. MS (M+H)$^+$ 513.1, 515.1.

Step 6: 8-chloro-3-(1-(5-chloro-2-ethoxy-4-methyl-3-(5-(trifluoromethyl)pyridin-3-yl)phenyl)ethyl)imidazo[1,5-a]pyrazine (39-6)

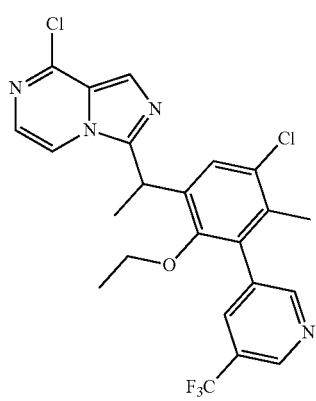 [SMILES: CCOc1c(C(C)c2ncc3c(Cl)nccn23)cc(Cl)c(C)c1-c1cncc(C(F)(F)F)c1]

Compound (39-6) was prepared in the similar manner as compound (38-9) described in example 38 from 2-(5-chloro-2-ethoxy-4-methyl-3-(5-(trifluoromethyl)pyridin-3-yl)phenyl)-N-((3-chloropyrazin-2-yl) methyl)propanamide. Afford Compound (39-6) (90 mg in 36.7% yield, for two steps). $^1$H NMR (400 MHz, CDCl$_3$) δ 8.95 (s, 1H), 8.74 (s, 1H), 7.88 (d, J=15.8 Hz, 2H), 7.71 (s, 1H), 7.34 (d, J=5.0 Hz, 1H), 7.28 (s, 1H), 4.81 (q, J=7.1 Hz, 1H), 3.59 (ds, 1H), 3.32 (dd, J=15.3, 7.8 Hz, 1H), 2.10 (s, 3H), 1.91 (d, J=7.1 Hz, 3H), 1.01 (brs, 3H), M S (M+H)$^+$ 495.1, 497.1.

Step 7: 1-bromo-8-chloro-3-(1-(5-chloro-2-ethoxy-4-methyl-3-(5-(trifluoromethyl)pyridin-3-yl)phenyl)ethyl)imidazo[1,5-a]pyrazine (39-7)

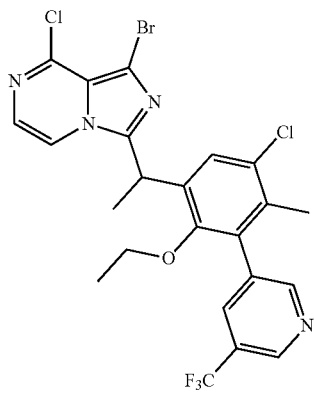

Compound (39-7) was prepared in the similar manner as compound (38-10) from 8-chloro-3-(1-(5-chloro-2-ethoxy-4-methyl-3-(5-(trifluoromethyl)pyridin-3-yl)phenyl)ethyl)imidazo[1,5-a]pyrazine (90 mg). Afford Compound (39-7) (57 mg) as a colorless oil which solidified at room temperature. MS (M+H)+ 573.0, 575.0.

Step 8: 1-bromo-3-(1-(5-chloro-2-ethoxy-4-methyl-3-(5-(trifluoromethyl)pyridin-3-yl)phenyl)ethyl)imidazo[1,5-a]pyrazin-8-amine (39-8)

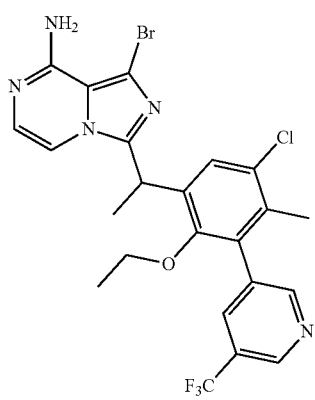 [SMILES: CCOc1c(C(C)c2nc(Br)c3c(Cl)nccn23)cc(Cl)c(C)c1-c1cncc(C(F)(F)F)c1]

Compound (39-8) was prepared in the similar manner as compound (38-11) described in example 38 from 1-bromo-8-chloro-3-(1-(5-chloro-2-ethoxy-4-methyl-3-(5-(trifluoromethyl)pyridin-3-yl)phenyl)ethyl)imidazo[1,5-a]pyrazine (57 mg). Afford compound (39-8) (28 mg in 50% yield) as off-white solid. $^1$H NMR (400 MHz, CDCl$_3$) δ 8.94 (d, J=1.3 Hz, 1H), 8.73 (s, 1H), 7.89 (s, 1H), 7.29 (s, 1H), 7.24 (d, J=5.1 Hz, 1H), 6.99 (d, J=5.0 Hz, 1H), 4.70 (q, J=7.1 Hz, 1H), 3.55 (ds, 1H), 3.31 (dq, J=14.2, 7.0 Hz, 1H), 2.10 (s, 3H), 1.84 (d, J=7.1 Hz, 3H), 1.00 (t, J=7.0 Hz, 3H). MS (M+H)+ 554.1.

Example 40

1-chloro-3-(1-(5-chloro-4-fluoro-2-isopropoxy-3-(6-(trifluoromethyl)pyridin-3-yl)phenyl)ethyl)imidazo[1,5-a]pyrazin-8-amine (Compound 40)

Compound 40

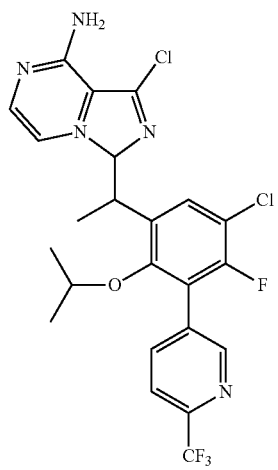

Compound 40A

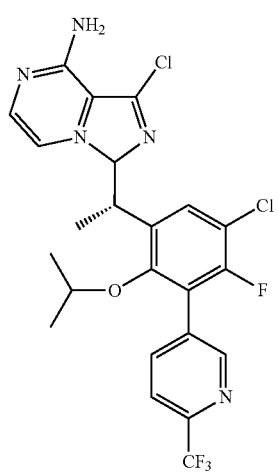

Compound 40B

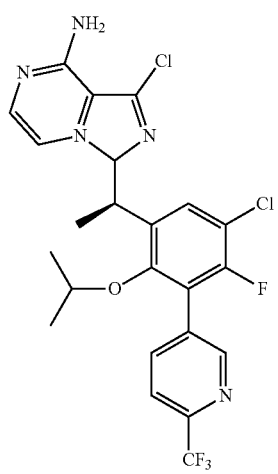

Step 1: 1-(5-chloro-4-fluoro-2-hydroxyphenyl)ethan-1-one (40-1)

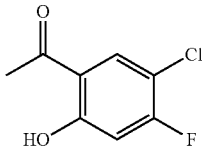

The reaction mixture of 4-chloro-3-fluorophenol (146.5 g, 1 mol) and acetyl chloride (157 g, 2 mol) was stirred at 60° C. for 2 hrs. Then the mixture was cooled to 0° C. and AlCl$_3$ (240 g, 1.8 mol) was added in portions. The reaction mixture was stirred at 180° C. for 2 hrs. The mixture was cooled to room temperature and 1N HCl (1.5 L) was added. The resulting mixture was extracted with ethyl acetate. The combined organic layers were washed with brine, dried over Na$_2$SO$_4$, filtered and evaporated in vacuo. The residue was dissolved in hexane and filtered through silica gel. The solvent was evaporated in vacuo to give the product (177 g in 93% yield) as a yellow solid. $^1$H NMR (400 MHz, DMSO-d6) δ 12.16 (s, 1H), 8.07 (d, J=8.6 Hz, 1H), 7.05 (d, J=10.9 Hz, 1H), 2.64 (s, 3H).

Step 2: 1-(5-chloro-4-fluoro-2-hydroxy-3-iodophenyl)ethan-1-one (40-2)

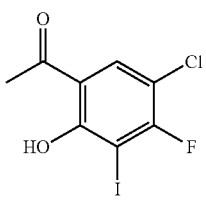

The reaction mixture of 1-(5-chloro-4-fluoro-2-hydroxyphenyl)ethan-1-one (88 g, 0.467 mol) and 1-iodopyrrolidine-2,5-dione (157 g, 0.7 mol) in A cOH (900 mL) was stirred at 80° C. for 20 hrs, then at 100° C. for 20 hrs. Then the solvent was evaporated in vacuo and the residue was dissolved with ethyl acetate. The mixture was washed with saturated Na$_2$CO$_3$ aqueous solution twice, saturated Na$_2$S$_2$O$_3$ aqueous solution and brine, dried over Na$_2$SO$_4$, filtered and evaporated in vacuo. The residue was purified by column chromatography (PE to PE/EA: 50/1) to give the product (43 g in 31% yield) as a yellow solid. $^1$H NMR (400 MHz, DMSO-d6) δ 13.36 (s, 1H), 8.28 (dd, J=8.4, 0.9 Hz, 1H), 2.70 (d, J=0.6 Hz, 3H). MS (M+H)$^+$ 314.9.

Step 3: 1-(5-chloro-4-fluoro-2-hydroxy-3-(6-(trifluoromethyl)pyridin-3-yl)phenyl)ethan-1-one (40-3)

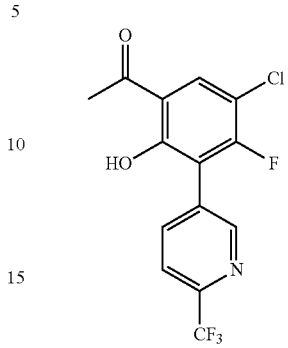

The reaction mixture of 1-(5-chloro-4-fluoro-2-hydroxy-3-iodophenyl)ethan-1-one (68 g, 216 mmol), (6-(trifluoromethyl)pyridin-3-yl)boronic acid (45 g, 238 mmol), Pd(dppf)Cl$_2$ (9.5 g, 13 mmol) and Na$_2$CO$_3$ (57 g, 106 mmol) in 1,4-dioxane/water (700 mL/100 mL) under nitrogen was stirred at 80° C. for overnight. After completed, the mixture was evaporated in vacuo. The residue was diluted with ethyl acetate and water then the resulting mixture was filtered. The organic layer was separated and the aqueous layer was extracted with ethyl acetate. The organic layers were combined, washed with brine, dried over Na$_2$SO$_4$, filtered and evaporated in vacuo. The residue was purified by column chromatography (PE/EA:50/1 to 10/1) to give the product as a yellow solid (59 g in 81% yield). $^1$H NMR (400 MHz, DMSO-d6) 313.01 (s, 1H), 8.88 (s, 1H), 8.39 (d, J=8.4 Hz, 1H), 8.24 (d, J=8.1 Hz, 1H), 8.07 (d, J=8.1 Hz, 1H), 2.74 (s, 3H), MS (M+H)$^+$ 334.0.

Step 4: 1-(5-chloro-4-fluoro-2-isopropoxy-3-(6-(trifluoromethyl)pyridin-3-yl)phenyl)ethan-1-one (40-4)

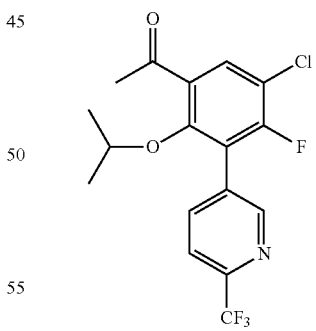

The reaction mixture of 1-(5-chloro-4-fluoro-2-hydroxy-3-(6-(trifluoromethyl)pyridin-3-yl)phenyl)ethan-1-one (59 g, 176.8 mmol), 2-Iodopropane (120 g, 707.2 mmol) and K$_2$CO$_3$ (49 g, 353.6 mmol) in DMF (150 mL) under N$_2$ was stirred at 70° C. for overnight. After completed, the mixture was filtered and the filtrate was evaporated in vacuo. The residue was purified by column chromatography (PE/EA: 6/1) to give the product as a brown oil (62 g in 93% yield). $^1$H NMR (400 MHz, DMSO-d6) δ 8.93 (s, 1H), 8.31 (d, J=8.3 Hz, 1H), 8.11 (d, J=8.2 Hz, 1H), 7.86 (d, J=8.6 Hz, 1H), 3.77-3.59 (m, 1H), 2.63 (s, 3H), 0.87 (d, J=6.1 Hz, 6H). MS (M+H)+ 376.0.

Step 5: 5-(3-chloro-2-fluoro-6-isopropoxy-5-(prop-1-en-2-yl)phenyl)-2-(trifluoromethyl)pyridine (40-5)

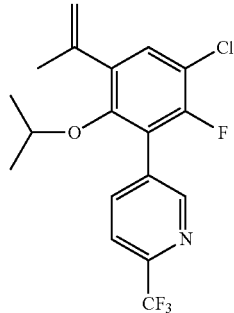 [SMILES: C=C(C)c1cc(Cl)c(F)c(-c2ccc(C(F)(F)F)nc2)c1OC(C)C]

To the solution of methyltriphenylphosphoniumbromide (177 g, 495 mmol) in THF (700 mL) at 0° C. was added n-BuLi (186 mL, 445.5 mmol) tinder N₂ and stirred for 1 hr. Then a solution of 1(5-chloro-4-fluoro-2-isopropoxy-3-(6-(trifluoromethyl)pyridin-3-yl)phenyl)ethan-1-one (62 g, 165 mmol) in THF (300 mL) was added and stirred at room temperature for overnight. The reaction was quenched with a saturated NH₄Cl aqueous solution and the mixture was extracted with ethyl acetate. The combined organic layers were washed with brine, dried over Na₂SO₄, filtered and evaporated in vacuo. The residue was purified by column chromatography (PE/EA:50/1) to give the product as a white solid (25 g in 40% yield) and recovered the original material, ¹H NMR (400 MHz, DMSO-d6) δ 8.85 (s, 1H), 8.23 (d, J=8.1 Hz, 1H), 8.06 (d, J=8.1 Hz, 1H), 7.55 (d, J=8.7 Hz, 1H), 5.29 (s, 1H), 5.22 (s, 1H), 3.90 (dt, J=12.2, 6.1 Hz, 1H), 2.14 (s, 3H), 0.82 (d, J=6.1 Hz, 6H). MS (M+H)+ 374.1.

Step 6: 2-(5-chloro-4-fluoro-2-isopropoxy-3-(6-(trifluoromethyl)pyridin-3-yl)phenyl)propan-1-ol (40-6)

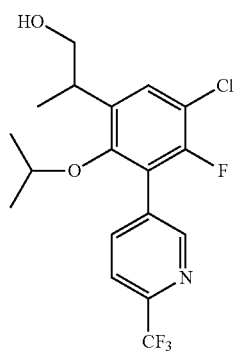 [SMILES: CC(C)Oc1c(C(C)CO)cc(Cl)c(F)c1-c1ccc(C(F)(F)F)nc1]

The reaction mixture of 5-(3-chloro-2-fluoro-6-isopropoxy-5-(prop-1-en-2-yl)phenyl)-2-(trifluoromethyl)pyridine (25 g, 66.9 mmol) and BH₃/THF (334 mL, 334 mmol) under nitrogen was stirred at room temperature for overnight. Then a solution of NaOH (5.25 g, 133.8 mmol) in water (1M) was added and followed by H₂O₂ (50 mL). The mixture was stirred at room temperature for 3 hrs. After completed, the reaction was quenched with a saturated Na₂SO₃ aqueous solution and the mixture was extracted with ethyl acetate. The combined organic layers were washed with brine, dried over Na₂SO₄, filtered and evaporated in vacuo. The residue was purified by column chromatography (CH₂Cl₂/MeOH=50/1, ammonia water) to give the product as a colorless oil which solidified at room temperature. MS (M+H)+ 392.1.

Step 7: 2-(5-chloro-4-fluoro-2-isopropoxy-3-(6-(trifluoromethyl)pyridin-3-yl)phenyl)propanoic Acid (40-7)

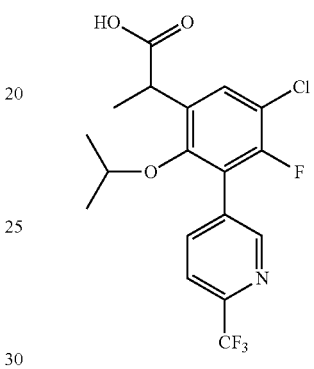

To the solution of 2-(5-chloro-4-fluoro-2-isopropoxy-3-(6-(trifluoromethyl)pyridin-3-yl)phenyl)propan-1-ol (6.7 g, 17.2 mmol) in MeCN (80 mL) was added buffer solution (80 mL, Na₂HPO₄ (0.25 M) and NaH₂PO₄ (0.5 M) in water), 2,2,6,6-Tetramethylpiperidinooxy (537 mg, 3.44 mmol), then a solution of NaClO₂ (16 g, 172 mmol) in NaClO (145 mL, 172 mmol) was added dropwise and stirred at room temperature for overnight. The mixture was diluted with water and extracted with ethyl acetate. The combined organic layers were washed with brine, dried over Na₂SO₄, filtered and evaporated in vacuo to give the product (6.2 g). MS (M+H)+ 406.0.

Step 8: 2-(5-chloro-4-fluoro-2-isopropoxy-3-(6-(trifluoromethyl)pyridin-3-yl)phenyl)-N-((3-chloro-pyrazin-2-yl)methyl)propanamide (40-8)

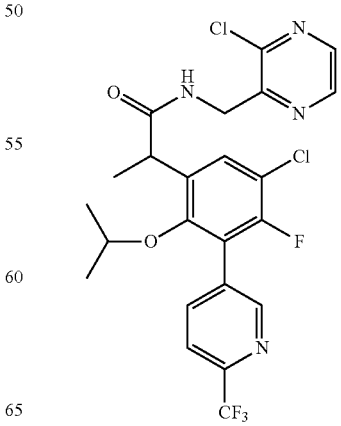

The reaction mixture of 2-(5-chloro-4-fluoro-2-isopropoxy-3-(6-(trifluoromethyl)pyridin-3-yl)phenyl)propanoic acid (520 mg, 1.28 mmol), (3-chloropyrazin-2-yl)methanamine hydrochloride (293 mg, 2.05 mmol), Benzotriazole-1-yl-oxytripyrrolidinophosphonium hexafluorophosphate (998 mg, 1.92 mmol) and N,N-Diisopropylethylamine (330 mg, 2.56 mmol) in DMF (20 mL) was stirred at room temperature for overnight. After completed, the solvent was evaporated in vacuo and the residue was dissolved with ethyl acetate. The mixture was washed with water and brine, dried over $Na_2SO_4$, filtered and evaporated in vacuo to give the product which was used directly for the next step without further purification. MS $(M+H)^+$ 531.1.

Step 9: 8-chloro-3-(1-(5-chloro-4-fluoro-2-isopropoxy-3-(6-(trifluoromethyl)pyridine-3-yl)phenyl)ethyl)imidazo[1,5-a]pyrazine (40-9)

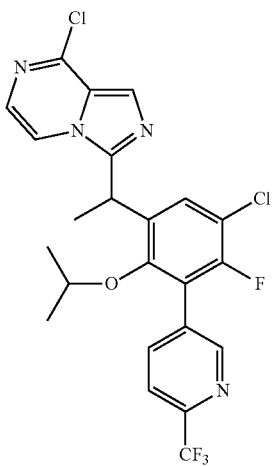 [SMILES: CC(C)Oc1c(C(C)c2ncc3c(Cl)nccn23)cc(Cl)c(F)c1-c1ccc(C(F)(F)F)nc1]

To the solution of 2-(5-chloro-4-fluoro-2-isopropoxy-3-(6-(trifluoromethyl)pyridin-3-yl)phenyl)-N-((3-chloropyrazin-2-yl)methyl)propanamide (crude) in $CH_2Cl_2$ (20 mL) was added trifluoromethanesulfonic anhydride (2 mL) at room temperature. Then pyridine (2 mL) was added dropwise slowly and the mixture was stirred for 20 mins. The mixture was washed with a saturated $NaHCO_3$ aqueous solution and brine, dried over $Na_2SO_4$, filtered and evaporated in vacuo. The residue was purified by column chromatography (PE/EA=6/1 to 1/1) to give the product (420 mg in 63% yield, for two steps) as an off-white solid, $^1H$ NMR (400 MHz, $CDCl_3$) δ 8.83 (s, 1H), 7.99 (d, J=8.1 Hz, 1H), 7.90-7.75 (m, 3H), 7.45 (d, J=8.3 Hz, 1H), 7.36 (d, J=5.1 Hz, 1H), 4.91 (q, J=7.1 Hz, 1H), 3.72 (dt, J=12.2, 6.1 Hz, 1H), 1.91 (d, J=7.2 Hz, 3H), 1.18 (d, J=6.1 Hz, 3H), 1.00 (d, J=6.1 Hz, 3H). MS $(M+H)^+$ 513.1, 515.0.

Step 10: 1,8-dichloro-3-(1-(5-chloro-4-fluoro-2-isopropoxy-3-(6-(trifluoromethyl)pyridin-3-yl)phenyl)ethyl)imidazo[1,5-a]pyrazine (40-10)

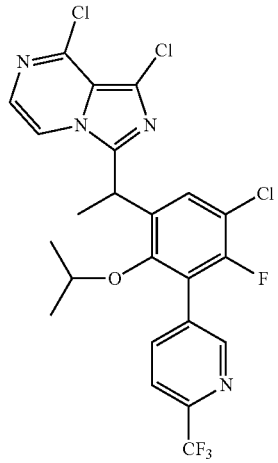 [SMILES: CC(C)Oc1c(C(C)c2nc(Cl)c3c(Cl)nccn23)cc(Cl)c(F)c1-c1ccc(C(F)(F)F)nc1]

The reaction mixture of 8-chloro-3-(1-(5-chloro-4-fluoro-2-isopropoxy-3-(6-(trifluoromethyl)pyridin-3-yl)phenyl)ethyl)imidazo[1,5-a]pyrazine (420 mg, 0.82 mmol) and 1-chloropyrrolidine-2,5-dione (131 mg, 0.98 mmol) in DMF (10 mL) was stirred at 50° C. for 1 h. After completed, the solvent was evaporated in vacuo and the residue was purified by column chromatography (PE/EA=3/1) to give the product (350 mg in 78% yield) as a yellow solid. LC-MS $(M+H)^+$ 547.0, 549.0.

Step 11: 1-chloro-3-(1-(5-chloro-4-fluoro-2-isopropoxy-3-(6-(trifluoromethyl)pyridin-3-yl)phenyl)ethyl)imidazo[1,5-a]pyrazin-8-amine (40-11)

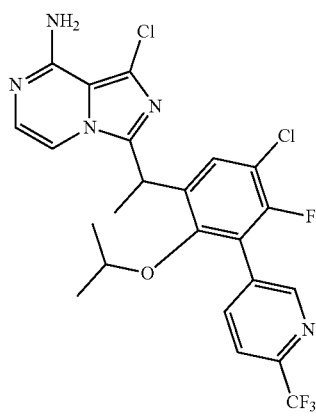 [SMILES: CC(C)Oc1c(C(C)c2nc(Cl)c3c(N)nccn23)cc(Cl)c(F)c1-c1ccc(C(F)(F)F)nc1]

The reaction mixture of 1,8-dichloro-3-(1-(5-chloro-4-fluoro-2-isopropoxy-3-(6-(trifluoromethyl)pyridin-3-yl)phenyl)ethyl)imidazo[1,5-a]pyrazine (350 mg, 0.64 mmol) and $NH_3$ in i-PrOH (10 mL) in a steel tube was stirred at 90° C. for overnight. After completed, the mixture was evaporated in vacuo. The residue was purified by column chromatography ($CH_2Cl_2$/MeOH=20/1) to obtain the desired product (200 mg), which was separated by chiral-HPLC to give two compounds, Compound 40A (66 mg, the first and fast isomer) and Compound 40B (68 mg, the second and slow isomer), as white solids. The absolute structure of the chiral center in compound 40A was shown in FIG. 1, it has been determined to as (S)-configuration.

Compound 40: ¹H NMR (400 MHz, DMSO-d6) δ 8.86 (s, 1H), 8.24 (d, J=8.0 Hz, 1H), 8.08 (d, J=8.2 Hz, 1H), 7.60 (d, J=8.5 Hz, 1H), 7.50 (d, J=4.9 Hz, 1H), 7.07 (s, 1H), 6.74 (s, 2H), 4.91 (q, J=6.8 Hz, 1H), 3.58 (dt, J=12.1, 6.0 Hz, 1H), 1.67 (d, J=7.1 Hz, 3H), 0.98 (d, J=6.1 Hz, 3H), 0.76 (d, J=6.1 Hz, 3H). LC-MS (M+H)⁺ 528.0.

Compound 40A: ¹H NMR (400 MHz, DMSO-d6) δ 8.86 (s, 1H), 8.24 (d, J=8.1 Hz, 1H), 8.08 (d, J=8.1 Hz, 1H), 7.60 (d, J=8.4 Hz, 1H), 7.49 (d, J=5.0 Hz, 1H). 7.06 (d, J=5.0 Hz, 1H), 6.74 (s, 2H), 4.91 (q, J=6.9 Hz, 1H), 3.58 (dt, J=12.1, 6.0 Hz, 1H), 1.67 (d, J=7.0 Hz, 3H), 0.98 (d, J=6.0 Hz, 3H), 0.76 (d, J=6.1 Hz, 3H). LC-MS (M+H)⁺ 528.0.

Compound 40B: ¹H NMR (400 MHz, DMSO-d6) δ 8.86 (s, 1H), 8.24 (d, J=8.0 Hz, 1H), 8.08 (d, J=8.1 Hz, 1H), 7.60 (d, J=8.4 Hz, 1H), 7.49 (d, J=5.0 Hz, 1H), 7.06 (d, J=5.0 Hz, 1H), 6.74 (s, 2H), 4.91 (q, J=6.9 Hz, 1H), 3.58 (dt, J=12.0, 6.0 Hz, 1H), 1.67 (d, J=7.0 Hz, 3H), 0.98 (d, J=6.0 Hz, 3H), 0.76 (d, J=6.0 Hz, 3H). LC-MS (M+H)⁺ 528.0.

| Column | CHIRALART Cellulose-SB |
| --- | --- |
| Column size | 2 cm × 25 cm |
| Injection | 0.3 ML |
| Mobile phase | Hex:EtOH = 95:5 |
| Flow rate | 20 ml/min |
| Wave length | UV 220 nm |
| Temperature | 35° C. |
| Sample solution | 30.9 mg/ml in mobile phase |
| Prep HPLC equipment | BJ-Prep-Gilson-HPLC |

Example 41

1-chloro-3-(1-(5-chloro-2-ethoxy-4-fluoro-3-(6-(trifluoromethyl)pyridin-3-yl)phenyl) ethyl)imidazo[1,5-a]pyrazin-8-amine (Compound 41)

Compound 41

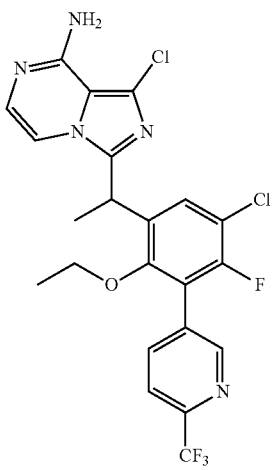

Compound 41A

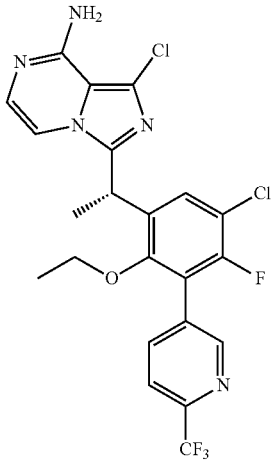

Compound 41B

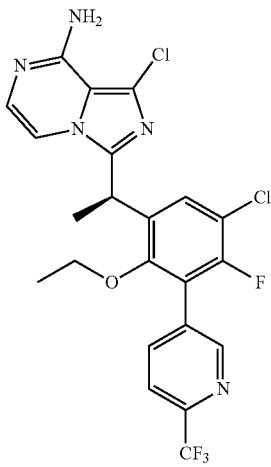

Step 1: 1-(5-chloro-2-ethoxy-4-fluoro-3-iodophenyl) ethan-1-one (41-1)

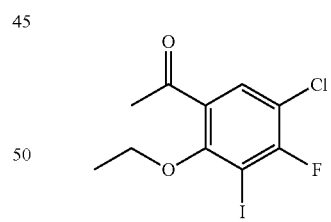

The reaction mixture of 1-(5-chloro-4-fluoro-2-hydroxy-3-iodophenyl)ethan-1-one (3.2 g, 10.2 mmol), iodoethane (3.17 g, 20.3 mmol) and K₂CO₃ (3.51 g, 25.4 mmol) in DMF was stirred at 70° C. for 2 hrs. After completed, the mixture was cooled to room temperature and poured into water. The resulting mixture was extracted with ethyl acetate. The combined organic layers were washed with water and brine, dried over Na₂SO₄, filtered and evaporated in vacuo. The residue was purified by column chromatography (PE/EA=10/1) to give the product (2.9 g in 83% yield). ¹H NMR (400 MHz, CDCl₃) δ 7.71 (d, J=8.4 Hz, 1H), 3.97 (q, J=7.0 Hz, 2H), 2.63 (s, 3H), 1.50 (t, J=7.0 Hz, 3H). MS (M+H)⁺ 342.9.

Step 2: 1-(5-chloro-2-ethoxy-4-fluoro-3-iodophenyl)ethan-1-ol (41-2)

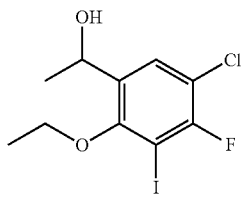

To the solution of 1-(5-chloro-2-ethoxy-4-fluoro-3-iodophenyl)ethan-1-one (2.9 g, 8.47 mmol) in MeOH (30 mL) under nitrogen atmosphere was added NaBH$_4$ (483 mg, 12.7 mmol) at 0° C. and stirred while the ice was melting for 3 hrs. Then the reaction was quenched with 1N hydrochloride to pH-7 and the mixture was evaporated in vacuo. The residue was purified by column chromatography to give the product (1.68 g, purity: 66%), MS (M+H)$^+$ 326.9.

Step 3: 1-(5-chloro-2-ethoxy-4-fluoro-3-(6-(trifluoromethyl)pyridin-3-yl)phenyl)ethan-1-ol (41-3)

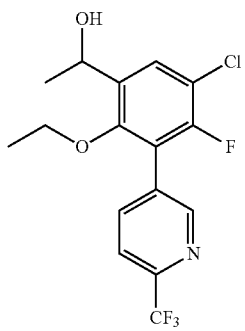 [SMILES: CCOc1c(C(C)O)cc(Cl)c(F)c1-c1ccc(C(F)(F)F)nc1]

Compound (41-3) was prepared in the similar manner as compound (38-2) described in example 38 from 1-(5-chloro-2-ethoxy-4-fluoro-3-iodophenyl)ethan-1-ol (1.68 g, purity: 66%). Afford Compound (41-3) (1.15 g in 97% yield) as a yellow oil. $^1$H NMR (400 MHz, CDCl$_3$) δ 8.86 (s, 1H), 8.15-7.94 (m, 1H), 7.80 (d, J=8.1 Hz, 1H), 7.63 (d, J=8.4 Hz, 1H), 5.20 (q, J=6.4 Hz, 1H), 3.58-3.37 (m, 2H), 1.54 (d, J=6.4 Hz, 3H), 1.08 (t, J=7.0 Hz, 3H). MS (M+H)$^+$ 364.1.

Step 4: 5-(3-chloro-5-(1-chloroethyl)-6-ethoxy-2-fluorophenyl)-2-(trifluoromethyl)pyridine (41-4)

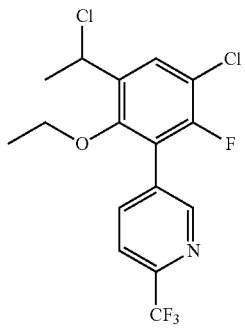 [SMILES: CCOc1c(C(C)Cl)cc(Cl)c(F)c1-c1ccc(C(F)(F)F)nc1]

Compound (41-4) was prepared in the similar manner as compound (38-5) from 1-(5-chloro-2-ethoxy-4-fluoro-3-(6-(trifluoromethyl)pyridin-3-yl)phenyl)ethan-1-ol (1.15 g). Afford crude product (1.2 g, Yield: 99%) as a brown oil. MS (M+H)$^+$ 382.0.

Step 5: 2-(5-chloro-2-ethoxy-4-fluoro-3-(6-(trifluoromethyl)pyridin-3-yl)phenyl)propanenitrile (41-5)

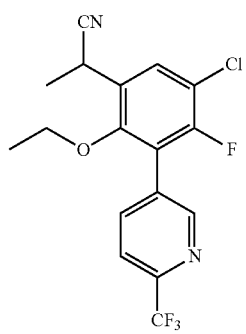

Compound (41-5) was prepared in the similar manner as compound (38-6) from 5-(3-chloro-5-(1-chloroethyl)-6-ethoxy-2-fluorophenyl)-2-(trifluoromethyl)pyridine (1.2 g). Afford Compound (41-5) (440 mg yield 38%) as a colorless oil which was solidified at room temperature. MS (M+H)$^+$ 373.0.

Step 6: 2-(5-chloro-2-ethoxy-4-fluoro-3-(6-(trifluoromethyl)pyridin-3-yl)phenyl) propanoic acid (41-6)

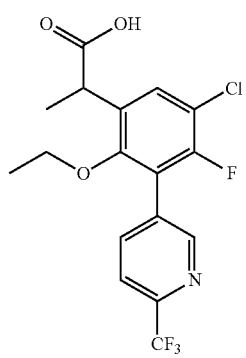 [SMILES: CCOc1c(C(C)C(=O)O)cc(Cl)c(F)c1-c1ccc(C(F)(F)F)nc1]

Compound (41-6) was prepared in the similar manner as compound (38-7) described in example 38 from 2-(5-chloro-2-ethoxy-4-fluoro-3-(6-(trifluoromethyl)pyridin-3-yl)phenyl)propanenitrile (440 mg). Afford the crude product (430 mg). MS (M+1)$^+$ 392.0.

Step 7: 2-(5-chloro-2-ethoxy-4-fluoro-3-(6-(trifluoromethyl)pyridin-3-yl)phenyl)-N-((3-chloropyrazin-2-yl)methyl)propanamide (41-7)

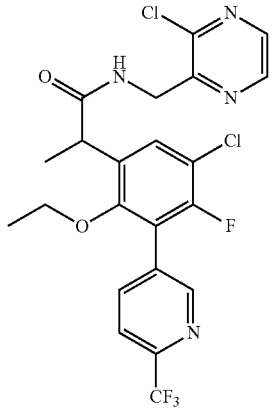 [SMILES: CCOc1c(C(C)C(=O)NCc2nccnc2Cl)cc(Cl)c(F)c1-c1ccc(C(F)(F)F)nc1]

Compound (41-7) was prepared in the similar manner as compound (38-8) described in example 38 from 2-(5-chloro-2-ethoxy-4-fluoro-3-(6-(trifluoromethyl)pyridin-3-yl)phenyl) propanoic acid (430 mg). Afford the crude product (560 mg) which was used directly for the next step without further purification. MS (M+H)$^+$ 517.0, 519.0.

Step 8: 8-chloro-3-(1-(5-chloro-2-ethoxy-4-fluoro-3-(6-(trifluoromethyl)pyridin-3-yl)phenyl)ethyl)imidazo[1,5-a]pyrazine (41-8)

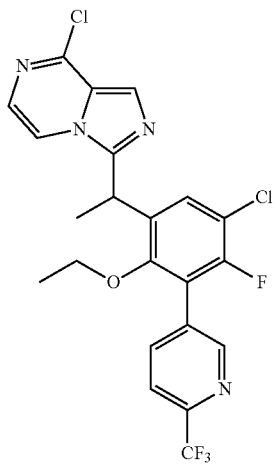 [SMILES: CCOc1c(C(C)c2ncc3c(Cl)nccn23)cc(Cl)c(F)c1-c1ccc(C(F)(F)F)nc1]

Compound (41-8) was prepared in the similar manner as compound (38-9) described in example 38 from 2-(5-chloro-2-ethoxy-4-fluoro-3-(6-(trifluoromethyl)pyridin-3-yl)phenyl)-N-((3-chloropyrazin-2-yl)methyl)propanamide (560 mg). Afford compound (41-8) (250 mg in 45% yield, for two steps) as a yellow solid. $^1$H NMR (400 MHz, CDCl$_3$) δ 8.85 (s, 1H), 8.01 (d, J=8.0 Hz, 1H), 7.87 (s, 1H), 7.82 (d, J=8.1 Hz, 1H), 7.72 (dd, J=5, 0, 0.8 Hz, 1H), 7.40 (d, J=8.2 Hz, 1H), 7.37 (d, J=5.0 Hz, 1H), 4.88 (q, J=7.1 Hz, 1H), 3.59 (dq, J=9.3, 7.0 Hz, 1H), 3.42 (dq, J=9.3, 7.0 Hz, 1H), 1.90 (d, J=7.2 Hz, 3H), 1.12 (t, J=7.0 Hz, 3H). MS (M+H)$^+$ 499.0, 501.0.

Step 9: 1,8-dichloro-3-(1-(5-chloro-2-ethoxy-4-fluoro-3-(6-(trifluoromethyl)pyridin-3-yl)phenyl)ethyl)imidazo[1,5-a]pyrazine (41-9)

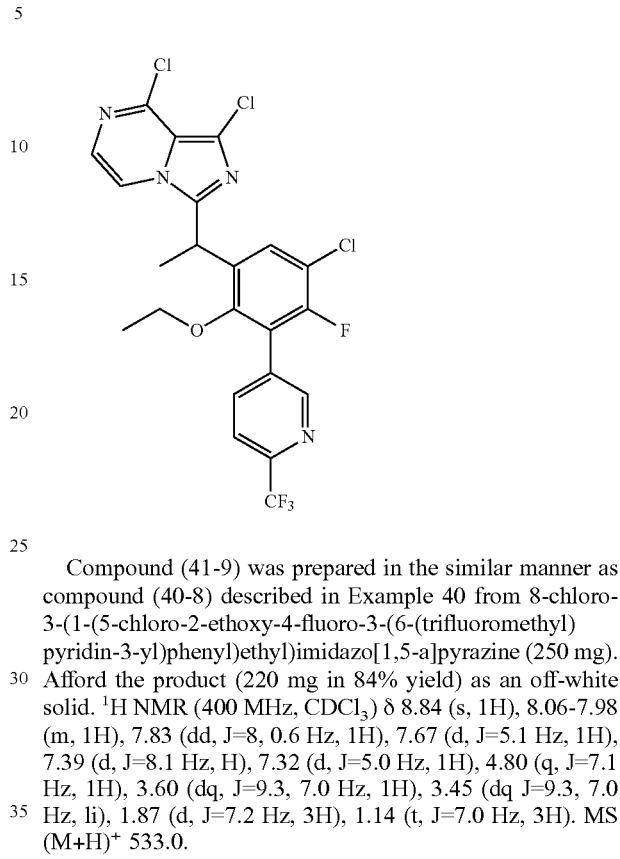

Compound (41-9) was prepared in the similar manner as compound (40-8) described in Example 40 from 8-chloro-3-(1-(5-chloro-2-ethoxy-4-fluoro-3-(6-(trifluoromethyl)pyridin-3-yl)phenyl)ethyl)imidazo[1,5-a]pyrazine (250 mg). Afford the product (220 mg in 84% yield) as an off-white solid. $^1$H NMR (400 MHz, CDCl$_3$) δ 8.84 (s, 1H), 8.06-7.98 (m, 1H), 7.83 (dd, J=8, 0.6 Hz, 1H), 7.67 (d, J=5.1 Hz, 1H), 7.39 (d, J=8.1 Hz, H), 7.32 (d, J=5.0 Hz, 1H), 4.80 (q, J=7.1 Hz, 1H), 3.60 (dq, J=9.3, 7.0 Hz, 1H), 3.45 (dq J=9.3, 7.0 Hz, li), 1.87 (d, J=7.2 Hz, 3H), 1.14 (t, J=7.0 Hz, 3H). MS (M+H)$^+$ 533.0.

Step 10: 1-chloro-3-(1-(5-chloro-2-ethoxy-4-fluoro-3-(6-(trifluoromethyl)pyridin-3-yl)phenyl)ethyl)imidazo[1,5-a]pyrazin-8-amine (41-10)

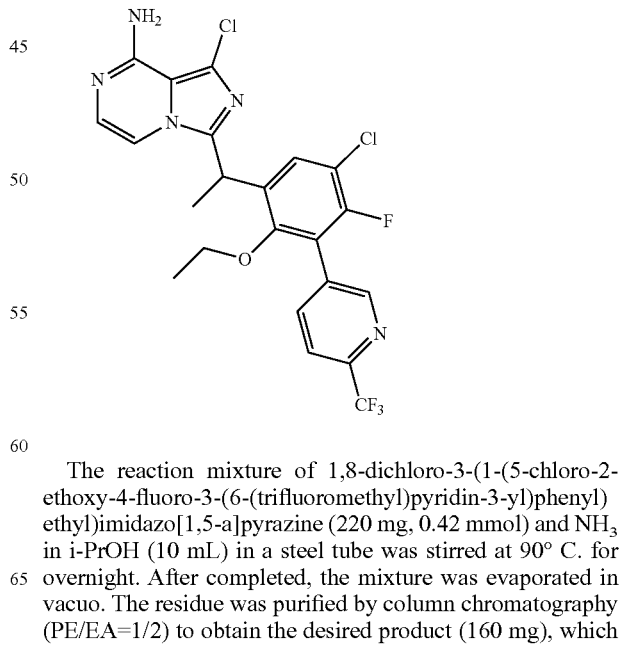

The reaction mixture of 1,8-dichloro-3-(1-(5-chloro-2-ethoxy-4-fluoro-3-(6-(trifluoromethyl)pyridin-3-yl)phenyl)ethyl)imidazo[1,5-a]pyrazine (220 mg, 0.42 mmol) and NH$_3$ in i-PrOH (10 mL) in a steel tube was stirred at 90° C. for overnight. After completed, the mixture was evaporated in vacuo. The residue was purified by column chromatography (PE/EA=1/2) to obtain the desired product (160 mg), which was separated by chiral-HPLC to give two compounds, Compound 41A (44 mg, the first and fast isomer) and Compound 41B (38 mg, the second and slow isomer) as white solid, Compound 41A was assigned as a (S)-configuration in a similar manner to Compound 40A.

Compound 41: $^1$H NMR (400 MHz, CDCl$_3$) δ 8.85 (s, 1H), 8.02 (d, J=8.1 Hz, 1H), 7.82 (d, J=7.8 Hz, 1H), 7.38 (d, J=8.2 Hz, 1H), 7.20 (d, J=5.1 Hz, 1H), 7.02 (d, J=5.1 Hz, 1H), 5.69 (s, 2H), 4.76 (q, J=7.1 Hz, 1H), 3.56 (dq, J=9.2, 7.0 Hz, 1H), 3.42 (dq, J=9.2, 7.0 Hz, 1H), 1.82 (d, J=7.2 Hz, 3H), 1.12 (t, J=7.0 Hz, 3H). LC-MS (M+H)$^+$ 514.1.

Compound 41A: $^1$H NMR (400 MHz, DMSO-d6) δ 8.88 (s, 1H), 8.25 (d, J=8.7 Hz, 1H), 8.07 (d, J=8.1 Hz, 1H), 7.55 (d, J=8.4 Hz, 1H), 7.45 (d, J=5.1 Hz, 1H), 7.03 (d, J=5.0 Hz, 1H), 6.76 (s, 2H), 4.90 (q, J=6.9 Hz, 1H), 3.51-3.39 (m, 1H), 3.26-3.16 (m, 1H), 1.66 (d, J=7.1 Hz, 3H), 0.86 (t, J=7.0 Hz, 3H). LC-MS (M+H)*514.1.

Compound 41B: $^1$H NMR (400 MHz, CDCl$_3$) δ 8.85 (s, 1H), 8.02 (d, J=8.0 Hz, 1H), 7.82 (d, J=8.1 Hz, 1H), 7.39 (d, J=8.2 Hz, 1H), 7.23 (d, J=5.3 Hz, 1H), 6.98 (d, J=5.2 Hz, 1H), 4.77 (q, J=7.1 Hz, 1H), 3.57 (dq, J=9.2, 7.0 Hz, 1H), 3.43 (dq, J=9.3, 7.0 Hz, 1H), 1.83 (d, J=7.1 Hz, 3H), 1.12 (t, J=7.0 Hz, 3H). LC-MS (M+H)$^+$ 514.1.

| Column | CHIRAL Cellulose-SB |
| --- | --- |
| Column size | 2*25 cm, 5 μm |
| Injection | 0.3 ML |
| Mobile phase | Hex:EtOH = 70:30 |
| Flow rate | 20 ml/min |
| Wave length | UV 220 nm |
| Temperature | 35° C. |
| Sample solution | 20.8 mg/ml in mobile phase |
| Prep-HPLC equipment | BJ-Prep-Gilson-HPLC |

Example 42

1-chloro-3-(1-(5-chloro-4-fluoro-2-propoxy-3-(6-(trifluoromethyl)pyridin-3-yl)phenyl)ethyl)imidazo[1,5-a]pyrazin-8-amine (Compound 42)

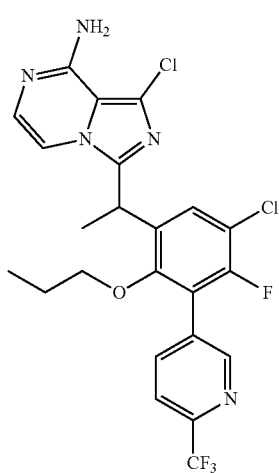

Compound 42

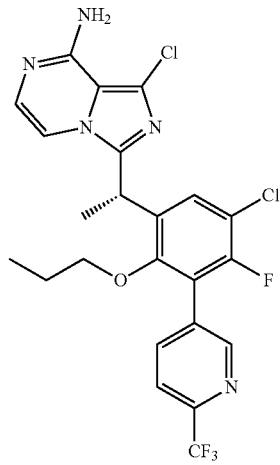

Compound 42A

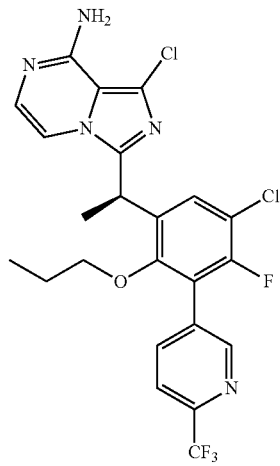

Compound 42B

Compound (42) was prepared in the similar manner as compound (40) described in example 40 from 1-(5-chloro-4-fluoro-2-hydroxy-3-iodophenyl)ethan-1-one. Afford the desired product (1.34 g), of which 200 mg was further separated by chiral-HPLC to give two compounds, Compound 42A (72 mg, the first and fast isomer) and Compound 42B (66 mg, the second and slow isomer) as white solids. Compound 42A was assigned as a (S)-configuration in a similar manner to Compound 40A.

Compound 42: $^1$H NMR (400 MHz, DMSO-d6) δ 8.87 (s, 1H), 8.25 (d, J=8.7 Hz, 1H), 8.07 (d, J=8.2 Hz, 1H), 7.56 (d, J=8.4 Hz, 1H), 7.44 (d, J=5.1 Hz, 1H), 7.03 (d, J=5.0 Hz, 1H), 6.76 (s, 2H), 4.88 (q, J=6.9 Hz, 1H), 3.47-3.21 (m, 1H), 3.05 (dt, J=9.0, 6.4 Hz, 1H), 1.67 (d, J=7.0 Hz, 3N), 1.25 (dt, J=13.7, 6.9 Hz, 2H), 0.53 (t, J=7.4 Hz, 3H). LC-MS (M+H)$^+$ 528.1.

Compound 42A: $^1$H NMR (400 MHz, DMSO-d6) δ 8.87 (s, 1), 8.25 (d, J=8.7 Hz, 1N), 8.07 (d, J=8.2 Hz, 1H), 7.56 (d, J=8.4 Hz, 1H), 7.44 (d, J=5.1 Hz, 1H), 7.03 (d, J=5.0 Hz, 1H), 6.76 (s, 2H), 4.88 (q, J=6.9 Hz, 1H), 3.47-3.21 (m, 1H), 3.05 (dt, J=9.0, 6.4 Hz, 1H), 1.67 (d, J=7.0 Hz, 3H), 1.25 (dt, J=13.7, 6.9 Hz, 2H), 0.53 (t, J=7.4 Hz, 3H). LC-MS (M+H)$^+$ 528.1.

Compound 42B: $^1$H NMR (400 MHz, DMSO-d6) δ 8.87 (s, 1H), 8.25 (d, J=8.3 Hz, 1H), 8.07 (d, J=8.1 Hz, 1H), 7.56 (d, J=8.4 Hz, 1H), 7.44 (d, J=5.1 Hz, 1H), 7.04 (d, J 5.0 Hz, 1H), 6.76 (s, 2H), 4.88 (q, J=7.0 Hz, 1H), 3.43-3.28 (m, 1H), 3.06 (dt, J=8.9, 6.3 Hz, 1H), 1.68 (d, J=7.0 Hz, 3H), 1.28-1.14 (m, 2H), 0.54 (t, J=7.4 Hz, 3H). LC-MS (M+H)+ 528.1.

| Column | CHIRALART Cellulose-SB |
|---|---|
| Column size | 2 cm × 25 cm, 5 μm |
| Injection | 0.3 ML |
| Mobile phase | Hex:EtOH = 90:10 |
| Flow rate | 20 ml/min |
| Wave length | UV 220 nm |
| Temperature | 35° C. |
| Sample solution | 51.2 mg/ml in mobile phase |
| Prep-HPLC equipment | BJ-Prep-Gilson-HPLC |

Example 43

1-chloro-3-(1-(5-chloro-2-ethoxy-4-fluoro-3-(2-methoxy-6-(trifluoromethyl)pyridin-3-yl)phenyl)ethyl)imidazo[1,5-a]pyrazin-8-amine (Compound 43)

Compound 43

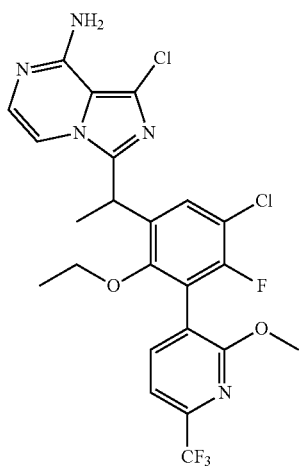

Compound 43A

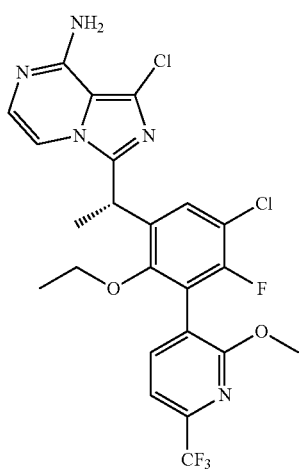

Compound 43B

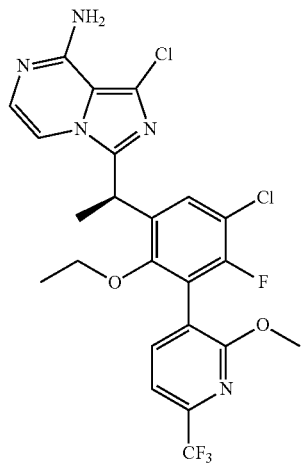

Step 1: 6-(trifluoromethyl)pyridin-2-ol (43-1)

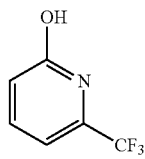

The reaction mixture of 2-fluoro-6-(trifluoromethyl)pyridine (660 mg, 4 mmol) and KOH (493 mmol, 8.8 mmol) in water (5 mL) was stirred at 100° C. for overnight. After completed, the mixture was neutralized with 1N hydrochloride to pH-7. Then the precipitate was filtered and dried to give the product as white solid (430 mg in 66% yield). MS (M+H)+ 164.0.

Step 2: 2-methoxy-6-(trifluoromethyl)pyridine (43-2)

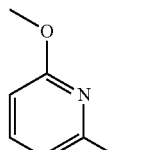

The suspension of 6-(trifluoromethyl)pyridin-2-ol (430 mg, 2.64 mmol), iodomethane (3.75 g, 26.4 mmol) and $Ag_2CO_3$ (982 mg, 3.56 mmol) in $CH_2Cl_2$ (8 mL) was stirred at room temperature in dark for 24 hrs. After completed, the mixture was filtered and the solvent was evaporated in vacuo at 30° C. The residue was purified by column chromatography (PE/EA=5/1) to give the product (80 mg in 17% yield). $^1$H NMR (400 MHz, $CDCl_3$) δ 7.76-7.59 (m, 1H), 7.24 (d, J=7.3 Hz, 1H), 6.91 (d, J=8.4 Hz, 1H), 3.98 (s, 3H).

Step 3: (2-methoxy-6-(trifluoromethyl)pyridin-3-yl) boronic Acid (43-3)

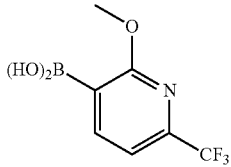

To the solution of 2-methoxy-6-(trifluoromethyl)pyridine (3.9 g, 22 mmol) in THF (80 mL) under nitrogen was added n-BuLi (11 mL, 26 mmol) at −78° C. dropwise and stirred at the same temperature for 30 mins. Then B(OiPr)$_3$ was added and stirred for 5 hrs while the temperature warmed to room temperature. Then 1N hydrochloride was added and stirred for 1 hr. The reaction was quenched with saturated NH$_4$Cl aqueous solution and the resulting mixture was extracted with ethyl acetate. The organic layers were washed with brine dried over Na$_2$SO$_4$, filtered and evaporated in vacuo to give the product (3.8 g) as yellow solid which was used directly for the next step without further purification.

Step 4: 1-(5-chloro-4-fluoro-2-hydroxy-3-(2-methoxy-6-(trifluoromethyl)pyridin-3-yl)phenyl)ethan-1-one (43-4)

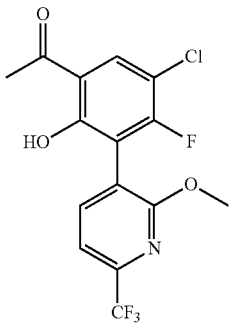 [SMILES: COc1nc(C(F)(F)F)ccc1-c1c(O)c(C(C)=O)cc(Cl)c1F]

The reaction mixture of 1-(5-chloro-4-fluoro-2-hydroxy-3-iodophenyl)ethan-1-one (1 g, 3.18 mmol), (2-methoxy-6-(trifluoromethyl)pyridin-3-yl)boronic acid (1.4 g, 6.36 mmol), Cs$_2$CO$_3$ (2.07 g, 6.36 mmol) and chloro(2-dicyclohexylphosphino-2',4',6'-triisopropyl-1,1'-biphenyl)[2-(2'-amino-1,1'-biphenyl)]palladium(II) (125 mg, 0.16 mmol) in 1,6-dioxane (30 mL) and water (6 mL) under nitrogen was stirred at 80° C. for overnight. After completed, the mixture was evaporated in vacuo and the residue was dissolved with ethyl acetate. The resulting mixture was filtered and the filtrate was evaporated in vacuo. The residue was purified by column chromatography (PE/EA=20/1) to give the product (460 mg in 40% yield) as a yellow solid. $^1$H NMR (400 MHz, DMSO-d6) δ 12.79 (s, 1H), 8.34 (dd, J=8.4, 0.8 Hz, 1H), 8.05 (d, J=7.5 Hz, 1H), 7.64 (d, J=7.6 Hz, 1H), 3.89 (d, J=0.8 Hz, 3H), 2.73 (d, J=0.7 Hz, 3H). MS (M+H)$^+$ 364.0.

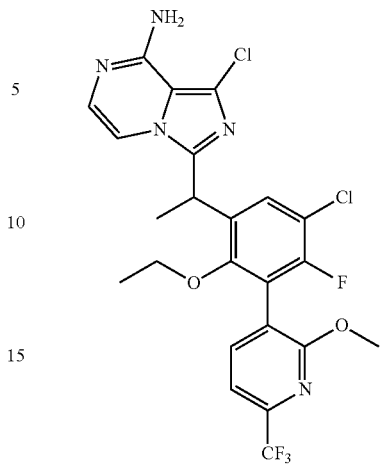

Compound (43) was prepared in the similar manner as Compound (40) described in Example 40 from 1-(5-chloro-4-fluoro-2-hydroxy-3-(2-methoxy-6-(trifluoromethyl)pyridin-3-yl)phenyl)ethan-1-one. Afford the desired product (320 mg), which was further separated by chiral-HPLC to give two compound, Compound 43A (134 mg, the first and fast isomer) and Compound 43B (127 mg, the second and slow isomer) as white solids. Compound 43A was assigned as a (S)-configuration in a similar manner to Compound 40A.

Compound 43: $^1$H NMR (400 MHz, DMSO-d6) δ 8.04 (dd, J=27.8, 7.5 Hz, 1H), 7.69-7.58 (m, 1H), 7.49 (dd, J=22.0, 8.4 Hz, 1H), 7.39 (dd, J=15.9, 5.1 Hz, 1H), 7.02 (t, J=4.7 Hz, 1H), 6.74 (s, 2H), 4.87 (q, J=6.8 Hz, 1H), 3.90 (d, J=13.6 Hz, 3H), 3.60-3.41 (m, 1H), 3.22-3.30 (m, 1H), 1.66 (d, J=7.0 Hz, 3H), 0.84 (dt, J=28.2, 7.0 Hz, 3H). LC-MS (M+H)$^+$ 544.1, 546.1.

Compound 43A: 134 mg, $^1$H NMR (400 MHz, DMSO-d6) δ 8.04 (dd, J=27.9, 7.5 Hz, 1H), 7.64 (dd, J=9.3, 7.7 Hz, 1H), 7.49 (dd, J=22.0, 8.4 Hz, 1H), 7.39 (dd, J=16.0, 5.1 Hz, 1H), 7.02 (t, J=4.7 Hz, 1H), 6.75 (s, 2H), 4.87 (p, J=6.9 Hz, 1H), 3.90 (d, J=13.6 Hz, 3H), 3.61-3.42 (m, 1H), 3.22-3.30 (m, 1H), 1.66 (d, J=7.0 Hz, 3H), 0.84 (dt, J=28.0, 7.0 Hz, 3H). LC-MS (M+H)$^+$ 544.1, 546.1.

Compound 43B: 127 mg, $^1$H NMR (400 MHz, DMSO-d6) δ 8.05 (dd, J=27.9, 7.5 Hz, 1H), 7.64 (dd, J=9.4, 7.7 Hz, 1H), 7.49 (dd, J=22.1, 8.4 Hz, 1H), 7.39 (dd, J=16.0, 5.1 Hz, 1H), 7.02 (t, J=4.7 Hz, 1H), 6.75 (s, 2H), 4.87 (p, J=6.9 Hz, 1H), 3.91 (d, J=13.6 Hz, 3H), 3.63-3.40 (m, 1H), 3.23-3.31 (m, 1H), 1.67 (d, J=7.0 Hz, 3H), 0.85 (dt, J=28.3, 7.0 Hz, 3H). LC-MS (M+H)$^+$ 544.1, 546.1.

| Column | CHIRALART Cellulose-SB |
|---|---|
| Column size | 2 cm × 25 cm, 5 μm |
| Injection | 0.3 ML |
| Mobile phase | Hex:EtOH = 90:10 |
| Flow rate | 20 ml/min |
| Wave length | UV 220 nm |
| Temperature | 35° C. |
| Sample solution | 39.2 mg/ml in mobile phase |
| Prep-HPLC equipment | BJ-Prep-Gilson-HPLC |

Example 44

3-(1-(5-chloro-2-ethoxy-4'-methoxy-6-methyl-[1,1'-biphenyl]-3-yl)ethyl)-1-(4-methoxyphenyl)imidazo[1,5-a]pyrazin-8-amine (Compound 44)

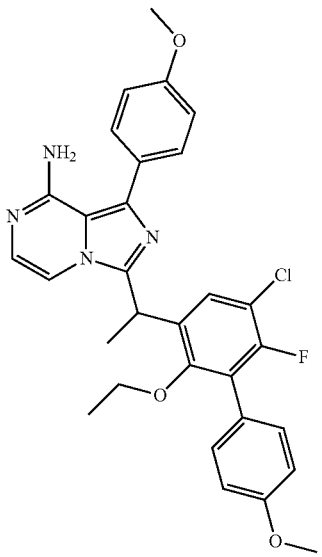 [SMILES: CCOc1c(C(C)c2nc(-c3ccc(OC)cc3)c3c(N)nccn23)cc(Cl)c(F)c1-c1ccc(OC)cc1]

Step 1: 6-(1-(8-amino-1-bromoimidazo[1,5-a]pyrazin-3-yl)ethyl)-4-chloro-2-iodo-3-methylphenol (44-1)

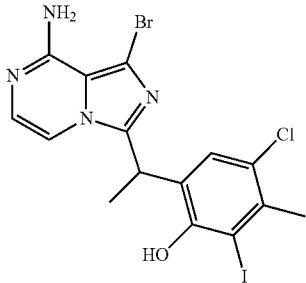 [SMILES: Cc1c(Cl)cc(C(C)c2nc(Br)c3c(N)nccn23)c(O)c1I]

To a mixture of 1-bromo-3-(1-(5-chloro-3-iodo-2-methoxy-4-methylphenyl)ethyl)imidazo[1,5-a]pyrazin-8-amine (0.8 g, 1.5 mmol) in dichloromethane (30 m L) was added BBr₃ (3.8 g, 15 mmol) at 0° C. The mixture was stirred for 30 mins. The mixture was quenched with water (30 mL), extracted with dichloromethane (3×30 mL). The combined organic layers were washed with brine, dried over anhydrous sodium sulfate (Na₂SO₄), filtered and concentrated. The residue was purified by silica gel column chromatography (elution with CH₂Cl₂/MeOH=20/1) to afford the product (260 mg in 34% yield) as a yellow solid. MS (ESI) m/e (M+1)⁺ 506.9, 508.9.

Step 2: 1-bromo-3-(1-(5-chloro-2-ethoxy-3-iodo-4-methylphenyl)ethyl)imidazo[1,5-a]pyrazin-8-anine (44-2)

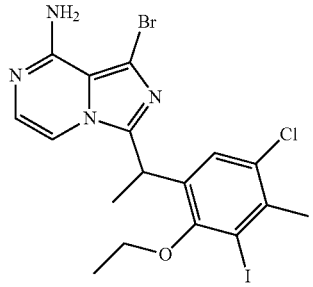 [SMILES: CCOc1c(C(C)c2nc(Br)c3c(N)nccn23)cc(Cl)c(C)c1I]

To a mixture of 6-(1-(8-amino-1-bromoimidazo[1,5-a]pyrazin-3-yl)ethyl)-4-chloro-2-iodo-3-methylphenol (260 mg, 0.51 mmol), diisopropyl azodicarboxylate (DIAD, 200 mg, 1.0 mmol) and EtOH (460 mg, 10 mmol) in THF (20 mL) was added PPh₃ (260 mg, 1.0 mmol). The mixture was stirred under N₂ for 18 hrs. The mixture was concentrated and the residue was purified by silica gel column chromatography (elution with hexane/ethyl acetate=1/1) to afford the product (160 mg in 58% yield) as a yellow solid. MS (ESI) m/e (M+1)⁺ 534.9, 536.9.

Step 3: 3-(1-(5-chloro-2-ethoxy-4'-methoxy-6-methyl-[151'-biphenyl]-3-yl)ethyl)-1-(4-methoxyphenyl)imidazo[1,5-a]pyrazin-8-amine (44-3)

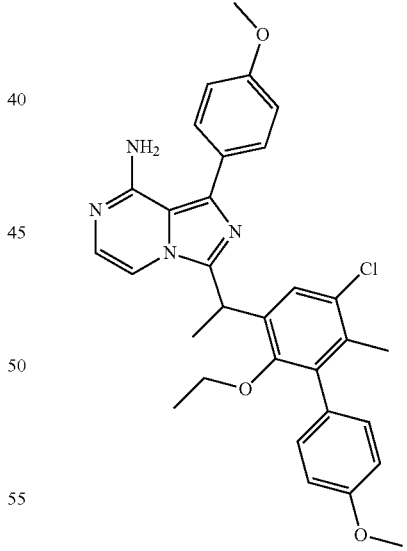

To a mixture of 1-bromo-3-(1-(5-chloro-2-ethoxy-3-iodo-4-methylphenyl)ethyl)imidazo[1,5-a]pyrazin-8-amine (160 mg, 0.3 mmol), (4-methoxyphenyl)boronic acid (90 mg, 0.6 mmol) and Cs₂CO₃ (290 mg, 0.9 mmol) in dioxane (20 mL) and water (10 mL) was added Pd(dppf)Cl₂ (20 mg, 0.03 mmol). The mixture was degassed and refilled with N₂, then stirred at 100° C. for 5 hrs. The mixture was cooled and diluted with water (20 mL), extracted with ethyl acetate (3×20 mL). The combined organic phase was washed with brine, dried over anhydrous sodium sulfate, filtered and concentrated. The residue was purified by silica gel column chromatography (elution with CH$_2$C$_2$/MeOH=20/1) to afford the product (60 mg in 36% yield) as a white solid. $^1$H NMR (400 MHz, DMSO-d6) δ 7.54 (d, J=8.5 Hz, 2H), 7.34 (d, J=5.0 Hz, 1H), 7.23 (d, J=7.5 Hz, 1H), 7.19-7.14 (m, 2H), 7.09 (d, J=8.6 Hz, 2H), 7.05-7.00 (m, 3H), 6.03 (brs, 2H), 4.86 (q, J=6.9 Hz, 1H), 3.83 (s, 3H), 3.81 (s, 3H), 3.49-3.40 (m, 1H), 3.33-3.24 (m, 1H), 2.02 (s, 3H), 1.72 (d, J=7.0 Hz, 3H), 0.86 (t, J=7.0 Hz, 3H). MS (ESI) m/e (M+1)$^+$ 543.2.

Example 45

1-chloro-3-(1-(5-chloro-2-ethoxy-4'-methoxy-6-methyl-[1,1'-biphenyl]-3-yl)ethyl)imidazo[1,5-a]pyrazin-8-amine (Compound 45)

Compound 45

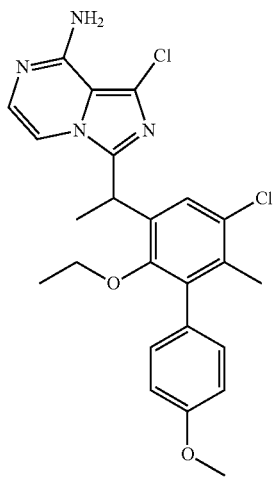

Compound 45A

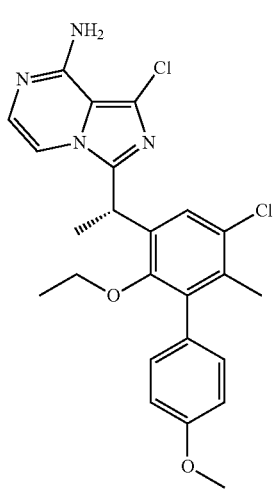

Compound 45B

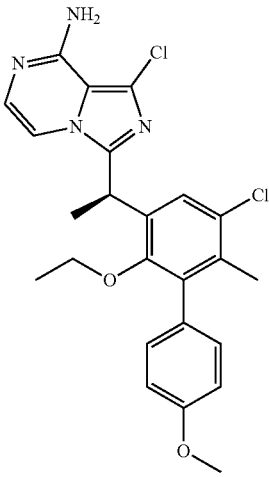

Step 1: 1-(5-chloro-2-hydroxy-3-iodo-4-methylphenyl)ethan-1-one (45-1)

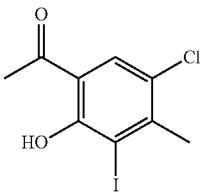

To a solution of 1-(5-chloro-2-hydroxy-4-methylphenyl)ethan-1-one (10.0 g, 54.2 mmol) in acetic acid (150 mL) was added 1-iodopyrrolidine-2,5-dione (NIS, 15.8 g, 70.2 mmol). The mixture was stirred at 80° C. for 15 hrs. The mixture was concentrated. The residue was diluted with ethyl acetate (200 mL), washed with saturated Na$_2$SO$_3$ solution (100 mL), saturated NaHCO$_3$ solution (100 mL), brine (100 mL), dried over Na$_2$SO$_4$, filtered and concentrated. The residue was purified by silica gel column chromatography (elution with hexane/ethyl acetate=20/1) to afford the product (12.0 g in 71% yield) as a yellow oil. MS (ESI) m/e (M+1)$^+$ 310.9.

Step 2: 1-(5-chloro-2-ethoxy-3-iodo-4-methylphenyl)ethan-1-one (45-2)

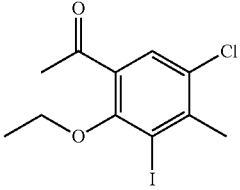

To a solution of 1-(5-chloro-2-hydroxy-3-iodo-4-methylphenyl)ethan-1-one (12.0 g, 38.6 mmol) and iodoethane (18.0 g, 115 mmol) in DMF (80 mL) was added K$_2$CO$_3$ (15.9 g, 115 mmol). The mixture was stirred at 80° C. for overnight. The mixture was cooled and diluted with ethyl acetate (200 mL), washed with water (3×30 mL), brine (30 mL), dried over Na$_2$SO$_4$, filtered and concentrated. The residue was purified by silica gel column chromatography (elution with hexane/ethyl acetate=20/1) to afford the product (8.6 g in 65% yield) as a yellow oil. $^1$H NMR (400 MHz, CDCl$_3$) δ 7.59 (s, 1H), 3.90 (q, J=7.0 Hz, 2H), 2.67 (s, 3H), 2.62 (s, 3H), 1.49 (t, J=7.0 Hz, 3H). MS (ESI) m/e (M+1)$^+$ 339.0.

Step 3: 1-(5-chloro-2-ethoxy-4'-methoxy-6-methyl-[1,1'-biphenyl]-3-yl)ethan-1-one (45-3)

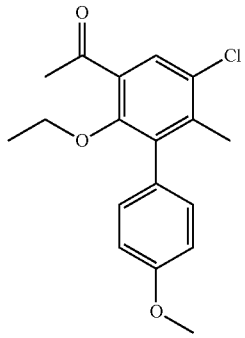 [SMILES: CCOc1c(C(C)=O)cc(Cl)c(C)c1-c1ccc(OC)cc1]

Compound (45-3) was prepared by the similar manner as compound (38-3) described in example 38. MS (ESI) m/e (M+1)$^+$ 319.1.

Step 4: 3-chloro-6-ethoxy-4'-methoxy-2-methyl-5-(prop-1-en-2-yl)-1,1'-biphenyl (45-4)

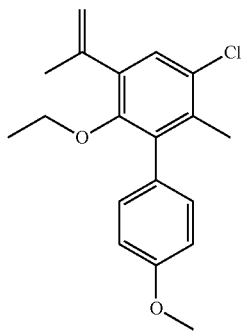 [SMILES: C=C(C)c1cc(Cl)c(C)c(-c2ccc(OC)cc2)c1OCC]

To a mixture of bromo(methyl)triphenyl-phosphane (3.4 g, 9.5 mmol) in THF (30 mL) was added n-BuLi (1.6 M in THF, 4.7 mL, 7.5 mmol) dropwise at −78° C. The mixture was stirred for 1 hr. A solution of 1-(5-chloro-2-ethoxy-4'-methoxy-6-methyl-[1,1'-biphenyl]-3-yl)ethan-1-one (1.5 g, 4.7 mmol) in THE (10 mL) was added dropwise to the mixture. The mixture was stirred at room temperature for 2 hrs. The mixture was diluted with water (50 mL), extracted with ethyl acetate (3×30 mL). The combined organic phase was washed with brine, dried over anhydrous sodium sulfate, filtered and concentrated. The residue was purified by silica gel column chromatography (elution with hexane/ethyl acetate=20/1) to afford the product (0.8 g in 53% yield) as a colorless oil. $^1$H NMR (400 MHz, CDCl$_3$) δ 7.21 (s, 1H), 7.15 (d, J=8.7 Hz, 2H), 6.95 (d, J=8.7 Hz, 2H), 5.16-5.11 (m, 2H), 3.86 (s, 3H), 3.47 (q, J=7.0 Hz, 2H), 2.14 (s, 3H), 2.11 (s, 3H), 0.90 (t, J=7.0 Hz, 3H).

Step 5: 2-(5-chloro-2-ethoxy-4'-methoxy-6-methyl-[1,1'-biphenyl]-3-yl)propan-1-ol (45-5)

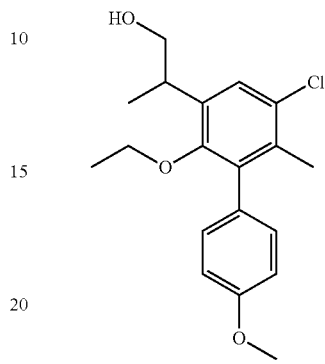

To a 100 mL flask were added 3-chloro-6-ethoxy-4'-methoxy-2-methyl-5-(prop-1-en-2-yl)-1,1'-biphenyl (0.8 g, 2.5 mmol) and BH$_3$-THF (1 M in THF, 25 ml, 25 mmol). The mixture was stirred for 15 hrs. Then a NaOH solution (0.25 M, 10 mL) was added to the mixture carefully, followed by H$_2$O$_2$ (30% w/w, 10 mL). The mixture was stirred for 1 hr. The mixture was extracted with ethyl acetate (3×20 mL). The combined organic phase was washed with brine, dried over anhydrous sodium sulfate, filtered and concentrated. The residue was purified by silica gel column chromatography (elution with hexane/ethyl acetate=10/1) to afford the product (0.7 g in 83% yield) as a colorless oil, MS (ESI) m/e (M+1)$^+$ 335.1.

Step 6: 2-(5-chloro-2-ethoxy-4'-methoxy-6-methyl-[1,1'-biphenyl]-3-yl)propanoic Acid (45-6)

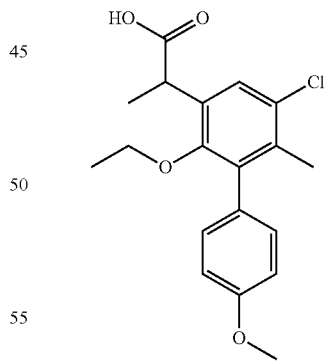

To a solution of 2-(5-chloro-2-ethoxy-4'-methoxy-6-methyl-[1,1'-biphenyl]-3-yl)propan-1-ol (0.7 g, 2.1 mmol) in acetonitrile (20 mL) was added tetramethylpiperdinyloxy free radical (TEMPO, 65 mg, 0.42 mmol), and then phosphate buffer solution (pH=6.7, 20 mL). To the mixture was added NaClO$_2$ (1.9 g, 21 mmol) and NaClO solution (6%, 26 mL). The mixture was stirred at 0° C. for 2 hrs. The mixture was extracted with ethyl acetate (3×20 mL). The combined organic phase was washed with brine, dried over anhydrous sodium sulfate, filtered and concentrated to afford the product 800 mg (crude) as a yellow oil. MS (ESI) m/e (M+1)+ 349.1.

Step 7: 2-(5-chloro-2-ethoxy-4'-methoxy-6-methyl-[1,1'-biphenyl]-3-yl)-N-((3-chloropyrazin-2-yl)methyl)propanamide (45-7)

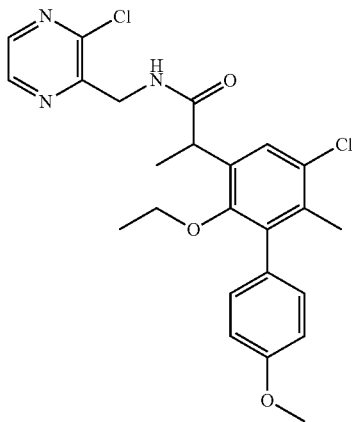 [SMILES: CCOc1c(C(C)C(=O)NCc2nccnc2Cl)cc(Cl)c(C)c1-c1ccc(OC)cc1]

To a solution of 2-(5-chloro-2-ethoxy-4'-methoxy-6-methyl-[1,1'-biphenyl]-3-yl)propanoic acid (800 mg, 2.3 mmol), (3-chloropyrazin-2-yl)methanamine 2 HCl salt (750 mg, 3.5 mmol) and Et$_3$N (1.2 g, 11.9 mmol) in CH$_2$C$_2$ (30 mL) were added 1-ethyl-3-(3-dimethylaminopropyl)carbodiimide hydrochloride (EDCI, 880 mg, 4.6 mmol) and 1-hydroxybenzotriazole (HOBT, 620 mg, 4.6 mmol). The mixture was stirred for 4 hrs. The mixture was diluted with water (50 mL), extracted with dichloromethane (3×20 mL). The combined organic phase was washed with brine, dried over anhydrous sodium sulfate, filtered and concentrated. The residue was purified by silica gel column chromatography (elution with hexane/ethyl acetate=5/1) to afford the product (800 mg in 73% yield) as a yellow oil. MS (ESI) m/e (M+1)+ 474.1.

Step 8: 8-chloro-3-(1-(5-chloro-2-ethoxy-4'-methoxy-6-methyl-[1'-biphenyl]-3-yl)ethyl)imidazo[1,5-a]pyrazine (45-8)

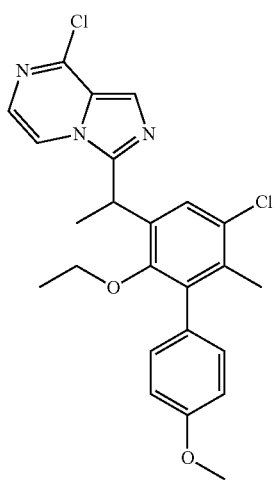 [SMILES: CCOc1c(C(C)c2ncc3c(Cl)nccn23)cc(Cl)c(C)c1-c1ccc(OC)cc1]

To a solution of 2-(5-chloro-2-ethoxy-4'-methoxy-6-methyl-[1,1'-biphenyl]-3-yl)-N-((3-chloropyrazin-2-yl)methyl)propanamide (800 mg, L 7 mmol) in dichloromethane (20 mL) was added trifluoromethanesulfonic anhydride (2.4 g, 8.5 mmol) dropwise. Then pyridine (1.4 g, 17.7 mmol) was added to the mixture dropwise. The mixture was stirred for 30 mins. The mixture was diluted with water (30 mL), extracted with dichloromethane (3×20 mL). The combined organic phase was washed with brine, dried over anhydrous sodium sulfate, filtered and concentrated. The residue was purified by silica gel column chromatography (elution with CH$_2$Cl$_2$/MeOH=30/1) to afford the product (500 mg in 64% yield) as a yellow oil. MS (ESI) m/e (M+1)+ 456.1, 4581.

Step 9: 1,8-dichloro-3-(1-(5-chloro-2-ethoxy-4'-methoxy-6-methyl-[1,1'-biphenyl]-3-yl)ethyl)imidazo[1,5-a]pyrazine (45-9)

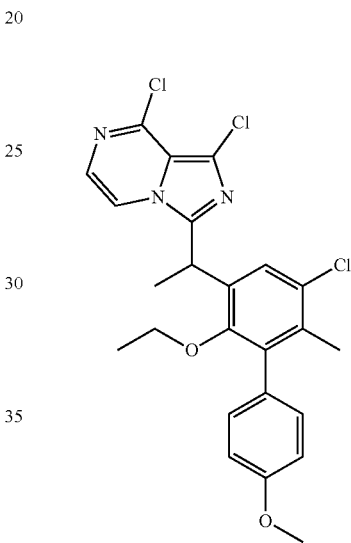

To a mixture of 8-chloro-3-(1-(5-chloro-2-ethoxy-4'-methoxy-6-methyl-[1,1'-biphenyl]-3-yl)ethyl)imidazo[1,5-a]pyrazine (500 mg, 1.1 mmol) in DMF (10 mL) was added 1-chloropyrrolidine-2,5-dione (NCS, 190 mg, 1.3 mmol). The mixture was stirred at 60° C. for 2 hrs. The mixture was cooled and diluted with ethyl acetate (80 mL), washed with water (3×20 mL), brine (20 mL), dried over anhydrous sodium sulfate, filtered and concentrated to afford the product 500 mg (crude) as a yellow oil. MS (ESI) m/e (M+1)+ 490.0, 492.1.

Step 10: 1-chloro-3-(1-(5-chloro-2-ethoxy-4'-methoxy-6-methyl-[1,1'-biphenyl]-3-yl)ethyl)imidazo[1,5-a]pyrazin-8-amine (45-10)

To a sealed tube were added 1,8-dichloro-3-(1-(5-chloro-2-ethoxy-4'-methoxy-6-methyl-[1,1'-biphenyl]-3-yl)ethyl)imidazo[1,5-a]pyrazine (500 mg, 1.0 mmol) and NH$_3$ in propan-2-ol (20% w/w, 15 mL). The mixture was stirred at 90° C. for 15 hrs, cooled and filtered. The filter cake was triturated with MeOH (10 mL), and filtered to afford 200 mg of product, which was separated by chiral prep-HPLC to give two compounds, Compound 45A (37 mg in 7% yield, the first and fast isomer) and Compound 45B (35 mg in 7% yield, the second and slow isomer), as a gray solids, Compound 45A was expected be in (S)-configuration.

Compound 45: $^1$H NMR (400 MHz, DMSO-d6) δ 7.31 (d, J=5.1 Hz, 1H), 7.25-7.11 (m, 3H), 7.03-6.99 (m, 3H), 6.73 (s, 2H), 4.81 (q, J=7.0 Hz, 1H), 3.80 (s, 3H), 3.43-3.36 (m, 1H), 3.25-3.17 (m, 1H), 2.02 (s, 3H), 1.64 (d, J=7.1 Hz, 3H), 0.82 (t, J=7.0 Hz, 3H). MS (ESI) m/e (M+1)$^+$ 4711.

Compound 45A: $^1$H NMR (400 MHz, DMSO-d6) δ 7.31 (d, J=5.1 Hz, 1H), 7.25-7.11 (m, 3H), 7.03-6.99 (m, 3H), 6.73 (s, 2H), 4.81 (q, J=7.0 Hz, 1H), 3.80 (s, 3H), 3.43-3.36 (m, 1H), 3.25-3.17 (m, 1H), 2.02 (s, 3H), 1.64 (d, J=7.1 Hz, 3H), 0.82 (t, J=7.0 Hz, 3H). MS (ESI) m/e (M+1)$^+$ 471.1.

Compound 45B: $^1$H NMR (400 MHz, DMSO-d$_6$) δ 7.31 (d, J=5.1 Hz, 1H), 7.24-7.12 (m, 3H), 7.03-6.99 (m, 3H), 6.73 (s, 2H), 4.81 (q, J=7.1 Hz, 1H), 3.80 (s, 3H), 3.43-3.35 (m, 1H), 3.25-3.18 (m, 1H), 2.02 (s, 3H), 1.64 (d, J=7.1 Hz, 3H), 0.82 (t, J=7.0 Hz, 3H). MS (ESI) m/e (M+1)$^+$ 471.1.

| Column | CHIRALART Cellulose-SB |
|---|---|
| Column size | 2 cm × 25 cm |
| Injection | 0.5 ML |
| Mobile phase | Hex:IPA = 90:10 |
| Flow rate | 20 ml/min |
| Wave length | UV 220 nm |
| Temperature | 35° C. |
| Sample solution | 18.3 mg/ml in mobile phase |
| Prep-HPLC equipment | BJ-Prep-Gilson-HPLC |

Example 46

4-(3-(1-(8-amino-1-chloroimidazo[1,5-a]pyrazin-3-yl)ethyl)-5-chloro-2-ethoxy-6-methylphenyl)pyrrolidin-2-one (Compound 46)

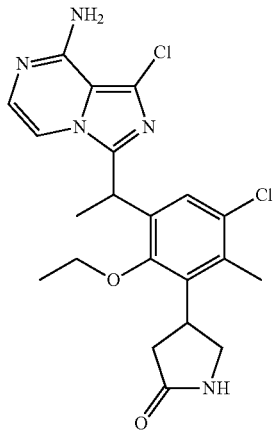 [SMILES: CCOc1c(C(C)c2nc(Cl)c3c(N)nccn23)cc(Cl)c(C)c1C1CNC(=O)C1]

Step 1: 2-(5-chloro-2-ethoxy-3-iodo-4-methylphenyl)propanenitrile (46-1)

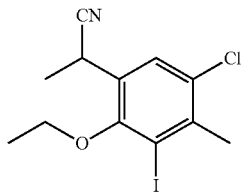

To a solution of 1-chloro-5-(1-chloroethyl)-4-ethoxy-3-iodo-2-methylbenzene (4.1 g, 11.4 mmol) in DMF (20 ml) was added NaCN (1.5 g, 30.6 mmol). The mixture was stirred at 70° C. for overnight. The mixture was cooled and diluted with water (80 mL), extracted with EtOAc (3×30 mL). The combined organic phase was washed with water (30 mL), brine (30 mL), dried over anhydrous sodium sulfate, filtered and concentrated. The residue was purified by silica gel column chromatography (elution with hexane/ethyl acetate=10/1) to afford the product (3.0 g in 75% yield) as a yellow oil. $^1$H NMR (400 MHz, CDCl$_3$) δ 7.47 (s, 1H), 4.19 (q, J=7.2 Hz, 1H), 4.09-4.01 (m, 1H), 3.95-3.87 (m, 1H), 2.62 (s, 3H), 1.60 (d, J=7.2 Hz, 3H), 1.51 (t, J=7.0 Hz, 3H).

Step 2: 2-(5-chloro-2-ethoxy-3-iodo-4-methylphenyl)propanoic Acid (46-2)

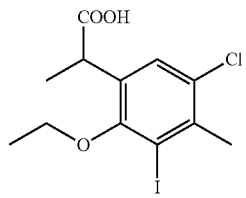 [SMILES: CCOc1c(C(C)C(=O)O)cc(Cl)c(C)c1I]

To a solution of 2-(5-chloro-2-ethoxy-3-iodo-4-methylphenyl)propanenitrile (3.0 g, 8.6 mmol) in AcOH (10 mL) was added conc. HCl (10 mL). The mixture was stirred at 100° C. for 6 hrs. The mixture was concentrated, the residue was purified by silica gel column chromatography (elution with hexane/ethyl acetate=10/1) to afford the product (3.0 g in 75% yield) as a yellow oil. MS (ESI) m/e [M−1]$^+$ 366.9.

Step 3: 2-(5-chloro-2-ethoxy-3-iodo-4-methylphenyl)-N-((3-chloropyrazin-2-yl)methyl)propanamide (46-3)

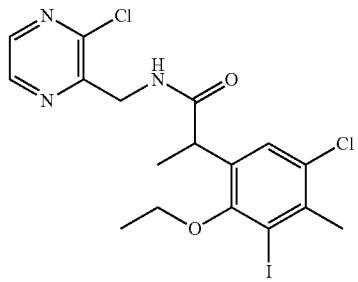 [SMILES: CCOc1c(C(C)C(=O)NCc2nccnc2Cl)cc(Cl)c(C)c1I]

Compound (46-3) was prepared by the similar manner as compound (11-7) described in example 11. MS (ESI) m/e (M+1)$^+$ 494.0.

Step 4: 8-chloro-3-(1-(5-chloro-2-ethoxy-3-iodo-4-methylphenyl)ethyl)imidazo[1,5-a]pyrazine (46-4)

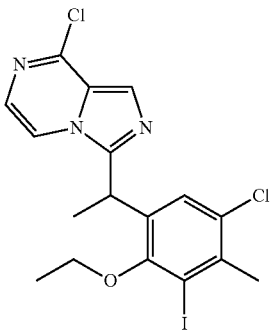 [SMILES: CCOc1c(C(C)c2ncc3c(Cl)nccn23)cc(Cl)c(C)c1I]

Compound (46-4) was prepared by the similar manner as compound (11-8) described in example 11, MS (ESI) m/e (M+1)⁺ 475.9.

Step 5: 1,8-dichloro-34(1-(5-chloro-2-ethoxy-3-iodo-4-methylphenyl)ethyl)imidazo[1,5-a]pyrazine (46-5)

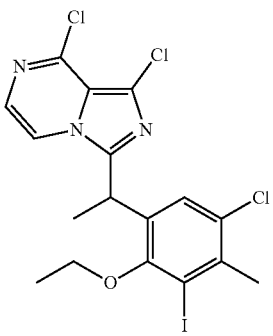 [SMILES: CCOc1c(C(C)c2nc(Cl)c3c(Cl)nccn23)cc(Cl)c(C)c1I]

Compound (46-5) was prepared by the similar manner as compound (11-9) described in example 11. MS (ESI) m/e (M+1)⁺ 509.9.

Step 6: 1-chloro-3-(1-(5-chloro-2-ethoxy-3-iodo-4-methylphenyl)ethyl)imidazo[1,5-a]pyrazin-8-amine (46-6)

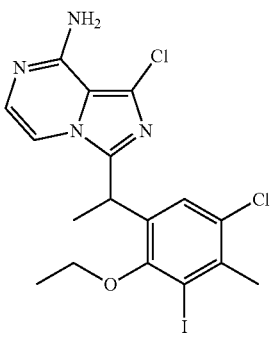 [SMILES: CCOc1c(C(C)c2nc(Cl)c3c(N)nccn23)cc(Cl)c(C)c1I]

Compound (46-6) was prepared by the similar manner as compound (11-10) described in example 11. MS (ESI) m/e (M+1)⁺ 491.0.

Step 7: di-tert-butyl (1-chloro-3-(1-(5-choro-2-ethoxy-3-iodo-4-methylphenyl)ethyl) imidazo[1,5-a]pyrazin-8-yl)iminodiformate (46-7)

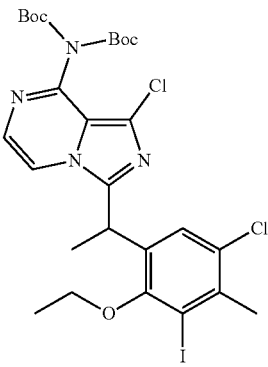 [SMILES: CCOc1c(C(C)c2nc(Cl)c3c(N(C(=O)OC(C)(C)C)C(=O)OC(C)(C)C)nccn23)cc(Cl)c(C)c1I]

To a mixture of 1-chloro-3-(1-(5-chloro-2-ethoxy-3-iodo-4-methylphenyl)ethyl) imidazo[1,5-a]pyrazin-8-amine (1.5 g, 3.0 mmol), di-tert-butyl dicarbonate (2.0 g, 9.1 mmol) and Et₃N (910 mg, 9.0 mmol) in THF (30 mL) was added dimethylaminopyridine (DMAP, 40 mg, 0.3 mmol). The mixture was stirred for 2 days at room temperature. The mixture was diluted with water (50 mL), extracted with EtOAc (3×30 mL), dried over anhydrous sodium sulfate, filtered and concentrated. The residue was purified by silica gel column chromatography (elution with hexane/ethyl acetate=10/1) to afford the product (1.2 g in 57% yield) as a yellow solid. MS (ESI) m/e (M+1)⁺ 691.1.

Step 8: ethyl 3-(3-(1-(8-((di-tert-butoxycarbonyl)amino)-1-chloroimidazo[1,5-a]pyrazin-3-yl)ethyl)-5-chloro-2-ethoxy-6-methylphenyl)acrylate (46-8)

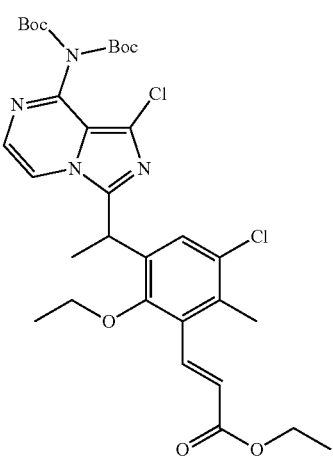 [SMILES: CCOC(=O)/C=C/c1c(C)c(Cl)cc(C(C)c2nc(Cl)c3c(N(C(=O)OC(C)(C)C)C(=O)OC(C)(C)C)nccn23)c1OCC]

To a mixture of di-tert-butyl (1-chloro-3-(1-(5-chloro-2-ethoxy-3-iodo-4-methylphenyl)ethyl)imidazo[1,5-a]pyrazin-8-yl)iminodiformate (1.2 g, 1.7 mmol), ethyl acrylate (3.4 g, 34 mmol), Et₃N (860 mg, 8.5 mmol) in acetonitrile (20 mL) were added Pd(OAc)₂ (40 mg, 0.18 mmol) and tri-o-tolylphosphine (110 mg, 0.36 mmol). The mixture was protected with nitrogen and refluxed for 15 hrs. The mixture was concentrated. The residue was purified by silica gel column chromatography (elution with $CH_2Cl_2$/ MeOH=100/1) to afford the product (160 mg, crude) as a yellow oil. MS (ESI) m/e (M+1)$^+$ 663.2.

Step 9: ethyl 3-(3-(1-(8-((di-tert-butoxycarbonyl) amino)-1-chloroimidazo[1,5-a]pyrazin-3-yl)ethyl)-5-chloro-2-ethoxy-6-methylphenyl)-4-nitrobutanoate (46-9)

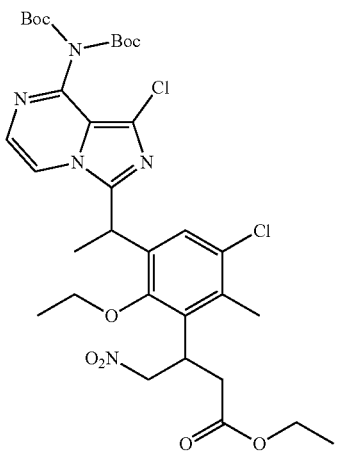 [SMILES: CCOC(=O)CC(C[N+](=O)[O-])c1c(C)c(Cl)cc(C(C)c2nc(Cl)c3c(N(C(=O)OC(C)(C)C)C(=O)OC(C)(C)C)nccn23)c1OCC]

To a solution of ethyl 3-(3-(1-(8-(((di-tert-butoxycarbonyl) amino)-1-chloroimidazo[1,5-a]pyrazin-3-yl)ethyl)-5-chloro-2-ethoxy-6-methylphenyl)acrylate (160 mg, 0.24 mmol) in nitromethane (10 mL) was added 1,8-diazabicyclo [5.4.0]undec-7-ene (DBU, 50 mg, 0.31 mmol). The mixture was stirred at 70° C. for 5 hrs. The mixture was concentrated to afford the product (200 mg, crude) as a brown oil. MS (ESI) m/e (M+1)$^+$ 724.2.

Step 10: 4-(3-(1-(8-amino-1-chloroimidazo[1,5-a] pyrazin-3-yl)ethyl)-5-chloro-2-ethoxy-6-methylphenyl)pyrrolidin-2-one (46-10)

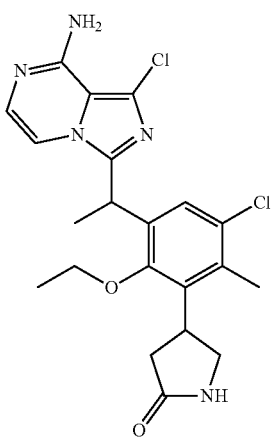 [SMILES: CCOc1c(C(C)c2nc(Cl)c3c(N)nccn23)cc(Cl)c(C)c1C1CNC(=O)C1]

To a mixture of ethyl 3-(3-(1-(8-(((di-tert-butoxycarbonyl) amino)-1-chloroimidazo[1,5-a]pyrazin-3-yl)ethyl)-5-chloro-2-ethoxy-6-methylphenyl)-4-nitrobutanoate (200 mg, 0.28 mmol) in AcOH (10 mL) was added Zn powder (180 mg, 2.8 mmol). The mixture was refluxed for 15 hrs. The mixture was filtered and concentrated. The residue was purified by prep-HPLC to afford 16 mg (12%) of 4-(3-(1-(8-amino-1-chloroimidazo[1,5-a]pyrazin-3-yl)ethyl)-5-chloro-2-ethoxy-6-methylphenyl)pyrrolidin-2-one as a yellow solid. $^1$H NMR (400 MHz, CDCl$_3$) δ 7.17 (s, 0.5H), 7.16-7.14 (m, 1H), 7.12 (d, J=5.2 Hz, 0.5H), 6.91 (t, J=4.9 l-z, 1H), 5.80 (d, J=10.5 Hz, 1H), 4.65-4.57 (m, 1H), 4.51-4.39 (m, 1H), 3.94-3.78 (m, 2H), 3.75 (t, J=9.9 Hz, 1H), 3.61-3.55 (m, 0.5H), 3.46-3.39 (m, 0.5H), 2.75-2.68 (m, 1.5H), 2.56-2.49 (m, 0.5H), 2.30 (s, 3H), 1.83-1.81 (m, 3H), 1.55-1.51 (m, 3H). MS (ESI) m/e (M+1)$^+$ 448.1.

| | |
|---|---|
| Instrument: | CXTH |
| Column: | Gemini-NX C18 |
| Column size: | 21.1 cm I.D. × 150 cm L, 5 μm |
| Flow rate: | 20 ml/min |
| Wavelength: | 214 nm |
| Mobile phase: | Solvent A: water (0.1% TFA) |
| | Solvent B: CH$_3$CN |

| Time table | |
|---|---|
| Time (min) | Solvent B % |
| 0.0 | 20 |
| 11.0 | 35 |
| 11.2 | 90 |
| 15.0 | 90 |
| 15.2 | 20 |
| 17.5 | 20 |

Example 47

5-(3-(1-(8-amino-1-chloroimidazo[1,5-a]pyrazin-3-yl)ethyl)-5-chloro-6-fluoro-2-isopropoxyphenyl) pyridin-2(1H)-one (Compound 47)

Compound 47

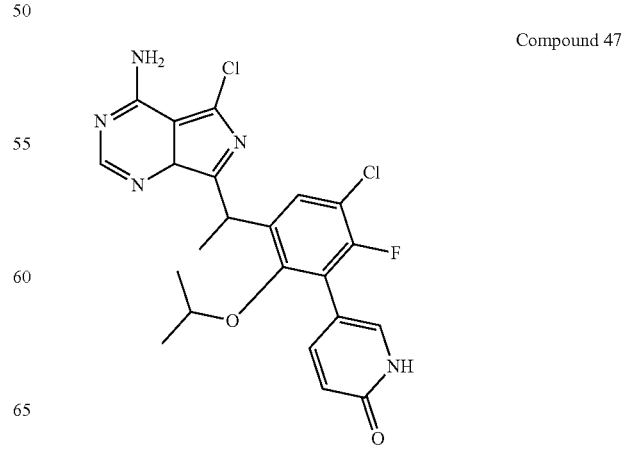

-continued

Compound 47A

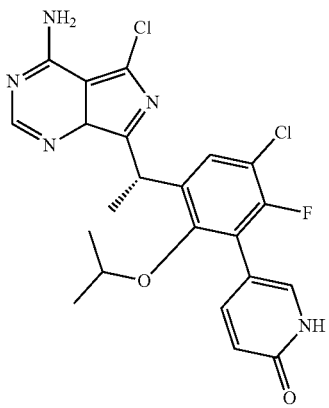

Compound 47B

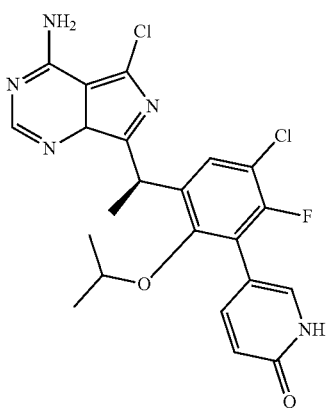

Step 1: 1-(3-bromo-5-chloro-4-fluoro-2-hydroxyphenyl)ethan-1-one (47-1)

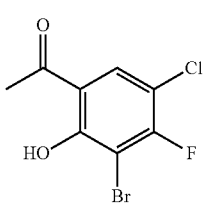

To a solution of 1-(5-chloro-4-fluoro-2-hydroxyphenyl)ethan-1-one (38.0 g, 201 mmol) in ACOH (500 mL) was added 1-bromopyrrolidine-2,5-dione (NBS, 53.8 g, 302 mmol). The mixture was stirred at 50° C. for 2 days. The mixture was concentrated. The residue was diluted with EtOAc (500 mL), washed with water (3×200 mL), brine (200 mL), dried over anhydrous sodium sulfate, filtered and concentrated. The residue was purified by silica gel column chromatography (elution with hexane/ethyl acetate=50/1) to afford 16.0 g (crude) of 1-(3-bromo-5-chloro-4-fluoro-2-hydroxyphenyl)ethan-1-one as a yellow oil. MS (ESI) m/e $(M+1)^+$ 266.9, 268.9.

Step 2: 1-(3-bromo-5-chloro-4-fluoro-2-isopropoxyphenyl)ethan-1-one (47-2)

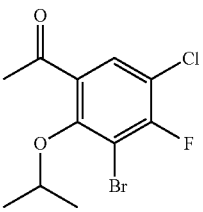 [SMILES: CC(=O)c1cc(Cl)c(F)c(Br)c1OC(C)C]

To a solution of 1-(3-bromo-5-chloro-4-fluoro-2-hydroxyphenyl)ethan-1-one (16.0 g, 60 mmol) and 2-iodopropane (20.4 g, 120 mmol) in DMF (100 mL) was added $NaHCO_3$ (10.0 g, 120 mmol). The mixture was stirred at 60° C. for 15 hrs. The mixture was diluted with water (100 mL), extracted with EtOAc (3×100 mL). The combined organic phase was washed with water (3×100 mL), brine (100 mL), dried over anhydrous sodium sulfate, filtered and concentrated. The residue was purified by silica gel column chromatography (elution with hexane/ethyl acetate=30/1) to afford (6.0 g in 32% yield) of 1-(3-bromo-5-chloro-4-fluoro-2-isopropoxyphenyl)ethan-1-one as a yellow oil. $^1$H NMR (400 MHz, $CDCl_3$) δ 7.57 (d, J=8.2 Hz, 1H), 4.48-4.37 (m, 1H), 2.61 (s, 3H), 1.32 (d, J=6.2 Hz, 6H).

Step 3: 3-bromo-1-chloro-2-fluoro-4-isopropoxy-5-(prop-1-en-2-yl)benzene (47-3)

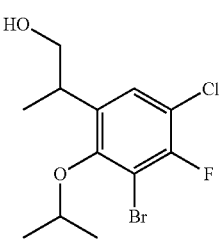 [SMILES: CC(C)Oc1c(C(C)CO)cc(Cl)c(F)c1Br]

Compound (47-3) was prepared by the similar manner as compound (11-4) described in example 11. $^1$H NMR (400 MHz, $CDCl_3$) δ 7.21-7.18 (m, 1H), 5.20-5.10 (m, 2H), 4.52-4.46 (m, 1H), 2.10-2.08 (m, 3H), 1.29-1.25 (m, 6H).

Step 4: 2-(3-bromo-5-chloro-4-fluoro-2-isopropoxyphenyl)propan-1-ol (47-4)

Compound (47-4) was prepared by the similar manner as compound (11-5) described in example 11. $^1$H NMR (400 MHz, $CDCl_3$) δ 7.23 (d, J=8.1 Hz, 1H), 4.63-4.52 (m, 1H), 3.71-3.59 (m, 2H), 3.52-3.41 (m, 1H), 1.41 (d, J=6.2 Hz, 3H), 1.29 (d, J=6.2 Hz, 3H), 1.23 (d, J=7.0 Hz, 3H).

Step 5: 2-(3-bromo-5-chloro-4-fluoro-2-isopropoxyphenyl)propanoic Acid (47-5)

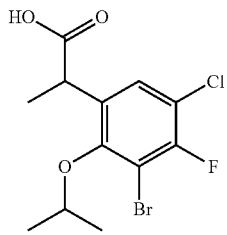

Compound (47-5) was prepared by the similar manner as compound (11-6) described in example 11. MS (ESI) m/e (M+1)+ 338.9, 340.9.

Step 6: 2-(3-bromo-5-chloro-4-fluoro-2-isopropoxyphenyl)-N-((3-chloropyrazin-2-yl)methyl)propanamide (47-6)

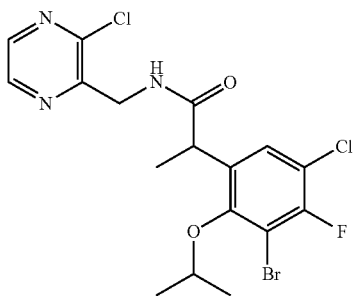 [SMILES: CC(C)Oc1c(C(C)C(=O)NCc2nccnc2Cl)cc(Cl)c(F)c1Br]

Compound (47-6) was prepared by the similar manner as compound (11-7) described in example 11. MS (ESI) m/e (M+1)+ 463.9, 466.0.

Step 7: 3-(1-(3-bromo-5-chloro-4-fluoro-2-isopropoxyphenyl)ethyl)-8-chloroimidazo[1,5-a]pyrazine (47-7)

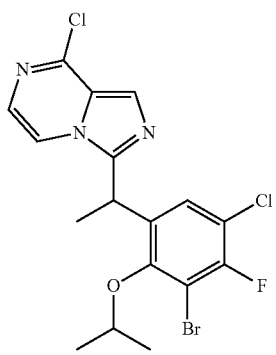 [SMILES: CC(C)Oc1c(C(C)c2ncc3c(Cl)nccn23)cc(Cl)c(F)c1Br]

Compound (47-7) was prepared by the similar manner as compound (11-8) described in example 11. MS (ESI) m/e (M+1)+ 445.9, 447.9.

Step 8: 3-(1-(3-bromo-5-chloro-4-fluoro-2-isopropoxyphenyl)ethyl)-1,8-dichloroimidazo[1,5-a]pyrazine (47-8)

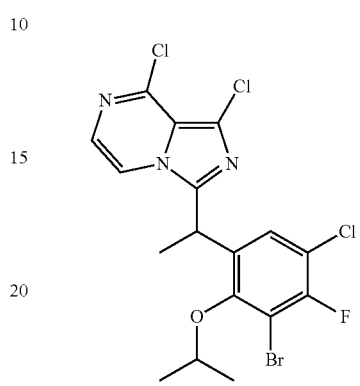

Compound (47-8) was prepared by the similar manner as compound (11-9) described in example 11. MS (ESI) m/e (M+1)+ 479.9, 481.9.

Step 9: 3-(1-(3-bromo-5-chloro-4-fluoro-2-isopropoxyphenyl)ethyl)-1-chloroimidazo[1,5-a]pyrazin-8-amine (47-9)

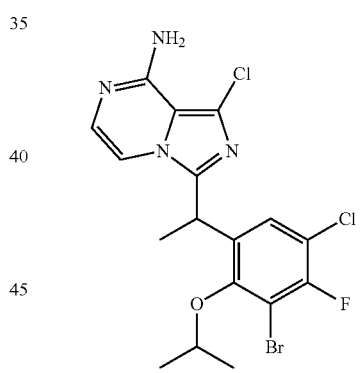

Compound (47-9) was prepared by the similar manner as compound (11-10) described in example 11. MS (ESI) m/e (M+1)+ 461.0, 463.0.

Step 10: 5-(3-(1-(8-amino-1-chloroimidazo[1,5-a]pyrazin-3-yl)ethyl)-5-chloro-6-fluoro-2-isopropoxyphenyl)pyridin-2(1H)-one (47-10)

To a mixture of 3-(1-(3-bromo-5-chloro-4-fluoro-2-isopropoxyphenyl)ethyl)-1-chloroimidazo[1,5-a]pyrazin-8-amine (250 mg, 0.54 mmol), 5-(4,4,5,5-tetramethyl-1,3,2-dioxaborolan-2-yl)pyridin-2-ol (140 mg, 0.63 mmol) and Na$_2$CO$_3$ (120 mg, 1.1 mmol) in dioxane (20 mL) and water (5 mL) was added Pd(PPh$_3$)$_4$ (30 mg, 0.026 mmol). The mixture was degassed and refilled with N$_2$, stirred at 100° C. for 2 hrs, then cooled and diluted with water (20 mL), extracted with ethyl acetate (3×20 mL). The combined organic phase was washed with brine, dried over anhydrous sodium sulfate (Na$_2$SO$_4$), filtered and concentrated. The residue was purified by silica gel column chromatography (elution with dichloromethane/MeOH=10/1) to afford 60 mg of desired product, which was separated by chiral prep-HPLC to give two compound, Compound 47A (15 mg in 5% yield, the first and fast isomer) and Compound 47B (22 mg in 8% yield, the second and slow isomer) as white solids, Compound 47A was expected to be in a (S)-configuration.

Compound 47: 1H NMR (400 MHz, CDCl$_3$) δ 7.57 (d, J=9.4 Hz, 1H), 7.44 (d, J=5.2 Hz, 1H), 7.40 (d, J=2.2 Hz, 1H), 7.33 (d, J=8.2 Hz, 1H), 6.89 (d, J=5.1 Hz, 1H), 6.70 (d, J=9.4 Hz, 1H), 4.79 (q, J=7.2 Hz, 1H), 4.03-3.97 (m, 1H), 1.84 (d, J=7.2 Hz, 3H), 1.23-1.20 (m, 6H).

Compound 47A: $^1$H NMR (400 MHz, DMSO-d6) δ 11.90 (s, 1H), 7.60-7.32 (m, 4H), 7.03 (d, J=4.9 Hz, 1H), 6.74 (s, 2H), 6.44 (d, J=9.4 Hz, 1H), 4.87 (q, J=6.8 Hz, 1H), 4.02-3.83 (m, 1H), 1.63 (d, J=7.0 Hz, 3H), 1.07 (d, J=6.0 Hz, 3H), 0.94 (d, J=6.0 Hz, 3H). MS (ESI) m/e (M+1)$^+$ 476.1.

Compound 47B: $^1$H NMR (400 MHz, DMSO-d6) δ 11.89 (s, 1H), 7.62-7.32 (m, 4H), 7.03 (d, J=5.0 Hz, 1H), 6.73 (s, 2H), 6.44 (d, J=9.4 Hz, 1H), 4.87 (q, J=7.0 Hz, 1H), 4.00-3.85 (m, 1H), 1.63 (d, J=7.0 Hz, 3H), 1.07 (d, J=6.0 Hz, 3H), 0.94 (d, J=6.0 Hz, 3H). MS (ESI) m/e (M+1)$^+$ 476.1.

| Column | CHIRALPAK IC |
| --- | --- |
| Column size | 2 cm × 25 cm, 5 μm |
| Injection | 3.0 ML |
| Mobile phase | 100% MeOH |
| Flow rate | 18 ml/min |
| Wave length | UV 220 nm |
| Temperature | 35° C. |
| Sample solution | 6 mg/ml in mobile phase |
| Prep-HPLC equipment | BJ-Prep-Gilson-HPLC |

Example 48

4-(3-(1-(8-amino-1-chloroimidazo[1,5-a]pyrazin-3-yl)ethyl)-5-chloro-6-fluoro-2-isopropoxyphenyl)pyrrolidin-2-one (Compound 48)

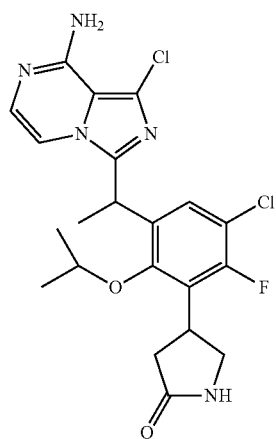

Compound 48

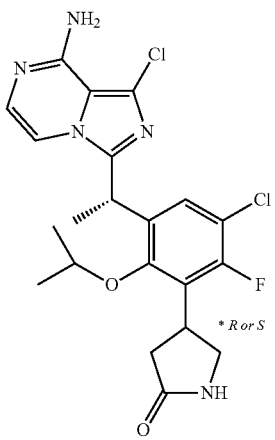

Compound 48A

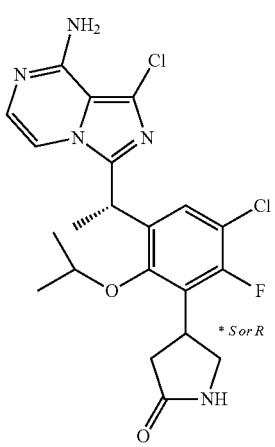

Compound 48B

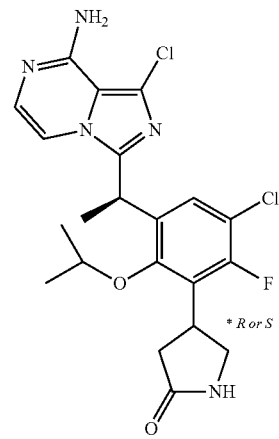

Compound 48C

-continued

Compound 48D

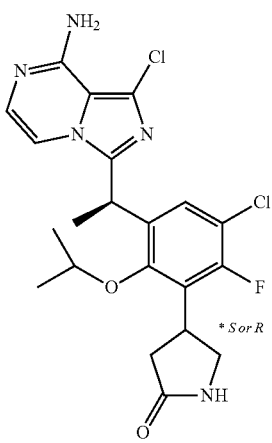

Step 1: 3-(1-(3-bromo-5-chloro-4-fluoro-2-isopropoxyphenyl)ethyl)-1-chloro-N-(2,4-dimethoxybenzyl)imidazo[1,5-a]pyrazin-8-amine (48-1)

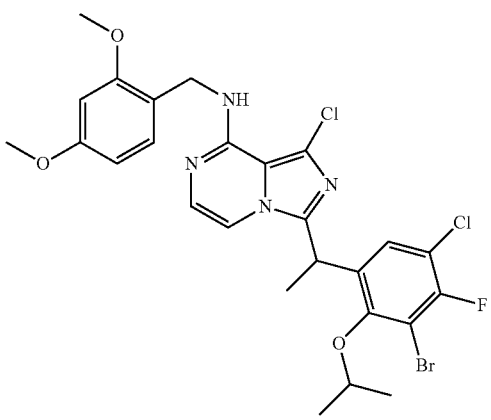 [SMILES: COc1ccc(CNc2nccn3c(C(C)c4cc(Cl)c(F)c(Br)c4OC(C)C)nc(Cl)c23)c(OC)c1]

Compound (47-8) (500 mg, 1.0 mmol), (2,4-dimethoxyphenyl)methanamine (200 mg, 1.2 mmol) and Na₂CO₃ (130 mg, 1.2 mmol) were dissolved in i-PrOH (5 mL). The mixture was stirred at 90° C. for 4 hrs. The mixture was cooled and concentrated. The residue was purified by silica gel column chromatography (elution with hexane/ethyl acetate=2/1) to afford 550 mg (in 89% yield) of 3-(1-(3-bromo-5-chloro-4-fluoro-2-isopropoxyphenyl)ethyl)-1-chloro-N-(2,4-dimethoxybenzyl)imidazo[1,5-a]pyrazin-8-amine as a yellow solid.

Step 2: ethyl 3-(3-chloro-5-(1-(1-chloro-8-((2,4-dimethoxybenzyl)amino)imidazo[1,5-a]pyrazin-3-yl)ethyl)-2-fluoro-6-isopropoxyphenyl)acrylate (48-2)

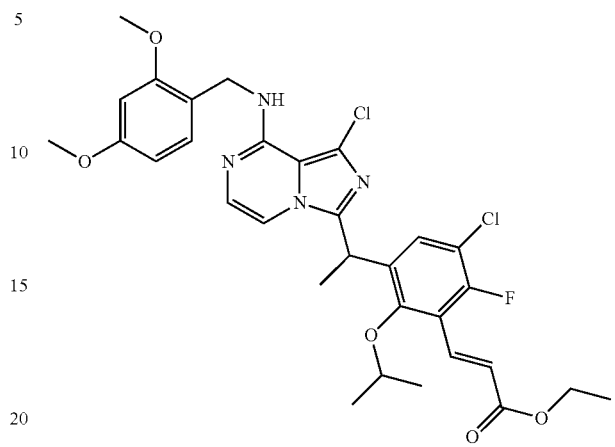

To a solution of 3-(1-(3-bromo-5-chloro-4-fluoro-2-isopropoxyphenyl)ethyl)-1-chloro-N-(2,4-dimethoxybenzyl)imidazo[1,5-a]pyrazin-8-amine (550 mg, 0.9 mmol) and ethyl acrylate (1.8 g, 18.0 mmol) in DMF (20 mL) were added Pd(OAc)₂ (20 mg, 0.09 mmol), tri-o-tolylphosphine (55 mg, 0.18 mmol) and NaHCO₃ (230 mg, 2.7 mmol). The mixture was protected with nitrogen, and stirred at 110° C. for 2 days. The mixture was cooled and diluted with water (50 mL), extracted with EtOAc (3×30 mL). The combined organic phase was washed with water (50 mL), brine (50 mL), dried over anhydrous sodium sulfate, filtered and concentrated. The residue was purified by silica gel column chromatography (elution with hexane/EtOAc=2/1) to afford 150 mg (in 26% yield) of ethyl 3-(3-chloro-5-(1-(1-chloro-8-((2,4-dimethoxybenzyl)amino)imidazo[1,5-a]pyrazin-3-yl)ethyl)-2-fluoro-6-isopropoxyphenyl)acrylate as a yellow solid, MS (ESI) m/e (M+1)⁺ 631.1, 633.1.

Step 3: ethyl 3-(3-chloro-5-(1-(1-chloro-8-((2,4-dimethoxybenzyl)amino)imidazo[1,5a]pyrazin-3-yl)ethyl)-2-fluoro-6-isopropoxyphenyl)-4-nitrobutanoate (48-3)

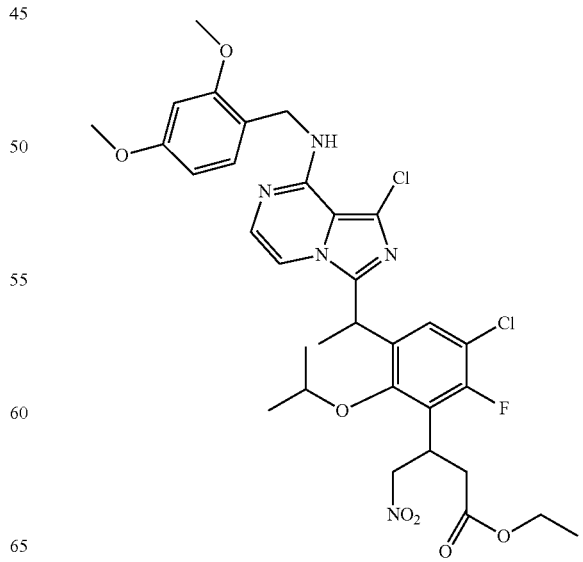

Compound (48-3) was prepared by the similar manner as compound (46-9) described in example 46. MS (ESI) m/e (M+1)⁺ 692.2, 694.2.

Step 4: 4-(3-(1-(8-amino-1-chloroimidazo[1,5-a]pyrazin-3-yl)ethyl)-5-chloro-6-fluoro-2-isopropoxyphenyl)pyrrolidin-2-one (48-4)

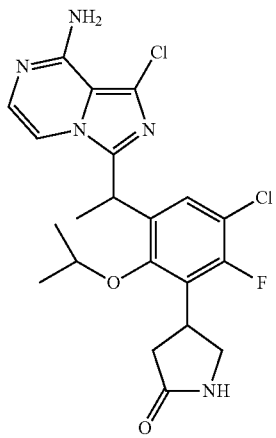 [SMILES: CC(C)Oc1c(C(C)c2nc(Cl)c3c(N)nccn23)cc(Cl)c(F)c1C1CNC(=O)C1]

Compound (48-4) was prepared by the similar manner as compound (46-10) described in Example 46, which was separated by chiral prep-HPLC to give four compounds, Compound 48A (the first isomer), 48B (the second isomer), 48C (the third isomer) and 48D (the fourth isomer) as white solids. Compound 48A and compound 48B was assigned as a (S)-configuration in a similar manner to Compound 40A.

Compound 48: ¹H NMR (400 MHz, CDCl₃) δ 7.29 (d, J=8.3 Hz, 1H), 7.23-7.19 (m, 1H), 6.94-6.88 (m, 1H), 5.75-5.70 (m, 1H), 4.63 (q, J=7.0 Hz, 1H), 4.19-4.08 (m, 2H), 3.73-3.55 (m, 2H), 3.49-3.42 (m, 1H), 2.78-2.72 (m, 1H), 2.66-2.47 (m, 2H), 1.84-1.81 (m, 3H), 1.46-1.43 (m, 3H), 1.42-1.39 m, 3H). MS (ESI) m/e (M+1)⁺ 466.1, 468.0.

Compound 48A: ¹H NMR (400 MHz, DMSO-d6) δ 7.83 (s, 1H), 7.37 (dd, J=12.5, 6.8 I-z, 2H), 7.01 (d, J=5.0 Hz, 1H), 6.73 (s, 2H), 4.78 (q, J=6.9 Hz, 1H), 4.05 (dt, J=13.0, 6.3 Hz, 2H), 3.62 (t, J=9.5 Hz, 1H), 3.31-3.22 (m, 1H), 2.56-2.44 (m, 1H), 2.21 (dd, J=17.0, 8.8 Hz, 1H), 1.62 (d, J=7.0 Hz, 3H), 1.30 (d, J=6.0 Hz, 3H), 1.24 (d, J=6.0 Hz, 3H). MS (M+H)⁺ 465.7.

Compound 48B: ¹H NMR (400 MHz, DMSO-d6) δ 7.81 (s, 1H), 7.37 (dd, J=11.1, 6.8 Hz, 2H), 7.01 (d, J=5.0 Hz, 1H), 6.74 (s, 2H), 4.78 (q, J=6.8 Hz, 1H), 4.24-3.93 (m, 2H), 3.53 (t, J=9.3 Hz, 1H), 3.19 (t, J=8.3 Hz, 1H), 2.57 (dd, J=16.9, 11.0 Hz, 1H), 2.33 (dd, J=17.0, 8.4 Hz, 1H), 1.63 (d, J=7.0 Hz, 3H), 1.31 (d, J=5.9 Hz, 3H), 1.24 (d, J=6.0 Hz, 3H). MS (M+H)⁺ 465.7.

Compound 48C: ¹H NMR (400 MHz, DMSO-d6) δ 7.83 (s, 1H), 7.37 (dd, J=12.5, 6.8 Hz, 2H), 7.01 (d, J=5.0 Hz, 1H), 6.74 (s, 2H), 4.78 (q, J=6.9 Hz, 1H), 4.05 (dt, J=13.0, 6.5 Hz, 2H), 3.62 (t, J=9.4 Hz, 1H), 3.31-3.20 (m, 1H), 2.61-2.41 (m, 1H), 2.21 (dd, J=16.7, 8.3 Hz, 1H), 1.62 (d, J=7.0 Hz, 3H), 1.30 (d, J=6.0 Hz, 3H), 1.24 (d, J=6.0 Hz, 3H). MS (M+H)⁺ 465.7.

Compound 48D: ¹H NMR (400 MHz, DMSO-d6) δ 7.82 (s, 1H), 7.37 (dd, J=11.3, 6.8 Hz, 2H), 7.01 (d, J=5.0 Hz, 1H), 6.74 (s, 2H), 4.78 (q, J=7.0 Hz, 1H), 4.29-3.93 (m, 2K), 3.53 (t, J=9.5 Hz, 1H), 3.19 (t, J=8.2 Hz, 1H), 2.57 (dd, J=17.7, 11.4 Hz, 1H), 2.33 (dd, J=17.3, 8.4 Hz, 1H), 1.63 (d, J=7.0 Hz, 3H), 1.32 (d, J=6.0 Hz, 3H), 1.25 (d, J=6.0 Hz, 3H). MS (M+H)⁺=465.7.

| Column | CHIRALPAK IC |
|---|---|
| Column size | 2 cm × 25 cm, 5 μm |
| Injection | 3.0 ML |
| Mobile phase | 100% MeOH |
| Flow rate | 18 ml/min |
| Wave length | UV 220 nm |
| Temperature | 35° C. |
| Sample solution | 6 mg/ml in mobile phase |
| Prep-HPLC equipment | BJ-Prep-Gilson-HPLC |

Example 49

1-chloro-3-(1-(5-chloro-2-ethoxy-4-fluoro-3-(tetrahydro-2H-pyran-4-yl)phenyl)ethyl)imidazo[1,5-a]pyrazin-8-anine (Compound 49)

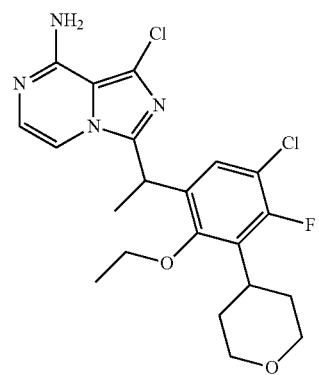

Compound 49

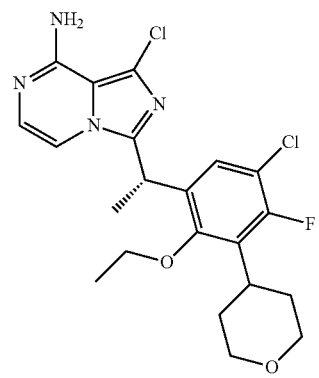

Compound 49A

Compound 49B

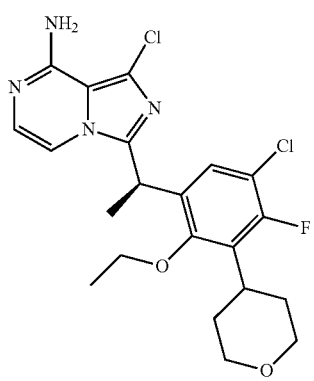

Step 1: 1-(5-chloro-3-(3,6-dihydro-2H-pyran-1-yl)-2-ethoxy-4-fluorophenyl)ethan-1-one (49-1)

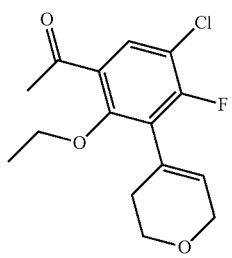 [SMILES: CCOc1c(C(C)=O)cc(Cl)c(F)c1C1=CCOCC1]

A solution of 1-(5-chloro-2-ethoxy-4-fluoro-3-iodophenyl)ethan-1-one (10 g, 29.24 mmol), 2-(3,6-dihydro-2H-pyran-4-yl)-4,4,5,5-tetramethyl-1,3,2-dioxaborolane (9.2 g, 43.86 mmol), Pd(dppf)Cl$_2$ (1.3 g, 1.75 mmol) and Na$_2$CO$_3$ (7.75 g, 73.1 mmol) in dioxane (250 mL) and H$_2$O (50 mL) was stirred at 80° C. for overnight under N$_2$ atmosphere. The reaction mixture was filtered over celite and extracted with ethyl acetate (100 mL×2). The combined organic layer was washed with brine (150 mL) and dried over Na$_2$SO$_4$. The solvent was evaporated to dryness. The residue was purified with column chromatography on silica gel (petroleum ether:ethyl acetate=10:1) to obtain compound as light-yellow solid (6.6 g in 76% yield). MS (ESI) m/e (M+1)$^+$ 299.1.

Step 2: 1-(5-chloro-3-(3,6-dihydro-2H-pyran-4-yl)-2-ethoxy-1-fluorophenyl)ethan-1-ol

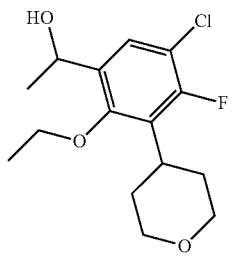 [SMILES: CCOc1c(C(C)O)cc(Cl)c(F)c1C1CCOCC1]

A suspension of 1-(5-chloro-3-(3,6-dihydro-2H-pyran-4-yl)-2-ethoxy-4-fluorophenyl)ethan-1-one (5 g, 16.78 mmol) and PtO$_2$ (190 mg, 0.84 mmol) in ethyl acetate (100 mL) was stirred at r.t for overnight under H$_2$ pressure (4 atm). The reaction mixture was filtered over celite. The solvent was evaporated to dryness. The residue was purified with column chromatography on silica gel (petroleum ether:ethyl acetate=5:1) to obtain the desired compound as light yellow solid (3.7 g in 74% yield). $^1$H NMR (400 MHz, CDCl$_3$) δ 7.38 (d, J=8.4 Hz, 1H), 5.13 (q, J=6.4 Hz, 1H), 4.10, 4.08 (dd, J=11.2 Hz, J=4.0 Hz, 1H), 3.88-3.80 (m, 2H), 3.52-3.47 (m, 2H), 3.23-3.17 (m, 1H), 2.32-2.20 (m, 2H), 1.57-1.53 (m, 2H), 1.49-1.45 (m, 6H). MS (ESI) m/e [M+1−H$_2$O]$^+$ 285.1, 287.1.

Step 3: 1-(5-chloro-2-ethoxy-4-fluoro-3-(tetrahydro-2H-pyran-4-yl)phenyl)ethan-1-one (49-3)

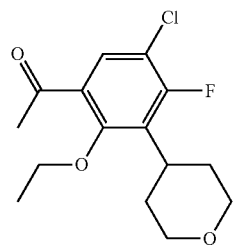 [SMILES: CCOc1c(C(C)=O)cc(Cl)c(F)c1C1CCOCC1]

To a solution of 1-(5-chloro-3-(3,6-dihydro-2H-pyran-4-yl)-2-ethoxy-4-fluorophenyl)ethan-1-ol (100 mg, 0.33 mmol) in DCM (50 mL) was added Dess-Martin reagent (210 mg, 0.495 mmol) at room temperature, the reaction mixture was stirred at room temperature for 1 h. The reaction mixture was evaporated in vacuo. The residue was purified with column chromatography on silica gel (petroleum ether:ethyl acetate=10:1) to obtain the desired compound as white solid (60 mg in 61% yield), $^1$H NMR (400 MHz, CDCl$_3$) δ 7.52 (d, J=8.4 Hz, 1H), 4.11 (dd, J=11.2 Hz, J=4.0 Hz, 2H), 3.83 (q, J=7.2 Hz, 2H), 3.53-3.47 (m, 2H), 3.35-3.28 (m, 1H), 2.60 (s, 3H), 2.30-2.25 (m, 2H), 1.57-1.55 (m, 2H), 1.44 (t, J=6.8 Hz, 3H). MS (ESI) m/e (M+1)$^+$ 301.1, 299.1.

Step 4: 2-(5-chloro-2-ethoxy-4-fluoro-3-(tetrahydro-2H-pyran-4-yl)phenyl)propan-2-ol (49-4)

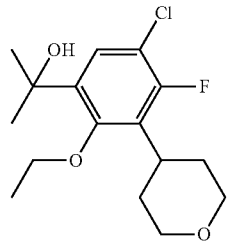 [SMILES: CCOc1c(C(C)(C)O)cc(Cl)c(F)c1C1CCOCC1]

To a solution of 1-(5-chloro-2-ethoxy-4-fluoro-3-(tetrahydro-2H-pyran-4-yl)phenyl)ethan-1-one (100 mg, 0.33 mmol) in THF (50 mL) was added CH$_3$MgBr (0.5 mL, 0.499 mmol, 1M in THF) at 0° C. The reaction mixture was stirred at rt for 2 hrs. NH$_4$Cl (aq, 20 mL) was added, the aqueous layer was extracted with ethyl acetate (50 mL×2). The combined organic layer was washed with brine (50 mL) and dried over Na$_2$SO$_4$. The solvent was evaporated in vacuo. The residue was purified with column chromatography on silica gel (petroleum ether:ethyl acetate=5:1) to obtain the desired compound as white solid (84 mg in 79% yield). $^1$H NMR (400 MHz, CDCl$_3$) δ 7.28 (d, J=8.4 Hz, 1H), 4.11 (dd, J=11.6 Hz, 4.4 Hz, 2H), 3.93 (q, J=7.2 Hz, 2H), 3.53-3.47 (m, 2H), 3.15-3.08 (m, 1H), 2.33-2.29 (m, 2H), 1.59-1.56 (m, 81H), 1.51 (t, J=6.8 Hz, 3H). MS (ESI) m/e (M+1)$^+$ 299.1.

Step 5: 4-(3-chloro-6-ethoxy-2-fluoro-5-(prop-1-en-2-yl)phenyl)tetrahydro-2H-pyran (49-5)

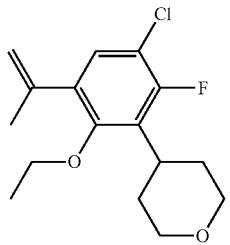 [SMILES: C=C(C)c1cc(Cl)c(F)c(C2CCOCC2)c1OCC]

To a solution of 2-(5-chloro-2-ethoxy-4-fluoro-3-(tetrahydro-2H-pyran-4-yl)phenyl)propan-2-ol (800 mg, 2.72 mmol) in CH$_2$Cl$_2$ (10 mL) was added TFA (5 mL, 6.73 mmol) at room temperature, the reaction mixture was stirred at room temperature for 2 hrs. The solvent was evaporated in vacuo. The residue was dissolved in CH$_2$Cl$_2$ (50 mL), NaHCO$_3$ (aq, 20 mL) was added, the aqueous layer was extracted with CH$_2$Cl$_2$ (50 mL×2). The combined organic layer was washed with brine (50 mL) and dried over Na$_2$SO$_4$. The solvent was evaporated in vacuo. The residue was purified with column chromatography on silica gel (petroleum ether:ethyl acetate=10:1) to obtain the desired compound as yellow-light oil (650 mg in 80% yield). $^1$H NMR (400 MHz, CDCl$_3$) δ 7.09 (d, J=8.4 Hz, 1H), 5.16-5.15 (m, 1H), 5.08-5.08 (m, 1H), 4.09 (dd, J=11.6 Hz, 4.0 Hz, 2H), 3.81 (q, J=7.2 Hz, 2H), 3.53-3.47 (m, 2H), 3.37-3.29 (m, 1H), 2.32-2.22 (m, 2H), 2.10 (s, 3H), 1.60-1.51 (m, 2H), 1.34 (t, J=7.2 Hz, 3H). MS (ESI) m/e (M+1)$^+$ 299.1.

Step 6: 2-(5-chloro-2-ethoxy-4-fluoro-3-(tetrahydro-2H-pyran-4-yl)phenyl)propan-1-ol (49-6)

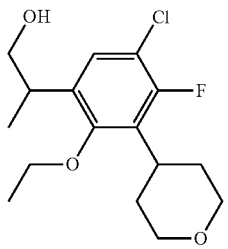 [SMILES: CCOc1c(C(C)CO)cc(Cl)c(F)c1C1CCOCC1]

BH$_3$ (20.2 mL, 1M in THF) was added to 4-(3-chloro-6-ethoxy-2-fluoro-5-(prop-1-en-2-yl)phenyl)tetrahydro-2H-pyran (600 mg, 2.02 mmol) at room temperature. The reaction mixture was stirred at room temperature for overnight, and NaOH (2M aq, 5 mL) was added, H$_2$O$_2$ (5 mL) was added and NaHSO$_3$ (aq, 20 mL) was added. The aqueous layer was extracted with ethyl acetate (50 mL×2). The combined organic layer was washed with brine (50 mL) and dried over Na$_2$SO$_4$. The solvent was evaporated to dryness. The residue was purified with column chromatography on silica gel (petroleum ether:ethyl acetate=5:1) to obtain the desired compound as white solid (440 mg in 68% yield). $^1$H NMR (400 MHz, CDCl$_3$) δ 7.13 (d, J=8.4 Hz, 1H), 4.11-4.07 (m, 2H), 3.85-3.77 (m, 2H), 3.72-3.68 (m, 2H), 3.52-3.46 (m, 2H), 3.34-3.21 (m, 2H), 2.33-2.24 (m, 2H), 1.64-1.55 (m, 2H), 1.47 (t, J=7.2 Hz, 3H), 1.22 (t, J=7.0 Hz, 3H). MS (ESI) m/e (M+1)$^+$ 317.1.

Step 7: 2-(5-chloro-2-ethoxy-4-fluoro-3-(tetrahydro-2H-pyran-4-yl)phenyl) propanal (49-7)

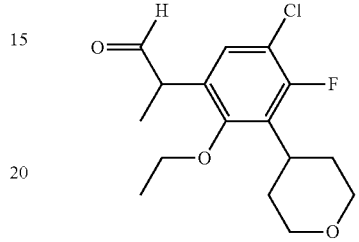

To a solution of 2-(5-chloro-2-ethoxy-4-fluoro-3-(tetrahydro-2H-pyran-4-yl)phenyl)propan-1-ol (200 mg, 0.63 mmol) in CH$_2$Cl$_2$ (50 mL) was added Dess-Martin reagent (401 mg, 0.946 mmol) at room temperature. The reaction mixture was stirred at room temperature, for 1 hr. The reaction mixture was evaporated in vacuo. The residue was purified with column chromatography on silica gel (petroleum ether:ethyl acetate=10:1) to obtain the desired compound as white solid (120 mg in 61% yield). $^1$H NMR (400 MHz, CDCl$_3$) δ 9.63 (d, J=0.8 Hz, 1H), 7.03 (d, J=8.0, 1H), 4.10 (dd, J=11.4, 4.1 Hz, 2H), 3.91 (q, J=7.1 Hz, 1H), 3.82-3.73 (m, 2H), 3.55-3.44 (m, 2H), 3.28-3.18 (m, 1H), 2.44-2.20 (m, 2H), 1.59 (dd, J=14.1, 12.3 Hz, 3H), 1.50-1.35 (m, 6H). MS (ESI) m/e (M+1)$^+$ 315.1.

Step 8: 2-(5-chloro-2-ethoxy-4-fluoro-3-(tetrahydro-2H-pyran-4-yl)phenyl) propanoic Acid (49-8)

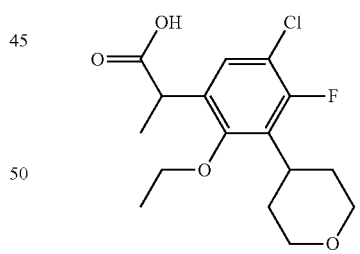

To a solution of 2-(5-chloro-2-ethoxy-4-fluoro-3-(tetrahydro-2H-pyran-4-yl)phenyl)propanal (180 mg, 0.57 mmol) in acetone (50 ml) was added KMnO$_4$ (181 mg, 1.15 mmol) at room temperature. The reaction mixture was stirred at room temperature for 1 hr. Na$_2$CO$_3$ (aq, 20 ml) was added to adjust pH to 9, the mixture was filtered over celite and extracted with MeOt$^-$Bu (50 mL). The aqueous layer was adjusted pH to 3-5 by 1N HCl, then extracted with ethyl acetate (50 mL×2) and dried over Na$_2$SO$_4$. The solvent was evaporated to obtain the desired compound as off-white solid (155 mg in 82% yield). $^1$H NMR (400 MHz, DMSO-d6) δ 12.44 (s, 1H), 7.32 (d, J=8.4 Hz, 1H), 3.96-3.91 (m, 3H), 3.87-3.73 (m, 2H), 3.45-3.33 (m, 2H), 3.24-3.17 (m, 1H), 2.08-1.99 (m, 2H), 1.59-1.53 (m, 2H), 1.42-1.31 (m, 6H). MS (ESI) m/e (M+1)+ 331.1.

Step 9: 2-(5-chloro-2-ethoxy-4-fluoro-3-(tetrahydro-2H-pyran-4-yl)phenyl)-N-((3-chloropyrazin-2-yl) methyl)propanamide (49-9)

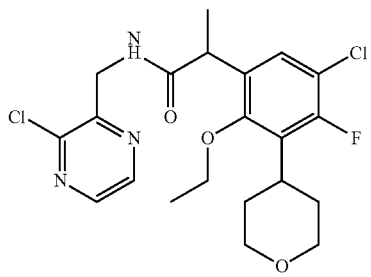 [SMILES: CCOc1c(C(C)C(=O)NCc2nccnc2Cl)cc(Cl)c(F)c1C1CCOCC1]

A solution of 2-(5-chloro-2-ethoxy-4-fluoro-3-(tetrahydro-2H-pyran-4-yl)phenyl)propanoic acid (180 mg, 0.57 mmol), (3-chloropyrazin-2-yl)methanamine dihydrochloride (95 mg, 0.44 mmol), EDCI (161 mg, 0.54 mmol), HOBt (73 mg, 0.54 mmol) and DIPEA (285 µL, 1.63 mmol) in CH$_2$Cl$_2$ (50 mL) was stirred at rt. for 3 hrs. The reaction mixture was added NH$_4$Cl (aq, 50 mL). The aqueous layer was extracted with CH$_2$Cl$_2$ (50 mL). The combined organic layer was washed with NaHCO$_3$ (aq, 50 mL), brine (50 mL) and dried over Na$_2$SO$_4$. The solvent was evaporated to dryness. The residue was purified with column chromatography on silica gel (CH$_2$Cl$_2$:MeOH=100:1) to obtain the desired compound as yellow foam. $^1$H NMR (400 MHz, CDCl$_3$) δ 8.37 (d, J=2.5 Hz, 1H), 8.30 (d, J=2.4 Hz, 1H), 7.34 (d, J=8.2 Hz, 1H), 4.64 (t, J=5.2 Hz, 1H), 4.14-3.99 (m, 3H), 3.90-3.80 (m, 2H), 3.62-3.47 (m, 2H), 3.26-3.19 (m, 1H), 2.26-2.19 (m, 2H), 1.62-1.45 (m, 8ll). MS (ESI) m/e (M+1)+ 456.1

Step 10: 8-chloro-3-(1-(5-chloro-2-ethoxy-4-fluoro-3-(tetrahydro-2H-pyran-4-yl)phenyl)ethyl)imidazo [1,5-a]pyrazine (49-10)

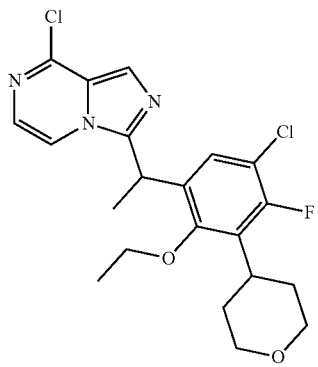 [SMILES: CCOc1c(C(C)c2ncc3c(Cl)nccn23)cc(Cl)c(F)c1C1CCOCC1]

To a solution of 2-(5-chloro-2-ethoxy-4-fluoro-3-(tetrahydro-2H-pyran-4-yl)phenyl)-N-((3-chloropyrazin-2-yl) methyl)propanamide (850 mg, 1.86 mmol) and pyridine (1.02 g, 13.02 mmol) in CH$_2$Cl$_2$ (150 mL) was added Tf$_2$O (2.62 g, 9.32 mmol) at room temperature. The reaction mixture was stirred at room temperature for 1 h. H$_2$O (50 mL) was added and the mixture was extracted with CH$_2$Cl$_2$ (50 ml). The organic layer was washed with brine (50 mL) and dried over Na$_2$SO$_4$. The solvent was evaporated to dryness. The residue was purified with column chromatography on silica gel (CH$_2$Cl$_2$:MeOH=100:1) to obtain the desired compound as yellow solid (650 mg, 80%). $^1$H NMR (400 MHz, CDCl$_3$) δ 7.84 (s, 1H), 7.62 (d, J=4.9 Hz, 1H), 7.28 (d, J=5.0 Hz, 1H), 7.13 (d, J=8.1 Hz, 1H), 4.78 (q, J=6.8 Hz, 1H), 4.17-4.02 (m, 2H), 3.90 (tt, J=16.1, 8.0 Hz, 2H), 3.51 (t, J=11.8 Hz, 2H), 3.24 (t, J=12.3 Hz, 1H), 2.27 (ddt, J=18.9, 9.4, 8.0 Hz, 2H), 1.89 (d, J=7.0 Hz, 3H), 1.63-1.46 (m, 5l). MS (ESI) m/e (M+1)+ 437.2.

Step 11: 1,8-dichloro-3-(1-(5-chloro-2-ethoxy-4-fluoro-3-(tetrahydro-2H-pyran-4-yl)phenyl)ethyl) imidazo[1,5-a]pyrazine (49-11)

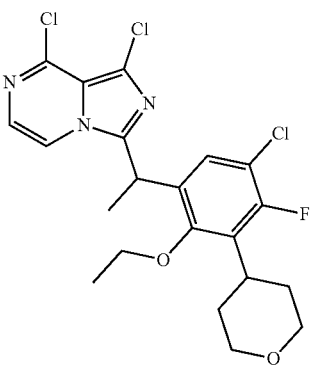 [SMILES: CCOc1c(C(C)c2nc(Cl)c3c(Cl)nccn23)cc(Cl)c(F)c1C1CCOCC1]

To a solution of 8-chloro-3-(1-(5-chloro-2-ethoxy-4-fluoro-3-(tetrahydro-2H-pyran-4-yl)phenyl)ethyl)imidazo [1,5-a]pyrazine (300 mg, 0.68 mmol) in DMF (10 mL) was added 1-chloropyrrolidine-2,5-dione (NCS, 137 mg, 1.03 mmol) at room temperature. The reaction mixture was stirred at 50° C. for 1 h. H$_2$O (50 mL) was added and the mixture was extracted with ethyl acetate (50 mL×2). The organic layer was washed with H$_2$O (50 mL×2), brine (50 mL) and dried over Na$_2$SO$_4$. The solvent was evaporated to dryness. The residue was purified with column chromatography on silica gel (CH$_2$Cl$_2$:MeOH=100:1) to obtain the desired compound as yellow solid (180 mg in 56% yield). $^1$H NMR (400 MHz, CDCl$_3$) δ 7.57 (d, J=5.0 Hz, 1H), 7.23 (d, J=5.0 Hz, 1H), 7.12 (d, J=8.0 Hz, 1H), 4.68 (q, J=7.2 Hz, 1H), 4.16-4.04 (m, 2H), 3.91 (q, J=6.8 Hz, 2H), 3.51 (t, J=11.7 Hz, 2H), 3.29-3.20 (m, 1H), 2.42-2.13 (m, 2H), 1.85 (d, J=7.1 Hz, 3H), 1.64-1.45 (m, 5H). MS (ESI) m/e (M+1)+ 472.1.

Step 12: 1-chloro-3-(1-(5-chloro-2-ethoxy-4-fluoro-3-(tetrahydro-2H-pyran-4-yl)phenyl)ethyl)imidazo [1,5-a]pyrazin-8-amine (49-12)

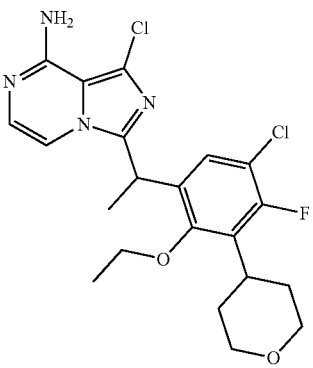 [SMILES: CCOc1c(C(C)c2nc(Cl)c3c(N)nccn23)cc(Cl)c(F)c1C1CCOCC1]

A solution of 1,8-dichloro-3-(1-(5-chloro-2-ethoxy-4-fluoro-3-(tetrahydro-2H-pyran-4-yl)phenyl)ethyl)imidazo[1,5-a]pyrazine (180 mg, 0.38 mmol) in NH$_3$/i-PrOH solution (5 mL) was stirred at 90° C. for overnight in sealed tube. The solution was evaporated to dryness. The residue was purified with column chromatography on silica gel (CH$_2$Cl$_2$:MeOH=50:1) to obtain compound as crude yellow solid, the solid was prepared by prep-HPLC to obtain the desired compound as white solid (95 mg in 55% yield). The compound was further separated by chiral column to give two compounds, Compound 49A (22 mg, the first and fast isomer) and Compound 49B (28 mg, the second and slow isomer). Compound 49A was assigned as a (S)-configuration in a similar manner to Compound 40A.

Compound 49: $^1$H NMR (400 MHz, DMSO-d6) δ 7.33 (d, J=5.0 Hz, 1H), 7.24 (d, J=8.3 Hz, 1H), 6.99 (d, =5.0 Hz, 1H), 6.78 (brs, 2H), 4.79 (q, J=6.9 Hz, 1H), 4.01-3.80 (m, 3H), 3.75-3.65 (m, 1H), 3.45-3.36 (m, 2H), 3.19 (t, J=12.0 Hz, 1H), 2.16-1.87 (m, 2H), 1.71-1.45 (m, 5H), 1.39 (t, J=6.9 Hz, 3H). MS (ESI) m/e (M+1)$^+$ 453.1.

Compound 49A: $^1$H NMR (400 MHz, DMSO-d6) δ 7.33 (d, J=5.0 Hz, 1H), 7.24 (d, J=8.3 Hz, 1H), 6.99 (d, J=5.0 Hz, 1H), 6.78 (brs, 2H), 4.79 (q, J=6.9 Hz, 1H), 4.01-3.80 (m, 3H), 3.75-3.65 (m, 1H), 3.45-3.36 (m, 2H), 3.19 (t, J=12.0 Hz, 1H), 2.16-1.87 (m, 2H), 1.71-1.45 (m, 5H), 1.39 (t, J=6.9 Hz, 3H). MS (ESI) nm/e (M+1)$^+$ 453.1.

Compound 49B: $^1$H NMR (400 MHz, DMSO-d6) δ 7.33 (d, J=5.0 Hz, 1H), 7.24 (d, J=8.3 Hz, 1H), 6.99 (d, J=5.0 Hz, 1H), 6.78 (brs, 2H), 4.79 (q, J=6.9 Hz, 1H), 4.01-3.80 (m, 3H), 3.75-3.65 (m, 1H), 3.45-3.36 (m, 2H), 3.19 (t, J=12.0 Hz, 1H), 2.16-187 (m, 2H), 1.71-1.45 (m, 5H), 1.39 (t, J=6.9 Hz, 3H). MS (ESI) nm/e (M+1)$^+$ 453.1.

| Column | CHIRALART Celluose-SB |
|---|---|
| Column size | 2 cm × 25 cm, 5 μm |
| Injection | 1.2 ML |
| Mobile phase | Hex:EtOH = 90:10 |
| Flow rate | 20 ml/min |
| Wave length | UV 220 nm |
| Temperature | 35° C. |
| Sample solution | 14.4 mg/ml in mobile phase |
| Prep-HPLC equipment | BJ-Prep-Gilson-HPLC |

Example 50

1-bromo-3-(1-(5-chloro-2-ethoxy-4-methylphenyl)ethyl)imidazo[1,5-a]pyrazin-8-amine (Compound 50)

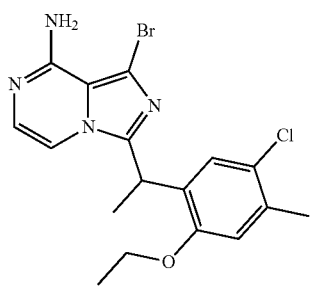 [SMILES: CCOc1cc(C)c(Cl)cc1C(C)c1nc(Br)c2c(N)nccn12]

Step 1: 1-(5-chloro-2-ethoxy-4-methylphenyl)ethan-1-one (50-1)

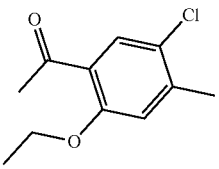

To a solution of 1-(5-chloro-2-hydroxy-4-methylphenyl)ethan-1-one (5.0 g, 27.08 mmol) and iodoethane (8.45 g, 54.17 mmol) in DMF (50 mL) was added K$_2$CO$_3$ (5.60 g, 40.62 mmol) at room temperature. The reaction mixture was stirred at 65° C. for overnight. H$_2$O (100 mL) was added and the mixture was extracted with ethyl acetate (100 mL×2). The organic layer was washed with H$_2$O (50 mL×3), brine (50 mL) and dried over Na$_2$SO$_4$, The solvent was evaporated to dryness. The residue was purified by column chromatography on silica gel (petroleum ether:ethyl acetate=20:1) to obtain the desired compound as yellow solid (4.4 g in 77% yield). $^1$H NMR (400 MHz, CDCl$_3$) δ 7.74 (s, 1H), 6.80 (s, 1H), 4.11 (q, J=7.0 Hz, 2H), 2.60 (s, 3H), 2.38 (s, 3H), 1.48 (t, J=7.0 Hz, 3H). MS (ESI) m/e (M+1)$^+$ 213.1.

Step 2: 1-(5-chloro-2-ethoxy-4-methylphenyl)ethan-1-ol (50-2)

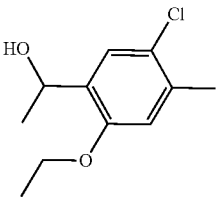

To a solution of 1-(5-chloro-2-ethoxy-4-methylphenyl)ethan-1-one (5.50 g, 25.94 mmol) in MeOH (50 mL) was added NaBH$_4$ (2.96 g, 77.8 mmol) at room temperature. The reaction mixture was stirred at rt for overnight. The solvent was evaporated to dryness. The residue was purified with column chromatography on silica gel (petroleum ether:ethyl acetate=5:1) to obtain the desired compound as yellow solid (5.6 g in 100% yield). $^1$H NMR (400 MHz, CDCl$_3$) δ 7.28 (s, 1H), 6.71 (s, 1H), 5.03 (q, J=6.5 Hz, 1H), 4.05 (q, J=7.0 Hz, 2H), 2.52 (brs, 3H), 2.33 (s, 3H), 1.55-1.36 (m, 6H).

Step 3: 1-chloro-5-(1-chloroethyl)-4-ethoxy-2-methylbenzene (50-3)

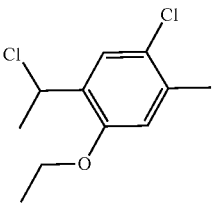

To a solution of 1-(5-chloro-2-ethoxy-4-methylphenyl)ethan-1-ol (5.60 g, 26.17 mmol) in CH$_2$Cl$_2$ (50 mL) was added SOCl$_2$ (3.70 mL, 52.14 mmol) at room temperature. The reaction mixture was stirred at room temperature for 2 hrs. The solvent was evaporated to dryness. To the residue was added NaHCO$_3$ (aq. 100 mL) and CH$_2$Cl$_2$ (100 mL). The organic layer was dried over Na$_2$SO$_4$ and evaporated in vacuo to obtain the desired compound as yellow oil (5.3 g in 87% yield). $^1$H NMR (400 MHz, CDCl$_3$) δ 7.45 (s, 1H), 6.71 (s, 1H), 5.51 (q, J=6.8 Hz, 1H), 4.04 (q, J=7.0 Hz, 2H). 2.34 (s, 3H), 1.78 (d, J=6.8 Hz, 3H), 1.43 (t, J=7.0 Hz, 3H).

Step 4: 2-(5-chloro-2-ethoxy-4-methylphenyl)propanenitrile (50-4)

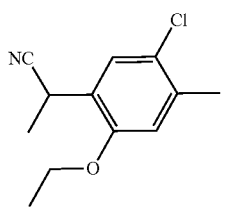

To a solution of 1-chloro-5-(1-chloroethyl)-4-ethoxy-2-methylbenzene (5.30 g, 22.84 mmol) and KI (2.27 g, 13.70 mmol) in DMF (50 mL) was added NaCN (1.75 g, 36.55 mmol) at room temperature. The reaction mixture was stirred at 65° C. for overnight. H$_2$O (150 mL) was added and the mixture was extracted with ethyl acetate (100 mL×2). The organic layer was washed with H$_2$O (50 mL×3), brine (50 ml) and dried over Na$_2$SO$_4$. The solvent was evaporated to dryness. The residue was purified by column chromatography on silica gel (petroleum ether:ethyl acetate=20:1) to obtain product as yellow solid (2.6 g in 51% yield). MS (ESI) m/e (M+1)$^+$ 224.1.

Step 5: 2-(5-chloro-2-ethoxy-4-methylphenyl)propanoic acid (50-5)

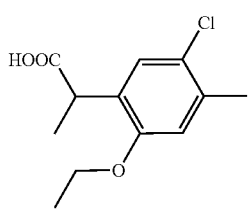 [SMILES: CCOc1cc(C)c(Cl)cc1C(C)C(=O)O]

To a solution of 2-(5-chloro-2-ethoxy-4-methylphenyl)propanenitrile (200 mg, 0.90 mmol) in EtOH (5 mL) was added NaOH (180 mg, 4.48 mmol) in H$_2$O (5 mL) at room temperature. The reaction mixture was stirred at reflux for 2 days. The solvent was evaporated. HCl (2M aq) was added to adjusted pH to 3-5. The aqueous layer was extracted with ethyl acetate (100 mL×2). The combined organic layer was dried over Na$_2$SO$_4$ and evaporated in vacuo to obtain the product as yellow solid (140 mg in 65% yield). $^1$H NMR (400 MHz, DMSO-d6) δ 7.15 (s, 1H), 6.97 (s, 1H), 4.07-3.96 (m, 2H), 3.81 (q, J=7.2 Hz, 1H), 2.28 (s, 3H), 1.29 (t, J=7.1 Hz, 6H), MS (ESI) m/e (M+1)$^+$ 243.1

Step 6: 2-(5-chloro-2-ethoxy-4-methylphenyl)-N-((3-chloropyrazin-2-yl)methyl) propanamide (50-6)

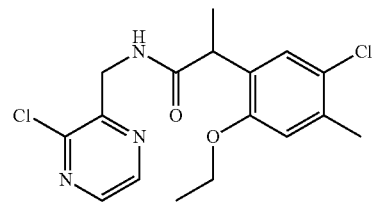 [SMILES: CCOc1cc(C)c(Cl)cc1C(C)C(=O)NCc1nccnc1Cl]

Compound (50-6) was prepared by the similar manner as compound (7-8) descried in example 1. $^1$H NMR (400 MHz, DMSO-d6) δ 8.60 (d, J=2.5 Hz, 1H), 8.43 (d, J=2.5 Hz, 1H), 8.28 (t, J=5.4 Hz, 1H), 7.24 (s, 1H), 6.95 (s, 1H), 4.49 (d, J=5.5 Hz, 2H), 4.08-3.88 (m, 3H), 2.28 (s, 3H), 1.34-1.25 (m, 6H). MS (ESI) m/e (M+1)$^+$ 368.1

Step 7: 8-chloro-3-(1-(5-chloro-2-ethoxy-4-methylphenyl)ethyl)imidazo[1,5-a]pyrazine (50-7)

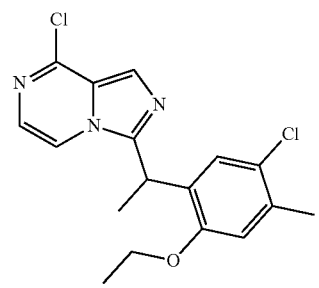 [SMILES: CCOc1cc(C)c(Cl)cc1C(C)c1ncc2c(Cl)nccn12]

Compound (50-7) was prepared by the similar manner as compound (7-9) descried in Example 1. $^1$H NMR (400 MHz, DMSO-d6) δ 8.06 (dd, J=5.0, 0.7 Hz, 1H), 7.85 (s, 1H), 7.40 (d, J=5.0 Hz, 1H), 7.08 (s, 1H), 6.97 (s, 1H), 4.92 (q, J=7.0 Hz, 1H), 4.05-3.85 (m, 21H), 2.26 (s, 3H), 1.65 (d, J=7.1 Hz, 3H) 1.16 (t, J=6.9 Hz, 3H). MS (ESI) m/e (M+1)$^+$ 350.1

Step 8: 1-bromo-8-chloro-3-(1-(5-chloro-2-ethoxy-4-methylphenyl)ethyl)imidazo[1,5-a]pyrazine (50-8)

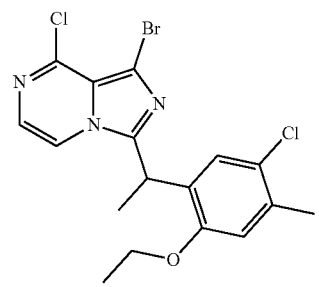 [SMILES: CCOc1cc(C)c(Cl)cc1C(C)c1nc(Br)c2c(Cl)nccn12]

Compound (50-8) was prepared by the similar manner as compound (7-10) descried in Example 1. $^1$H NMR (400 MHz, DMSO-d6) δ 8.13 (d, J=5.1 Hz, 1H), 7.41 (d, J=5.0 Hz, 1H), 7.15 (s, 1H), 6.96 (s, 1H), 4.88 (q, J=7.0 Hz, 1H), 4.00-3.80 (m, 2H), 2.27 (s, 3H), 1.61 (d, J=7.1 Hz, 3H), 1.12 (t, J=6.9 Hz, 3H). MS (ESI) m/e (M+1)+ 428.0

Step 9: 1-bromo-3-(1-(5-chloro-2-ethoxy-4-methylphenyl)ethyl)imidazo[1,5-a]pyrazin-8-amine (50-9)

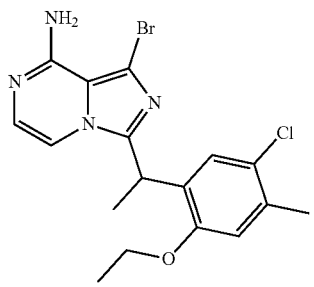 [SMILES: CCOc1cc(C)c(Cl)cc1C(C)c1nc(Br)c2c(N)nccn12]

Compound (50-9) was prepared by the similar manner as compound (7-11) descried in example 1. ¹H NMR (400 MHz, DMSO-d6) δ 7.29 (d, J=5.0 Hz, 1H), 6.99-6.65 (m, 3H), 6.71 (brs, 2H), 4.75 (q, J=6.9 Hz, 1H), 4.02-3.95 (m, 2H), 2.26 (s, 3H), 1.57 (d, J=70 Hz, 3H), 1.21 (t, J=6.9 Hz, 3H). MS (ESI) m/e (M+1)+ 428.0

Example 51

1-chloro-3-(1-(5-chloro-2-ethoxy-4-methyl-3-morpholinophenyl)ethyl)imidazo[1,5-a]pyrazin-8-amine (Compound 51)

Compound 51

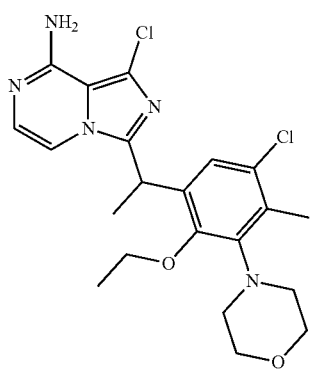

Compound 51A

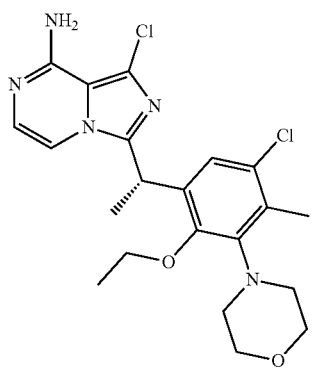

Compound 51B

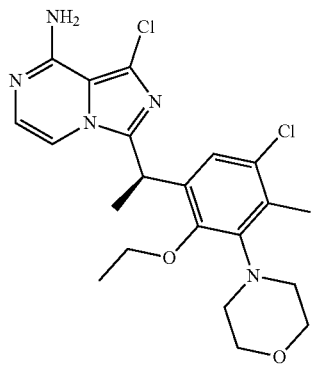

Step 1: 1-(5-chloro-2-hydroxy-/4-methyl-3-nitrophenyl)ethan-1-one (51-1)

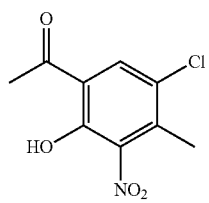

To a solution of 1-(5-chloro-2-hydroxy-4-methylphenyl)ethan-1-one (1 g, 5.42 mmol) in H₂SO₄ (5 mL) was added NaNO₂ (690 mg, 8.12 mmol) at 0° C. The reaction mixture was stirred at 0° C. for 0.5 hr. The reaction mixture was poured into ice, the resulting aqueous layer was extracted with ethyl acetate (250 mL×2). The organic layer was washed with brine (100 mL) and dried over Na₂SO₄. The solvent was evaporated to dryness. The residue was purified with column chromatography on silica gel (petroleum ether: ethyl acetate=10:1) to obtain the desired compound as yellow solid (770 mg in 62% yield). ¹H NMR (400 MHz, CDCl₃) δ 12.60 (s, 1H), 7.84 (s, 1H), 2.66 (s, 3H), 2.38 (s, 3H). MS (ESI) m/e (M+1)+ 230.0.

Step 2: 1-(5-chloro-2-ethoxy-4-methyl-3-nitrophenyl)ethan-1-one (51-2)

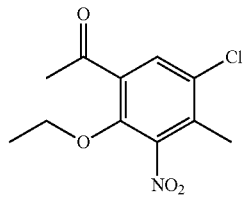

To a solution of 1-(5-chloro-2-hydroxy-4-methyl-3-nitrophenyl)ethan-1-one (450 mg, 1.96 mmol) and iodoethane (613 mg, 3.93 mmol) in DMF (20 mL) was added K₂CO₃ (676 mg, 4.90 mmol) at room temperature. The reaction mixture was stirred at 65° C. for overnight. H₂O (50 mL) was added and the mixture was extracted with ethyl acetate (100 mL×2). The organic layer was washed with H₂O (100 mL×3), brine (50 mL) and dried over Na$_2$SO$_4$. The solvent was evaporated to dryness. The residue was purified with column chromatography on silica gel (petroleum ether:ethyl acetate=10:1) to obtain product as yellow solid (384 mg in 76% yield). $^1$H NMR (400 MHz, CDCl$_3$) δ 7.73 (s, 1H), 4.02 (q, J=7.0 Hz, 2H), 2.63 (s, 3H), 2.34 (s, 3H), 1.37 (t, J=7.0 Hz, 3H), MS (ESI) m/e (M+1)$^+$ 258.0.

Step 3: 1-(3-amino-5-chloro-2-ethoxy-4-methylphenyl)ethan-1-one (51-3)

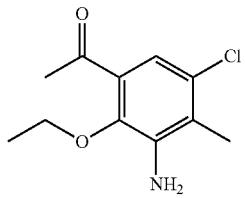

To a solution of 1-(5-chloro-2-ethoxy-4-methyl-3-nitrophenyl)ethan-1-one (360 mg, 1.40 mmol) and NH$_4$Cl (600 mg, 11.2 mmol) in EtOH:H$_2$O (1:1, 50 mL/50 mL) was added Zn power (364 mg, 5.60 mmol) at 65° C. The reaction mixture was stirred at 65° C. for 5 hrs. The reaction mixture was filtered over celite, the mixture was extracted with ethyl acetate (100 mL×2). The organic layer was washed with brine (100 mL) and dried over Na$_2$SO$_4$. The solvent was evaporated to dryness. The residue was purified with column chromatography on silica gel (petroleum ether:ethyl acetate=5:1 to 3:1) to obtain product as brown solid (206 mg in 65% yield). $^1$H NMR (400 MHz, CDCl$_3$) δ 7.26 (s, 1H), 3.90 (q, J=7.0 Hz, 2H), 2.59 (s, 3H), 2.27 (s, 3H), 1.41 (t, J=7.0 Hz, 3H). MS (ESI) m/e (M+1)$^+$ 228.0.

Step 4: 1-(5-chloro-2-ethoxy-4-methyl-3-morpholinophenyl)ethan-1-one (51-4)

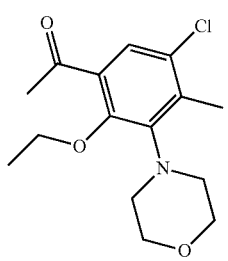 [SMILES: CCOc1c(C(C)=O)cc(Cl)c(C)c1N1CCOCC1]

To a solution of 1-(3-amino-5-chloro-2-ethoxy-4-methylphenyl)ethan-1-one (4.8 g, 21.14 mmol) and 1-bromo-2-(2-bromoethoxy)ethane (24.5 g, 105.73 mmol) in DMA (100 mL) was added K$_2$CO$_3$ (6.08 g, 44.06 mmol) at room temperature. The reaction mixture was stirred at 65° C. for overnight. H$_2$O (50 mL) was added and the mixture was extracted with ethyl acetate (100 mL×2). The organic layer was washed with H$_2$O (100 mL×3), brine (50 mL) and dried over Na$_2$SO$_4$. The solvent was evaporated to dryness. The residue was purified with column chromatography on silica gel (petroleum ether:ethyl acetate=4:1) to obtain product as yellow solid (2.5 g in 76% yield). MS (ESI) m/e (M+1)$^+$ 98.1.

Step 5: 1-(5-chloro-2-ethoxy-4-methyl-3-morpholinophenyl)ethan-1-ol (51-5)

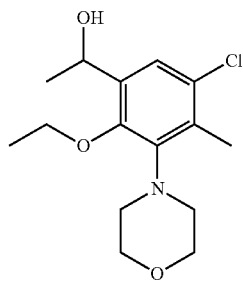 [SMILES: CCOc1c(C(C)O)cc(Cl)c(C)c1N1CCOCC1]

Compound (51-5) was prepared by the similar manner as compound (2-2) descried in Example 2, in 94.5% yield. $^1$H NMR (400 MHz, CDCl$_3$) δ 7.23 (s, 1H), 5.10 (q, J=6.4 Hz, 1H), 3.99-3.67 (m, 6H), 3.28-2.78 (m, 4H), 2.34 (s, 3H), 1.51-1.38 (m, 6H). MS (ESI) m/e (M+1)$^+$ 300.1.

Step 6: 4-(3-chloro-5-(1-chloroethyl)-6-ethoxy-2-methylphenyl)morpholine (51-6)

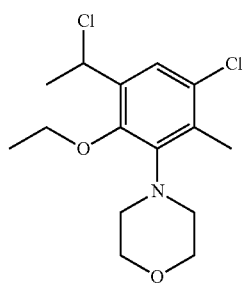 [SMILES: CCOc1c(C(C)Cl)cc(Cl)c(C)c1N1CCOCC1]

Compound (51-6) was prepared by the similar manner as compound (2-3) descried in Example 2. $^1$H NMR (400 MHz, CDCl$_3$) δ 7.26 (s, 1H), 5.44 (q, J=6.8 Hz, 1H), 4.01-3.69 (m, 6H), 3.33-2.93 (m, 2H), 2.37 (s, 3H), 1.79 (d, J=6.8 Hz, 3H), 1.49 (t, J=6.8 Hz, 3H). MS (ESI) m/e [M+1−Cl+OH]$^+$ 300.1.

Step 7: 2-(5-chloro-2-ethoxy-4-methyl-3-morpholinophenyl)propanenitrile (51-7)

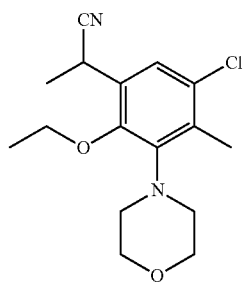 [SMILES: CCOc1c(C(C)C#N)cc(Cl)c(C)c1N1CCOCC1]

Compound (51-7) was prepared by the similar manner as compound (2-4) descried in example 2. MS (ESI) m/e (M+1)$^+$ 309.1.

Step 8: 2-(5-chloro-2-ethoxy-4-methyl-3-morpholinophenyl)propanoic Acid (51-8)

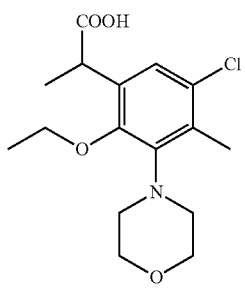 [SMILES: CCOc1c(C(C)C(=O)O)cc(Cl)c(C)c1N1CCOCC1]

Compound (51-8) was prepared by the similar manner as compound (2-5) descried in example 2, ¹H NMR (400 MHz, CDCl₃) δ 7.13 (s, 1H), 4.12-4.03 (m, 1H), 3.94-3.87 (m, 1H), 3.86-3.76 (m, 5H), 3.14-3.12 (m, 3H), 2.35 (s, 3H), 1.51-1.40 (m, 6H). MS (ESI) m/e (M+1)⁺ 328.1.

Step 9: 2-(5-chloro-2-ethoxy-4-methyl-3-morpholinophenyl)-N-((3-chloropyrazin-2-yl)methyl)propanamide (51-9)

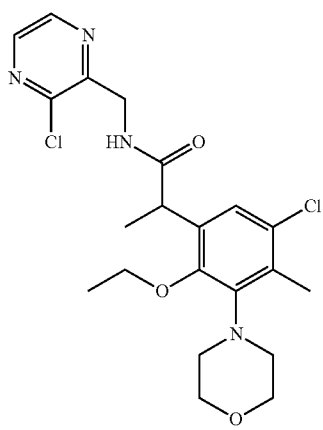 [SMILES: CCOc1c(C(C)C(=O)NCc2nccnc2Cl)cc(Cl)c(C)c1N1CCOCC1]

Compound (51-9) was prepared by the similar manner as compound (2-6) descried in example 2. ¹H NMR (400 MHz, CDCl₃) δ 8.35 (d, J=2.4 Hz, 1H), 8.28 (s, 1H), 7.38 (s, 1H), 7.04 (s, 1H), 4.63 (t, J=3.2 Hz, 2H), 4.07-3.90 (m, 2H), 3.87-3.74 (m, 5H), 3.30-2.94 (m, 4H), 2.36 (s, 3H), 1.61-1.43 (m, 6H). MS (ESI) m/e (M+1)⁺ 453.1.

Step 10: 4-(3-chloro-5-(1-(8-chloroimidazo[1,5-a]pyrazin-3-yl)ethyl)-6-ethoxy-2-methylphenyl)morpholine (51-10)

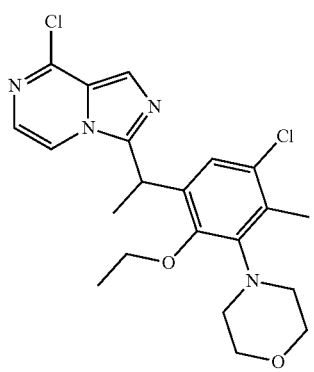 [SMILES: CCOc1c(C(C)c2ncc3c(Cl)nccn23)cc(Cl)c(C)c1N1CCOCC1]

Compound (51-10) was prepared by the similar manner as compound (2-7) descried in example 2. ¹H NMR (400 MHz, CDCl₃) δ 7.81 (s, 1H), 7.66 (d, J=4.9 Hz, 1H), 7.22 (d, J=5.0 Hz, 1H), 6.97 (s, 1H), 4.74 (q, J=7.0 Hz, 1H), 4.02-3.96 (m, 1H), 3.91-3.81 (m, 5H), 3.23-2.77 (m, 4H), 2.30 (s, 3H), 1.89 (d, J=7.1 Hz, 3H), 1.55 (t, J=7.0 Hz, 3H). MS (ESI) m/e (M+1)⁺ 435.1.

Step 11: 4-(3-chloro-5-(1-(1,8-dichloroimidazo[1,5-a]pyrazin-3-yl)ethyl)-6-ethoxy-2-methylphenyl)morpholine (51-11)

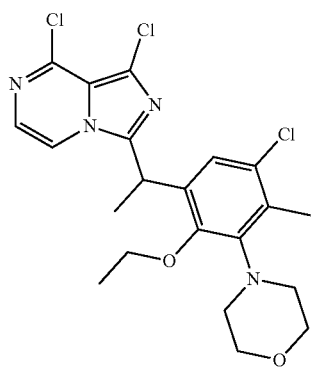 [SMILES: CCOc1c(C(C)c2nc(Cl)c3c(Cl)nccn23)cc(Cl)c(C)c1N1CCOCC1]

Compound (51-11) was prepared by the similar manner as compound (2-8) descried in example 2. MS (ESI) m/e (M+1)⁺ 469.1.

Step 12: 1-chloro-3-(1-(5-chloro-2-ethoxy-4-methyl-3-morpholinophenyl)ethyl)imidazo[1,5-a]pyrazin-8-amine (51-12)

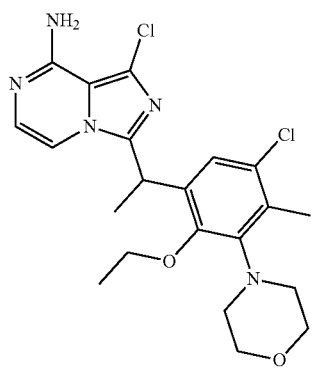 [SMILES: CCOc1c(C(C)c2nc(Cl)c3c(N)nccn23)cc(Cl)c(C)c1N1CCOCC1]

Compound (51-12) was prepared by the similar manner as compound (2-9) descried in example 2. And then, the compound was separated by chiral column to give two compounds, Compound 51A (the first and fast isomer) and Compound 51B (the second and slow isomer). Compound 51A was assigned as a (S)-configuration in a similar manner to Compound 40A.

Compound 51: ¹H NMR (400 MHz, DMSO-d6) δ 7.26 (d, J=5.0 Hz, 1H), 6.96 (d, J=5.0 Hz, 1H), 6.72 (brs, 2H), 4.74 (q, J=6.9 Hz, 1H), 3.82-3.61 (m, 6H), 3.21-2.77 (m, 4H), 2.27 (s, 3H), 1.62 (d, J=7.0 Hz, 3H), 1.40 (t, J=6.9 Hz, 3H). MS (ESI) m/e (M+1)⁺ 450.1, 452.1.

Compound 51A: 1H NMR (400 MHz, DMSO-d6) δ 7.26 (d, J=5.0 Hz, 1H), 6.96 (d, J=5.0 Hz, 1H), 6.72 (brs, 2H), 4.74 (q, J=6.9 Hz, 1H), 3.82-3.61 (m, 614), 3.21-2.77 (m, 4H), 2.27 (s, 3H), 1.62 (d, J=7.0 Hz, 3H), 1.40 (t, J=6.9 Hz, 3H). MS (ESI) m/e (M+1)⁺ 450.1, 452.1.

Compound 51B: ¹H NMR (400 MHz, DMSO-d6) δ 7.26 (d, J=5.0 Hz, 1H), 6.96 (d, J=5.0 Hz, 1H), 6.72 (brs, 2H), 4.74 (q, J=6.9 Hz, 1H), 3.82-3.61 (m, 61H), 3.21-2.77 (m, 4H), 2.27 (s, 3H), 1.62 (d, J=7.0 Hz, 3H), 1.40 (t, J=6.9 Hz, 3H). MS (ESI) m/e (M+1)⁺ 450.1, 452.1.

Chiral Separation Condition

| Column | CHIRALART Cellulose-SB |
|---|---|
| Column size | 2 cm × 25 cm |
| Injection | 0.8 ML |
| Mobile phase | Hex:EtOH = 85:15 |
| Flow rate | 20 ml/min |
| Wave length | UV 220 nm |
| Temperature | 35° C. |
| Sample solution | 9.4 mg/ml in mobile phase |
| Prep-HPLC equipment | BJ-Prep-Gilson-HPLC |

Example 52

3-(1-(5-chloro-2-methoxy-4-methyl-3-(pyridin-3-yl)phenyl)ethyl)-1-methyl imidazo[1,5-a]pyrazin-8-amine (Compound 52)

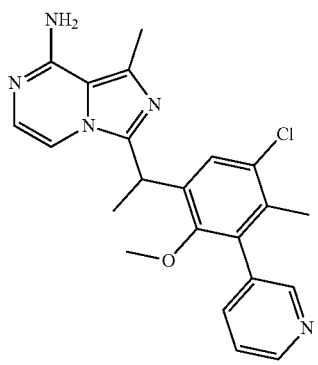 [SMILES: COc1c(C(C)c2nc(C)c3c(N)nccn23)cc(Cl)c(C)c1-c1cccnc1]

Step 1: 5-chloro-2-methoxy-4-methyl-3-(pyridin-3-yl)benzoic Acid (52-1)

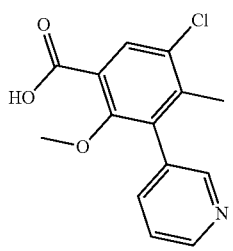 [SMILES: COc1c(C(=O)O)cc(Cl)c(C)c1-c1cccnc1]

Compound (52-1) was prepared by the similar manner as compound (2-5) descried in example 2, in 63% yield, MS (ESI) m/e (M+1)⁺ 278.1

Step 2: 2-(5-chloro-2-methoxy-4-methyl-3-(pyridin-3-yl)phenyl)-N-(1-(3-chloropyrazin-2-yl)ethyl)propanamide (52-2)

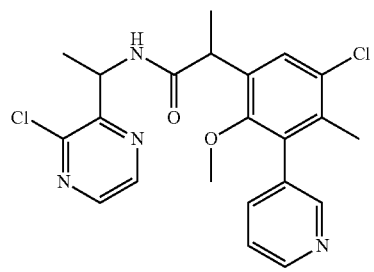 [SMILES: COc1c(C(C)C(=O)NC(C)c2nccnc2Cl)cc(Cl)c(C)c1-c1cccnc1]

Compound (52-2) was prepared by the similar manner as compound (2-6) descried in example 2, in 74% yield. ¹H NMR (400 MHz, CDCl₃) δ 8.81 (d, J=4.9 Hz, 1H), 8.67 (s, 1H), 8.44-8.22 (m, 2H), 8.04 (d, J=7.4 Hz, 1H), 7.75-7.62 (m, 1H), 7.55 (d, J=8.5 Hz, 1H), 7.56-7.39 (m, 1H), 5.60-5.46 (m, 1H), 4.04-3.89 (m, 1H), 3.26 (d, J=8.4 Hz, 3H), 2.13 (s, 3H), 1.56 (d, J=7.1 Hz, 3H), 1.49 (d, J=6.8 Hz, 3H). MS (ESI) m/e (M+1)⁺ 445.1

Step 3: 8-chloro-3-(1-(5-chloro-2-methoxy-4-methyl-3-(pyridin-3-yl)phenyl)ethyl)-1-methylimidazo[1,5-a]pyrazine (52-3)

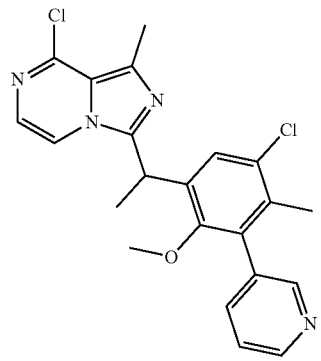 [SMILES: COc1c(C(C)c2nc(C)c3c(Cl)nccn23)cc(Cl)c(C)c1-c1cccnc1]

Compound (52-3) was prepared by the similar manner as compound (2-7) descried in example 2, in 76% yield, MS (ESI) m/e (M+1)⁺ 427.1

Step 4: 3-(1-(5-chloro-2-methoxy-4-methyl-3-(pyridin-3-yl)phenyl)ethyl)-1-methylimidazo[1,5-a]pyrazin-8-amine (52-4)

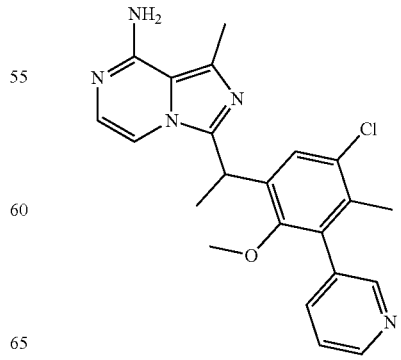

Compound (52-4) was prepared by the similar manner as compound (2-9) descried in example 2, in 14% yield. ¹H NMR (400 MHz, DMSO-d6) δ 8.62 (dd, J=4.8, 1.7 Hz, 1H), 8.49 (d, J=33.1 Hz, 1H), 7.84-7.66 (m, 1H), 7.54-7.49 (m, 1H), 7.21-7.18 (m, 2H), 6.85-6.83 (m, 1H), 6.56 (brs, 2H), 4.75 (q, J=7.0 Hz, 1H), 3.18 (s, 3H), 2.61 (s, 3H), 2.01 (s, 3H), 1.66 (d, J=7.1 Hz, 3H). MS (ESI) m/e (M+1)⁺ 408.1.

Example 53

3-(1(5-chloro-2-methoxy-4-methyl-3-(pyridin-3-yl) phenyl)ethyl)-1-cyclopropyl imidazo[1,5-a]pyrazin-8-amine (Compound 53)

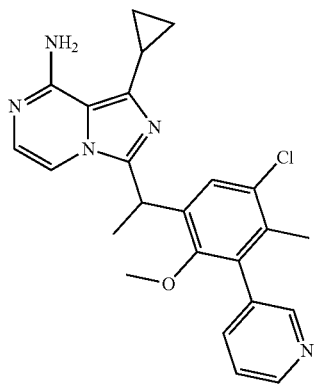 [SMILES: COc1c(C(C)c2nc(C3CC3)c3c(N)nccn23)cc(Cl)c(C)c1-c1cccnc1]

The desired compound was prepared by the similar manner as compound 52 descried in example 52. ¹H NMR (400 MHz, DMSO-d6) δ 8.63 (s, 1H), 8.49 (d, J=33.4 Hz, 1H), 7.75 (d, J=34.8 Hz, 1H), 7.52 (s, 1H), 7.15 (d, J=3.9 Hz, 2H), 6.85 (s, 1H), 6.66 (s, 2H), 4.73 (q, J=7.1 Hz, 1H), 3.19 (s, 3H), 2.50 (s, 3H), 2.43 (brs, 1H), 1.64 (d, J=6.7 Hz, 3H), 1.02-0.71 (m, 4H), MS (ESI) m/e (M+1)⁺ 434.1.

Example 54

6-(1-(4-amino-5-bromo-7H-pyrrolo[2,3-d]pyrimidin-7-yl)ethyl)-4-chloro-2-oxo-1-phenyl-1,2-dihydropyridine-3-carbonitrile (Compound 54)

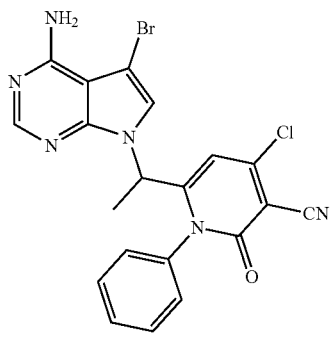 [SMILES: CC(c1cc(Cl)c(C#N)c(=O)n1-c1ccccc1)n1cc(Br)c2c(N)ncnc21]

Step 1: methyl 3-(phenylamino)pent-2-enoate (54-1)

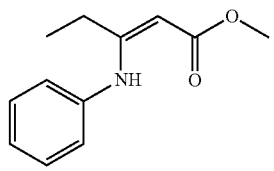

To a solution of aniline (9.31 g 100 mmol) and methyl 3-oxopentanoate (13.01 g, 100 mmol) in hexane (30 mL) was added TsOH (172 mg, 1 mmol). The mixture was refluxed for overnight under Nitrogen atmosphere. After completed, the mixture was cooled and concentrated. The residue was purified by silica gel column chromatography (elution with hexane/ethyl acetate=50/1) to afford methyl 3-(phenylamino)pent-2-enoate (11.0 g, yield 53%) as a yellow oil. ¹H NMR (400 MHz, CDCl₃) δ 7.37-7.29 (m, 2H), 7.17 (m, 1H), 7.10 (d, J=7.5 Hz, 2H), 4.74 (s, 1H), 3.69 (s, 3H), 2.33 (q, J=7.5 Hz, 2H), 1.04 (t, J=7.5 Hz, 3H).

Step 2: methyl 3-(phenylamino)pentanoate (54-2)

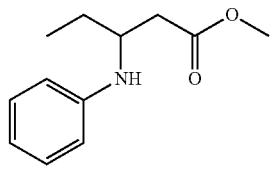

To a solution of methyl 3-(phenylamino)pent-2-enoate (10.0 g, 48.7 mmol) in MeOH (200 mL) was added Pd/C (w/w, 10%, 1.0 g). The mixture was stirred under H₂ (4 atm) for 48 hrs. After completed, the mixture was filtered and concentrated to afford methyl 3-(phenylamino)pentanoate (8.6 g, crude) as a yellow oil. ¹H NMR (400 MHz, CDCl₃) δ 7.20-7.14 (m, 2H), 6.73-6.67 (m, 1H), 6.67-6.61 (m, 2H), 3.78-3.71 (m, 1H), 3.66 (s, 3H), 2.62-2.46 (m, 2H), 1.68-1.56 (m, 2H), 0.98 (t, J=7.4 Hz, 3H). MS (ESI) m/e [M+1]⁺ 207.7.

Step 3: methyl 3-(2-cyano-N-phenylacetamido)pentanoate (54-3)

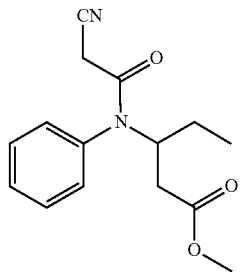 [SMILES: CCC(CC(=O)OC)N(C(=O)CC#N)c1ccccc1]

To a solution of methyl 3-(phenylamino)pentanoate (3.0 g, 14.5 mmol) and Et₃N (14.7 g, 145 mmol) in THF (200 mL) was added a solution of 2-cyanoacetyl chloride (9.0 g, 87 mmol) in THF (50 mL) by dropwise. The mixture was stirred at 40° C. for overnight. After completed, the mixture was diluted with EtOAc (500 mL), washed with NaHCO₃ solution (200 mL), brine (200 mL), dried over anhydrous Na₂SO₄, filtered and concentrated in vacuo. The residue was purified by silica gel column chromatography (elution with hexane/ethyl acetate=5/1) to afford methyl 3-(2-cyano-N-phenylacetamido)pentanoate (3.0 g, yield 75%) as a white solid. MS (ESI) m/e [M+1]⁺ 274.6.

Step 4: 6-ethyl-4-hydroxy-2-oxo-1-phenyl-1,2,5,6-tetrahydropyridine-3-carbonitrile (54-4)

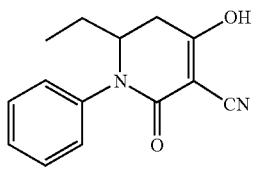 [SMILES: CCC1CC(O)=C(C#N)C(=O)N1c1ccccc1]

To a solution of methyl 3-(2-cyano-N-phenylacetamido)pentanoate (3.0 g, 10.9 mmol) in EtOH (200 mL) was added a solution of EtONa in EtOH (20%, 18.5 g, 54.5 mmol). The mixture was stirred at 50° C. for 3 hrs. After completed, the mixture was concentrated, the residue was diluted with water (50 mL), acidified with HCl (6 M) to pH=2. The mixture was extracted with EtOAc (3×50 mL). The combined organic phase was dried over Na₂SO₄, filtered and concentrated to afford 6-ethyl-4-hydroxy-2-oxo-1-phenyl-1,2,5,6-tetrahydropyridine-3-carbonitrile (2.2 g, yield 83%) as a yellow solid. ¹H NMR (400 MHz, CDCl₃) δ 7.40 (t, J=7.7 Hz, 2H), 7.32-7.27 (m, 1H), 7.27-7.23 (m, 2H), 3.86-3.77 (m, 1H), 3.09 (dd, J=17.7, 6.8 Hz, 1H), 2.66-2.61 (m, 2H), 1.75-1.63 (m, 2H), 0.84 (t, J=7.5 Hz, 3H). MS (ESI) m/e [M+1]⁺ 242.7.

Step 5: 6-ethyl-4-hydroxy-2-oxo-1-phenyl-1,2-dihydropyridine-3-carbonitrile (54-5)

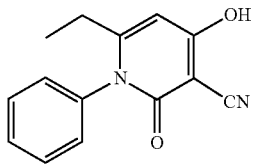 [SMILES: CCc1cc(O)c(C#N)c(=O)n1-c1ccccc1]

To a mixture of 6-ethyl-4-hydroxy-2-oxo-1-phenyl-1,2,5,6-tetrahydropyridine-3-carbonitrile (2.5 g, 10.3 mmol) in dioxane (50 mL) was added 2,3-Dichloro-5,6-dicyano-1,4-benzoquinone (DDQ, 4.7 g, 20.7 mmol). The mixture was refluxed for overnight. After completed, the mixture was cooled and concentrated. The residue was triturated with EtOAc (30 mL) and filtered to afford 6-ethyl-4-hydroxy-2-oxo-1-phenyl-1,2-dihydropyridine-3-carbonitrile (800 mg, yield 32%) as a yellow solid. ¹H NMR (400 MHz, CD₃OD) δ 7.60-7.43 (m, 3H), 7.26-7.19 (m, 2H), 6.10 (s, 1H), 2.28-2.23 (m, 2H), 1.05 (t, J=7.4 Hz, 3H). MS (ESI) m/e [M+1]⁺ 240.6.

Step 6: 4-chloro-6-ethyl-2-oxo-1-phenyl-1,2-dihydropyridine-3-carbonitrile (54-6)

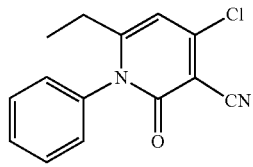 [SMILES: CCc1cc(Cl)c(C#N)c(=O)n1-c1ccccc1]

To a 50 mL flask was added DMF (10 mL) and then POCl₃ (13 g, 8.5 mmol) was added into the flask by dropwise at 0° C. The mixture was stirred at 0° C. for 30 mins. A solution of 6-ethyl-4-hydroxy-2-oxo-1-phenyl-1,2-dihydropyridine-3-carbonitrile (100 mg, 0.42 mmol) in DMF (10 mL) was added to the mixture by dropwise. The mixture was stirred at 80° C. for 3 hrs. After completed, the mixture was cooed to 0° C. and quenched with water carefully. The mixture was extracted with EtOAc (100 mL), the organic phase was washed with water (3×20 mL), brine (20 mL), dried over anhydrous Na₂SO₄, filtered and concentrated in vacuo. The residue was purified by Prep-TLC (elution with hexane/ethyl acetate=1/1) to afford 4-chloro-6-ethyl-2-oxo-1-phenyl-1,2-dihydropyridine-3-carbonitrile (70 mg, yield 64%) as a yellow solid. ¹H NMR (400 MHz, CD₃OD) δ 7.62-7.50 (m, 3H), 7.32-7.24 (m, 2H), 6.65 (s, 1H), 2.34 (qd, J=7.4, 0.5 Hz, 2H), 1.08 (t, J=7.4 Hz, 3H). MS (ESI) m/e [M+1]⁺ 258.6.

Step 7: 6-(1-bromoethyl)-4-chloro-2-oxo-1-phenyl-1,2-dihydropyridine-3-carbonitrile (54-7)

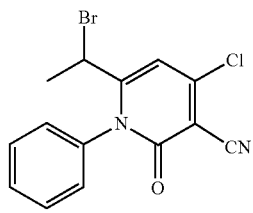 [SMILES: CC(Br)c1cc(Cl)c(C#N)c(=O)n1-c1ccccc1]

To a mixture of 4-chloro-6-ethyl-2-oxo-1-phenyl-1,2-dihydropyridine-3-carbonitrile (800 mg, 3.1 mmol) and N-bromosuccinimide (NBS, 820 mg, 4.6 mmol) in CCl₄ (30 mL) was added AlBN (60 mg, 0.36 mmol). The mixture was refluxed for 3 hrs. After completed, the mixture was concentrated in vacuo, the residue was purified by silica gel column chromatography (elution with hexane/ethyl acetate=2/1) to afford 6-(1-bromoethyl)-4-chloro-2-oxo-1-phenyl-1,2-dihydropyridine-3-carbonitrile (800 mg, yield 76%) as a yellow solid. MS (ESI) m/e [M+1]⁺ 337.1, 339.

Step 8: 6-(1-(4-amino-5-bromo-7H-pyrrolo[2,3-d]pyrimidin-7-yl)ethyl)-4-chloro-2-oxo-1-phenyl-1,2-dihydropyridine-3-carbonitrile (54-8)

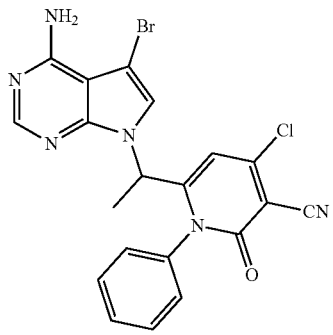 [SMILES: CC(c1cc(Cl)c(C#N)c(=O)n1-c1ccccc1)n1cc(Br)c2c(N)ncnc21]

To a mixture of 6-(1-bromoethyl)-4-chloro-2-oxo-1-phenyl-1,2-dihydropyridine-3-carbonitrile (600 mg, 1.8 mmol) and 5-bromo-7H-pyrrolo[2,3-d]pyrimidin-4-amine (570 mg, 2.7 mmol) in acetonitrile (50 mL) was added $K_2CO_3$ (750 mg, 5.4 mmol). The mixture was stirred at 70° C. for 3 hrs, After completed, the mixture was cooled and diluted with water (50 mL) and extracted with EtOAc (3×30 mL). The combined organic phase was washed with brine, dried over anhydrous $Na_2SO_4$, filtered and concentrated in vacuo. The residue was purified by silica gel column chromatography (elution with hexane/ethyl acetate from 3/1 to 1/2) to afford title compound (50 mg, yield 5.9%) as a yellow solid. $^1$H NMR (400 MHz, DMSO-d6) 7.91 (s, 1H), 7.55-7.50 (m, 2H), 7.45 (s, 1H), 7.38-7.32 (m, 1H), 7.17 (t, J=7.6 Hz, 1H), 6.87 (d, J=8.0 Hz, 1H), 6.73 (s, 1H), 5.44 (q, J=6.9 Hz, 1H), 1.62 (d, J=7.0 Hz, 3H). MS (ESI) m/e [M+1]$^+$ 468.9, 470.9.

Example 55

6-(1-(4-amino-3-methyl-1H-pyrazolo[3,4-d]pyrimidin-1-yl)ethyl)-4-chloro-2-oxo-1-phenyl-1,2-dihydropyridine-3-carbonitrile (Compound 55)

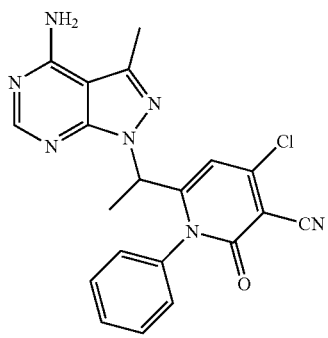 [SMILES: Cc1nn(C(C)c2cc(Cl)c(C#N)c(=O)n2-c2ccccc2)c2ncnc(N)c12]

The desired product was prepared using a procedure similar to step 8 for example 54 starting with 6-(1-bromoethyl)-4-chloro-2-oxo-1-phenyl-1,2-dihydropyridine-3-carbonitrile and 3-methyl-1H-pyrazolo[3,4-d]pyrimidin-4-amine. $^1$H NMR (400 MHz, CDCl$_3$) δ 8.87 (brs, 1H), 8.00 (brs, 1H), 7.93 (brs, 1H), 7.59 (t, J=7.4 Hz, 1H), 7.46 (t, J=7.4 Hz, 1H), 7.35-7.27 (m, 1H), 6.85 (brs, 1H), 5.72 (q, J=5.7 Hz, 1H), 2.70 (s, 3H), 1.76 (d, J=6.9 Hz, 3H). MS (ESI) m/e [M+1]$^+$ 405.5.

Example 56

6-(1-(4-amino-3-methyl-1H-pyrazolo[3,4-d]pyrimidin-1-yl)ethyl)-4-methoxy-2-oxo-1-phenyl-1,2-dihydropyridine-3-carbonitrile (Compound 56)

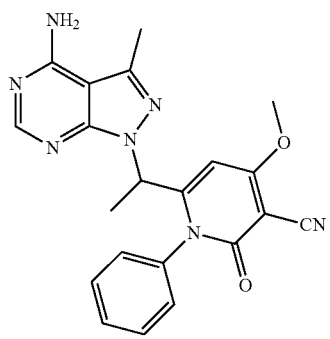 [SMILES: COc1cc(C(C)n2nc(C)c3c(N)ncnc32)n(-c2ccccc2)c(=O)c1C#N]

Step 1: 6-ethyl-4-methoxy-2-oxo-1-phenyl-1,2-dihydropyridine-3-carbonitrile (56-1)

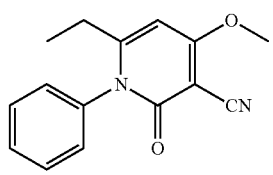 [SMILES: CCc1cc(OC)c(C#N)c(=O)n1-c1ccccc1]

To a solution of 6-ethyl-4-hydroxy-2-oxo-1-phenyl-1,2-dihydropyridine-3-carbonitrile (54-5) (240 mg, 1 mmol) and CH$_3$I (280 mg, 2 mmol) in acetonitrile (20 mL) was added K$_2$CO$_3$ (280 mg, 2 mmol). The mixture was stirred at 80° C. for 1 h. After completed, the mixture was cooled and concentrated in vacuo. The residue was diluted with water (20 mL) and extracted with EtOAc (3×20 mL). The combined organic phase was washed with brine, dried over Na$_2$SO$_4$, filtered and concentrated to afford 6-ethyl-4-methoxy-2-oxo-1-phenyl-1,2-dihydropyridine-3-carbonitrile (200 mg, 78%) as a yellow solid. $^1$H NMR (400 MHz, CD$_3$OD) δ 7.59-7.48 (m, 3H), 7.29-7.20 (m, 2H), 6.45 (s, 1H), 4.10 (s, 3H), 2.36 (q, J=7.5 Hz, 2H), 1.09 (t, J=7.5 Hz, 3H). MS (ESI) m/e [M+1]$^+$ 254.7.

Step 2: 6-(1-bromoethyl)-4-methoxy-2-oxo-1-phenyl-1,2-dihydropyridine-3-carbonitrile (56-2)

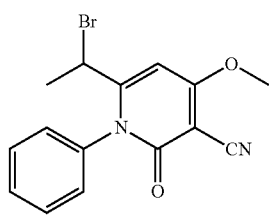 [SMILES: COc1cc(C(C)Br)n(-c2ccccc2)c(=O)c1C#N]

The desired product was prepared using a procedure similar to step 7 for example 54. MS (ESI) m/e [M+1]$^+$ 332.9, 334.9.

Step 3: 6-(1-(4-amino-3-methyl-1H-pyrazolo[3,4-d]pyrimidin-1-ethyl)-4-methoxy-2-oxo-1-phenyl-1,2-dihydropyridine-3-carbonitrile (56-3)

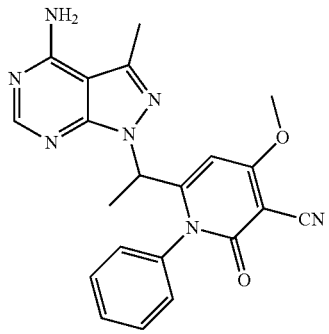 [SMILES: COc1cc(C(C)n2nc(C)c3c(N)ncnc32)n(-c2ccccc2)c(=O)c1C#N]

The desired product was prepared using a procedure similar to step 8 for example 54 starting with 3-methyl-1H-pyrazolo[3,4-d]pyrimidin-4-amine. $^1$H NMR (400 MHz, CD$_3$OD) δ 7.79 (s, 1H), 7.43-7.39 (m, 1H), 7.29-7.25 (m, 1H), 7.21-7.17 (m, 1H), 6.97-6.92 (in, 1H), 6.60 (s, 1H), 6.47-6.43 (m, 1H), 5.62 (q, J=6.9 Hz, 1H), 4.05 (s, 3H), 2.48 (s, 3H), 1.64 (d, J=6.9 Hz, 3H). MS (ESI) m/e [M+1]$^+$ 401.6.

Example 57

6-(1-(4-amino-5-bromo-7H-pyrrolo[2,3-d]pyrimidin-7-yl)ethyl)-4-methoxy-2-oxo-1-phenyl-1,2-dihydropyridine-3-carbonitrile (Compound 57)

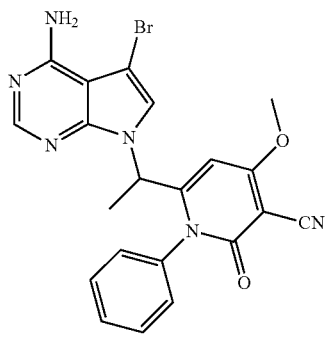 [SMILES: COc1cc(C(C)n2cc(Br)c3c(N)ncnc32)n(-c2ccccc2)c(=O)c1C#N]

The desired product was prepared using a procedure similar to step 8 for example 54 starting with 5-bromo-7H-pyrrolo[2,3-d]pyrimidin-4-amine, $^1$H NMR (400 MHz, DMSO-d6) δ 7.84 (s, 1H), 7.52-7.47 (m, 1H), 7.44-7.41 (m, 2H), 7.29 (t, J=7.3 Hz, 1H), 7.04 (t, J=7.6 Hz, 1H), 6.73 (brs, 2H), 6.62 (d, J=7.3 Hz, 1H), 6.51 (s, 1H), 5.48 (q, J=7.1 Hz, 1H), 4.09 (s, 3H), 1.64 (d, J=6.8 Hz, 3H). MS (ESI) m/C [M+1]$^+$ 465.1, 467.0.

Example 58

(S)-3-(1-(5-chloro-4-fluoro-2-isopropoxy-3-(6-(trifluoromethyl)pyridin-3-yl)phenyl)ethyl)-1-methyl-imidazo[1,5-a]pyrazin-8-amine (Compound 58)

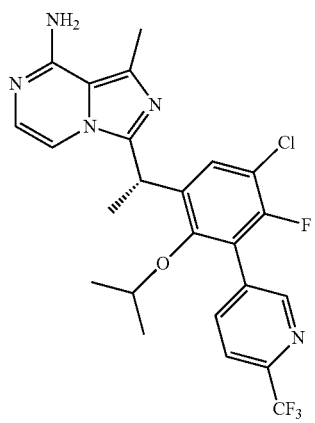 [SMILES: Cc1nc([C@@H](C)c2cc(Cl)c(F)c(-c3ccc(C(F)(F)F)nc3)c2OC(C)C)n2ccnc(N)c12]

Step 1: 1-(5-chloro-4-fluoro-2-hydroxyphenyl)ethan-1-one (58-1)

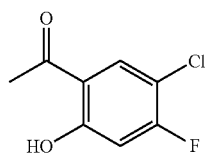

The reaction mixture of 4-chloro-3-fluorophenol (146.5 g, 0.78 mol) and acetyl chloride (157 g, 2 mol) was stirred at 60° C. for 2 hrs. Then the mixture was cooled to 0° C. and AlCl$_3$ (240 g, 1.8 mol) was added portionwise. The reaction mixture was stirred at 180° C. for 2 hrs. The mixture was cooled to room temperature and 1N HCl (1.5 L) was added. The resulting mixture was extracted with ethyl acetate. The combined organic layers were washed with brine, dried over Na$_2$SO$_4$, filtered and evaporated in vacuo. The residue was dissolved with petroleum and filtered through silica gel. The solvent was evaporated in vacuo to give the crude product (177 g, 93%) as a yellow solid. $^1$H NMR (400 MHz, DMSO-d6) δ 12.16 (s, 1H), 8.07 (d, J=8.6 Hz, 1H), 7.05 (d, J=10.9 Hz, 1H), 2.64 (s, 3H).

Step 2: 1-(5-chloro-4-fluoro-2-hydroxy-3-iodophenyl)ethan-1-one (58-2)

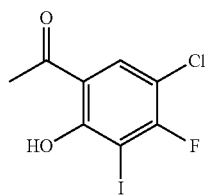

The reaction mixture of 1-(5-chloro-4-fluoro-2-hydroxyphenyl)ethan-1-one (88 g, 0.467 mol) and NIS (157 g, 0.7 mol) in AcOH (900 ml) was stirred at 80° C. for 20 hrs then 110° C. for 20 hrs. Then the solvent was evaporated in vacuo and the residue was dissolved with ethyl acetate. The mixture was washed with saturated Na₂CO₃ aqueous solution twice, saturated Na₂S₂O₃ aqueous solution and brine, dried over Na₂SO₄, filtered and evaporated in vacuo. The residue was purified by column chromatography (PE to PE/EA: 50/1) to give the product (43 g, 31%; 37 g, impure) as a yellow solid. ¹H NMR (400 MHz, DMSO-d6) δ 13.36 (s, 1H), 8.28 (dd, J=8.4, 0.9 Hz, 1H), 2.70 (d, J=0.6 Hz, 3H). LC-MS (M+H)⁺ 314.9.

Step 3: 1-(5-chloro-4-fluoro-2-hydroxy-3-(6-(trifluoromethyl)pyridin-3-yl)phenyl)ethan-1-one (58-3)

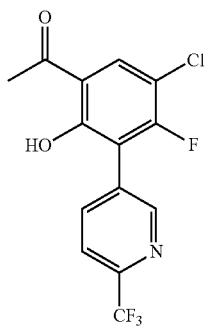

The reaction mixture of 1-(5-chloro-4-fluoro-2-hydroxy-3-iodophenyl)ethan-1-one (68 g, 216 mmol), (6-(trifluoromethyl)pyridin-3-yl)boronic acid (45 g, 238 mmol), Pd(dppf)Cl₂ (9.5 g, 13 mmol) and Na₂CO₃ (57 g, 106 mmol) in 1,4-dioxane/water (700 mL/100 mL) under nitrogen was stirred at 80° C. for overnight. After completed, the mixture was evaporated in vacuo. The residue was diluted with ethyl acetate and water then the resulting mixture was filtered. The organic layer was separated and the aqueous layer was extracted with ethyl acetate. The organic layers was combined, washed with brine, dried over Na₂SO₄, filtered and evaporated in vacuo. The residue was purified by column chromatography (PE/EA:50/1 to 10/1) to give the product as a yellow solid (59 g, 81%). ¹H NMR (400 MHz, DMSO-d6) δ 13.01 (s, 1H), 8.88 (s, 1H), 8.39 (d, J=8.4 Hz, 1H), 8.24 (d, J=8.1 Hz, 1H), 8.07 (d, J=8.1 Hz, 1H), 2.74 (s, 3H), LC-MS (M+H)⁺=334.0.

Step 4: 1-(5-chloro-4-fluoro-2-isopropoxy-3-(6-(trifluoromethyl)pyridin-3-yl)phenyl)ethan-1-one (58-4)

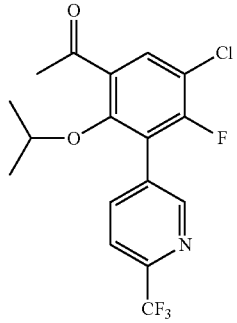

The reaction mixture of 1-(5-chloro-4-fluoro-2-hydroxy-3-(6-(trifluoromethyl)pyridin-3-yl)phenyl)ethan-1-one (59 g, 176.8 mmol), 2-Iodopropane (120 g, 707.2 mmol) and K₂CO₃ (49 g, 353.6 mmol) in DMF (150 mL) under N₂ was stirred at 70° C. for overnight. After completed, the mixture was filtered and the filtrate was evaporated in vacuo. The residue was purified by column chromatography (PE/EA: 6/1) to give the product as a brown oil (62 g, 93%). ¹H NMR (400 MHz, DMSO-d6) δ 8.93 (s, 1H), 8.31 (d, J=8.3 Hz, 1H), 8.11 (d, J=8.2 Hz, 1H), 7.86 (d, J=8.6 Hz, 1H), 3.77-3.59 (m, 1H), 2.63 (s, 3H), 0.87 (d, J=6.1 Hz, 6H), LC-MS (M+H)⁺=376.0.

Step 5 5-(3-chloro-2-fluoro-6-isopropoxy-5-(prop-1-en-2-yl)phenyl)-2-(trifluoromethyl)pyridine (58-5)

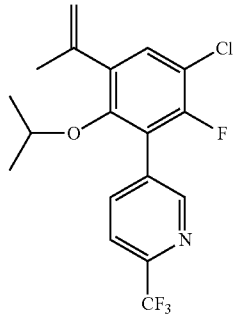 [SMILES: C=C(C)c1cc(Cl)c(F)c(-c2ccc(C(F)(F)F)nc2)c1OC(C)C]

To the solution of methyltriphenylphosphoniumbromide (177 g, 495 mmol) in THF (700 mL) at 0° C. was added nBuLi (186 mL, 445.5 mmol) under N₂ and stirred for 1 hr. Then a solution of 1-(5-chloro-4-fluoro-2-isopropoxy-3-(6-(trifluoro methyl)pyridin-3-yl)phenyl)ethan-1-one (62 g, 165 mmol) in THF (300 mL) was added and stirred at room temperature for overnight. The reaction was quenched with a saturated NH₄Cl aqueous solution and the mixture was extracted with ethyl acetate. The combined organic layers were washed with brine, dried over Na₂SO₄, filtered and evaporated in vacuo. The residue was purified by column chromatography (PE/EA:50/1) to give the product as a white solid (25 g, 40%) and recovered the original material. ¹H NMR (400 MHz, DMSO-d6) δ 8.85 (s, 1H), 8.23 (d, J=8.1 Hz, 1H), 8.06 (d, J=8.1 Hz, 1H), 7.55 (d, J=8.7 Hz, 1H), 5.29

(s, 1H), 5.22 (s, 1H), 3.90 (dt, J=12.2, 6.1 Hz, 1H), 2.14 (s, 3H), 0.82 (d, J=6.1 Hz, 61H), LC-MS (M+H)⁺=374.1.

Step 6 2-(5-chloro-4-fluoro-2-isopropoxy-3-(6-(trifluoromethyl)pyridin-3-yl)phenyl)propan-1-ol (58-6)

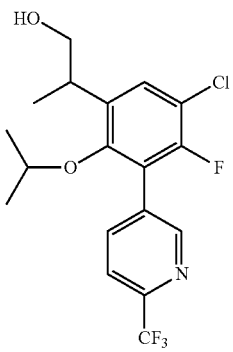

The reaction mixture of 5-(3-chloro-2-fluoro-6-isopropoxy-5-(prop-1-en-2-yl)phenyl)-2-(trifluoromethyl)pyridine (25 g, 66.9 mmol) and BH₃/THF (334 mL, 334 mmol) under nitrogen was stirred at room temperature for overnight. Then a solution of NaOH (5.25 g, 133.8 mmol) in water was added and H₂O₂ (50 mL) was added. The mixture was stirred at room temperature for 3 hrs. After completed, the reaction was quenched with a saturated Na₂SO₃ aqueous solution and the mixture was extracted with ethyl acetate. The combined organic layers were washed with brine, dried over Na₂SO₄, filtered and evaporated in vacuo. The residue was purified by column chromatography (DCM/MeOH=50/1, ammonia water) to give the product as a colorless oil which solidified at room temperature. LC-NMS (M+H)= 392.1

Step 7: 2-(5-chloro-4-fluoro-2-isopropoxy-3-(6-(trifluoromethyl)pyridin-3-yl)phenyl)propanoic acid (58-7)

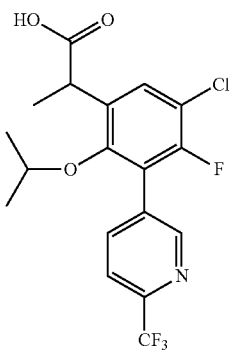 [SMILES: CC(C)Oc1c(C(C)C(=O)O)cc(Cl)c(F)c1-c1ccc(C(F)(F)F)nc1]

To the solution of 2-(5-chloro-4-fluoro-2-isopropoxy-3-(6-(trifluoromethyl)pyridin-3-yl)phenyl)propan-1-ol (6.7 g, 17.2 mmol, leg) in MeCN (80 mL) was added buffer solution (80 mL, Na₂HPO₄ (0.25 M) and NaH₂PO₄ (0.5 M) in water), 2,2,6,6-Tetramethylpiperidinooxy (537 mg, 3.44 mmol). Then a solution of NaClO₂ (16 g, 172 mmol) in NaClO (145 mL, 172 mmol) was added by dropwise and stirred at room temperature for overnight. The mixture was diluted with water and extracted with ethyl acetate. The combined organic layers were washed with brine, dried over Na₂SO₄, filtered and evaporated in vacuo to give the crude product (6.2 g). LC-MS (M+H)⁺=406.0.

Step 8: Chiral separation of 2-(5-chloro-4-fluoro-2-isopropoxy-3-(6-(trifluoromethyl)pyridin-3-yl)phenyl)propanoic Acid (58-8)

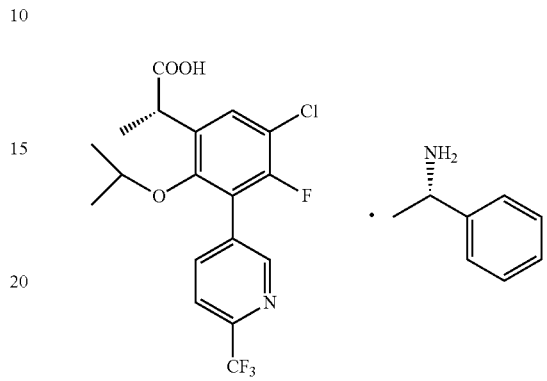

A mixture of 2-(5-chloro-4-fluoro-2-isopropoxy-3-(6-(trifluoromethyl)pyridin-3-yl)phenyl)propanoic acid (49.55 g, 122.42 mmol) and (S)-1-phenylethan-1-amine (19.4 g, 159.17 mmol) in EtOH (250 mL) was stirred at 78° C. until the solid was dissolved. Then Water (300 ml) was partially added and stirred at 78° C. for 20 min. After cooling to room temperature, the reaction mixture was stranded at room temperature for 24 hrs. The solid was collected by filtration and dried to give the product (48.4 g) as a white solid.

A mixture of the solid (48.4 g) in 230 mL of EtOH was stirred at 78° C. until the solid was dissolved. Then Water (450 ml) was partially added and stirred at 78° C. for 20 min. After cooling to room temperature, the reaction mixture was stranded at room temperature for 24 hrs. The solid was collected by filtration and dried to give the product as a white solid. And repeat this procedure one time, the solid was freed by 3N HCl to give product (19.5 g, 39.7%) as a white solid.

Step 9: (2S)-2-(5-chloro-4-fluoro-2-isopropoxy-3-(6-(trifluoromethyl)pyridin-3-yl)phenyl)-N-(1-(3-chloropyrazin-2-yl)ethyl)propanamide (58-9)

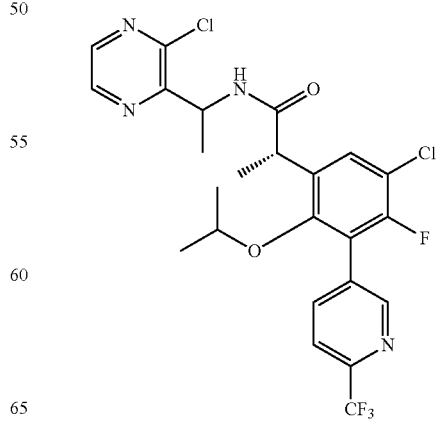

(S)-2-(5-chloro-4-fluoro-2-isopropoxy-3-(6-(trifluoromethyl)pyridin-3-yl)phenyl)propanoic acid (19.5 g, 48.1 mmol), 1-(3-chloropyrazin-2-yl)ethan-1-amine (12.1 g, 76.4 mmol), HOBt (8.45 g, 62.5 mmol), EDCI (11.99 g, 62.5 mmol) and DIPEA (24 mL, 144.3 mmol) were dissolved in DCM (200 ml) and the mixture was stirred at room temperature for overnight under $N_2$. Then 100 mL of DCM was added and washed with water (200 mL×2). The organic layers was washed with brine, dried over $Na_2SO_4$, evaporated in vacuo, The residue was purified by a silica gel pad (50 g), washed with PE:EA=1:1 (500 mL) to give the product (29 g, nearly 100%) as a light yellow oil without further purification Step 10: (S)-8-chloro-3-(1-(5-chloro-4-fluoro-2-isopropoxy-3-(6-(trifluoromethyl)pyridin-3-yl)phenyl)ethyl-1-methylimidazo[1,5-a]pyrazine (58-10)

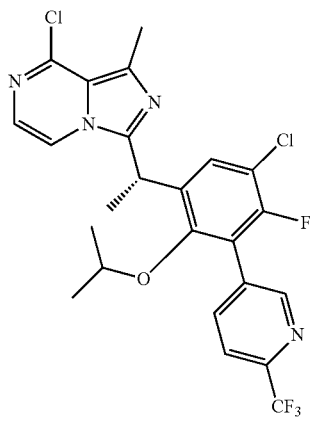 [SMILES: Cc1nc([C@@H](C)c2cc(Cl)c(F)c(-c3ccc(C(F)(F)F)nc3)c2OC(C)C)n2ccnc(Cl)c12]

To the solution of compound 58-9 (29 g, crude) in DCM (250 mL) was added trifluoromethanesulfonic anhydride (15.4 ml) slowly at room temp. Then pyridine (15.4 mL) was added dropwise slowly and the mixture was stirred for 20 mins. The mixture was washed with water (200 mL×2) and brine, dried over $Na_2SO_4$, filtered and evaporated in vacuo. The residue was purified by a silica gel pad (45 g), washed with PE:EA=1:1 (500 mL) to give the crude product, then the crude product was stirred at PE:EA=5:1 (50 mL) and filtrated to give the product (16.7 g, 66% for two steps) as an off-white solid.

Step 11: (S)-3-(1-(5-chloro-4-fluoro-2-isopropoxy-3-(6-(trifluoromethyl)pyridin-3-yl)phenyl)ethyl)-1-methylimidazo[1,5-a]pyrazin-8-amine (58-11)

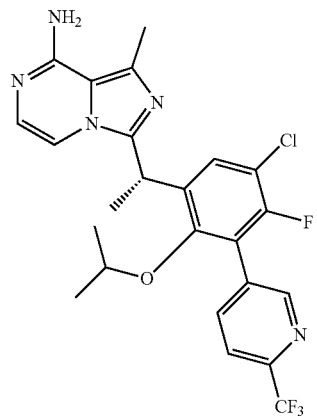 [SMILES: Cc1nc([C@@H](C)c2cc(Cl)c(F)c(-c3ccc(C(F)(F)F)nc3)c2OC(C)C)n2ccnc(N)c12]

A mixture of compound 58-10 (16.7 g, 31.74 mmol) and $NH_3$ in iPrOH (150 mL) in a steel tube was stirred at 90° C. for 48 hrs. After completed, the mixture was evaporated in vacuo. The residue was added 300 mL of ethyl acetate, washed with water (200 mL×2), dried over $Na_2SO_4$, filtered and evaporated in vacuo. to give the crude product, then the crude product was stirred in petroleum (250 mL) and filtrated to give the product (14.98 g, 93.1%) as a white solid. $^1$H NMR (400 MHz, DMSO-$d_6$): δ 8.86 (s, 1H), 8.23-8.25 (d, J=8.0 Hz, 1H), 8.07-8.09 (d, J=8.4 Hz, 1H), 7.53-7.55 (d, J=8.0 Hz, 1H), 7.34-7.36 (d, J=5.2 Hz, 1H), 6.91-6.92 (d, J=4.8 Hz, 1H), 6.52 (brs, 2H), 4.83-4.85 (q, 1H), 3.59-3.62 (m, 1H), 2.60 (s, 3H), 1.66-1.68 (d, J=6.8 Hz, 3H), 0.99-1.01 (d, J=6.0 Hz, 3H), 0.78-0.79 (d, J=6.0 Hz, 3H). MS (ESI) m/e [M+1]+ 508.1.

Example 59

5-(3-(1-(8-amino-1-methylimidazo[1,5-a]pyrazin-3-yl)ethyl)-5-chloro-6-fluoro-2-isopropoxyphenyl)picolinonitrile (59)

Compound 59

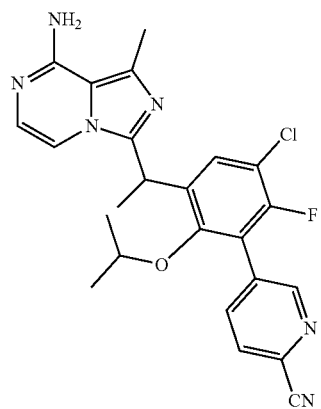

-continued

Compound 59A

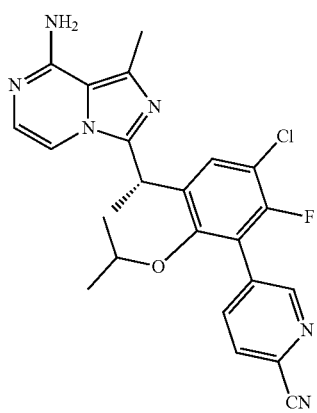

Compound 59B

Step 1: 1-(5-chloro-4-fluoro-2-hydroxyphenyl)ethan-1-one (59-1)

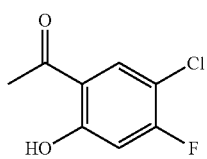

To a 2 L three necks flask, equipped with a magnetic stirrer was added 4-chloro-3-fluorophenol (160 g, 1.1 mol) and acetyl chloride (129 g, 0.69 mol). The mixture was stirred for 1 h. Then aluminum chloride (219 g, 1.6 mol) was added into the mixture in portions. The mixture was heated to 160° C. and kept at 150° C. for 2 hrs. The mixture was cooled and diluted with HCl (2 M, 500 mL). The resulting hot liquid was cooled and extracted with ethyl acetate (3×500 mL). The combined organic phase was washed with water (500 mL) and brine (500 mL), dried over anhydrous sodium sulfate, filtered and concentrated to afford 200 g (crude) of 1-(5-chloro-4-fluoro-2-hydroxyphenyl)ethan-1-one as a yellow solid. $^1$H NMR (400 MHz, CDCl$_3$) δ 12.48-12.41 (m, 1H), 7.78 (d, J=8.1 Hz, 1H), 6.77 (d, J=10.3 Hz, 1H), 2.61 (s, 3H).

Step 2: 1-(3-bromo-5-chloro-4-fluoro-2-hydroxyphenyl)ethan-1-one (59-2)

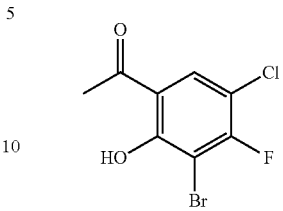

To a solution of 1-(5-chloro-4-fluoro-2-hydroxyphenyl)ethan-1-one (110 g, 412 mmol) in DMF (1 L) was added NBS (114 g, 640 mmol) in portions. The mixture was stirred at room temperature for 1 h. The mixture was diluted with water (3 L), extracted with ethyl acetate (3×1 L). The combined organic phase was washed with brine (3×1 L), dried over anhydrous sodium sulfate, filtered and concentrated to afford 150 g (crude) of 1-(5-chloro-4-fluoro-2-hydroxyphenyl)ethan-1-one as a yellow solid. $^1$H NMR (400 MHz, CDCl$_3$) δ 13.21 (d, J=1.8 Hz, 1H), 7.80 (d, J=7.8 Hz, 1H), 2.66 (s, 3H).

Step 3: 1-(3-bromo-5-chloro-4-fluoro-2-isopropoxyphenyl)ethan-1-one (59-3)

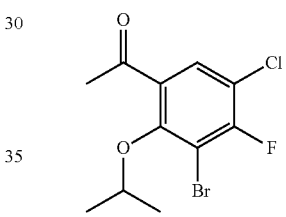

To a solution of 1-(3-bromo-5-chloro-4-fluoro-2-hydroxyphenyl)ethan-1-one (150 g, 560 mmol) and 2-iodopropane (143 g, 841 mmol) in DMF (1 L) was added NaHCO$_3$ (71 g, 845 mmol). The mixture was stirred at 60° C. overnight. The mixture was cooled and diluted with water (3 L), extracted with ethyl acetate (3×1 L). The combined organic phase was washed with brine (3×1 L), dried over anhydrous sodium sulfate, filtered and concentrated. The residue was purified by silica gel column chromatography (elution with hexane/ethyl acetate=50/1) to afford 140 g (80%) of 1-(3-bromo-5-chloro-4-fluoro-2-isopropoxyphenyl)ethan-1-one as a yellow oil. $^1$H NMR (400 MHz, CDCl$_3$) δ 7.57 (d, J=8.2 Hz, 1H), 4.45-4.39 (m, 1H), 2.61 (s, 3H), 1.31 (t, J=6.7 Hz, 6H).

Step 4: 3-bromo-1-chloro-2-fluoro-4-isopropoxy-5-(prop-1-en-2-yl)benzene (59-4)

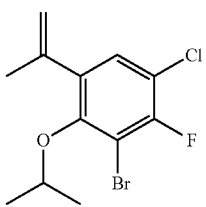 [SMILES: C=C(C)c1cc(Cl)c(F)c(Br)c1OC(C)C]

To a mixture of bromo(methyl)triphenylphosphane (41 g, 115 mmol) in THE (400 mL) was added n-BuLi (1.6 M, 72 mL, 115 mmol) dropwise at 0° C. The mixture was stirred at 0° C. for 30 mins. A solution of 1-(3-bromo-5-chloro-4-fluoro-2-isopropoxy phenyl)ethan-1-one (30 g, 97 mmol) in THF (100 mL) was added to the mixture by dropwise at 0° C. The mixture was stirred at 0° C. for 4 hrs. The mixture was quenched with water (500 mL), extracted with ethyl acetate (3×200 mL). The combined organic phase was washed with brine, dried over anhydrous sodium sulfate, filtered and concentrated. The residue was purified by silica gel column chromatography (elution with hexane/ethyl acetate=100/1) to afford 5.0 g (17%) of 3-bromo-1-chloro-2-fluoro-4-isopropoxy-5-(prop-1-en-2-yl)benzene as a yellow oil. $^1$H NMR (400 MHz, CDCl$_3$) δ 7.21-7.17 (ma, 1H), 5.20-5.16 (m, 1H), 5.13-5.10 (m, 1H), 4.54-4.44 (m, 1H), 2.10-2.08 (m, 3H), 1.29-1.25 (m, 6H).

Step 5: 2-(3-bromo-5-chloro-4-fluoro-2-isopropoxyphenyl)propan-1-ol (59-5)

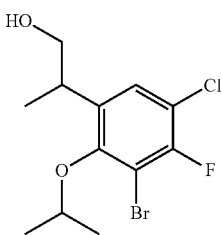

To a 3 L flask equipped with a magnetic stirrer was added 3-bromo-1-chloro-2-fluoro-4-isopropoxy-5-(prop-1-en-2-yl)benzene (170 g, 553 mmol) and BH$_3$.THF (1M, 1660 mL). The mixture was stirred for overnight at room temperature. The mixture was quenched with water (100 mL) carefully. A solution of NaOH (22 g, 550 mmol) in water (400 mL) was added to the mixture by dropwise at 0° C., then H$_2$O$_2$ (30%, 188 mL) was added to the mixture by dropwise at 0° C. The mixture was stirred at room temperature for 4 hrs. The mixture was quenched with NaHSO$_3$ solution (1 L) carefully in ice-water bath. Then the mixture was extracted with ethyl acetate (3×1000 mL). The combined organic phase was washed with brine, dried over anhydrous sodium sulfate, filtered and concentrated to afford 200 g (crude) of 2-(3-bromo-5-chloro-4-fluoro-2-isopropoxyphenyl)propan-1-ol as a yellow oil.

Step 6: 2-(3-bromo-5-chloro-4-fluoro-2-isopropoxyphenyl)propanoic Acid (59-6)

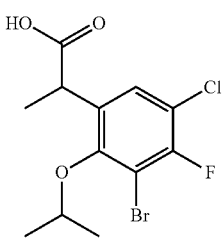 [SMILES: CC(C)Oc1c(C(C)C(=O)O)cc(Cl)c(F)c1Br]

To a solution of 2-(3-bromo-5-chloro-4-fluoro-2-isopropoxyphenyl)propan-1-ol (200 g, 614 mmol) and TEMPO (0.8 g, 5.1 mmol) in acetonitrile (1 L) was added phosphate buffer (PH=6.7, 1 L). The mixture was cooled in water bath. A mixture of NaClO (10%, 500 mL) and NaClO$_2$ (180 g in water 500 mL) was added dropwise to the mixture during 30 mins. The mixture was stirred for 2 hrs, then the mixture was extracted with ethyl acetate (2×1000 mL). The combined organic phase was treated with HCl (2M, 500 mL), the organic phase was separated, washed with brine, dried over anhydrous sodium sulfate, filtered and concentrated. The residue was triturated with acetonitrile (150 mL), the precipitate was collected by filtration to afford 90 g (43%) of 2-(3-bromo-5-chloro-4-fluoro-2-isopropoxyphenyl)propanoic acid as a white solid. $^1$H NMR (400 MHz, d6-DMSO) δ 12.55 (s, 1H), 7.51 (d, J=8.4 Hz, 1H), 4.60-4.50 (m, 1H), 4.03 (q, J=7.2 Hz, 1H), 2.08 (s, 3H), 1.37 (d, J=7.3 Hz, 3H), 1.31-1.27 (m, 6H). MS (ESI) m/e [M–H]$^-$ 336.9, 338.9.

Step 7: 2-(3-bromo-5-chloro-4-fluoro-2-isopropoxyphenyl)-N-(1-(3-chloropyrazin-2-yl)ethyl)propanamide (59-7)

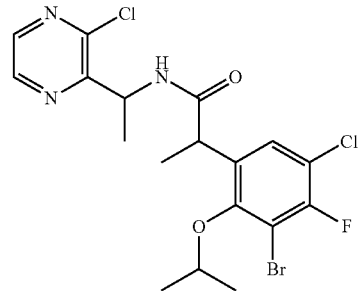 [SMILES: CC(C)Oc1c(C(C)C(=O)NC(C)c2nccnc2Cl)cc(Cl)c(F)c1Br]

To a solution of 2-(3-bromo-5-chloro-4-fluoro-2-isopropoxyphenyl)propanoic acid (13.0 g, 38.3 mmol) and 1-(3-chloropyrazin-2-yl)ethan-1-amine (6.0 g, 38.1 mmol) in dichloromethane (150 mL) were added Et$_3$N (11.6 g, 114.6 mmol), HOBT (6.2 g, 45.9 mmol) and EDCI (8.8 g, 45.9 mmol). The mixture was stirred for 3 hrs. The mixture was diluted with water (300 mL), extracted with dichloromethane (3×100 mL). The combined organic phase was dried and concentrated. The residue was purified by silica gel column chromatography (elution with dichloromethane/ethyl acetate from 20/1 to 5/1) to afford 11.4 g (62%) of 2-(3-bromo-5-chloro-4-fluoro-2-isopropoxyphenyl)-N-(1-(3-chloropyrazin-2-yl)ethyl)propanamide as a yellow solid. $^1$H NMR (400 MHz, CDCl$_3$) δ 8.30 (d, J=2.4 Hz, 1H) 8.26 (d, J=2.4 Hz, 1H), 7.31 (d, J=8.1 Hz, 1H), 6.96 (d, J=7.6 Hz, 1H), 5.47-5.39 (m, 1H), 4.73-4.63 (m, 1H), 4.15-4.07 (m, 1H), 1.51-1.42 (m, 9H), 1.32 (d, J=6.2 Hz, 3H). MS (ESI) m/e [M+1]$^+$ 478.0, 480.0.

Step 8: 3-(1-(3-bromo-5-chloro-4-fluoro-2-isopropoxyphenylethyl)-8-chloro-1-methylimidazo[1,5-a]pyrazine (59-8)

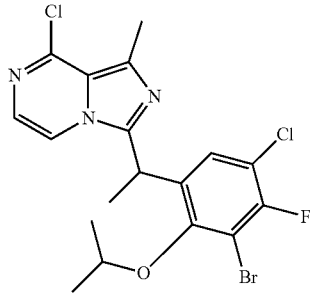 [SMILES: Cc1nc(C(C)c2cc(Cl)c(F)c(Br)c2OC(C)C)n2ccnc(Cl)c12]

To a solution of 2-(3-bromo-5-chloro-4-fluoro-2-isopropoxyphenyl)-N-(1-(3-chloropyrazin-2-yl)ethyl)propanamide (11.4 g, 23.8 mmol) in dichloromethane (130 mL) was added a solution of Tf$_2$O in dichloromethane (30 mL) dropwise. Then a solution of pyridine (9.4 g, 119 mmol) in dichloromethane (40 mL) was added by dropwise to the mixture. The mixture was stirred at room temperature for 1 h. The mixture was quenched with water (200 mL)), extracted with dichloromethane (3×100 mL). The combined organic phase was dried and concentrated. The residue was purified by silica gel column chromatography (elution with dichloromethane/ethyl acetate from 20/1 to 5/1) to afford 8.0 g (73%) of 3-(1-(3-bromo-5-chloro-4-fluoro-2-isopropoxyphenyl)ethyl)-8-chloro-1-methylimidazo[1,5-a]pyrazine as a yellow solid. $^1$H NMR (400 MHz, CDCl$_3$) δ 7.57 (d, J=4.8 Hz, 1H), 7.30 (d, J=7.8 Hz, 1H), 7.15 (d, J=4.6 Hz, 1H), 4.84-4.69 (m, 2H), 2.82 (s, 3H), 1.86 (d, J=7.0 Hz, 3H), 1.53 (d, J=6.1 Hz, 3H), 1.38 (d, J=6.1 Hz, 3H). MS (ESI) m/e [M+1]$^+$459.9, 462.0.

Step 9: 3-(1-(3-bromo-5-chloro-4-fluoro-2-isopropoxyphenyl)ethyl)-1-methylimidazo[1,5-a]pyrazin-8-amine (59-9)

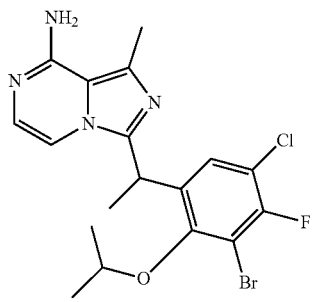 [SMILES: Cc1nc(C(C)c2cc(Cl)c(F)c(Br)c2OC(C)C)n2ccnc(N)c12]

A mixture of 3-(1-(3-bromo-5-chloro-4-fluoro-2-isopropoxyphenyl)ethyl)-8-chloro-1-methylimidazo[1,5-a]pyrazine (1.01 g, 2.2 mmol) and NH$_3$ in iPrOH (20 mL) in a steel tube was stirred at 90° C. for 48 hrs. After completed, the mixture was evaporated in vacuo. The residue was added 50 mL ethyl acetate, washed with water (30 mL×2), dried over Na$_2$SO$_4$, filtered and evaporated in vacuo to give the crude product, then the crude product was stirred in petroleum (250 mL) and filtrated to give the product (0.96 g, 98.3%) as a white solid.

Step 10: 5-(3-(1-(8-amino-1-methylimidazo[1,5-a]pyrazin-3-yl)ethyl)-5-chloro-6-fluoro-2-isopropoxyphenyl)picolinonitrile (59-10)

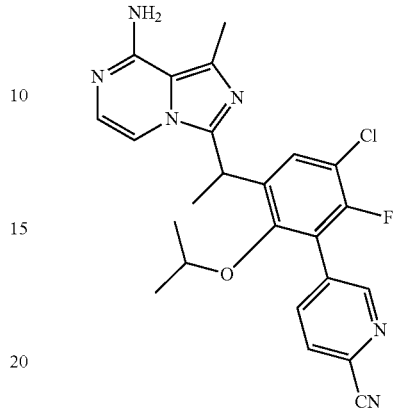

The reaction mixture of 3-(1-(3-bromo-5-chloro-4-fluoro-2-isopropoxyphenyl)ethyl)-1-methylimidazo[1,5-a]pyrazin-8-amine (0.6 g, 1.36 mmol), (6-cyanopyridin-3-yl)boronic acid (0.32 g, 1.5 mmol), Pd(dppf)Cl$_2$ (60 mg, 0.08 mmol) and Na$_2$CO$_3$ (0.36 g, 3.41 mmol) in 1,4-dioxane/water (35 mL/5 mL) under nitrogen was stirred at 80° C. for overnight. After completed, the mixture was evaporated in vacuo. The residue was diluted with ethyl acetate and water then the resulting mixture was filtered. The organic layer was separated and the aqueous layer was extracted with ethyl acetate. The organic layers was combined, washed with brine, dried over Na$_2$SO$_4$, filtered and evaporated in vacuo. The residue was purified by column chromatography (PE/EA:2/1 to EA) to give the product as a white solid (251 mg, 49.2%). $^1$H NMR (400 MHz, DMSO-d6): δ8.84 (s, 1H), 8.21 (s, 2H), 7.53-7.55 (d, J=8.0 Hz, 1H), 7.32-7.33 (d, J=5.2 Hz 1H), 6.90-6.91 (d, J=4.8 Hz 1H), 6.47 (brs, 2H), 4.82-4.83 (q, 1H), 3.59-3.61 (m, 1H), 2.59 (s, 3H), 1.65-1.67 (d, J=6.8 Hz, 3H), 0.99-1.01 (d, J=6.0 Hz, 3H), 0.79-0.80 (d, J=6.0 Hz, 3H). MS (ESI) m/e [M+1]$^+$ 465.1.

Compound 59 was separated by chiral column to afford two compounds, Compound 59A (the first and fast isomer) and Compound 59B (the second and slow isomer), as white solids. Compound 59A was assigned as a (S)-configuration in a similar manner to Compound 40A.

Compound 59A: $^1$H NMR (400 MHz, DMSO-d6): δ8.84 (s, 1H), 8.21 (s, 2-H), 7.53-7.55 (d, J=8.0 Hz, 1H), 7.32-7.33 (d, J=5.2 Hz 1H), 6.90-6.91 (d, J=4.8 Hz 1H), 6.47 (brs, 21), 4.82-4.83 (q, 1H), 3.59-3.61 (m, 1H), 2.59 (s, 3H), 1.65-1.67 (d, J=6.8 Hz, 3H), 0.99-1.01 (d, J=6.0 Hz, 3H), 0.79-0.80 (d, J=6.0 Hz, 3H). MS (ESI) m/e [M+1]$^+$ 465.1.

Compound 59B: $^1$H NMR (400 MHz, DMSO-d6): δ8.84 (s, 1H), 8.21 (s, 2H), 7.53-7.55 (d, J=8.0 Hz, 1H), 7.32-7.33 (d, J=5.2 Hz 1H), 6.90-6.91 (d, J=4.8 Hz 1H), 6.47 (brs, 21), 4.82-4.83 (q, 1H), 3.59-3.61 (m, 1H), 2.59 (s, 3H), 1.65-1.67 (d, J=6.8 Hz, 3H), 0.99-1.01 (d, J=6.0 Hz, 3H), 0.79-0.80 (d, J=6.0 Hz, 3H). MS (ESI) m/e [M+1]$^+$ 465.1.

| Column | CHIRALPAK IE |
|---|---|
| Column size | 2 cm × 25 cm, 5um |
| Injection | 0.2 ML |
| Mobile phase | Hex:EtOH = 50:50 |

| Column | CHIRALPAK IE |
|---|---|
| Flow rate | 15 ml/min |
| Wave length | UV 220 nm |
| Temperature | 25° C. |
| Sample solution | 58 mg/ml in EtOH |
| Prep-HPLC equipment | Prep-Gilson-HPLC |

Example 60

(S)-5-(3-(1-(8-amino-1-methylimidazo[1,5-a]pyrazin-3-v)ethyl)-5-chloro-6-fluoro-2-isopropoxyphenyl-N'-hydroxypicolinimidamide (60)

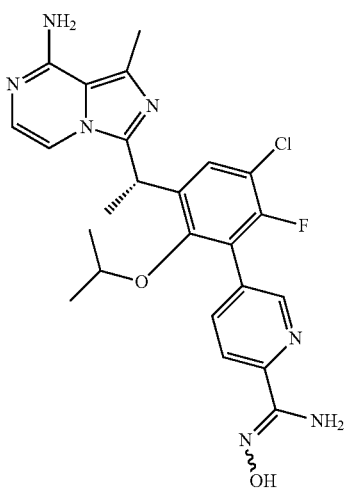 [SMILES: Cc1nc([C@@H](C)c2cc(Cl)c(F)c(-c3ccc(C(N)=NO)nc3)c2OC(C)C)n2ccnc(N)c12]

Step 1: 5-(3-(1-(8-amino-1-methylimidazo[1,5-a]pyrazin-3-yl)-5-chloro-6-fluoro-2-isopropoxyphenyl)-N'-hydroxypicolinimidamide (60-1)

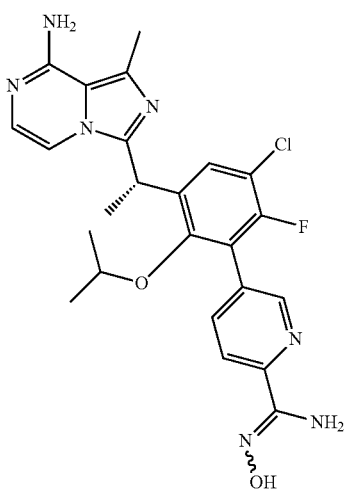 [SMILES: Cc1nc([C@@H](C)c2cc(Cl)c(F)c(-c3ccc(C(N)=NO)nc3)c2OC(C)C)n2ccnc(N)c12]

The reaction mixture of compound 59A (30 mg, 0.065 mmol), hydroxylamine (10 mg, 0.30 mmol) and triethylamine (0.05 mL) in EtOH (10 mL) was stirred at 78° C. for 2 hrs. After completed, the mixture was evaporated in vacuo. The residue was washed with petroleum. The solid was collected by filtration to give the product as a white solid (9.3 mg, 29%). $^1$H NMR (400 MHz, DMSO-d6): δ10.05 (s, 1H), 8.62 (s, 1H), 7.98-8.00 (d, J=8.0 Hz, 1H), 7.89-7.92 (d, J=8.8 Hz, 1H), 7.45-7.47 (d, J=8.0 Hz, 1H), 7.33-7.34 (d, J=5.2 Hz, 1H), 6.90-6.91 (d, J=4.8 Hz, 1H), 6.52 (brs, 2H), 5.91 (s, 2H), 4.83-4.84 (q, 1H), 3.63-3.67 (m, 1H), 2.59 (s, 3H), 1.65-1.67 (d, J=6.8 Hz, 31-1), 1.00-1.01 (d, J=6.0 Hz, 3H), 0.80-0.82 (d, J=6.0 Hz, 3H). MS (ESI) m/e [M+1]$^+$ 498.1.

Example 61

(S)-(5-(3-(1-(8-amino-1-methylimidazo[1,5-a]pyrazin-3-yl)ethyl)-5-chloro-6-fluoro-2-isopropoxyphenyl)pyridin-2-yl)(4-hydroxypiperidin-1-yl)methanone (61)

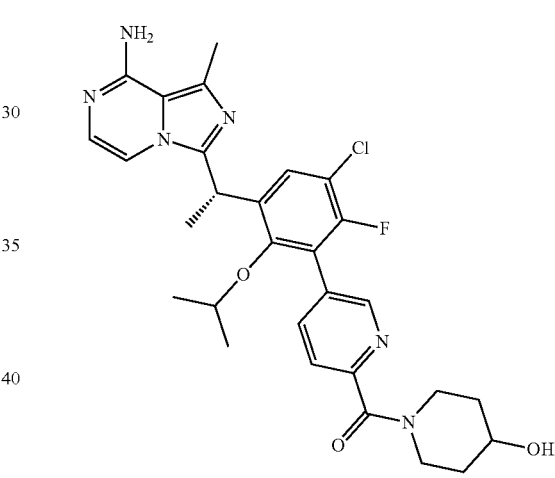

Step 1: 1-(5-chloro-4-fluoro-2-hydroxyphenyl)ethan-1-one (61-1)

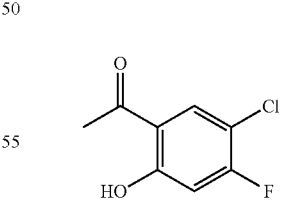

4-chloro-3-fluorophenol (241 g, 1.644 mol) was dissolved in acetyl chloride (193.64 g, 2.467 mole). AlCl$_3$ (328 g, 2.247 mol) was added and heated to 180° C. for 2 hrs. Cool to room temperature, HCl (1 N, 1 L) was added slowly and stirred at room temperature for 2 hrs. The solid was got by filtration and dissolved in ethyl acetate. The organic layers were washed with water and brine and dried over Na$_2$SO$_4$. The product (309.2 g, 100%) was got.

Step 2: 1-(5-chloro-4-fluoro-2-hydroxy-3-iodophenyl)ethan-1-one (61-2)

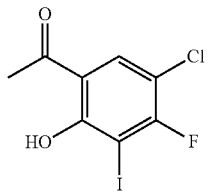

1-(5-chloro-4-fluoro-2-hydroxyphenyl)ethan-1-one (100 g, 53.03 mmol) was dissolved in DMF (1 L), NIS (131.5 g, 58.33 mmol) was added and stirred at room temperature for 18 hrs, water (2 L) was added and extracted with ethyl acetate. The combined organic layers was washed with brine and dried over $Na_2SO_4$. The product (165 g, 99%) was got by chromatography column on silica gel. MS (ESI) m/e $(M+H)^+$ 315.0.

Step 3: 1-(5-chloro-3-(6-chloropyridin-3-yl)-4-fluoro-2-hydroxyphenyl)ethan-1-one (61-3)

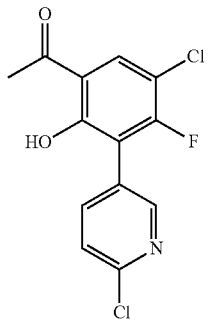 [SMILES: CC(=O)c1cc(Cl)c(F)c(-c2ccc(Cl)nc2)c1O]

1-(5-chloro-4-fluoro-2-hydroxy-3-iodophenyl)ethan-1-one (60 g, 190.8 mmol), (6-chloropyridin-3-yl)boronic acid (36 g, 228.95 mmol), $Pd(PPh_3)_4$ (11.03 g, 9.54 mmol) and $K_2CO_3$ (52.7 g, 381.6 mmol) were dissolved in 1,4-dioxane/$H_2O$ (600 ml/300 ml) and refluxed under $N_2$ for 36 hrs, solvent was removed by reduced pressure and extracted with ethyl acetate. The combined organic layers were washed with brine and dried over $Na_2SO_4$, the product (36 g, 63%) was got by chromatography column on silica gel.

Step 4: 1-(5-chloro-3-(6-chloropyridin-3-yl)-4-fluoro-2-isopropoxyphenyl)ethan-1-one

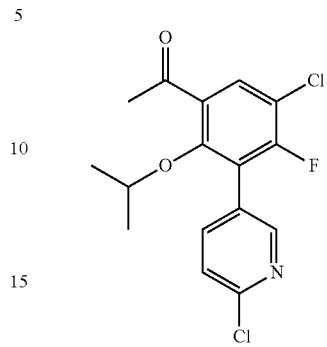

1-(5-chloro-3-(6-chloropyridin-3-yl)-4-fluoro-2-hydroxyphenyl)ethan-1-one (72 g, 241 mmol) was dissolved in DMF (600 mL), $K_2CO_3$ (99.7 g, 723 mmol) and 2-iodopropane (81.9 g, 482 mmole) was added. The reaction was heated to 60° C. for 2 hrs, DMF was removed in vacuo and extracted with ethyl acetate. The combined organic layers were washed with brine and dried over $Na_2SO_4$. The product (48 g, 58.6%) was got by chromatography column on silica gel. $^1$H NMR (400 MHz, DMSO-d6) δ 8.56 (s, 1H), 8.05 (dd, J=8.2, 1.8 Hz, 1H), 7.81 (d, J=8.6 Hz, 1H), 7.71 (d, J=8.3 Hz, 1H), 3.79-3.60 (m, 1H), 2.60 (s, 3H), 0.89 (d, J=6.1 Hz, 6H). MS (ESI) m/e $(M+H)^+$ 342.0.

Step 5: 2-chloro-5-(3-chloro-2-fluoro-6-isopropoxy-5-(prop-1-en-?-yl)phenyl)pyridine (61-5)

$CH_3PPh_3Br$ (173.3 g, 485.1 mmol) was dissolved in dry THF (830 ml), nBuLi (2.5M, 155.3 mL, 388.1 mmol) was added dropwise under $N_2$ at −65° C. and stirred for 1 hr.

Compound 61-4 (83 g, 242.6 mmol) in dry THF (300 mL) was added dropwise at −65° C. and stirred for 17 hrs, water (500 ml) was added and extracted with ethyl acetate. The combined organic layers were washed with brine and dried over $Na_2SO_4$. The product (43 g, 52.12%) was got by chromatography column on silica gel.

Step 6: 2-(5-chloro-3-(6-chloropyridin-3-yl)-4-fluoro-2-isopropylphenyl)propan-1-ol (61-6)

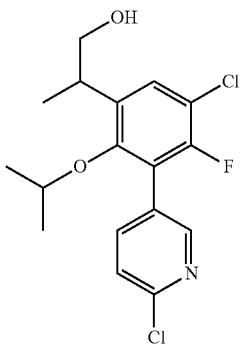 [SMILES: CC(C)Oc1c(C(C)CO)cc(Cl)c(F)c1-c1ccc(Cl)nc1]

2-chloro-5-(3-chloro-2-fluoro-6-isopropoxy-5-(prop-1-en-2-yl)phenyl)pyridine (102 g, 299.81 mmol) was dissolved in BH₃/THF (1M, 900 mL) and stirred at room temperature for 48 hrs, NaOH (1N, 250 mL) was added dropwise at 0° C., H₂O₂ (200 mL, 30%) was added and stirred at room temperature for 2 hrs. The reaction was extracted with ethyl acetate, the combined organic layers were washed with brine and dried over Na₂SO₄. The crude product (107.4 g, 100%) was got. MS (ESI) m/e (M+1)⁺ 358.0.

Step 7: 2-(5-chloro-3-(6-chloropyridin-3-yl)-4-fluoro-2-isopropoxyphenyl)propanoic Acid (61-7)

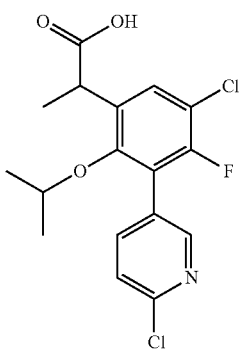 [SMILES: CC(C)Oc1c(C(C)C(=O)O)cc(Cl)c(F)c1-c1ccc(Cl)nc1]

TEMPO (468.5 mg, 2.998 mmol) and 2-(5-chloro-3-(6-chloropyridin-3-yl)-4-fluoro-2-isopropoxyphenyl)propan-1-ol (107.4 g 299.81 mmol) were dissolved in CH₃CN (550 mL). Na₂HPO₄/NaH₂PO₄ (0.25 mol/0.5 mmol/L, 550 mL) were added and stirred under room temperature, NaClO₂ (86.8 g, 959.4 mmol) in water (400 mL) and NaClO (10%, 245 mL, 329.8 mmol) were added dropwise at room temperature and stirred at room temperature for 30 min. The reaction was extracted with ethyl acetate. The combined organic layers were washed with brine and dried over Na₂SO₄. The product (103 g, 92.3%) was got. MS (ESI) m/e (M+H)⁺ 372.0.

Step 8: (S) 5-chloro-3-(6-chloropyridin-3-yl)-4-fluoro-2-isopropoxyphenyl)propanoic Acid (61-8)

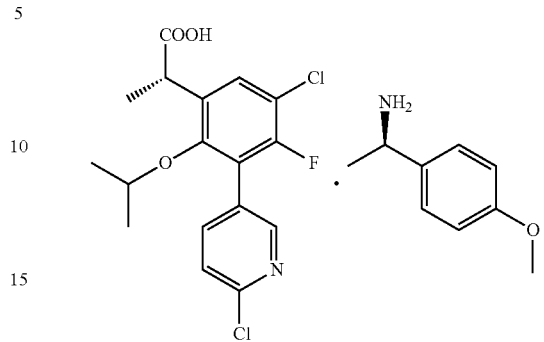

2-(5-chloro-3-(6-chloropyridin-3-yl)-4-fluoro-2-isopropoxyphenyl)propanoic acid (103 g, 276.72 mol) was dissolved in EtON (750 mL), (R)-1-(4-methoxyphenyl)ethan-1-amine (50.2 g, 332.1 mmol) was added slowly and refluxed for 30 mins, the reaction was cooled to room temperature and kept at −5° C. for overnight. The salt (43 g, ee: 97.5%) was got by filtration, the salt was recrystallized, the salt (31 g, ee: 100%) was got. The salt (37.64 g) was dissolved in ethyl acetate (500 mL) and HCl (2N, 500 mL) and stirred at room temperature for 30 mins. The reaction was extracted with ethyl acetate, washed with brine and dried over Na₂SO₄. The product (26.77 g) was got.

Step 9: (2S)-2-(5-chloro-3-(6-chloropyridin-3-yl)-4-fluoro-2-isopropoxyphenyl)-N-(1-(3-chloropyrazin-2-yl)ethyl)propanamide (61-9)

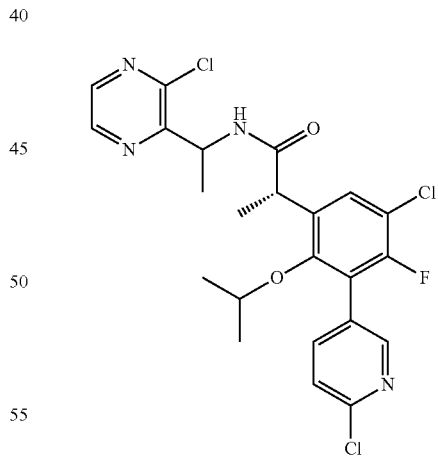

Compound 61-8 (17.6 g, 47.284 mmol), 1-(3-chloropyrazin-2-yl)ethan-1-amine (8.942 g, 56.74 mmol), HOBt (7.7 g, 56.741 mmol), EDCI (10.85 g, 56.741 mmol) and DIPEA (12.22 g, 94.568 mmol) were dissolved in THF (200 ml) and stirred at room temperature for overnight, water (100 mL) was added and extracted with ethyl acetate. The combined organic layers were washed with brine and dried over Na)SO₄. The product (24.2 g, 100%) was got by chromatography column on silica gel. MS (ESI) m/e (M+H)⁺ 511.0.

Step 10: (S)-8-chloro-3-(1-(5-chloro-3-(6-chloro-pyridin-3-yl)-4-fluoro-2-isopropoxyphenyl)ethyl)-1-methylimidazo[1,5-a]pyrazine (61-10)

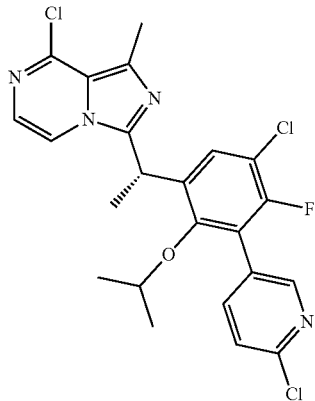 [SMILES: Cc1nc([C@@H](C)c2cc(Cl)c(F)c(-c3ccc(Cl)nc3)c2OC(C)C)n2ccnc(Cl)c12]

Compound 61-9 (24.2 g, 47.284 mmol) was dissolved in DCM (242 mL). Tf$_2$O (24.2 mL) was added dropwise slowly and stirred at room temperature for 15 mins, pyridine (36.3 mL) was added dropwise slowly and stirred at room temperature for 30 mins, water (500 mL) was added at 0° C. and extracted with ethyl acetate. The combined organic layers were washed with brine and dried over Na$_2$SO$_4$. The product (18.3 g, 78.4%) was got by chromatography column on silica gel. MS (ESI) m/e (M+H)$^+$ 493.0.

Step 11: (S)-3-(1-(5-chloro-3-(6-chloropyridin-3-yl)-4-fluoro-2-isopropoxyphenyl)ethyl)-1-methyl-imidazo[1,5-a]pyrazin-8-amine (61-11)

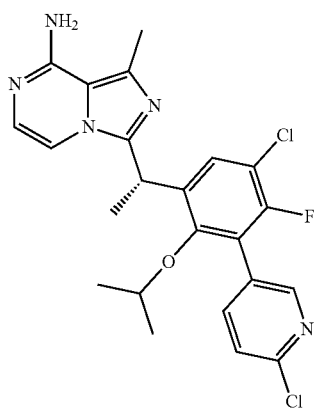 [SMILES: Cc1nc([C@@H](C)c2cc(Cl)c(F)c(-c3ccc(Cl)nc3)c2OC(C)C)n2ccnc(N)c12]

Compound 61-10 (18.3 g, 37.06 mmol) was dissolved in NH$_3$/propan-2-ol (7 N, 300 mL in tube and heated to 90° C. for 48 hrs, solvent was removed by in vacuo, DCM (300 mL) and water (200 mL) were added and extracted with DCM. The combined organic layers were washed with brine and dried over Na$_2$SO$_4$. The product (14 g, 79.55%) was got by chromatography column on silica gel. MS (ESI) m/e (M+H)$^+$ 474.0.

Step 12: ethyl (S)-5-(3-(1-(8-amino-1-methylimidazo[1,5-a]pyrazin-3-yl)ethyl)-5-chloro-6-fluoro-2-isopropoxyphenyl)picolinate (61-12)

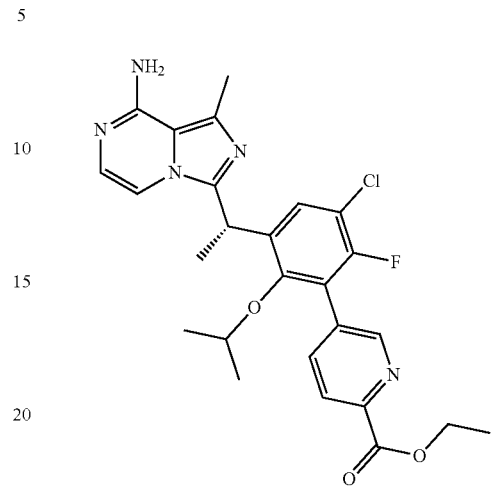

Compound 61-11 (7 g, 14.76 mmol), Pd(OAc)$_2$ (331.3 mg, 1.476 mmol), dppp (608.76 mg, 1.476 mmol) and Et$_3$N (350 mL) were dissolved in EtOH (350 mL). The reaction was refluxed under CO in balloon for overnight. Solvent was removed in vacuo and the product (5.5 g, 72.8%) was got by chromatography column on silica gel. $^1$H NMR (400 MHz, DMSO-d6) δ 8.79 (s, 1H), 8.16 (dd, J=29.9, 7.9 Hz, 2H), 7.52 (d, J=8.5 Hz, 1H), 7.35 (d, J=4.9 Hz, 1H), 6.92 (d, J=4.8 Hz, 1H), 6.51 (s, 2H), 4.84 (q, J=6.8 Hz, 1H), 4.39 (q, J=7.1 Hz, 2H), 3.62 (m, 1H), 2.60 (s, 3H), 1.67 (d, J=6.9 Hz, 3H), 1.36 (t, J=7.1 Hz, 3H), 1.00 (d, J=6.0 I-z, 3H), 0.81 (t, J=12.2 Hz, 3H). MS (ESI) m/e (M+1)$^+$ 512.0.

Step 13: (S)-5-(3-(1-(8-amino-1-methylimidazo[1,5-a]pyrazin-3-yl)ethyl)-5-chloro-6-fluoro-2-isopropoxyphenyl)picolinic Acid (61-13)

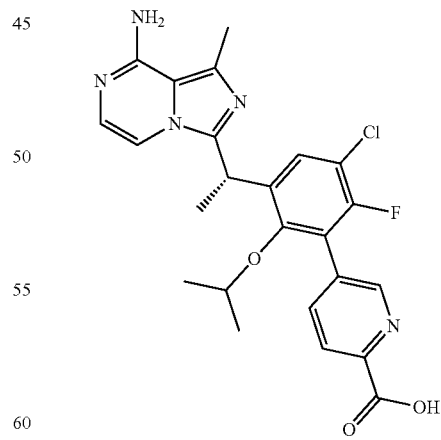

Compound 61-12 (5.5 g, 10.74 mmol) was dissolved in EtOH/NaOH (1.72 g, 42.97 mmol) in water (50 mL), the reaction was heated to 65° C. for 2 hrs, EtOH was removed in vacuo and the pH was regulated to 6-7, the product (5.1 g, 98%) was got by filtration. MS (ESI) m/e (M+H)$^+$ 484.0.

Step 14: (S)-(5-(3-(1-(8-amino-1-methylimidazo[1,5-a]pyrazin-3-yl)ethyl)-5-chloro-6-fluoro-2-isopropoxyphenyl)pyridin-2-yl)(4-hydroxypiperidin-1-yl)methanone (61-14)

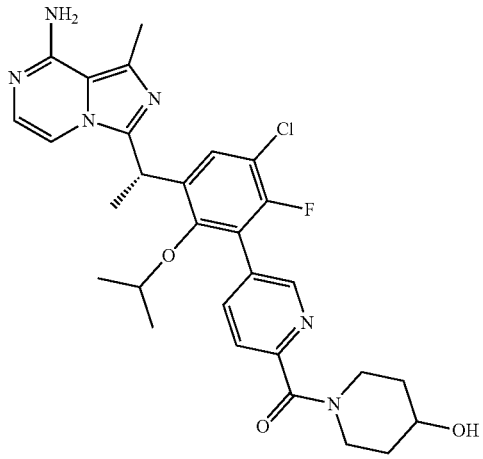 [SMILES: Cc1nc([C@@H](C)c2cc(Cl)c(F)c(-c3ccc(C(=O)N4CCC(O)CC4)nc3)c2OC(C)C)n2ccnc(N)c12]

Compound 61-13 (1,107 g, 2.27 mmol), piperidin-4-ol (463 mg, 4.58 mmol), HOBt (464 mg, 3.43 mmol), EDCI (655.71 mg, 3.43 mmol) and DIPEA (888 mg, 16.87 mmol) were dissolved in THF (50 mL) and stirred at room temperature for overnight, water (30 mL) was added and extracted with ethyl acetate. The combined organic layers were washed with brine and dried over $Na_2SO_4$. The product (470 mg, 36.2%) was got by chromatography column on silica gel. $^1$H NMR (400 MHz, DMSO-d6) δ 8.63 (s, 1H), 8.03 (d, J=8.3 Hz, 1H), 7.69 (d, J=8.1 Hz, 1H), 7.48 (d, J=8.5 Hz, 1H), 7.33 (d, J=5.0 Hz, 1H), 6.91 (d, J=5.0 Hz, 1H), 6.49 (s, 21H), 4.94-4.68 (m, 2H), 4.07-4.02 (m, 1H), 3.76-3.75 (m, 1H), 3.64-3.60 (dd, J=12.1, 6.0 Hz, 1H), 3.55-3.52 (m, 1H), 3.30-3.21 (m, 1H), 3.16 (t, J=10.0 Hz, 1H), 2.59 (s, 3H), 1.76 (d, J=44.4 Hz, 2H), 1.66 (d, J=7.0 Hz, 3H), 1.51-1.29 (m, 2H), 1.01 (d, J=5.9 Hz, 3H), 0.79 (d, J=5.9 Hz, 3H). MS (ESI) m/e (M+1)$^+$ 567.0.

Example 62

(S)-5-(3-(1-(8-amino-1-methylimidazo[1,5-a]pyrazin-3-yl)ethyl)-5-chloro-6-fluoro-2-isopropoxyphenyl)-N-(2-hydroxyethyl)picolinamide (64)

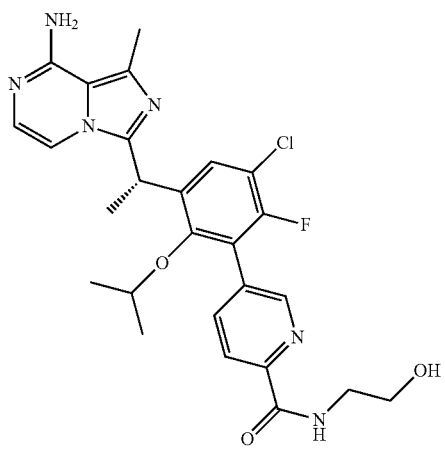 [SMILES: Cc1nc([C@@H](C)c2cc(Cl)c(F)c(-c3ccc(C(=O)NCCO)nc3)c2OC(C)C)n2ccnc(N)c12]

Compound 62 was prepared by similar manner as compound 61 starting from compound 61-13. $^1$H NMR (400 MHz, DMSO-d6) δ 11.55 (s, 1H), 8.75-8.69 (m, 3H), 8.13 (dd, J=26.9, 8.0 Hz, 2H), 7.62 (t, J=6.5 Hz, 2H), 7.02 (d, J=5.7 Hz, 1H), 5.04-4.87 (m, 1H), 3.64-3.47 (m, 3H), 3.46-3.33 (m, 2H), 2.67 (s, 3H), 1.69 (d, J=6.9 Hz, 3H), 1.00 (d, J=5.9 Hz, 3H), 0.80 (d, J=6.0 Hz, 3H). MS (ESI) m/e (M+1)$^+$ 527.0.

Example 63

(S)-(5-(3-(1-(8-amino-1-methylimidazo[1,5-a]pyrazin-3-yl)ethyl)-5-chloro-6-fluoro-2-isopropoxyphenyl)pyridin-2-yl)(3-hydroxyazetidine-1-yl)methanone (63)

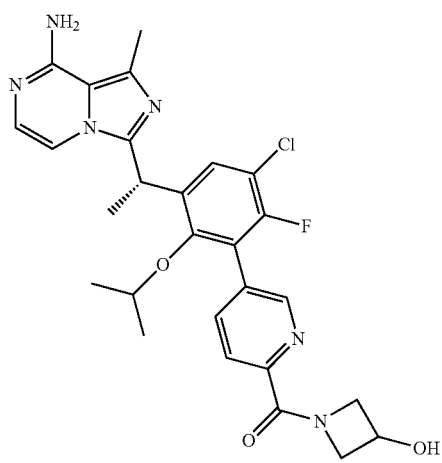 [SMILES: Cc1nc([C@@H](C)c2cc(Cl)c(F)c(-c3ccc(C(=O)N4CC(O)C4)nc3)c2OC(C)C)n2ccnc(N)c12]

Compound 63 was prepared by similar manner as compound 61 starting from compound 61-13. $^1$H NMR (400 MHz, DMSO-d6) δ 8.67 (s, 1H), 8.06 (brs, 2H), 7.50 (d, J=8.4 Hz, 1H), 7.38 (d, J=4.8 Hz, 1H), 6.94 (brs, 3H), 5.73 (d, J=6.2 Hz, 1H), 4.91-4.70 (m, 21H), 4.53-4.51 (m, 1H), 4.38-4.22 (m, 2H), 3.83 (d, J=7.4 Hz, 1H), 3.69-3.41 (m, 1H), 2.61 (s, 3H), 1.67 (d, J=6.9 Hz, 3H), 1.00 (d, J=5.9 Hz, 3H), 0.79 (d, J=5.9 Hz, 3H), MS (ESI) m/e (M+H)$^+$ 539.0.

Example 64

(5-(3-((S)-1-(8-amino-1-methylimidazo[1,5-a]pyrazin-3-yl)ethyl)-5-chloro-6-fluoro-2-isopropoxyphenyl)pyridin-2-yl)((R)-3-hydroxypyrrolidin-1-yl)methanone (64)

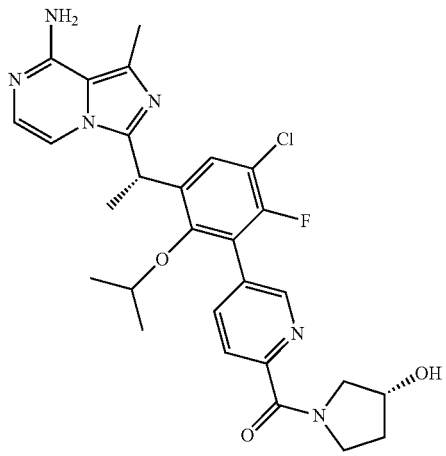 [SMILES: Cc1nc([C@@H](C)c2cc(Cl)c(F)c(-c3ccc(C(=O)N4CC[C@@H](O)C4)nc3)c2OC(C)C)n2ccnc(N)c12]

Compound 64 was prepared by similar manner as compound 61 starting from compound 61-13. $^1$H NMR (400 MHz, DMSO-d6) δ 8.66 (s, 1H), 8.04 (d, J=7.9 Hz, 1H), 7.87 (t, J=7.7 Hz, 1H), 7.52 (d, J=8.4 Hz, 1H), 7.42 (d, J=5.0 Hz, 1H), 7.37-6.98 (m, 3H), 6.95 (d, J=5.1 Hz, 1H), 4.99 (d, J=19.1 Hz, 1H), 4.87 (d, J=6.9 Hz, 1H), 4.33-4.29 (m, 1H), 3.89-3.40 (m, 5H), 2.62 (s, 3H), 2.04-1.74 (m, 2H), 1.67 (d, J=6.8 Hz, 3H), 1.01 (d, J=5.7 Hz, 3H), 0.82 (d, J=11.0 Hz, 3H). MS (ESI) m/e (M+1)$^+$ 553.0.

Example 65

(S)-1-(5-(3-(1-(8-amino-1-methylimidazo[1,5-a]pyrazin-3-yl)ethyl)-5-chloro-6-fluoro-2-isopropoxyphenyl)picolinoyl)azetidine-3-carboxylic Acid (65)

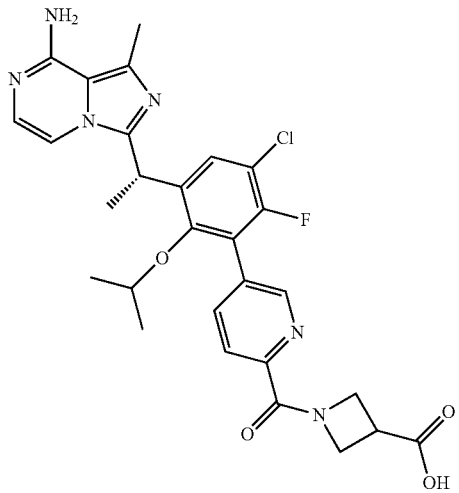 [SMILES: Cc1nc([C@@H](C)c2cc(Cl)c(F)c(-c3ccc(C(=O)N4CC(C(=O)O)C4)nc3)c2OC(C)C)n2ccnc(N)c12]

Step 1: methyl (S)-1-(5-(3-(1-(8-amino-1-methylimidazo[1,5-a]pyrazin-3-yl)ethyl)-5-chloro-6-fluoro-2-isopropoxyphenyl)picolinoyl)azetidine-3-carboxylate (65-1)

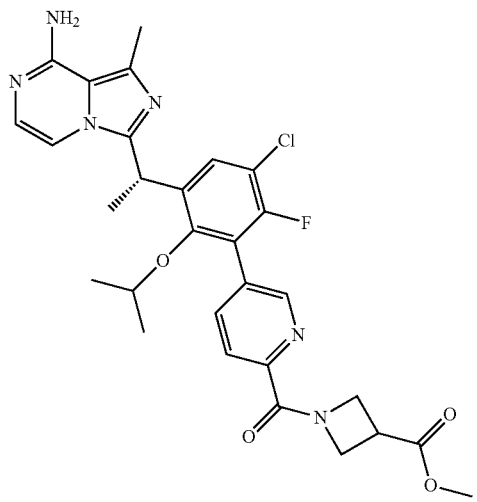 [SMILES: COC(=O)C1CN(C(=O)c2ccc(-c3c(F)c(Cl)cc([C@H](C)c4nc(C)c5c(N)nccn45)c3OC(C)C)cn2)C1]

Compound 61-13 (500 mg, 1.0332 mmol), methyl azetidine-3-carboxylate hydrochloride (470 mg, 3.01 mmol), HOBt (279.21 mg, 2.0664 mmol), EDCI (395.034 mg, 2.0664 mmol) and DIPEA (667.5 mg, 5,165 mmol) were dissolved in THF (15 mL) and stirred at room temperature for overnight, water (50 mL) was added and extracted with ethyl acetate. The combined organic layers were washed with brine and dried over Na$_2$SO$_4$. The product (236 mg, 39.53%) was got by chromatography column on silica gel. MS (ESI) m/e (M+H)$^+$ 581.0.

Step 2: (S)-1-(5-(3-(1-(8-amino-1-methylimidazo[1,5-a]pyrazin-3-yl)ethyl)-5-chloro-6-fluoro-2-isopropoxyphenyl)picolinoyl)azetidine-3-carboxylic Acid (65-2)

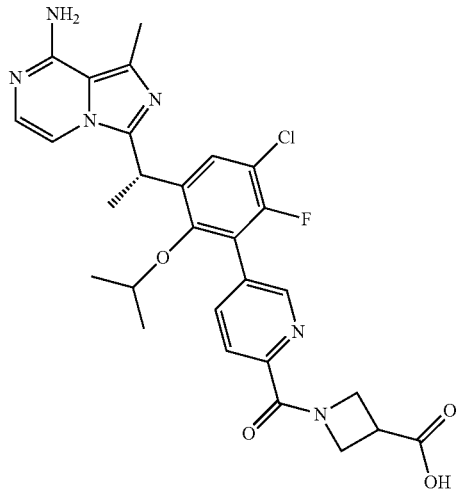 [SMILES: Cc1nc([C@@H](C)c2cc(Cl)c(F)c(-c3ccc(C(=O)N4CC(C(=O)O)C4)nc3)c2OC(C)C)n2ccnc(N)c12]

Compound 65-1 (200 mg, 0.3442 mmol) was dissolved in MeOH (10 mL), NaOH (41.3 mg, 1.03 mmol) in water (10 mL) was added and stirred at room temperature for 48 hrs, MeOH was removed in vacuo, the PH was regulated to 6.5-7. The product (30 mg, 15.4%) was got by filtration. ¹H NMR (400 MHz, DMSO-d6) δ 8.69 (s, 1H), 8.09 (brs, 2H), 7.48 (d, J=8.5 Hz, 1H), 7.33 (d, J=5.1 Hz, 1H), 6.91 (d, J=5.0 Hz, 1H), 6.56 (s, 2H), 4.81 (dd, J=16.7, 8.3 Hz, 1H), 4.68 (dd, J=10.1, 6.1 Hz, 1H), 4.28 (t, J=9.6 Hz, 1H), 4.13 (dd, J=10.1, 5.8 Hz, 1H), 3.68-3.55 (m, 1H), 3.49 (dd, J=10.3, 4.4 Hz, 1H), 2.60 (s, 3H), 1.66 (d, J=7.1 Hz, 3H), 1.00 (d, J=6.1 Hz, 3H), 0.79 (d, J=5.9 Hz, 3H). MS (ESI) m/e (M+H)⁺ 567.0.

Example 66

(S)-5-(3-(1-(8-amino-1-methylimidazo[1,5-a]pyrazin-3-yl)ethyl)-5-chloro-6-fluoro-2-isopropoxyphenyl)-N-(1-(hydroxymethyl)cyclopropyl)picolinamide (66)

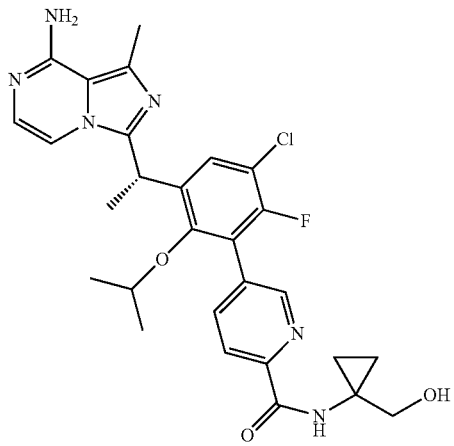 [SMILES: Cc1nc([C@@H](C)c2cc(Cl)c(F)c(-c3ccc(C(=O)NC4(CO)CC4)nc3)c2OC(C)C)n2ccnc(N)c12]

Compound 66 was prepared by similar manner as compound 61 starting from compound 61-13, afford desired compound as a white solid (45 mg, 39%). ¹H NMR (DMSO-d6) δ 8.83 (s, 1H), 8.68 (s, 1H), 8.16-8.08 (m, 2H), 7.49 (d, J=8.4 Hz, 1H), 7.33 (d, J=4.9 Hz, 1H), 6.90 (d, J=4.8 Hz, 1H), 6.48 (s, 2H), 4.83 (d, J=7.1 Hz, 1H), 4.75 (t, J=5.5 Hz, 1H), 3.69-3.57 (m, 1H), 3.53 (d, J=5.5 Hz, 2H), 2.59 (s, 3H), 1.66 (d, J=6.9 Hz, 3H), 0.99 (d, J=5.9 Hz, 3H), 0.80-0.79 (m, 7H). MS (ESI) m/e [M+1]⁺553.2.

Example 67

(5-(3-((S)-1-(8-amino-1-methylimidazo[1,5-a]pyrazin-3-yl)ethyl)-5-chloro-6-fluoro-2-isopropoxyphenyl)picolinoyl)-L-proline (67)

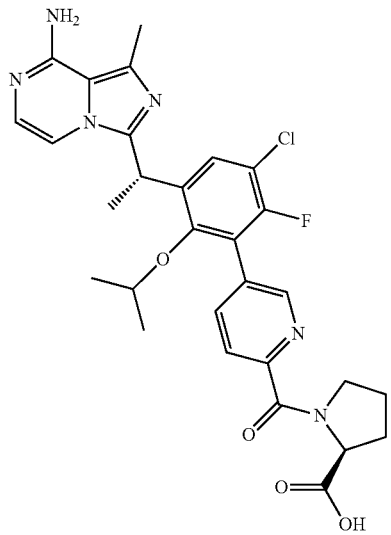 [SMILES: Cc1nc([C@@H](C)c2cc(Cl)c(F)c(-c3ccc(C(=O)N4CCC[C@H]4C(=O)O)nc3)c2OC(C)C)n2ccnc(N)c12]

Compound 67 was prepared by similar manner as compound 65 starting from compound 61-13, afford desired compound as a white solid (7 mg, 18%). ¹H NMR (400 MHz, CD₃OD) δ 8.68 (s, 0.471), 8.60 (s, 0.54H), 8.07-8.02 (m, 1.5H), 7.94 (d, J=8.1 Hz, 0.5H), 7.62 (t, J=5.7 Hz, 1H), 7.51 (dd, J=8.2, 5.2 Hz, 1H), 7.02-6.85 (m, 1H), 5.23-5.21 (m, 0.6H), 5.08-4.96 (m, 1.3H), 4.67-4.63 (m, 0.6H), 4.03-3.63 (m, 3H), 2.75 (s, 3H), 2.48-2.29 (m, 1H), 2.20 (dd, J=13.8, 6.4 Hz, 1H), 2.15-1.91 (m, 3H), 1.81 (dd, J=6.9, 3.7 Hz, 3H), 1.23-1.08 (m, 3H), 1.04-0.83 (m, 3H). MS (ESI) m/e [M+H]⁺ 581.2.

Example 68

(S)-1-(5-(3-(1-(8-amino-1-methylimidazo[1,5-a]pyrazin-3-yl)ethyl)-5-chloro-6-fluoro-2-isopropoxyphenyl)picolinamido)cyclopropane-1-carboxylic Acid (68)

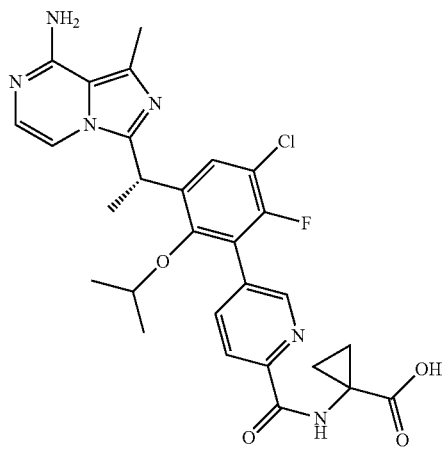 [SMILES: Cc1nc([C@@H](C)c2cc(Cl)c(F)c(-c3ccc(C(=O)NC4(C(=O)O)CC4)nc3)c2OC(C)C)n2ccnc(N)c12]

Compound 68 was prepared by similar manner as compound 65 starting from compound 61-13, afford desired compound as a white solid (25 mg, 40%). ¹H NMR (400 MHz, CD₃OD) δ 8.69 (s, 1H), 8.22 (d, J=8.1 Hz, 1H), 8.06 (d, J=8.0 Hz, 1H), 7.63 (d, J=5.8 Hz, 1H), 7.53 (d, J=8.1 Hz, 1H), 6.93 (d, J=5.7 Hz, 1H), 5.00 (dd, J=13.8, 6.8 Hz, 1H), 3.83-3.65 (m, 1H), 2.75 (s, 3H), 1.81 (d, J=: 6.9 I-z, 3H), 1.64 (brs, 2H), 1.31 (brs, 2H), 1.13 (d, J=5.8 Hz, 3H), 0.94 (d, J=5.9 Hz, 3H), MS (ESI) m/e [M+H]⁺ 567.2.

Example 69

(5-(3-((S)-1-(8-amino-1-methylimidazo[1,5-a]pyrazin-3-yl)ethyl)-5-chloro-6-fluoro-2-isopropoxyphenyl)picolinoyl)-D-proline (69)

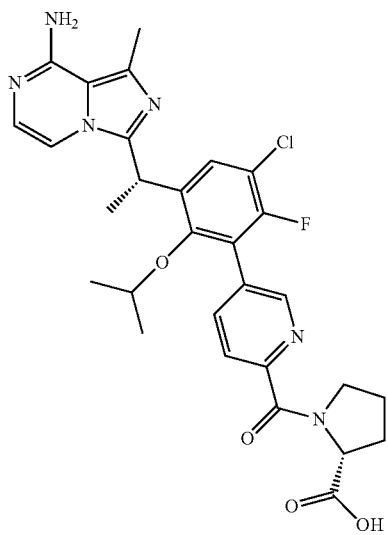 [SMILES: Cc1nc([C@@H](C)c2cc(Cl)c(F)c(-c3ccc(C(=O)N4CCC[C@@H]4C(=O)O)nc3)c2OC(C)C)n2ccnc(N)c12]

Compound 69 was prepared by similar manner as compound 65 starting from compound 61-13, afford desired compound as a white solid (25 mg, 32%). ¹H NMR (400 MHz, (CD)₃OD) δ 8.65 (s, 0.25H), 8.51 (s, 1H), 8.09 (d, J=8.0 Hz, 1H), 8.01 (m, 0.31H), 7.94 (d, J=8.2 Hz, 0.5H), 7.79-7.77 (m, 1H), 7.49-7.46 (m, 1H), 7.38-7.22 (m, 2H), 6.89 (s, 0.29H), 6.52-6.51 (m, 1H), 5.31-5.14 (m, 1H), 3.90-3.85 (m, 2.68H), 3.73-3.71 (m, 1.48H), 2.73 (s, 3H), 2.71 (s, 1H), 2.48-2.43 (m, 1H), 2.19-2.14 (m, 1H), 2.08-1.91 (m, 3H) 1.79 (d, J=7.0 Hz, 1H), 1.75-1.73 (m, 3H), 1.10 (dd, J=11.9, 6.0 Hz, 3H), 0.91 (t, J=5.3 Hz, 3H). MS (ESI) m/e [M+H]⁺ 581.1.

Example 70

(S)-2-(5-(3-(1-(8-amino-1-methylimidazo[1,5-a]pyrazin-3-yl)ethyl)-5-chloro-6-fluoro-2-isopropoxyphenyl)picolinamido)-2-methylpropanoic Acid (70)

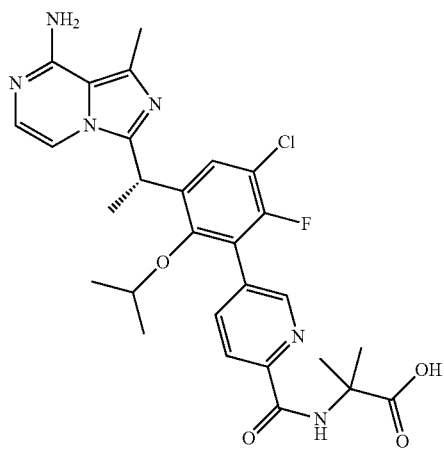 [SMILES: Cc1nc([C@@H](C)c2cc(Cl)c(F)c(-c3ccc(C(=O)NC(C)(C)C(=O)O)nc3)c2OC(C)C)n2ccnc(N)c12]

Compound 70 was prepared by similar manner as compound 65 starting from compound 61-13, afford desired compound as a white solid (30 mg, 44%). ¹H NMR (400 MHz, CD₃OD) δ 8.71 (s, 1H), 8.19 (d, J=8.1 Hz, 1H), 8.06 (d, J=8.2 Hz, 1H), 7.48-7.44 (m, 2H), 6.95 (d, J=5.5 Hz, 1H), 4.99-4.93 (m, 1H), 3.80-3.74 (m, 1H), 2.74 (s, 3H), 1.81 (d, J=7.1 Hz, 3H), 1.70 (ds, 6H), 1.14 (d, J=6.1 Hz, 3H), 0.92 (d, J=8.7 Hz, 3H). MS (ESI) m/e [M+1]⁺ 569.2.

Example 71

(S)-(5-(3-(1-(8-amino-1-methylimidazo[1,5-a]pyrazin-3-ylethyl)-5-chloro-6-fluoro-2-isopropoxyphenyl)pyridin-2-yl)(4,4-difluoropiperidin-1-yl)methanone (71)

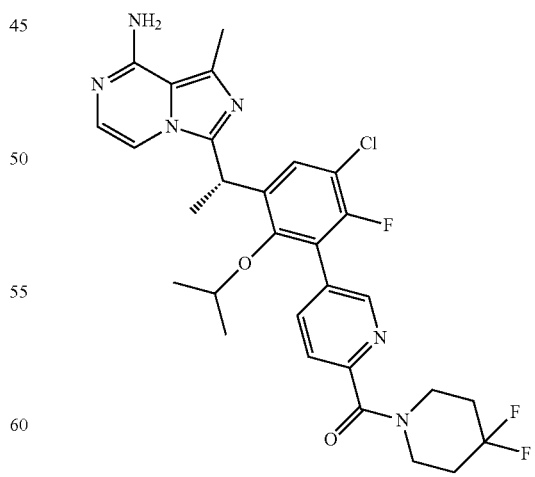

Compound 71 was prepared by similar manner as compound 61 starting from compound 61-13, afford desired compound as a white solid (25 mg, 14%). ¹H NMR (DMSO-d₆) δ 8.66 (s, 1H), 8.06 (d, J=8.2 Hz, 1H), 7.79 (d, J=8.1 Hz, 1H), 7.49 (d, J=8.5 Hz, 1H), 7.32 (d, J=5.0 Hz, 1H), 6.90 (d, J=5.0 Hz, 1H), 6.44 (s, 2H), 4.83 (q, J=6.8 Hz, 1H), 3.79 (brs, 2H), 3.66-3.60 (m, 1H), 3.55 (brs, 2H), 2.59 (s, 3H), 2.17-1.96 (m, 4H), 1.66 (d, J=7.0 Hz, 3H), 1.01 (d, J=6.0 Hz, 3H), 0.80 (d, J=6.1 Hz, 3H). MS (ESI) m/e [M+1]$^+$ 587.2.

Biological Assays

I. PI3Kδ Assay

Compounds disclosed herein were tested for inhibition of PI3Kδ kinase activity using commercial ADP-Glo™ Kinase Assay (Promega Corporation) and following the manufacture's instruction. Briefly, recombinant PI3K (p110δ/p85α) enzyme, lipid kinase substrate and a serial dilution of compounds disclosed herein were incubated for 0.5 hr at room temperature. ATP was added to initiate the kinase reaction. After incubation for 1 hr at room temperature, ADP-Glo™ reagent was added to terminate the kinase reaction and deplete the remaining ATP. After incubation for 1 hr at room temperature, kinase detection reagent was added to simultaneously convert ADP to ATP and allow the newly synthesized ATP to be measured using a luciferase/luciferin reaction. After incubation for 0.5 hr at room temperature, the luminescence generated was measured on a PHERAstar FS plate reader (BMG LABTECH), The residual enzyme activity in presence of increasing concentrations of compounds was calculated based on the luminescence. The IC$_{50}$ for each compound was derived from fitting the data to the four-parameter logistic equation by Graphpad Prism software.

II. PI3Kα, β and γ Assays

Compounds disclosed herein were tested for inhibition of recombinant PI3K (p110α/p85α), PI3K (p110β/p85α) and PI3K (p110γ) using the same method as PI3K (p110δ/p85α) except that incubation of 2 hrs was applied to PI13K (p110β/p85α) kinase reaction.

TABLE 1

Enzyme Activity IC$_{50}$ or max inhibition (%) at 0.5 μM for the compounds disclosed herein Enzyme activity IC$_{50}$ (nM) or max inhibition (%) at 0.5 μM

| Compound | PI3Kα | PI3Kβ | PI3Kδ | PI3Kγ |
|---|---|---|---|---|
| 1 | — | 6% | 150 | −27% |
| 2 | 560 | — | 1.5 | 37% |
| 2A | — | — | 1600 | — |
| 2B | 360 | — | 0.59 | 150 |
| 3 | — | — | 150 | — |
| 4 | 20% | — | 7.5 | 9% |
| 5 | 19% | — | 18 | 44% |
| 6 | 34% | — | 2.0 | 52% |
| 7 | 420 | — | 1.9 | 200 |
| 7A | 580 | 180 | 1.3 | 210 |
| 7B | — | — | 43 | — |
| 8 | 1400 | 350 | 1.1 | 260 |
| 8A | 1300 | 580 | 0.51 | 300 |
| 8B | — | — | 170 | — |
| 9 | — | — | 100 | — |
| 10 | 3200 | 2700 | 9.1 | 1500 |
| 11 | 540 | 360 | 0.54 | 190 |
| 12 | 1300 | 870 | 1.7 | 67 |
| 13 | 1200 | 400 | 1.2 | 480 |
| 14 | 1100 | 250 | 0.73 | 240 |
| 15 | 830 | 320 | 1.2 | 320 |
| 16A | 790 | 870 | 0.71 | 440 |
| 16B | — | — | 62 | — |
| 17 | 3100 | 1600 | 1.5 | 1900 |
| 17A | — | — | 91 | — |
| 17B | 970 | 670 | 0.28 | 520 |
| 18 | 7100 | 1100 | 1.3 | 340 |
| 18A | 4600 | 190 | 0.56 | 160 |
| 18B | — | — | 26 | — |
| 19 | 580 | 180 | 1.3 | 210 |
| 20 | 2300 | 930 | 3.2 | 740 |
| 21 | 2000 | — | 3.3 | 1500 |
| 22 | 1400 | 390 | 1.5 | 760 |
| 23 | 16% | 12% | 15 | −19% |
| 24 | 4000 | 1600 | 2.9 | 2100 |
| 25 | 3000 | 2600 | 2.6 | 1400 |
| 26 | 1500 | 330 | 1.4 | 500 |
| 27 | 3300 | 1800 | 2.5 | 1400 |
| 27A | 2200 | 400 | 1.1 | 1000 |
| 27B | — | — | 500 | — |
| 28 | 2300 | 930 | 3.2 | 740 |
| 29 | 2900 | 820 | 2.1 | 1100 |
| 30 | 1800 | 530 | 2.3 | 450 |
| 31 | 2200 | 620 | 2.5 | 430 |
| 32 | 7400 | 3500 | 8.5 | 2100 |
| 33 | 1800 | 1800 | 5.7 | 750 |
| 34 | — | — | 43 | — |
| 35 | 23000 | 79000 | 11 | 5900 |
| 36 | 1300 | 580 | 2.2 | 730 |
| 37 | 11000 | 1900 | 4.2 | 900 |
| 38 | >200000 | 30000 | 19 | 2800 |
| 38A | >200000 | 28000 | 5.4 | 740 |
| 38B | — | — | 2100 | — |
| 39 | 3200 | 2000 | 5.7 | 1600 |
| 40 | >50000 | >50000 | 5.5 | >50000 |
| 40A | 33000 | 6800 | 1.0 | 3800 |
| 40B | — | — | 150 | — |
| 41 | 2700 | 3100 | 3.2 | 2100 |
| 41A | 2200 | 1200 | 2.1 | 730 |
| 41B | — | — | 350 | — |
| 42 | >50000 | >50000 | 7.4 | 1600 |
| 42A | 26000 | 2200 | 4.1 | 810 |
| 42B | — | — | 330 | — |
| 43 | >50000 | >50000 | 59 | >50000 |
| 43A | >50000 | >50000 | 28 | >50000 |
| 43B | — | — | >1000 | — |
| 44 | — | — | 380 | — |
| 45 | 1100 | 930 | 17 | 1200 |
| 46 | 5600 | 470 | 0.7 | 920 |
| 47 | 810 | 190 | 0.20 | 170 |
| 48 | 540 | 580 | 0.42 | 530 |
| 48A | 4800 | 440 | 0.40 | 800 |
| 48B | 1300 | 1200 | 0.31 | 630 |
| 48C | — | — | 160 | — |
| 48D | — | — | 6.8 | — |
| 49 | — | — | 3.1 | — |
| 49A | 2100 | 260 | 0.49 | 440 |
| 49B | — | — | 26 | — |
| 50 | 36000 | 670 | 17 | 2600 |
| 51 | 2900 | 2700 | 1.6 | 1700 |
| 51A | 2100 | 480 | 0.79 | 1200 |
| 51B | — | — | 320 | — |
| 52 | 6% | — | 7.7 | −11% |
| 53 | — | — | 1900 | — |
| 54 | 29000 | 1700 | 15 | 4200 |
| 55 | — | — | 450 | — |
| 56 | — | — | 1000 | — |
| 57 | 83000 | 1237 | 20 | 1900 |
| 58 | 14000 | 17000 | 5.6 | 13000 |
| 59 | 10000 | 3500 | 2.5 | 6300 |
| 59A | 6300 | 1400 | 1.2 | 2700 |
| 59B | — | — | 240 | — |
| 60 | 4300 | 4200 | 1.6 | 2800 |
| 61 | 2900 | 6100 | 0.58 | 3800 |
| 62 | 5200 | 3600 | 0.82 | 2600 |
| 63 | 2600 | 2300 | 0.56 | 2400 |
| 64 | 1400 | 1600 | 0.37 | 2100 |
| 65 | 5400 | 1200 | 0.71 | 1600 |

TABLE 1-continued

Enzyme Activity $IC_{50}$ or max inhibition (%) at
0.5 µM for the compounds disclosed herein Enzyme activity $IC_{50}$ (nM) or max inhibition (%) at 0.5 µM

| Compound | PI3Kα | PI3Kβ | PI3Kδ | PI3Kγ |
|---|---|---|---|---|
| 66 | 4100 | 3400 | 0.72 | 2600 |
| 67 | 5200 | 460 | 0.47 | 1200 |
| 68 | 3400 | 400 | 0.33 | 960 |
| 69 | 7100 | 610 | 0.71 | 620 |
| 70 | 4400 | 540 | 0.33 | 840 |
| 71 | 4700 | 2700 | 0.96 | 3200 |

III. Pharmacokinetic Properties of Compounds in Sprague-Dawley Rats after Intravenous (IV) and Oral Administrations (PO)

Dose Formulation Preparation The injection dosing solution was prepared as follows: 1.0 mg of a test compound was weighted and dissolved in 0.32 mL of dimenthyl acetamide (DMA). The solution was then further diluted by 0.36 mL of ethanol and 0.32 mL of propylene glycol. The final concentration of the test compound was 1.0 mg·mL$^{-1}$.

The oral dosing solution was prepared as follows: 5.0 mg of a test compound was weighed and dispersed in 10 mL of 0.5% methyl cellulose (MC). The final concentration of the test compound is 1 mg·mL$^{-1}$.

Animals

The animal information is summarized in Table 2. The animals were housed in solid bottom polypropylene cages with sterilized bedding and receive sterilized diet and sterilized water. The room was controlled and monitored for humidity (targeted mean range 40% to 70%) and temperature (targeted mean range 18° C. to 26° C.) with 10 to 20 air changes/hour. The light cycle was maintained at 12-h light and 12-h dark, Only animals that appeared to be healthy were selected for this study based on overall health, body weight, or other relevant information. The animal treatment schedule is summarized in Table 3.

Study Design

All procedures performed on animals were in accordance with established guidelines and reviewed and approved by an independent institutional review board.

The male Sprague-Dawley rats were fasted overnight with free access to drinking water prior to treatment. On day 1, the animals were weighed and actual dose volume for each animal was calculated using the formula below:

$$\text{Dose Volume (mL)} = [\text{Nominal Dose (mg·kg}^{-1})/\text{Dose Concentration (mg·mL}^{-1})] \times \text{Animal Body Weight (kg)} \quad (1)$$

Three rats were given a single IV dose of 1 mg·kg$^{-1}$ via tail vein injection and other three rats were given a single oral dose of 5 mg·kg$^{-1}$. The dosing solutions were freshly prepared prior to dose administration. The actual body weights and actual volume injected were recorded accordingly. Four hours after dosing, the rats were allowed to intake food.

Blood samples (~150 L) were collected at different times from the jugular vein catheter into EDTA-K$_2$ coated tubes, Whole blood was processed by centrifugation at 3000 g for 10 min. Plasma samples were collected and kept at −80° C. freezer prior to analysis. The blood sampling time was recorded accordingly.

Sample Test

The dose samples of IV and PO were diluted with MeOH:H$_2$O (4:1, v/v) to achieve the concentration of 2 µg·mL$^{-1}$, respectively. Then, 2.5 µL of the diluted samples were added with 47.5 µL blank plasma, and then were handled as the plasma sample procedure. An aliquot of 10 µL of the mixture was injected into the LC-MS/MS system.

Results

The pharmacokinetic (PK) data of the test compounds are shown in Table 4.

TABLE 2

Animal Information Sheet

| Genus | Gender | Species | Source | Age | Weight (g) | Reserved | Selected |
|---|---|---|---|---|---|---|---|
| Rat | Male | Sprague Dawley (SD) | Vital River | 8 weeks | 220-250 | 7 | 6 |

TABLE 3

Animal Treatment Schedule

| Groups | Quantity | Dose Level (mg · kg$^{-1}$) | Conc. (mg · mL$^{-1}$) | Vehicle | Dosing Route | Regimen | Fasted/Fed | Sampling Time |
|---|---|---|---|---|---|---|---|---|
| 1-3 | 3 | 1.0 | 1.0 | 32% DMA, 36% ethanol, 32% propylene glycol | Tail Vein IV | Single | Fasted | Pre-dose, 5, 15, 30 min, 1, 2, 4, 8, 24 h |
| 4-6 | 3 | 5.0 | 1.0 | 0.5% MC | Oral | Single | Fasted | Pre-dose, 15, 30 min, 1, 2, 4, 8, 24 h |

TABLE 4

Rat PK data of Compounds

| Compound | IV (1 mpk) | | | | PO (5 mpk) | | | | |
|---|---|---|---|---|---|---|---|---|---|
| | $t_{1/2}$ (h) | Cl (mL·kg$^{-1}$·min$^{-1}$) | AUC$_{0\text{-}inf}$ (h·ng·mL$^{-1}$) | V$_{dSS}$ (L·kg$^{-1}$) | $t_{1/2}$ (h) | $t_{max}$ (h) | C$_{max}$ (ng·mL$^{-1}$) | AUC$_{0\text{-}inf}$ (h·ng·mL$^{-1}$) | F % |
| 16A | 1.3 | 16.0 | 1065.0 | 1.8 | 1.9 | 1.0 | 495.5 | 2186.0 | 41.1 |
| 40A | 9.0 | 22.2 | 768.5 | 14.8 | 6.6 | 2.7 | 178.6 | 1721.4 | 51 |
| 48B | 1.4 | 39.2 | 425.3 | 4.3 | 2.1 | 0.8 | 254.4 | 1001.2 | 47 |

IV. Brain Penetration of Compounds in Male C57BL/6 Mice after Oral Administration Dose Formulation Preparation Approximately 4 mg of a test compound was weighed and dispersed in 0.5% methyl cellulose (MC). After that, the whole mixture were vortexed until a solution or suspension was formed. The final concentration of the test compound was 1 mg·mL$^{-1}$. The concentration of test compound in dosing formulations was determined within 85% to 115% of nominal values.

Animals:

The animal information is summarized in Table 5. The mice were housed in solid bottom polypropylene cages with sterilized bedding. The room was controlled and monitored for humidity (targeted mean range 40% to 70%) and temperature (targeted mean range 20° to 25° C.) with 10 to 20 air changes/hour. The room was on a 12-hour light/dark cycle except when interruptions were necessitated by study activities. The mice were supplied with sterilized diet and water. All animals were examined upon receipt and were acclimated for at least 3 days. Only animals that appeared to be healthy were selected for the study based on overall health, body weight, or other relevant data as appropriate.

TABLE 5

Animal Information Sheet

| Genus | Gender | Species | Number | Source | Weight (g) |
|---|---|---|---|---|---|
| Mouse | Male | C57BL/6 | 9 | Vital River Laboratory Technology Co., Ltd. | 18-30 |

Study Design

All procedures performed on animals were in accordance with established guidelines and reviewed and approved by an independent institutional review board. The study design is summarized in Table 6.

TABLE 6

Animal Treatment Schedule

| Test Article | Quantity | Dose Level (mg·kg$^{-1}$) | Volume (mL kg$^{-1}$) | Dosing Route | Fasted/Fed | Sampling Time |
|---|---|---|---|---|---|---|
| Test compound | 9 | 10 | 10 | PO | Fasted | 1, 2 and 4 h |

The male mice were fasted overnight with free access to drinking water prior to treatment. On day 1, the animals were weighed and actual dose volume for each animal was calculated using the formula below:

Dose Volume (mL)=[Nominal Dose (mg·kg$^{-1}$)/Dose Concentration (mg·mL$^{-1}$)]×Animal Body Weight (kg)   (1)

The mice were administrated with test compound at 10 mg·kg$^{-1}$ via oral gavage, respectively. The dosing formulations were freshly prepared. The actual body weights and actual volume administered were recorded accordingly.

Three mice were sacrificed under carbon dioxide for sample collection at 1, 2 and 4 hours post dose, respectively. Blood samples (~0.2 mL) were collected via cardiac puncture into anticoagulant tubes (coated with EDTA-Ka). The tubes were gently inverted several times to ensure mixing. Whole blood was processed for plasma by centrifugation at 5,500 rpm for 10 min. The brain was collected immediately after euthanasia. The sample collection time was recorded accordingly. After the removal of excess water, the brain was weighed and homogenized with 5× water (w/v) in an ice bath. The samples were kept below −20° C. freezer prior to analysis.

Sample Test

For plasma samples: An aliquot of 10 µL of sample was added with 500 µL ACN which contained IS (Verapamil, 5 ng·mL$^{-1}$ and (Glibenclamide, 50 ng·mL$^{-1}$) for protein precipitation, the mixture was vortexed for 1 min, then centrifuged at 13000 rpm for 8 min, then 70 µL of supernatant was added with 70 µL water, then vortexed for 10 min. An aliquot of 10 µL of the mixture was injected into the LC-MS/MS system.

For brain samples: An aliquot of 50 µL of sample was added with 250 µL ACN which contained IS (Verapamil, 5 ng·mL$^{-1}$ and Glibenclamide, 50 ng·mL$^{-1}$) for protein precipitation, the mixture was vortexed for 1 min, then centrifuged at 13000 rpm for 8 min, then 70 µL of supernatant was added with 70 µL water, then vortexed for 10 min. An aliquot of 10 µL of the mixture was injected into the LC-MS/MS system.

Results

The blood-brain barrier (BBB) data of the test compounds are shown in Table 7.

TABLE 7

Mouse BBB data of Compounds

| Compound | BBB (Brain/Plasma Conc. Ratio) |
|---|---|
| 16 A | 0.05 |
| 40 A | 0.29 |

Compound 40A was found to have a much better Brain/Plasma Conc, Ratio, suggesting the compounds disclosed herein as a potentially important diagnostic and therapeutic agent to the brain.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention as claimed.

The invention claimed is:

1. A method for treating glioblastoma (GBM) in a subject, comprising administering to the subject a compound of Formula (I),

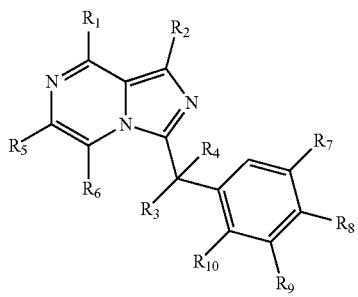

(I)

or a stereoisomer thereof, or a pharmaceutically acceptable salt thereof, wherein:

- $R_1$ is $-NR_aR_b$, wherein $R_a$ and $R_b$ are each independently hydrogen or $C_{1-6}$alkyl;
- $R_2$ is hydrogen, F, Cl, Br, $-C_{1-6}$alkyl, $-C_{2-6}$alkenyl, $-C_{2-6}$alkynyl, cycloalkyl, heterocyclyl, aryl, heteroaryl, $-CN$, $-NO_2$, $-OR_{12}$, $-SO_2R_{12}$, $-COR_{12}$, $-CO_2R_{12}$, $-CONR_{12}R_{13}$, $-C(=NR_{12})NR_{13}R_{14}$, $-NR_{12}R_{13}$, $-NR_{12}COR_{13}$, $-NR_{12}CONR_{13}R_{14}$, $-NR_{12}CO_2R_{13}$, $-NR_{12}SONR_{13}R_{14}$, $-NR_{12}SO_2NR_{13}R_{14}$, or $-NR_{12}SO_2R_{13}$; wherein said $-C_{1-6}$alkyl, $-C_{2-6}$alkenyl, $-C_{2-6}$alkynyl, cycloalkyl, heterocyclyl, aryl or heteroaryl are each independently optionally substituted with at least one substituent $R_{11a}$;
- $R_3$ is hydrogen, $-C_{1-6}$alkyl, cycloalkyl, heterocyclyl, aryl, or heteroaryl;
- $R_4$ is $-C_{1-6}$alkyl, cycloalkyl, heterocyclyl, aryl, or heteroaryl;
- $R_5$ and $R_6$, which may be the same or different, are each independently hydrogen, halogen, $-C_{1-6}$alkyl, $-C_{2-6}$alkenyl, $-C_{2-6}$alkynyl, cycloalkyl, heterocyclyl, aryl, heteroaryl, $-CN$, $-NO_2$, $-OR_{12}$, $-SO_2R_{12}$, $-COR_{12}$, $-CO_2R_{12}$, $-CONR_{12}R_{13}$, $-C(=NR_{12})NR_{13}R_{14}$, $-NR_{12}R_{13}$, $-NR_{12}COR_{13}$, $-NR_{12}CONR_{13}R_{14}$, $-NR_{12}CO_2R_{13}$, $-NR_{12}SONR_{13}R_{14}$, $-NR_{12}SO_2NR_{13}R_{14}$, or $-NR_{12}SO_2R_{13}$; wherein said $-C_{1-6}$alkyl, $-C_{2-6}$alkenyl, $-C_{2-6}$alkynyl, cycloalkyl, heterocyclyl, aryl or heteroaryl are each independently optionally substituted with at least one substituent $R_{11b}$;
- $R_7$, $R_8$ and $R_{10}$, which may be the same or different, are each independently hydrogen, halogen, $-C_{1-6}$alkyl, $-C_{2-6}$alkenyl, $-C_{2-6}$alkynyl, cycloalkyl, heterocyclyl, aryl, heteroaryl, $-CN$, $-NO_2$, $-OR_{12}$, $-SO_2R_{12}$, $-COR_{12}$, $-CO_2R_{12}$, $-CONR_{12}R_{13}$, $-C(=NR_{12})NR_{13}R_{14}$, $-NR_{12}R_{13}$, $-NR_{12}COR_{13}$, $-NR_{12}CONR_{13}R_{14}$, $-NR_{12}CO_2R_{13}$, $-NR_{12}SONR_{13}R_{14}$, $-NR_{12}SO_2NR_{13}R_{14}$, or $-NR_{12}SO_2R_{13}$; wherein said $-C_{1-6}$alkyl, $-C_{2-6}$alkenyl, $-C_{2-6}$alkynyl, cycloalkyl, heterocyclyl, aryl or heteroaryl are each independently optionally substituted with at least one substituent $R_{11c}$;
- $R_9$ is 5- to 6-membered heterocyclyl comprising one nitrogen atom and 0 or 1 additional heteroatom selected from N, O and S, or 5- to 6-membered heteroaryl comprising one nitrogen atom and 0 or 1 additional heteroatom selected from N, O and S; wherein said heterocyclyl or heteroaryl are each independently optionally substituted with at least one substituent $R_{11d}$;
- $R_{11a}$, $R_{11b}$, $R_{11c}$ and $R_{11d}$, which may be the same or different, are each independently hydrogen, halogen, $-C_{1-6}$alkyl, $-C_{2-6}$alkenyl, $-C_{2-6}$alkynyl, haloC$_{1-6}$alkyl, haloC$_{2-6}$alkenyl, haloC$_{2-6}$alkynyl, cycloalkyl, heterocyclyl, aryl, heteroaryl, $-CN$, $-NO_2$, oxo, $-OR_{12}$, $-SO_2R_{12}$, $-COR_{12}$, $-CO_2R_{12}$, $-CONR_{12}R_{13}$, $-C(=NR_{12})NR_{13}R_{14}$, $-NR_{12}R_{13}$, $-NR_{12}COR_{13}$, $-NR_{12}CONR_{13}R_{14}$, $-NR_{12}CO_2R_{13}$, $-NR_{12}SONR_{13}R_{14}$, $-NR_{12}SO_2NR_{13}R_{14}$, or $-NR_{12}SO_2R_{13}$;
- $R_{12}$, $R_{13}$, and $R_{14}$, which may be the same or different, are each independently hydrogen, $-C_{1-6}$alkyl, $-C_{2-6}$alkenyl, $-C_{2-6}$alkynyl, $C_{1-6}$alkyloxyC$_{1-6}$alkyl-, cycloalkyl, heterocyclyl, aryl, heteroaryl or $-OR_{15}$, wherein $R_{15}$ is hydrogen, $C_{1-6}$alkyl, $-C_{2-6}$alkenyl, $-C_{2-6}$alkynyl, $C_{1-6}$alkyloxyC$_{1-6}$alkyl-, cycloalkyl, heterocyclyl, aryl, or heteroaryl, and wherein said $C_{1-6}$alkyl, $-C_{2-6}$alkenyl, $-C_{2-6}$alkynyl, $C_{1-6}$alkyloxyC$_{1-6}$alkyl-, cycloalkyl, heterocyclyl, aryl, or heteroaryl as $R_{12}$, $R_{13}$, or $R_{14}$, or as a moiety of $-OR_{15}$ are each independently optionally substituted with at least one substituent $R_{16}$;
- alternatively, ($R_{12}$ and $R_{13}$), ($R_{13}$ and $R_{14}$), or ($R_{12}$ and $R_{14}$), together with the atom(s) to which they are attached, form a 3- to 8-membered saturated, partially or fully unsaturated ring comprising 0, 1 or 2 additional heteroatoms independently selected from $-NH$, $-O-$, $-S-$, $-SO-$ or $-SO_2-$, and said ring is optionally substituted with at least one substituent $R_{16}$; and
- $R_{16}$, at each of its occurrences, is independently hydrogen, halogen, $-C_{1-6}$alkyl optionally substituted with hydroxyl, $-C_{2-6}$alkenyl, $-C_{2-6}$alkynyl, haloC$_{1-6}$alkyl, haloC$_{2-6}$alkenyl, haloC$_{2-6}$alkynyl, cycloalkyl, heterocyclyl, aryl, heteroaryl, $-CN$, $-NO_2$, oxo, $-OR_a$, $-SO_2R_a$, $-COR_a$, $-CO_2R_a$, $-CONR_aR_b$, $-C(=NR_a)NR_bR_c$, $-NR_aR_b$, $-NR_aCOR_b$, $-NR_aCONR_bR_c$, $-NR_aCO_2R_b$, $-NR_aSONR_bR_c$, $-NR_aSO_2NR_bR_c$, or $-NR_aSO_2R_b$, wherein $R_a$, $R_b$, or $R_c$ is independently hydrogen, halogen, $-C_{1-6}$alkyl, $-C_{2-6}$alkenyl, $-C_{2-6}$alkynyl, haloC$_{2-6}$alkyl, haloC$_{2-6}$alkenyl, haloC$_{2-6}$alkynyl, cycloalkyl, heterocyclyl, aryl, or heteroaryl; or ($R_a$ and $R_b$), or ($R_a$ and $R_b$), or ($R_b$ and $R_c$), together with the atom(s) to which they are attached, form a 3- to 8-membered saturated, partially or fully unsaturated ring comprising 0, 1 or 2 additional heteroatoms independently selected from $-NH$, $-O-$, $-S-$, $-SO-$ or $-SO_2-$.

2. The method of claim 1, which is a compound of Formula (II),

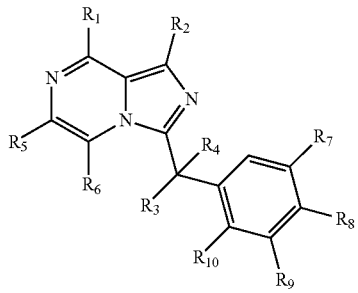

(II)

or a stereoisomer thereof, or a pharmaceutically acceptable salt thereof, wherein:

$R_1$ is —$NR_aR_b$, wherein $R_a$ and $R_b$ are each independently hydrogen or $C_{1-6}$alkyl;

$R_2$ is hydrogen, F, Cl, Br, —$C_{1-6}$alkyl, —$C_{2-6}$alkenyl, —$C_{2-6}$alkynyl, cycloalkyl, heterocyclyl, aryl, heteroaryl, —CN, —$NO_2$, —$OR_{12}$, —$SO_2R_{12}$, —$COR_{12}$, —$CO_2R_{12}$, —$CONR_{12}R_{13}$, —$C(=NR_{12})NR_{13}R_{14}$, —$NR_{12}R_{13}$, —$NR_{12}COR_{13}$, —$NR_{12}CONR_{13}R_{14}$, —$NR_{12}CO_2R_{13}$, —$NR_{12}SONR_{13}R_{14}$, —$NR_{12}SO_2NR_{13}R_{14}$, or —$NR_{12}SO_2R_{13}$; wherein said —$C_{1-6}$alkyl, —$C_{2-6}$alkenyl, —$C_{2-6}$alkynyl, cycloalkyl, heterocyclyl, aryl or heteroaryl are each independently optionally substituted with at least one substituent $R_{11a}$;

$R_3$ is hydrogen, —$C_{1-6}$alkyl, cycloalkyl, heterocyclyl, aryl, or heteroaryl;

$R_4$ is —$C_{1-6}$alkyl, cycloalkyl, heterocyclyl, aryl, or heteroaryl;

$R_5$ and $R_6$, which may be the same or different, are each independently hydrogen, halogen, —$C_{1-6}$alkyl, —$C_{2-6}$alkenyl, —$C_{2-6}$alkynyl, cycloalkyl, heterocyclyl, aryl, heteroaryl, —CN, —$NO_2$, —$OR_{12}$, —$SO_2R_{12}$, —$COR_{12}$, —$CO_2R_{12}$, —$CONR_{12}R_{13}$, —$C(=NR_{12})NR_{13}R_{14}$, —$NR_{12}R_{13}$, —$NR_{12}COR_{13}$, —$NR_{12}CONR_{13}R_{14}$, —$NR_{12}CO_2R_{13}$, —$NR_{12}SONR_{13}R_{14}$, —$NR_{12}SO_2NR_{13}R_{14}$, or —$NR_{12}SO_2R_{13}$; wherein said —$C_{1-6}$alkyl, —$C_{2-6}$alkenyl, —$C_{2-6}$alkynyl, cycloalkyl, heterocyclyl, aryl or heteroaryl are each independently optionally substituted with at least one substituent Rub;

$R_7$, $R_8$ and $R_{10}$, which may be the same or different, are each independently hydrogen, halogen, —$C_{1-6}$alkyl, —$C_{2-6}$alkenyl, —$C_{2-6}$alkynyl, cycloalkyl, heterocyclyl, aryl, heteroaryl, —CN, —$NO_2$, —$OR_{12}$, —$SO_2R_{12}$, —$COR_{12}$, —$CO_2R_{12}$, —$CONR_{12}R_{13}$, —$C(=NR_{12})NR_{13}R_{14}$, —$NR_{12}R_{13}$, —$NR_{12}COR_{13}$, —$NR_{12}CONR_{13}R_{14}$, —$NR_{12}CO_2R_{13}$, —$NR_{12}SONR_{13}R_{14}$, —$NR_{12}SO_2NR_{13}R_{14}$, or —$NR_{12}SO_2R_{13}$; wherein said —$C_{1-6}$alkyl, —$C_{2-6}$alkenyl, —$C_{2-6}$alkynyl, cycloalkyl, heterocyclyl, aryl or heteroaryl are each independently optionally substituted with at least one substituent $R_{11c}$;

$R_9$ is 5- to 6-membered heterocyclyl comprising one nitrogen atom and 0 or 1 additional heteroatom selected from N, O and S, or 5- to 6-membered heteroaryl comprising one nitrogen atom and 0 or 1 additional heteroatom selected from N, O and S; wherein said heterocyclyl or heteroaryl are each independently optionally substituted with at least one substituent id;

$R_{11a}$, $R_{11b}$, $R_{11c}$ and $R_{11d}$, which may be the same or different, are each independently hydrogen, halogen, —$C_{1-6}$alkyl, —$C_{2-6}$alkenyl, —$C_{2-6}$alkynyl, halo$C_{1-6}$alkyl, halo$C_{2-6}$alkenyl, halo$C_{2-6}$alkynyl, cycloalkyl, heterocyclyl, aryl, heteroaryl, —CN, —$NO_2$, oxo, —$OR_{12}$, —$SO_2R_{12}$, —$COR_{12}$, —$CO_2R_{12}$, —$CONR_{12}R_{13}$, —$C(=NR_{12})NR_{13}R_{14}$, —$NR_{12}R_{13}$, —$NR_{12}COR_{13}$, —$NR_{12}CONR_{13}R_{14}$, —$NR_{12}CO_2R_{13}$, —$NR_{12}SONR_{13}R_{14}$, —$NR_{12}SO_2NR_{13}R_{14}$, or —$NR_{12}SO_2R_{13}$; and $R_{12}$, $R_{13}$, and $R_{14}$, which may be the same or different, are each independently hydrogen, —$C_{1-6}$alkyl, —$C_{2-6}$alkenyl, —$C_{2-6}$alkynyl, halo$C_{1-6}$alkyl, halo$C_{2-6}$alkenyl, halo$C_{2-6}$alkynyl, $C_{1-6}$alkyloxy$C_{1-6}$alkyl-, cycloalkyl, heterocyclyl, aryl, or heteroaryl.

3. The method of claim 1, wherein $R_1$ is —$NH_2$.

4. The method of claim 1, wherein $R_2$ is independently hydrogen, F, Cl, Br, —$C_{1-6}$alkyl, $C_{3-6}$cycloalkyl or $C_{6-10}$aryl, and wherein —$C_{1-6}$alkyl, $C_{3-6}$cycloalkyl and $C_{6-10}$aryl are each independently optionally substituted with at least one substituent $R_{11a}$.

5. The method of claim 4, wherein $R_2$ is Cl, Br or methyl.

6. The method of claim 1, wherein $R_3$ is hydrogen, and $R_4$ is —$C_{1-6}$alkyl.

7. The method of claim 1, wherein $R_5$ and $R_6$, which may be the same or different, are each independently hydrogen, halogen, —$C_{1-6}$alkyl, —$C_{2-6}$alkenyl, —$C_{2-6}$alkynyl, cycloalkyl, heterocyclyl, aryl, or heteroaryl, wherein said —$C_{1-6}$alkyl, —$C_{2-6}$alkenyl, —$C_{2-6}$alkynyl, cycloalkyl, heterocyclyl, aryl or heteroaryl are each independently optionally substituted with at least one substituent Rub, wherein Rub is halogen.

8. The method of claim 1, wherein $R_5$ and $R_6$ are each independently hydrogen, halogen, or —$C_{1-6}$alkyl.

9. The method of claim 8, wherein $R_5$ and $R_6$ are both hydrogen.

10. The method of claim 1, wherein $R_7$, $R_8$ and $R_{10}$, which may be the same or different, are each independently hydrogen, halogen, —$C_{1-6}$alkyl, —$C_{2-6}$alkenyl, —$C_{2-6}$alkynyl, cycloalkyl, heterocyclyl, aryl, heteroaryl, or —$OR_{12}$; wherein said —$C_{1-6}$alkyl, —$C_{2-6}$alkenyl, —$C_{2-6}$alkynyl, cycloalkyl, heterocyclyl, aryl or heteroaryl are each independently optionally substituted with at least one substituent $R_{11c}$, wherein $R_{11c}$ is halogen.

11. The method of claim 10, wherein $R_7$ and $R_8$, are each independently hydrogen, halogen or —$C_{1-6}$alkyl, and $R_{10}$ is —$OR_{12}$.

12. The method of claim 1, wherein $R_9$ is 5-membered heterocyclyl comprising one nitrogen atom, or 6-membered heterocyclyl comprising one or two nitrogen atoms, or 5- or 6-membered heteroaryl comprising one nitrogen atom, wherein said heterocyclyl or heteroaryl are each independently optionally substituted with at least one substituent Ruud.

13. The method of claim 1, wherein $R_{11d}$ is hydrogen, halogen, —$C_{1-6}$alkyl, halo$C_{1-6}$alkyl, oxo, —$OR_{12}$, —$CO_2R_{12}$, —$CONR_{12}R_{13}$ or 5- to 6-membered heterocyclyl comprising 1 or 2 heteroatoms selected from N and O, wherein $R_{12}$ and $R_{13}$ are each independently hydrogen, —$C_{1-6}$alkyl, or $C_{1-6}$alkyloxy$C_{1-6}$alkyl-.

14. The method of claim 1, wherein $R_9$ is 5- or 6-membered heteroaryl comprising one nitrogen atom, wherein said heteroaryl is optionally substituted with a substituent $R_{11d}$.

15. The method of claim 14, wherein Rim is —CONR$_{12}$R$_{13}$.

16. The method of claim 15, wherein:
   a) R$_{12}$ is hydrogen and R$_{13}$ is cycloalkyl optionally substituted with at least one substituent R$_{16}$; or
   b) R$_{12}$ and R$_{13}$ together with the nitrogen atom to which they are attached, form a 3- to 8-membered saturated, partially or fully unsaturated ring comprising 0, 1 or 2 additional heteroatoms independently selected from —NH, —O—, —S—, —SO— or —SO$_2$—, and said ring is optionally substituted with at least one substituent R$_{16}$.

17. The method of claim 16, wherein R$_{12}$ is hydrogen and R$_{13}$ is a C$_3$-C$_8$ cycloalkyl optionally substituted with at least one substituent R$_{16}$.

18. The method of claim 17, wherein R$_{13}$ is a cyclopropyl optionally substituted with at least one substituent R$_{16}$.

19. The method of claim 16, wherein R$_{12}$ and R$_{13}$ together with the nitrogen atom to which they are attached, form a 4- to 6-membered saturated ring comprising 0 or 1 additional heteroatoms independently selected from —NH, —O—, —S—, —SO— or —SO$_2$—, and said ring is optionally substituted with at least one substituent R$_{16}$.

20. The method of claim 16, wherein R$_{16}$, at each of its occurrences, is independently hydrogen, halogen, —C$_{1-6}$ alkyl optionally substituted with hydroxyl, —OH, or —CO$_2$H.

21. The method of claim 13, wherein R$_{11d}$ is methyl, trifluoromethyl, chloro, N,N-dimethylaminocarbonyl, N,N-diethylaminocarbonyl, aminocarbonyl, carboxyl, hydroxyl, oxo, methoxy, or 2-methoxyethoxy.

22. The method of claim 1, wherein R$_9$ is

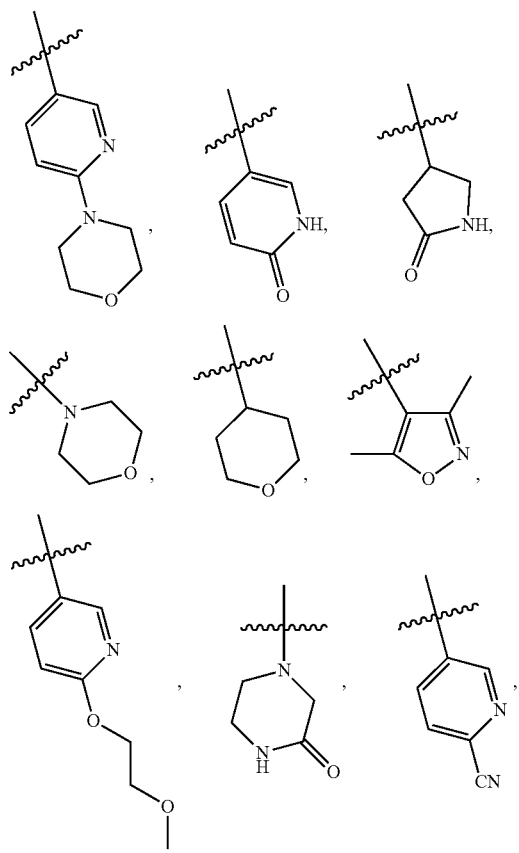

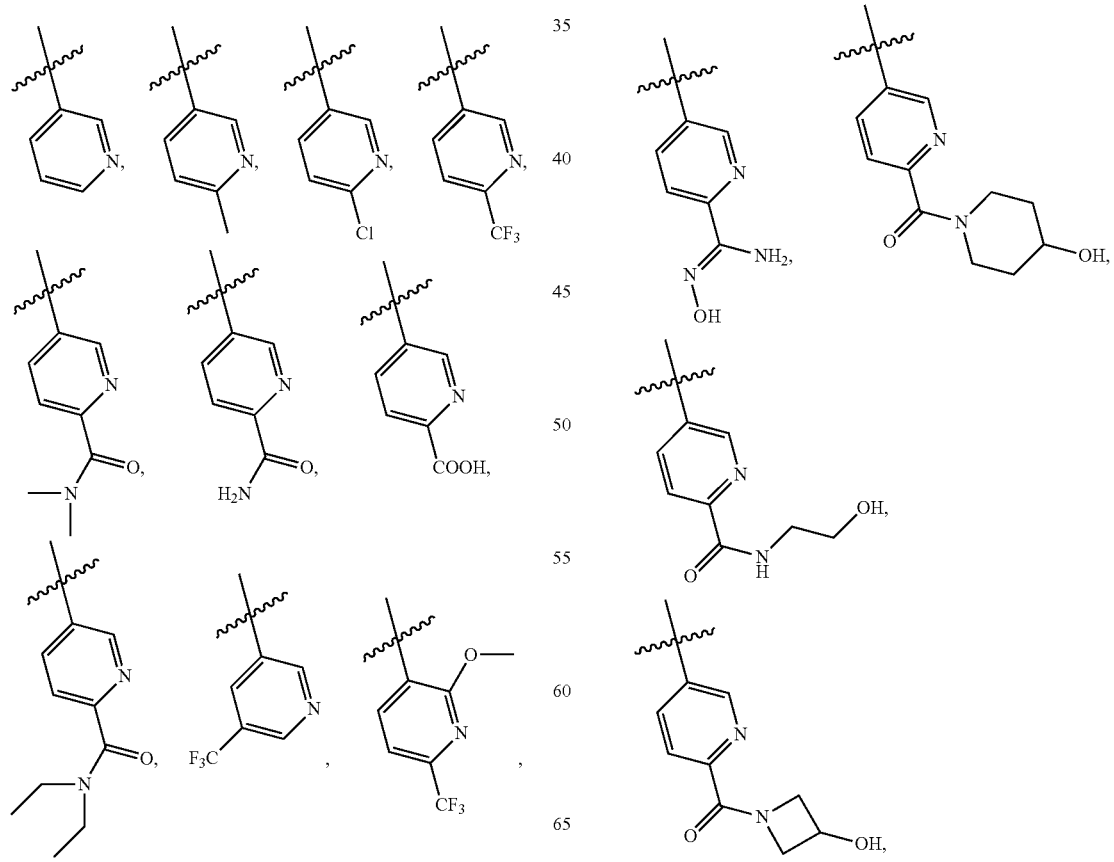

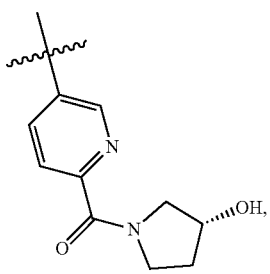

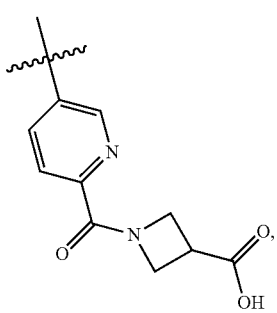

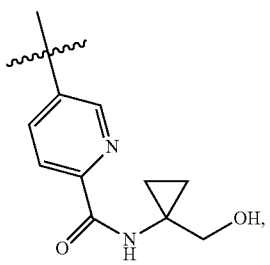 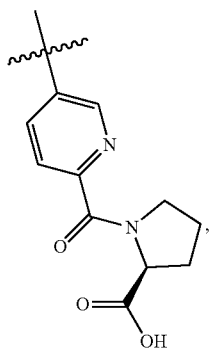

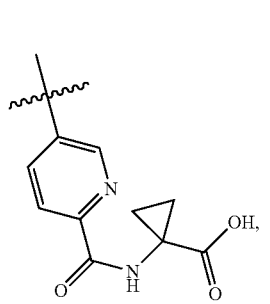 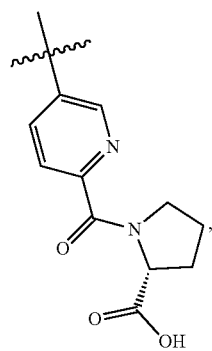

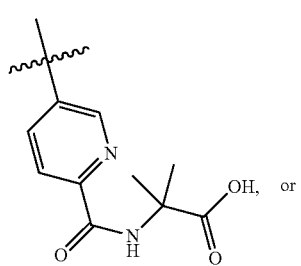 or

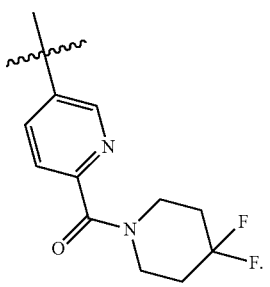

23. The method of claim 1, wherein $R_{10}$ is methoxy, ethoxy, propoxy, or isopropoxy.

24. The method of claim 23, wherein $R_{10}$ is isopropoxy.

25. The method of claim 1, wherein the compound is in (S)-configuration in case that $R_3$ and $R_4$ are different.

26. A method for treating glioblastoma (GBM) in a subject, comprising administering to the subject a compound having the structure:

Compound 1

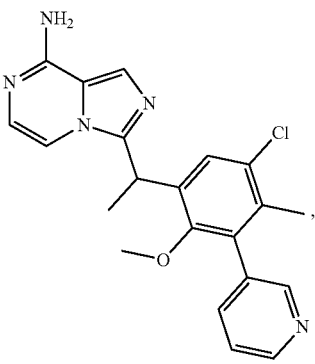

Compound 2

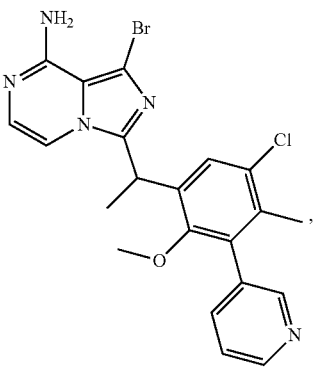

-continued
Compound 3
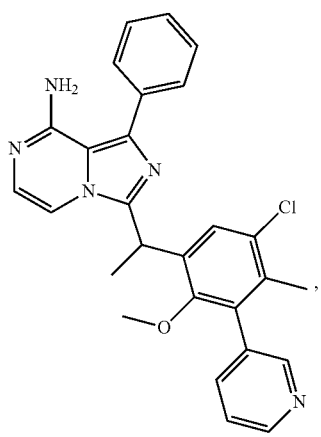
Compound 4
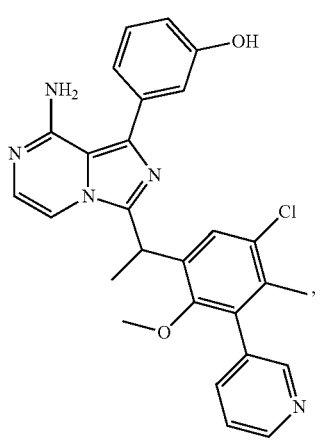
Compound 5
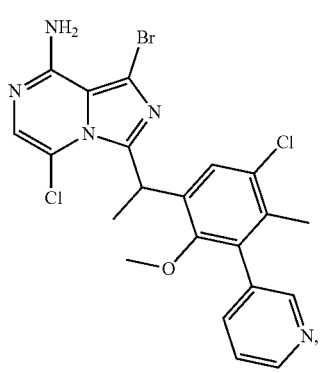
Compound 6
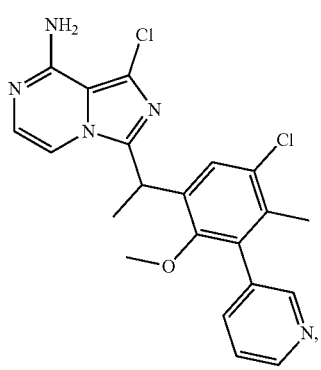
-continued
Compound 7
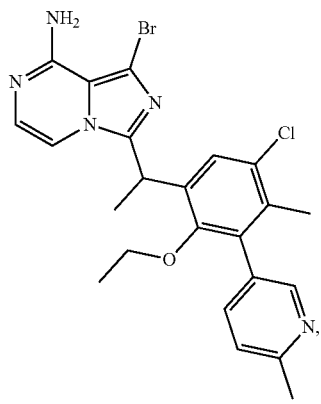
Compound 8
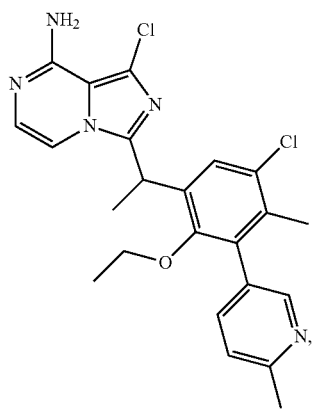
Compound 9
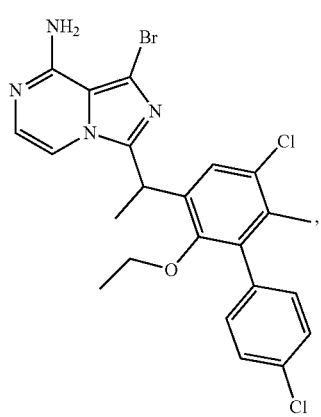

Compound 10
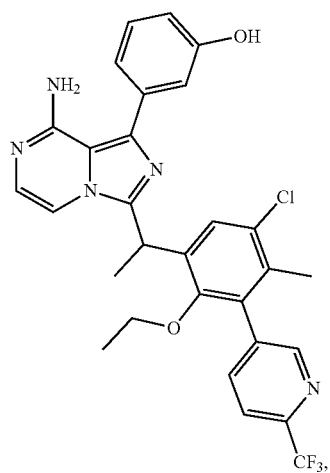
Compound 11
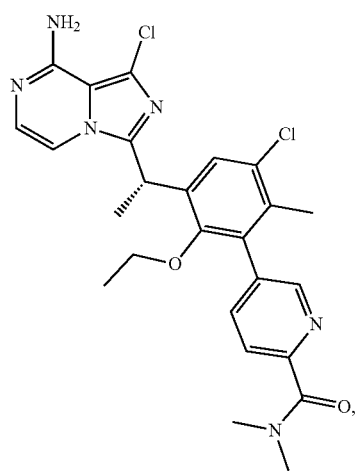
Compound 12
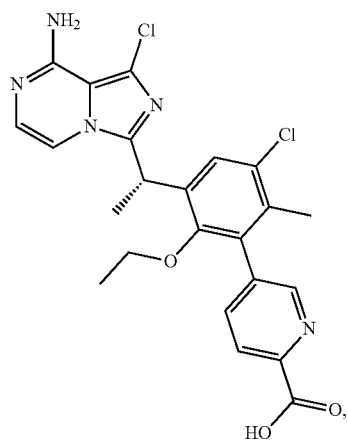
Compound 13
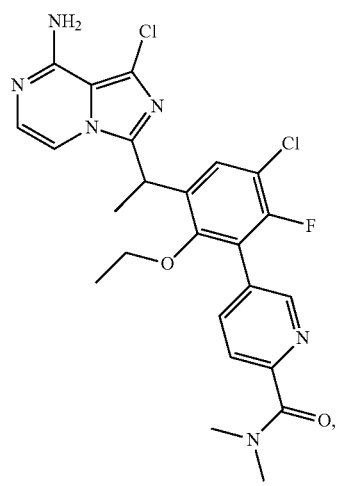
Compound 14
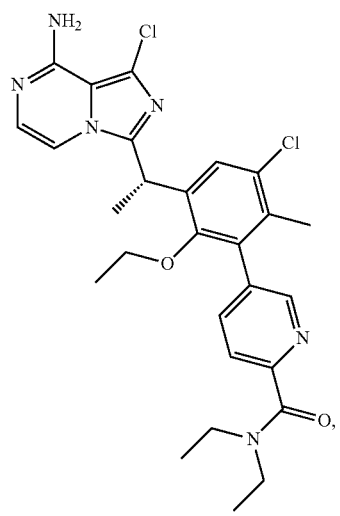
Compound 15
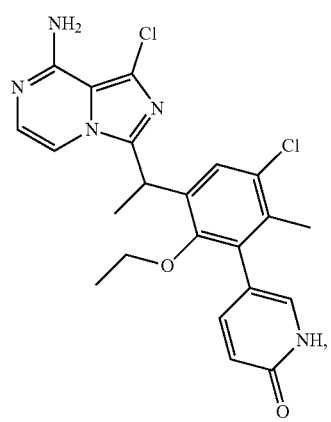

215
-continued
Compound 16
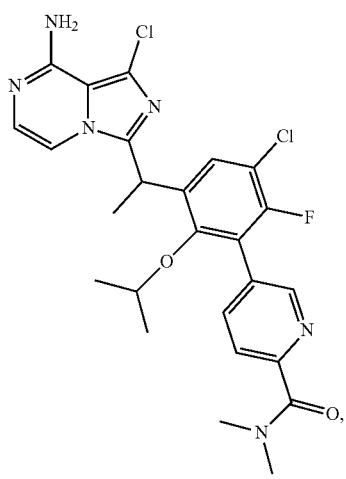
Compound 17
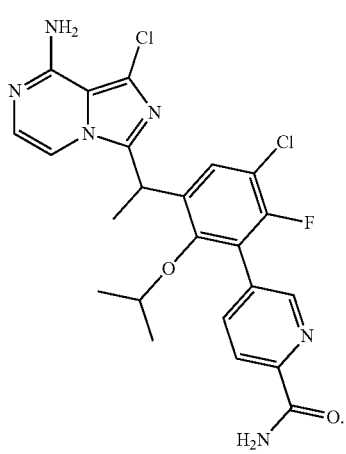
Compound 18
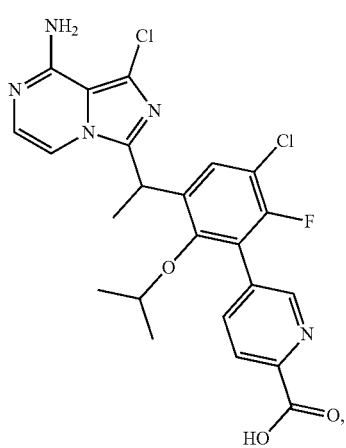
216
-continued
Compound 19
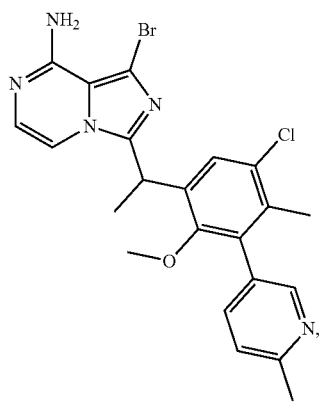
Compound 20
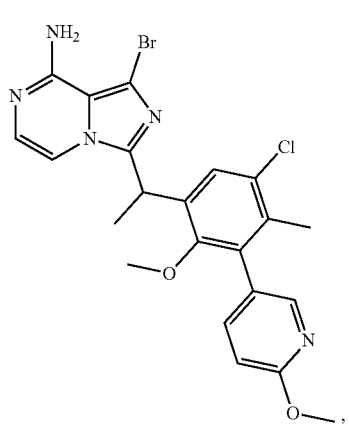
Compound 21
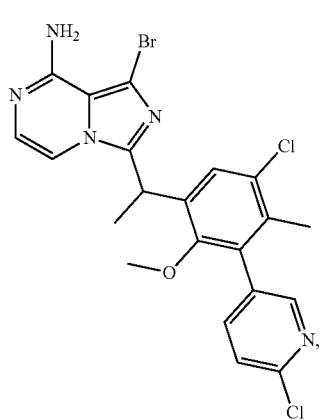
Compound 22

Compound 23
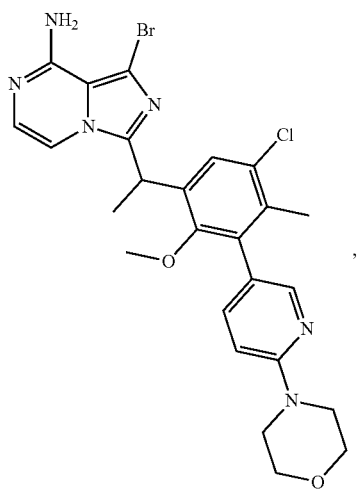
Compound 24
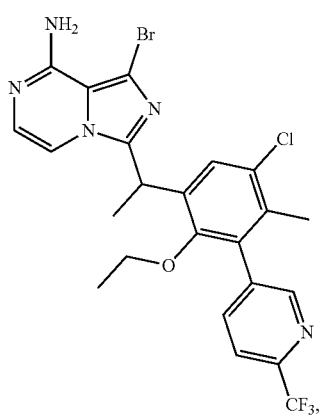
Compound 25
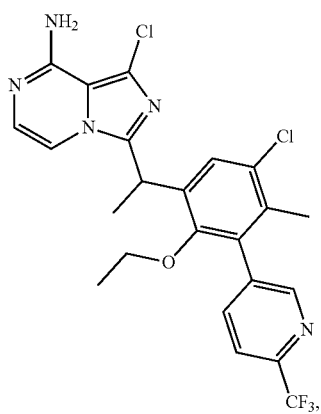
Compound 26
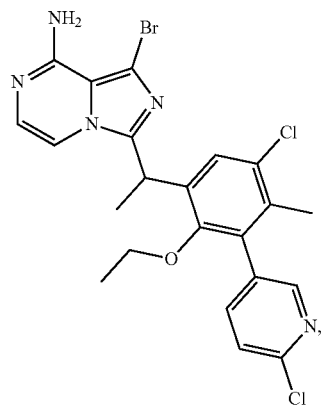
Compound 27
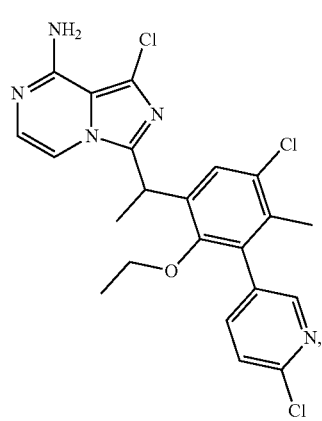
Compound 28
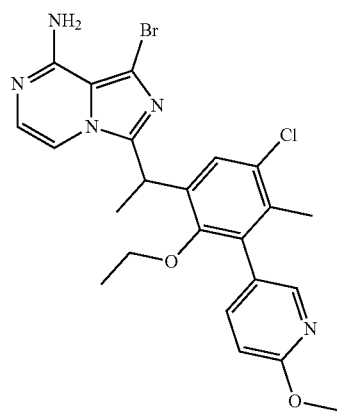
Compound 29
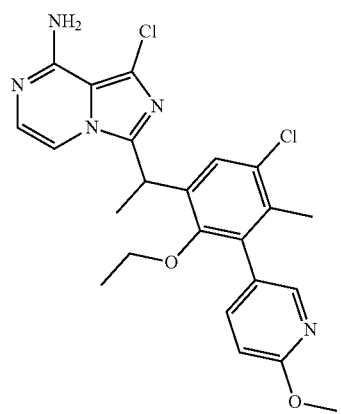

Compound 30
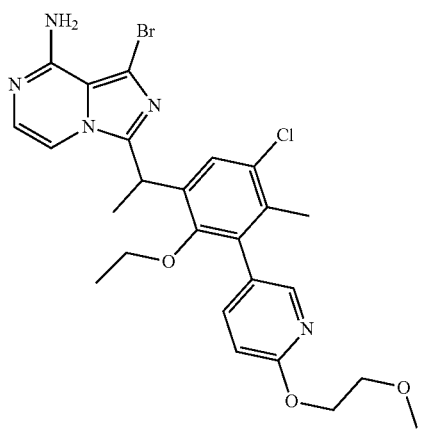
Compound 31
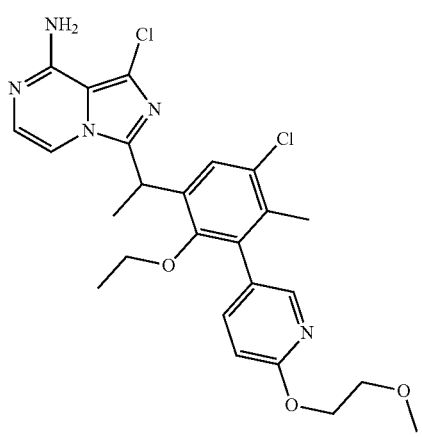
Compound 32
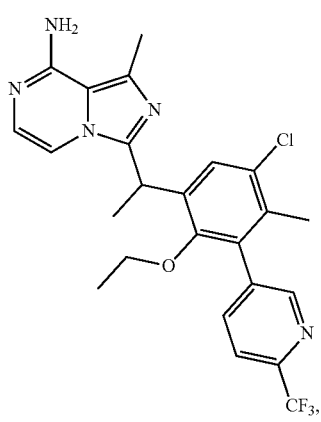
Compound 33
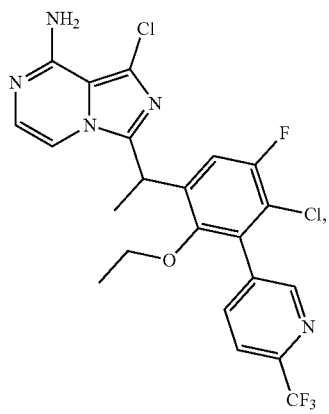
Compound 34
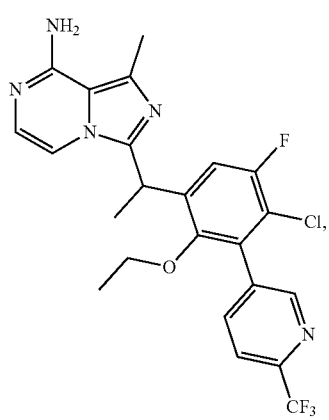
Compound 35
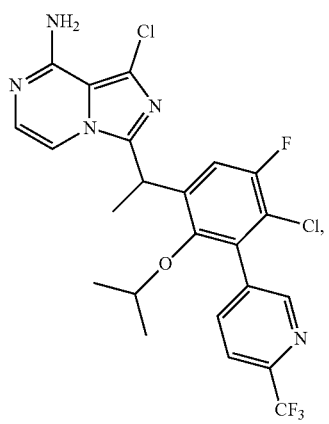
Compound 36
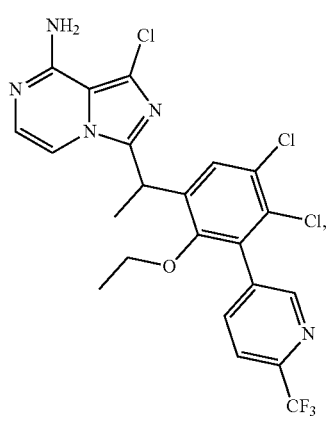

-continued
Compound 37
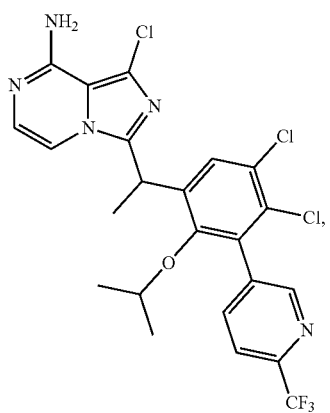
Compound 38
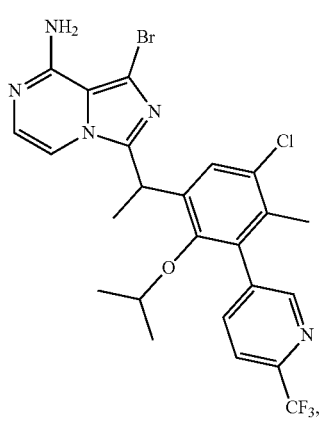
Compound 39
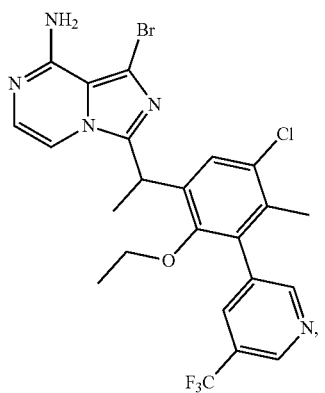
-continued
Compound 40
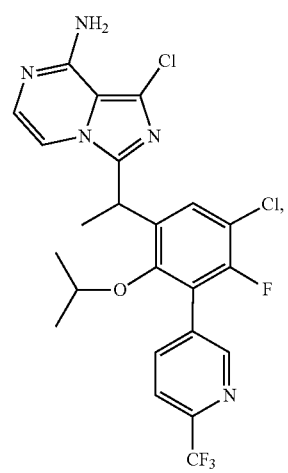
Compound 41
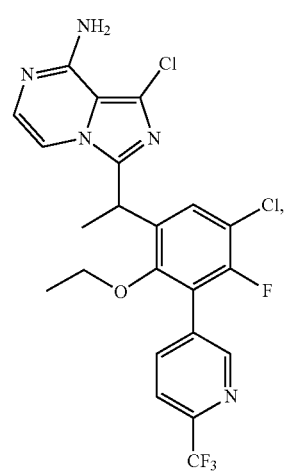
Compound 42
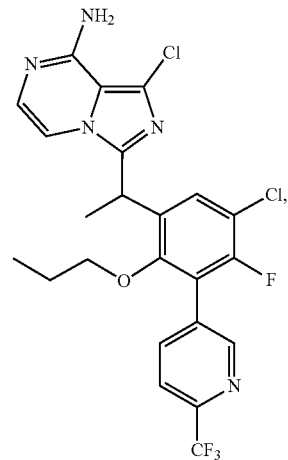

Compound 43
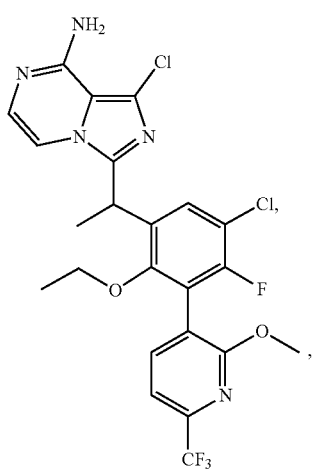
Compound 44
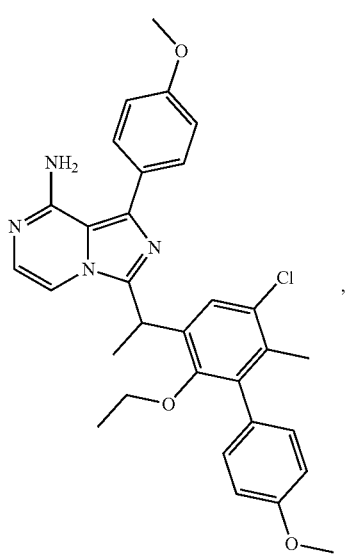
Compound 45
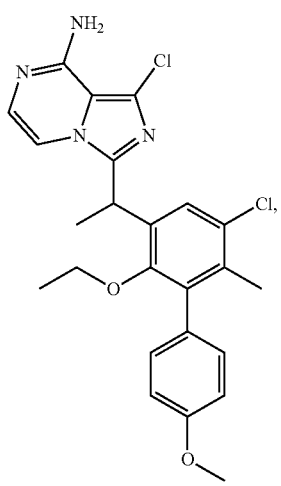
Compound 45A
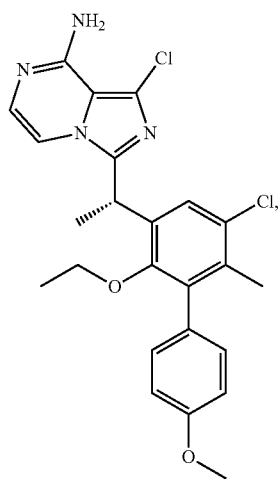
Compound 45B
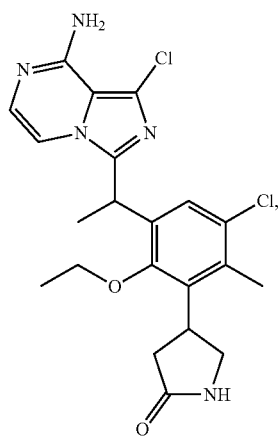
Compound 46

-continued
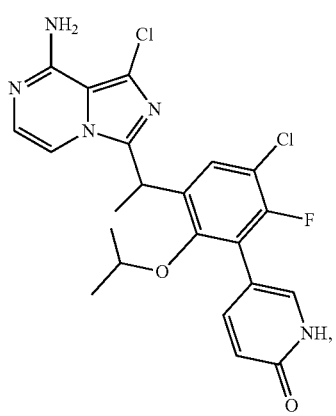
Compound 47
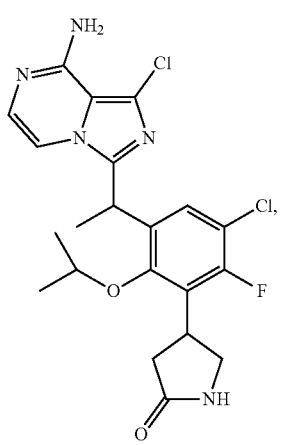
Compound 48
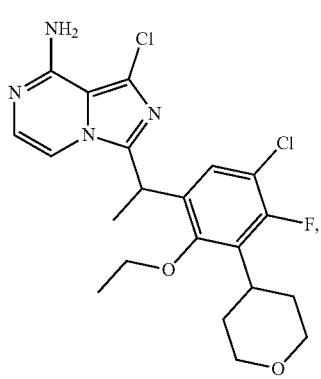
Compound 49
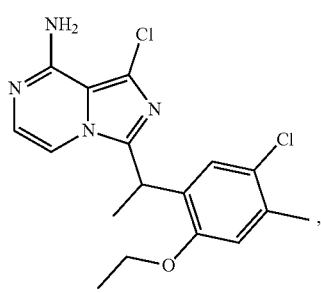
Compound 50
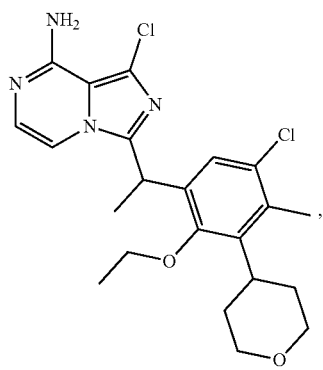
Compound 51
Compound 52
Compound 53
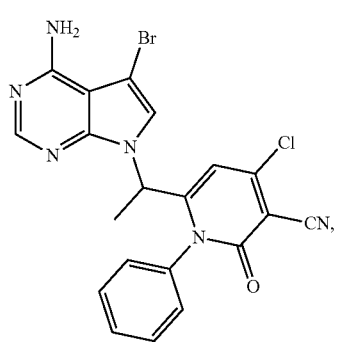
Compound 54

Compound 55
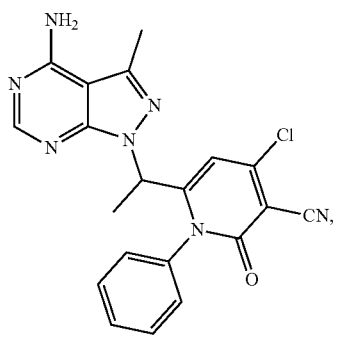
Compound 56
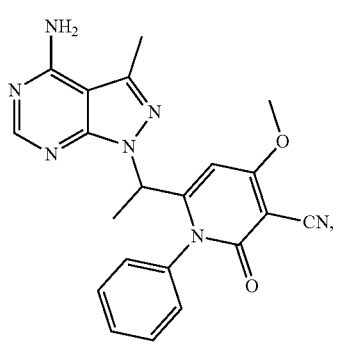
Compound 57
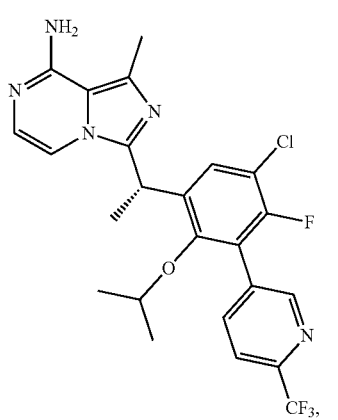
Compound 58
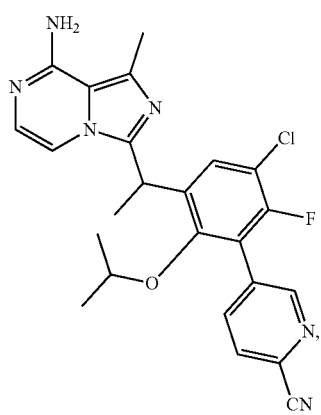
Compound 59
Compound 60
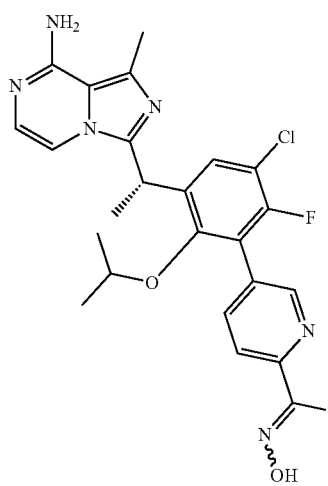
Compound 61
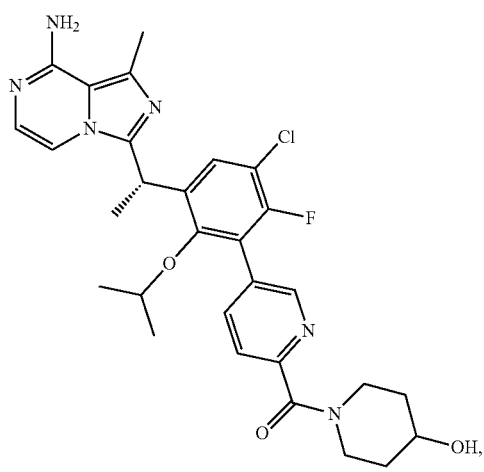

-continued
Compound 62
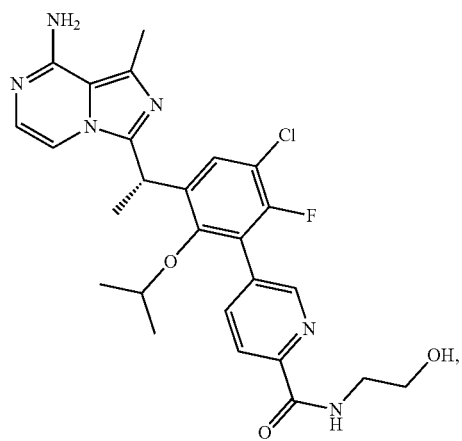
Compound 63
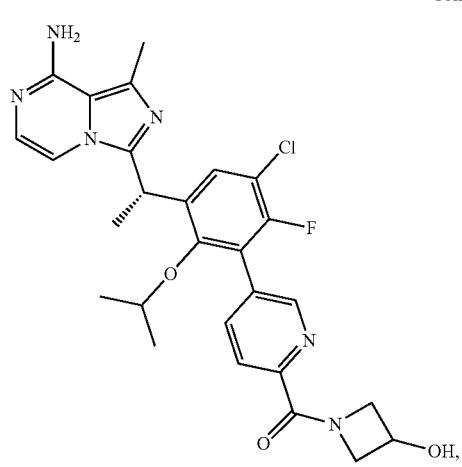
Compound 64
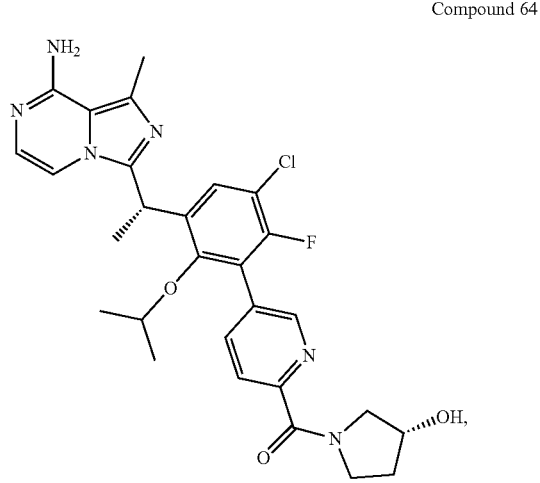
-continued
Compound 65
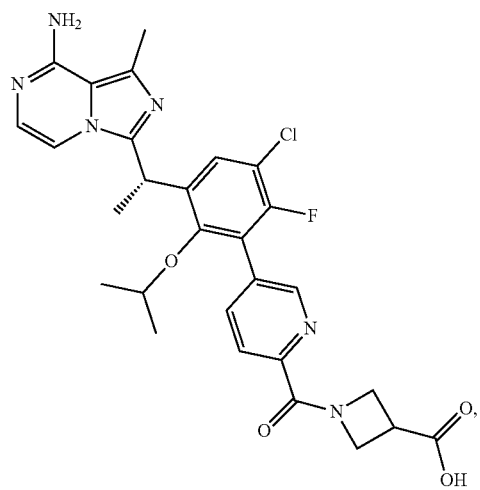
Compound 66
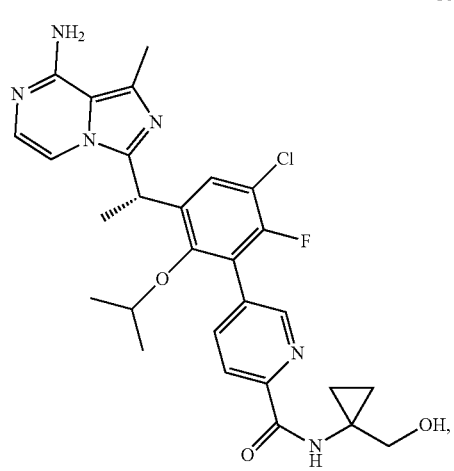
Compound 67
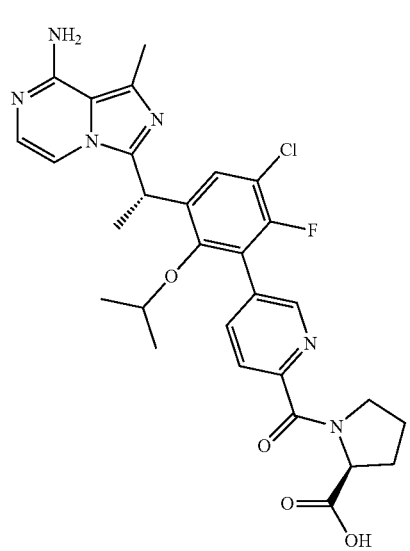

Compound 68
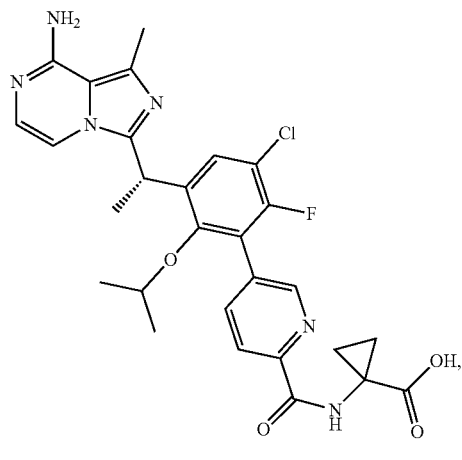
Compound 69
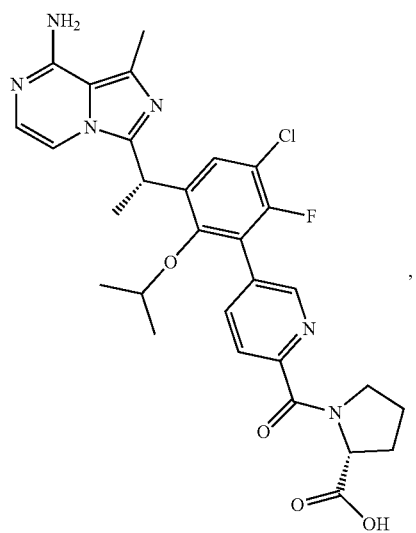
Compound 70
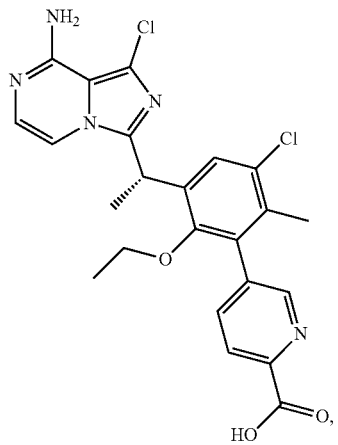, or
Compound 71
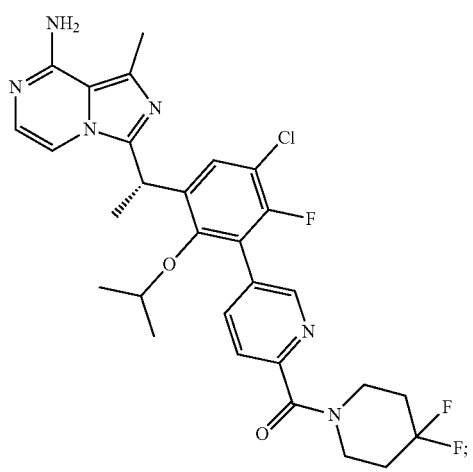
or a pharmaceutically acceptable salt thereof.
27. The method of claim 1, wherein the compound is:
Compound 11
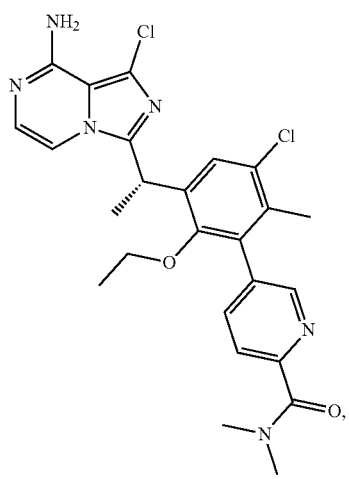
Compound 12

Compound 14
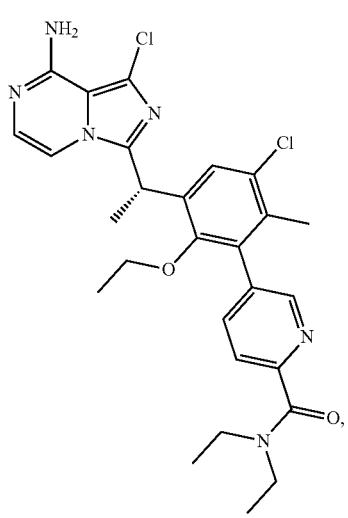
Compound 58
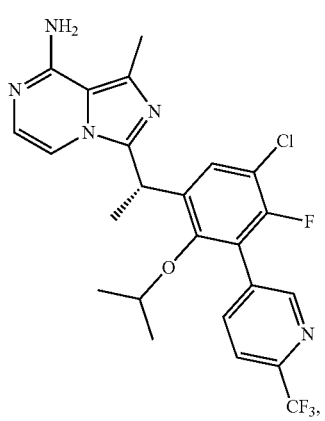
Compound 60
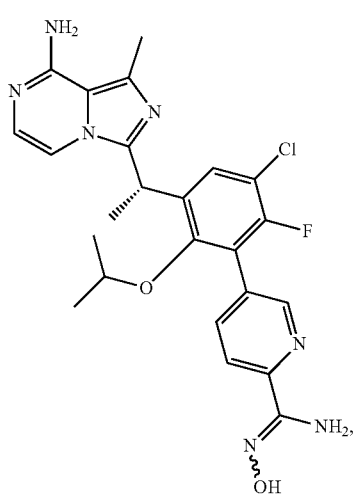
Compound 61
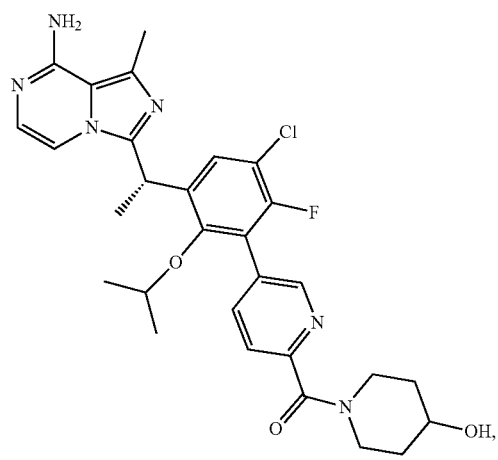
Compound 62
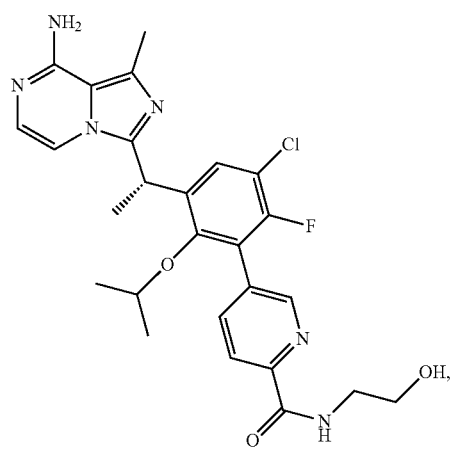
Compound 63
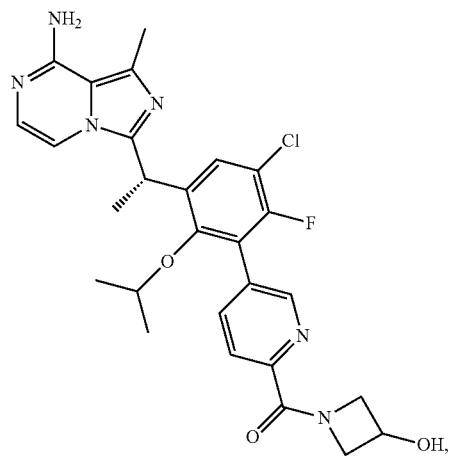

-continued
Compound 64
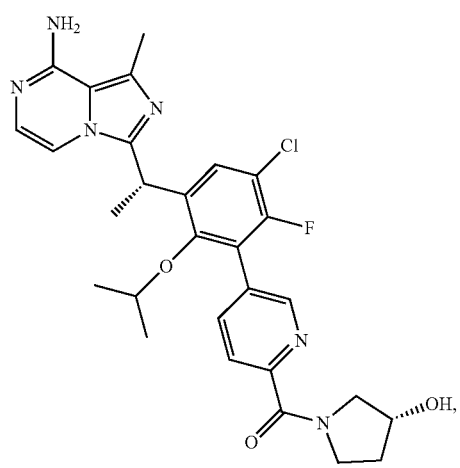
Compound 65
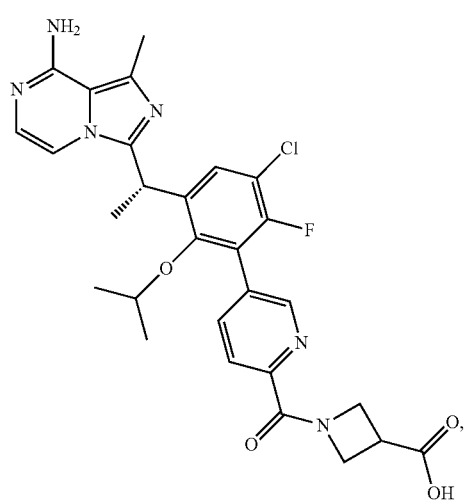
Compound 66
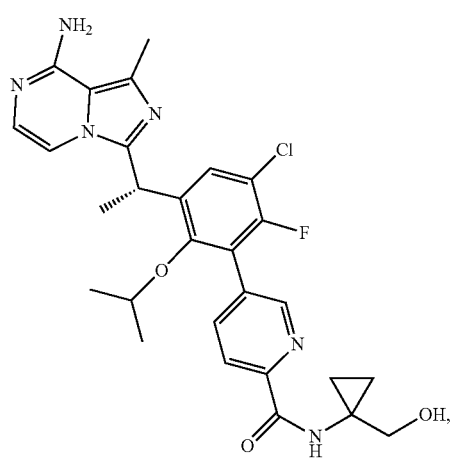
-continued
Compound 67
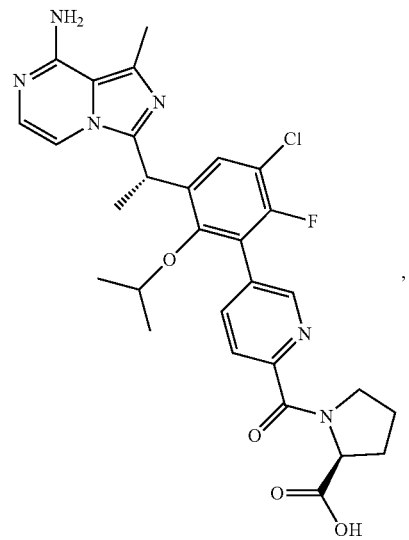
Compound 68
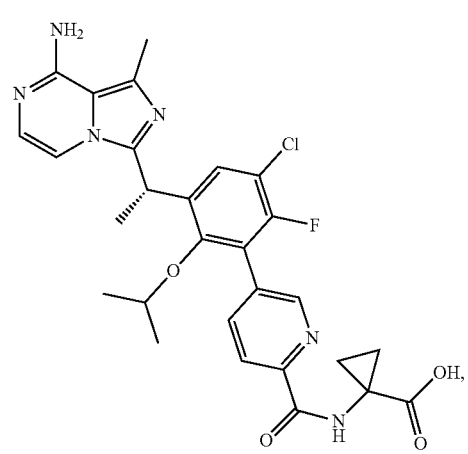
Compound 69
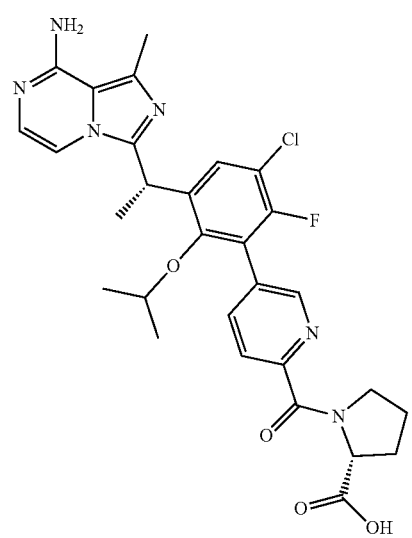

Compound 70
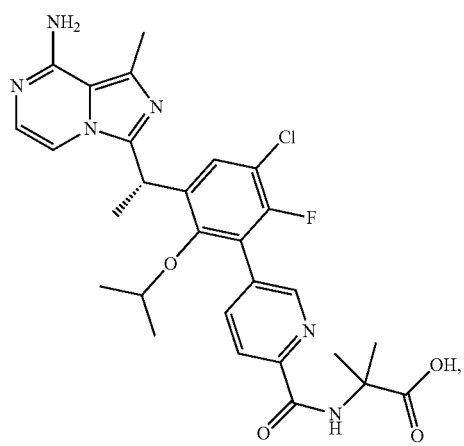
Compound 71
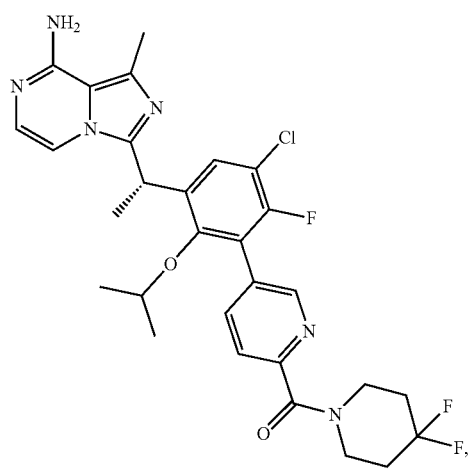
Compound 2A
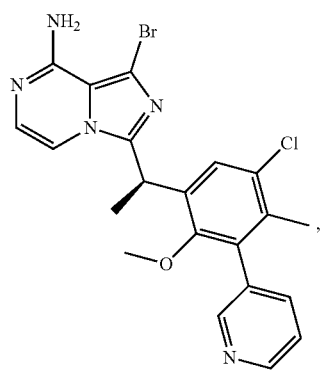
Compound 2B
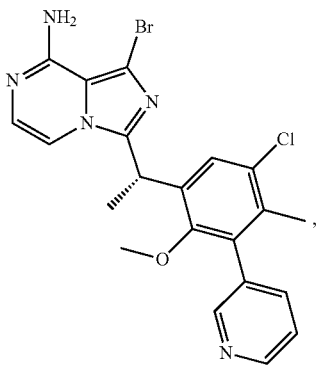
Compound 7A
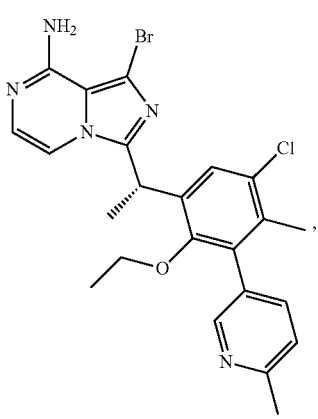
Compound 7B
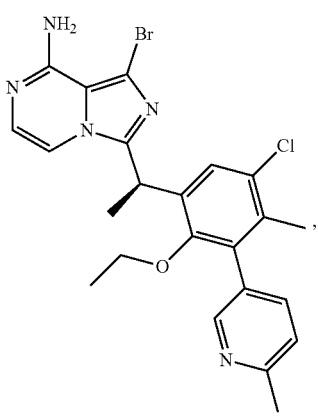
Compound 8A
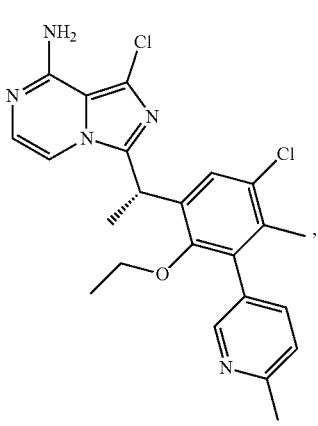

Compound 8B
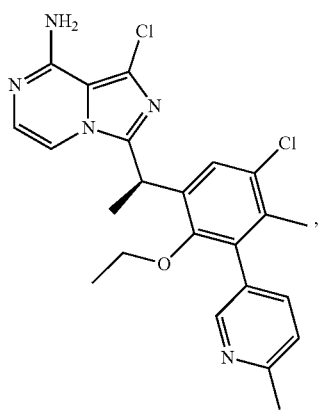
Compound 17A
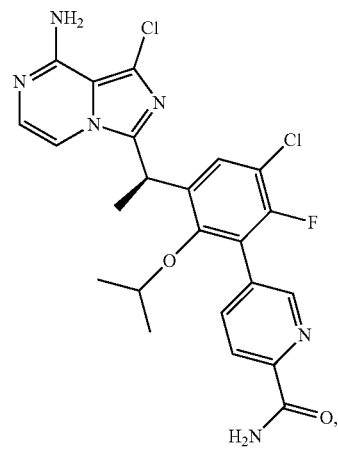
Compound 16A
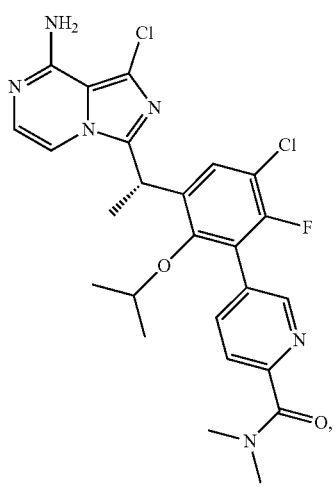
Compound 17B
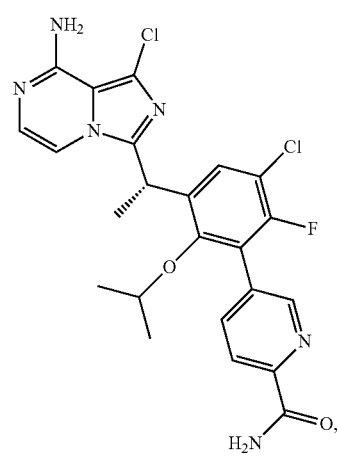
Compound 16B
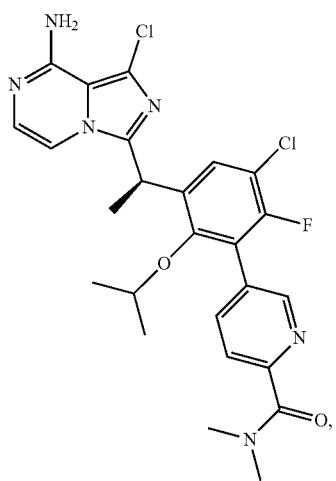
Compound 18A
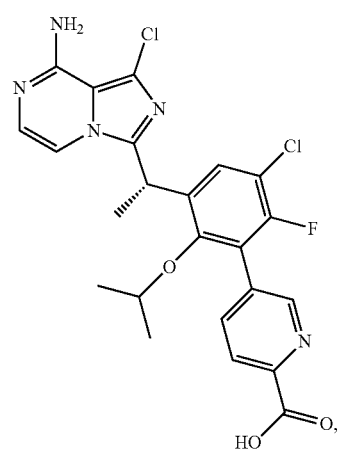

Compound 18B
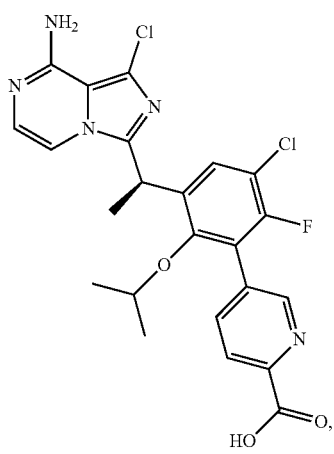
Compound 27A
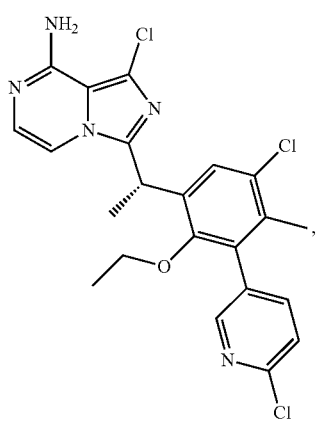
Compound 27B
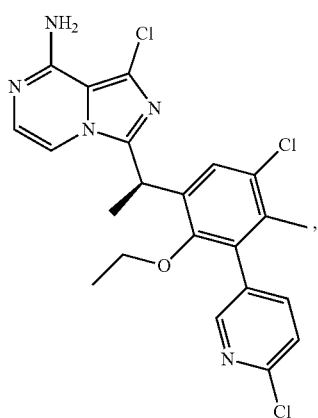
Compound 38A
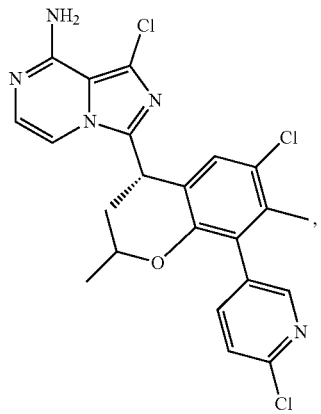
Compound 38B
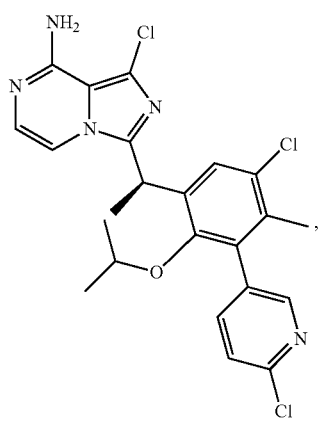
Compound 40A
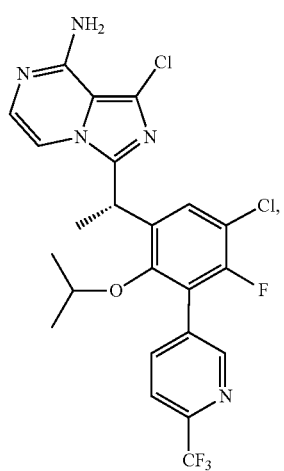

Compound 40B
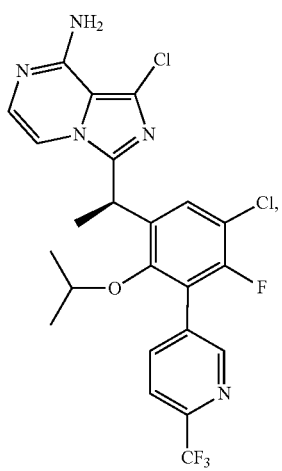
Compound 42A
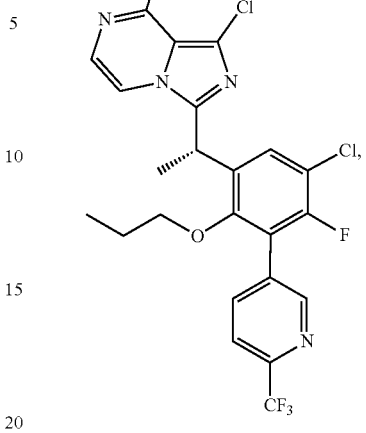
Compound 41A
Compound 42B
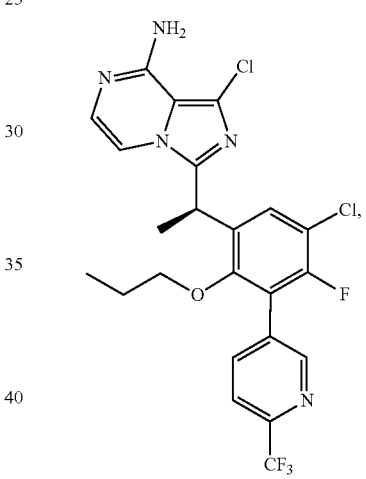
Compound 41B
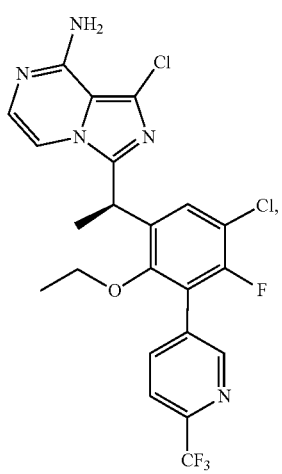
Compound 43A
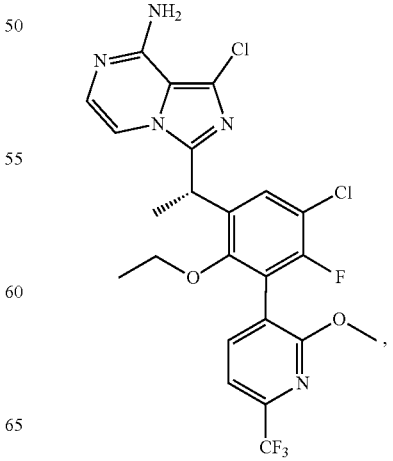

Compound 43B
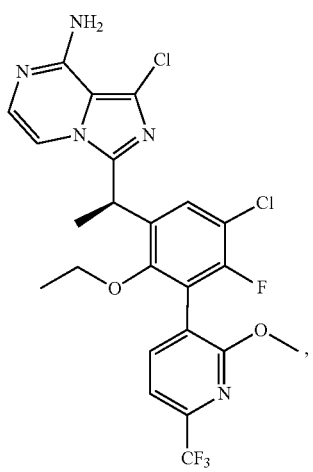
Compound 47A
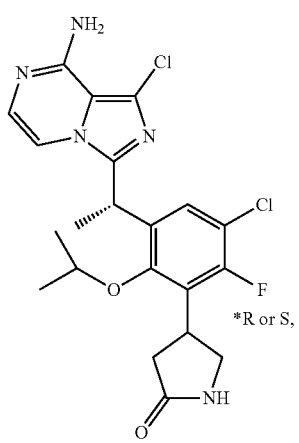
Compound 47B
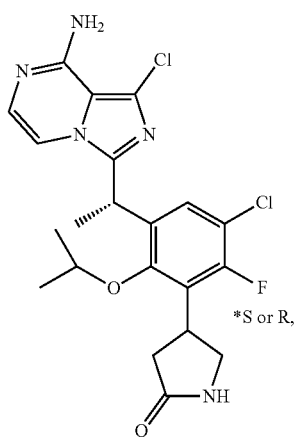
Compound 48A
*R or S,
Compound 48B
*S or R,
Compound 48C
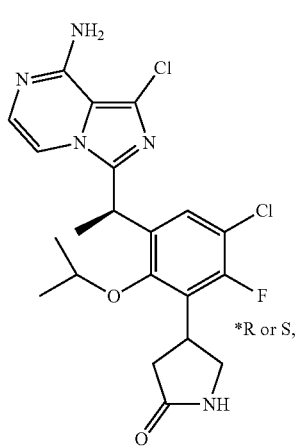
*R or S, 247
-continued
Compound 48D
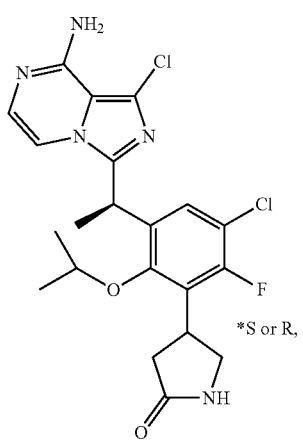
*S or R,
Compound 49A
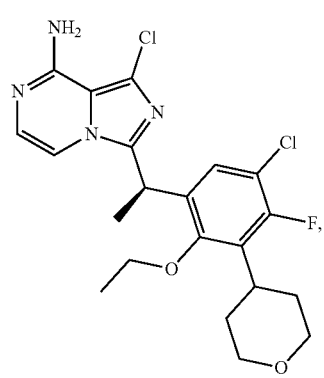
Compound 49B
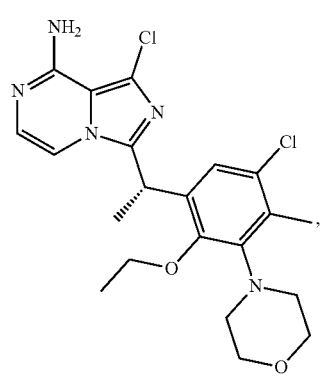
Compound 51A
248
-continued
Compound 51B
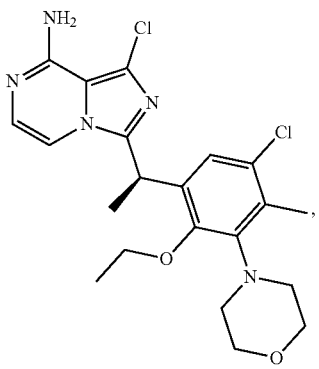
Compound 59A
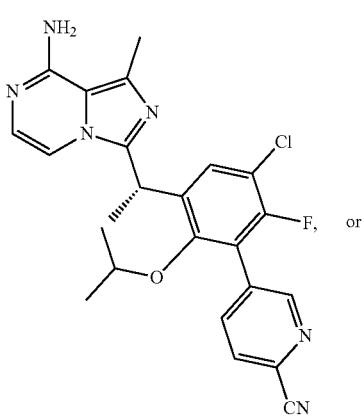
or
Compound 59B
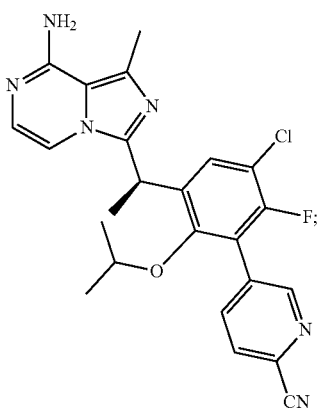
or a pharmaceutically acceptable salt thereof.

28. The method of claim 1, wherein the compound is:
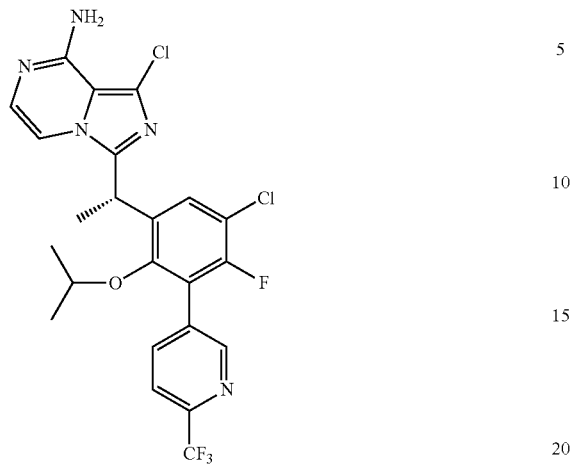
or a pharmaceutically acceptable salt thereof.
* * * * *